United States Patent
Evans et al.

(10) Patent No.: US 6,355,245 B1
(45) Date of Patent: Mar. 12, 2002

(54) C5-SPECIFIC ANTIBODIES FOR THE TREATMENT OF INFLAMMATORY DISEASES

(75) Inventors: Mark J. Evans, Cheshire; Louis A. Matis, Southport; Eileen Elliott Mueller, East Haven, all of CT (US); Steven H. Nye, Mequon, WI (US); Scott Rollins, Monroe, CT (US); Russell P. Rother; Jeremy P. Springhorn, both of Cheshire, CT (US); Stephen P. Squinto, Bethany, CT (US); Thomas C. Thomas, Madison, CT (US); James A. Wilkins, Woodbridge, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 0 days.

(21) Appl. No.: 08/487,283

(22) Filed: Jun. 7, 1995

Related U.S. Application Data

(63) Continuation of application No. PCT/US95/05688, filed on May 1, 1995, which is a continuation-in-part of application No. 08/236,208, filed on May 2, 1994, now Pat. No. 6,074,642.

(51) Int. Cl.$^7$ ..................... A61K 39/395; C07K 16/36; C12N 5/12

(52) U.S. Cl. ................... 424/145.1; 424/130.1; 424/133.1; 424/135.1; 424/141.1; 424/145.1; 424/158.1; 424/139.1; 424/130; 530/387.1; 530/387.3; 530/387.9; 530/388.1; 530/388.23; 530/388.25; 530/388.7; 435/326; 435/328; 435/331; 435/33 L; 435/337; 435/343; 435/346

(58) Field of Search ............... 530/387.1, 387.3, 530/388.1, 388.7, 387.9, 388.23; 435/69.1, 172.3, 328, 343, 70.21, 325, 331, 332, 346; 424/130.1, 141.1, 139, 133.1, 145.1

(56) References Cited

U.S. PATENT DOCUMENTS

| | | | |
|---|---|---|---|
| 4,578,335 A | 3/1986 | Urdal et al. ............ 435/68 |
| 4,686,100 A | 8/1987 | Raffin et al. ............ 424/85 |
| 4,816,397 A | 3/1989 | Boss et al. ............. 435/68 |
| 4,816,565 A | 3/1989 | Honjo et al. ............ 530/351 |
| 4,816,567 A | 3/1989 | Cabilly et al. ........... 530/387 |
| 4,845,198 A | 7/1989 | Urdal et al. ............. 530/387 |
| 4,867,973 A | 9/1989 | Goers et al. ............. 424/85.91 |
| 5,135,916 A | 8/1992 | Sims et al. ............. 514/21 |
| 5,173,490 A | 12/1992 | Sindelar et al. ............ 514/462 |
| 5,198,359 A | 3/1993 | Taniguchi et al. ........ 435/252.3 |
| 5,225,539 A | 7/1993 | Winter ................. 530/387.3 |
| 5,395,760 A | 3/1995 | Smith et al. ............ 435/240.1 |
| 5,506,247 A | 4/1996 | Sindelar et al. ........... 514/374 |
| 5,530,101 A * | 6/1996 | Queen et al. |
| 5,585,089 A | 12/1996 | Queen et al. ........... 424/133.1 |
| 5,610,279 A | 3/1997 | Brockaus et al. ........ 530/387.3 |
| 5,635,178 A | 6/1997 | Sims et al. ............. 424/145.1 |
| 5,693,761 A | 12/1997 | Queen et al. ........... 536/23.53 |
| 5,693,762 A | 12/1997 | Queen et al. ........... 530/387.3 |
| 5,808,029 A | 9/1998 | Brockaus et al. ......... 536/23.5 |
| 5,859,205 A | 1/1999 | Adair et al. ............ 530/387.3 |

OTHER PUBLICATIONS

Fitch et al. Circulation 100: 2499–2506 (1999).*
Rollins et al. Immunopharmacology 49: 69 (2000).*
Jain et al. Arthritis and Rheumatism 42: 577 (1999).*
Rollins et al. Molecular Immunology 35: 397 (1998).*
Wurzner et al. Complement. Inflamm. 8:328–340 (1991).*
Ames et al., "Isolation of neutralizing anti–C5a monoclonal antibodies from a filamentous phage monovalent fab display library" *J. Immunol.*152:4572–4581, 1994.
Auda et al., "Measurement of complement activation products in patients with chronic rheumatic diseases" *Rheumatol Int* 10:185–189, 1990.
Baker et al., "Depletion of C6 prevents development of proteinuria in experimental membranous nephropathy in rats" *Am J Path* 135:185–194, 1989.
Bhakdi et al., "Electroimmunoassy–immunoblotting (EIA–IB) for utilization of monoclonal antibodies in quantitative immunoelectrophoresis: the method and its applications" *J Immunol Methods*, 80:25–32, 1985.
Biesecker et al., "The release of C5a in complement–activated serum does not require C6" *J Immunol*, 143:1228–1232, 1989.
Cochrane et al., "A role of polymorphonuclear leukocytes and complement in nephrotoxic nephritis" *J Exp Med*, 122:99–116, 1965.
Couser et al., "C6 depletion reduces proteinuria in experimental nephropathy induced by a nonglomerular antigen" *J Am Soc Nephrol*, 2:894–901, 1991.
Couser et al., "Complement and the direct mediation of immune glomerular injury: A new perspective" *Kidney Internat*, 28:879–890, 1985.
Couser et al., "Role of $C_{5b-9}$ in experimental membranous nephropathy" *Nephrol Dial Transplant*, Suppl 1:25–31, 1992.
Dalmasso et al., "Complement channels in membranes: inhibition with a monoclonal antibody to a neoantigen of polymerized C9" *Biochem Biophys Res Commun*, 125:1013–1019, 1984.

(List continued on next page.)

Primary Examiner—Phillip Gambel

(57) ABSTRACT

The use of anti-C5 antibodies, e.g., monoclonal antibodies, to treat glomerulonephritis (GN) is disclosed. The administration of such antibodies at low dosage levels has been found to significantly reduce glomerular inflammation/enlargement and other pathologic conditions associated with GN. Also disclosed are anti-C5 antibodies and anti-C5 antibody-encoding nucleic acid molecules. These antibodies are useful in the treatment of GN and other inflammatory conditions involving pathologic activation of the complement system.

23 Claims, 19 Drawing Sheets

OTHER PUBLICATIONS

Discipio et al., "The activation of human complement component C5 by a fluid phase C5 convertase." 258(17), 10629–10636, 1983.

Discipio et al., "The conversion of human complement component C5 into fragment C5b by the alternative–pathway C5 convertase" *Biochem J*, 199:497–504, 1981.

Discipio, "Formation and structure of the C5b–7 complex of the lytic pathway of complement" *J Biol Chem* 267:17087–17094, 1992.

Falk and Jennette, "Immune complex induced glomerular lesions in C5 sufficient and deficient mice" *Kidney Internat*, 30:678–686, 1986.

Floege et al., "Markers of complement–dependent and complement–independent glomerular visceral epithelial cell injury in vivo" *Lab Invest*, 67:486–497, 1992.

Frei et al., "Generation of a monoclonal antibody to mouse C5 application in an ELISA assay for detection of anti–C5 antibodies" *Mol Cell Probes*, 1:141–149, 1987.

Garrad et al., "Synthesis of C3, C5, C6, C7, C8, and C9 by human fibroblast." *Scand J. Immunol* 32(5): 555–560, 1990.

Giclas et al., "Preparation and characterization of monoclonal antibodies against the fifth component of rabbit complement (C5)" *J Immunol Meth* 105:201–209, 1987.

Goldman and Goldman, "Antibody–induced suppression of the fifth component of complement in mice" *J Immunol*, 120:400–407, 1978.

Groggel et al., "Role of the terminal complement pathway in experimental membranous nephropathy in the rabbit" *J Clin Invest*, 72:1948–1957, 1983.

Hong et al., "An anticomplement agent, K–76 monocarboxylic acid: Its site and mechanism of inhibition of the complement activation cascade." *J. Immunol* 122:2418–2433, 1979.

Hugo et al., "Monoclonal antibodies against neoantigens of the terminal C5b–9 complex of human complement" *BioScience Rep*, 5:649–658, 1985.

Hugo et al., "Sensitive ELISA fo quantitating the terminal membrane C5b–9 and fluid–phase SC5b–9 complex of human complement" *J Immunol Methods* 99:243–251 1987.

Inoue, "C5 neoepitopes appearing during activation." *Complement Inflamm* 6(3):219–222, 1989.

Jennette et al., "Amelioration of immune complex–mediated glomerulonephritis b synthetic protease inhibitors" *Am J Path*, 127:499–506, 1987.

Jones et al., "Replacing the complementarity–determining regions in a human antibody with those from a mouse." *Nature*, 321:522–525, 1986.

Kitamura et al., "The activation of C5 in the fluid phase and in the absense of C3 through the classical pathway of the complement system." *Immumology* 58(3): 459–465, 1986.

Klos et al., "Detection of native human complement components C3 and C5 and their primary activation peptides C3a and C5a (anaphylatoxic peptides) by ELISAs with monoclonal antibodies" *J Immuno Methods* 111:241–252, 1988.

Knicker and Cochrane, "Pathogenic factors in vascular lesions of experimental serum sickness" *J Exp Med*, 122:83–97, 1965.

Kolb and Muller–Eberhard, "The Membrane Attack Mechanism of Complement" *J Exper Med*, 141:724–735, 1975.

Minta and Man, "Cleavage of Human C5 By Trypsin: Characterization of the Digestion Products by Gel Electrophoresis" *J Immunol*, 119:1597–1602, 1977.

Mollnes et al., "Identification of a human C5 β–chain epitope exposed in the native complement component but concealed in the SC5b–9 complex" *Scand J. Immunol*, 28:307–312, 1988.

Mollnes et al., "Quantification of the terminal complement complex in human plasma by an enzyme–linked immunosorbent assay based on monoclonal antibodies against a neoantigen of the complex." *Scand J Immunol*, 22(2): 197–202, 1985.

Montz et al., "Regulation of the human autologous T cell proliferation by endogeneously generated C5a" *Cell Immunol*, 127:337–351, 1990.

Moongkarndi et al., "Monoclonal antibodies against the fifth component of human complement" *Immunobiol* 162:397, 1982.

Moongkarndi et al., "Immunological and functional properties of two monoclonal antibodies against human C5." *Immunobiol* 165:323, 1983.

Morrison, "In vitro antibodies strategies for production and application" *Ann Rev Immunol* 10:239–265, 1992.

Morgan, "Clinical complementology recent progress and future trends." *EPO J. Clinical Invesg.* 24: 219–228, 1994.

Morgan et al., "Inhibition of complement–induced [14C] sucrose release by intracellular and extracellular monoclonal antibodies to C9: evidence that C9 is a transmembrane protein." *Biochem Biophys Res Commun*, 118(2):616–622, 1984.

Passwell et al., "Local extrahepatic expression of complement genes C3, factor B, C2, and C4 is increased in murine lupus nephritis" *J Clin Invest*, 82:1676–1684, 1988.

Peake et al., "Differences in the metabolism of C4 in patients with complement activation." *Clin Exp Immunol* 78:49–53, 1989.

Perez et al., "Complement (C5)–derived chemotactic activity in serum form patients with pancreatitis" *J Lab Clin Med*, 101:123–129, 1983.

Perez et al., "Radioimmunoelectrophoresis, a sensitive method of detecting cleavage of the fifth component of human complement (C5)" *J Immunol Methods*, 56:55–62, 1983.

Reed et al., "Synthesis of complement component C5 by human B and T lymphoblastoid cell lines" *Immunogenetics*, 31:145–151, 1990.

Riechmann et al., "Reshaping human antibodies for therapy." *Nature*, 332: 323–327, 1988.

Rinder et al., "Blockade of C5 and C5b–9 generation Inhibits leukocyte and platelet activation during extracorporeal circulation." *J. Clinical Invesg.* 96(3): 1564–1572.

Rodrigues et al., "Engineering fab' fragments for efficient F(ab)$_2$ formation in *escherichia coli* and for improved in vivo stability." *J. Immunology*, 151(12): 6954–6961, 1993.

Rottini et al., "Monoclonal antibodies as probes to investigate the molecular changes of C5 associated with the different stability of the molecule on sheep erythrocytes and *Escherichia coli* 0111:B4" *J. Immunol* 146:643–647, 1991.

Salant et al., "A new role for complement in experimental membranous nephropathy in rats" *J Clin Invest*, 66:1339–1350, 1980.

Schrijver et al., "Anti–GBM nephritis in the mouse: role of granulocytes in the heterologous phase" *Kidney Internat*, 38:86–95, 1990.

Schrijver et al., "Antiglomerular basement membrane nephritis in the mouse" *Lab Invest*, 59:484–491, 1988.

Seeger et al., "Noncytolytic terminal complement complexes may serve as calcium gates to elicit leukotriene B4 generation in human polymorphonuclear leukocytes." *J. Immunol*, 137(4): 1286–1293, 1986.

Stahl et al., "Role of granulocytes and C5 in myocardial response to zymosan–activated serum." *Am J. Physiol*, 261(1 Pt2): H29–H37, 1991.

Sundsmo, "Leukocyte complement: a possible role for C5 in lymphocyte stimulation" *J Immunol*, 131:886–891, 1983.

Takeda et al., "Rapid and simple measurement of human C5a–des–Arg level in plasma or serum using monoclonal antibodes" *J Immunol Methods*, 101:265–270, 1987.

Unanue and Dixon, "Participation of complement in nephrotoxic nephritis" *J Exp Med*, 119:965–982, 1964.

Vogt et al., "'Inactivated' third component of complement (C3b–like C3; C3i) acquires C5 binding capacity and supports C5 activation upon covalent fixation to a solid surface" *Complement*, 1:87–96, 1984.

Vogt et al., "Non–enzymic activation of the fifth component of human complement. by oxygen radicals. some properties of the activation product. C5b–like C5" *Mol Immunol* 26(12): 1133–1142, 1989.

Wetsel and Kolb, "Complement–independent activation of the fifth component (C5) of human complement: limited trypsin digestion resulting in the expression of biologic activity" *J Immunol* 128:2209–2216, 1982.

Wurzner et al., "Inhibition of terminal complement complex formation and cell lysis by monoclonal antibodies" *Complement Inflamm*, 8:328–340, 1991.

* cited by examiner

```
1                                                                                    20
GAC ATC CAG ATG ACT CAG TCT CCA GCT TCA CTG TCT GCA TCT GTG GGA GAA ACT GTC ACC
 D   I   Q   M   T   Q   S   P   A   S   L   S   A   S   V   G   E   T   V   T 24                          30                  34                       40
ATC ACA TGT GGA GCA AGT GAG AAT ATT TAC GGT GCT TTA AAT TGG TAT CAG CGG AAA CAG
 I   T   C   G   A   S   E   N   I   Y   G   A   L   N   W   Y   Q   R   K   Q
                        ─────────────────────────────
                                   CDR-L1

50                          56                   60
GGA AAA TCT CCT CAG CTC CTG ATC TAT TAT GGT GCA ACC AAC TTG GCA GAT GGC ATG TCG
 G   K   S   P   Q   L   L   I   Y   Y   G   A   T   N   L   A   D   G   M   S
                                        ─────────────────
                                              CDR-L2

70                              80
AGG TTC AGT GGC AGT GGA TCT GGT AGA CAG TAT TAT CTC AAG ATC AGT AGC CTG CAT CCT
 R   F   S   G   S   G   S   G   R   Q   Y   Y   L   K   I   S   S   L   H   P 89                              97                        100
GAC GAT GTT GCA ACG TAT TAC TGT CAA AAT GTG TTA AAT ACT CCT CTC ACG TTC GGT GCT
 D   D   V   A   T   Y   Y   C   Q   N   V   L   N   T   P   L   T   F   G   A
                                    ───────────────────────
                                              CDR-L3

GGG ACC AAG TTG GAG CTG AAA
 G   T   K   L   E   L   K
```

FIG.18

```
-19                                                                      -1 +1
atg aaa tgg agc tgg gtt att ctc ttc ctc ctg tca gta act gca ggt gtc cac tcc cag
 M   K   W   S   W   V   I   L   F   L   L   S   V   T   A   G   V   H   S   Q
                                    10                                        20
GTT CAG CTG CAG CAG TCT GGA GCT GAG CTG ATG AAG CCT GGG GCC TCA GTG AAG ATG TCC
 V   Q   L   Q   Q   S   G   A   E   L   M   K   P   G   A   S   V   K   M   S
              26                                  35                          40
TGC AAG GCT ACT GGC TAC ATA TTC AGT AAC TAC TGG ATA CAG TGG ATA AAG CAG AGG CCT
 C   K   A   T   G   Y   I   F   S   N   Y   W   I   Q   W   I   K   Q   R   P
                                CDR-H1
                                50  52a                                       60
GGA CAT GGC CTT GAG TGG ATT GGT GAG ATT TTA CCT GGA AGT GGT TCT ACT GAG TAC ACT
 G   H   G   L   E   W   I   G   E   I   L   P   G   S   G   S   T   E   Y   T
                                           CDR-H2
              65                                  70                          80
GAG AAC TTC AAG GAC AAG GCC ACA TTC ACT GCA GAT ACA TCC TCC AAC ACA GCC TAC ATG
 E   N   F   K   D   K   A   T   F   T   A   D   T   S   S   N   T   A   Y   M
      82a 82b 82c                                 90                          95
CAA CTC AGC AGC CTG ACA TCA GAG GAC TCT GCC GTC TAT TAC TGT GCA AGA TAT TTC TTC
 Q   L   S   S   L   T   S   E   D   S   A   V   Y   Y   C   A   R   Y   F   F
             100 a   b   c   d   e                102                        110
GGT AGT AGC CCC AAC TGG TAC TTC GAT GTC TGG GGC GCA GGG ACC ACG GTC ACC GTC TCC
 G   S   S   P   N   W   Y   F   D   V   W   G   A   G   T   T   V   T   V   S
     CDR-H3

TCA
 S
```

FIG.19

C5-SPECIFIC ANTIBODIES FOR THE TREATMENT OF INFLAMMATORY DISEASES

This is a continuation in part of International application Ser. No. PCT/US95/05688, filed May 1, 1995, which is a continuation in part of U.S. application Ser. No. 08/236,208, filed May 2, 1994, which issued as U.S. Pat. No. 6,074,642 on Jun. 13, 2000. International application Serial No. PCT/US95/05688 was published in English under PCT Article 21(2) on Nov. 9, 1995 as WO 95/29697.

FIELD OF THE INVENTION

The present invention relates to the treatment of glomerulonephritis (GN) and other inflammatory diseases, and more generally to therapeutic treatments involving the pharmacologic inhibition of a patient's complement system. In particular, the invention relates to the use of antibodies specific to human complement component C5 to accomplish such therapeutic treatment. The invention also relates to compositions comprising native monoclonal antibodies (mAbs) specific to human complement component C5 that block complement hemolytic activity and C5a generation at concentrations that substantially reach the theoretical one to two stoichiometric limit of antibody to antigen that can be achieved by a bivalent antibody. The invention further provides recombinant mabs that are derivatives (including monovalent derivatives) of these native mAbs that provide substantially the same blocking activities as the native mabs.

BACKGROUND OF THE INVENTION

I. Immune Complex Mediated Disease

The formation of immune complexes is the typical consequence of the interaction of antigens with specific antibodies. The inflammatory response that ensues when such complexes accumulate in a limited area is an important element of normal host defenses, leading to immune complex clearance and antigen destruction by phagocytic cells. In contrast, immune complex diseases are reflections of excess complex formation or retarded clearance, usually under conditions of exceptional antigen challenge or immunologic dysregulation. Under such circumstances, immune complexes are deposited or formed at specific tissue sites and resulting inflammatory responses lead to disease states due to localized or systemic tissue damage. The kidney, and more specifically the kidney structure known as the glomerulus, is a particularly important site of immune complex deposition resulting in the development of serious disease conditions.

Human studies, and studies using animal models of human diseases, have implicated the complement system in the pathologies associated with a number of immune complex associated disorders. The activation of complement that mediates the pathology associated with these disorders may be a consequence of an autoimmune mechanism, or can be non-immunologic in origin.

The hypersensitivity response that occurs when antibodies bind to antigens either in tissues or in the circulation results from the activation of complement and the release of molecules that mediate inflammation. This process is classified as either being mediated by the binding of antibody to fixed tissue or cell bound antigens (Type II hypersensitivity) or to circulating antigens, resulting in the formation of circulating immune complexes and their subsequent pathogenic deposition in tissues (Type III hypersensitivity).

Type II hypersensitivity is mediated through the activation of complement following the binding of antibodies to fixed tissue antigens. The inflammatory response that ensues results from the activation of the proinflammatory and lytic components of the complement system and the subsequent recruitment of stimulated leukocytes to the sites of immune complex formation. The increased vascular permeability that results from the anaphylatoxic activities of C3a and C5a further enhances immune complex deposition and leukocyte recruitment.

The cross-linking of antibody bound cells or tissues to effector cells such as neutrophils, platelets, NK cells, and monocytes via their Fc receptors also plays a proinflammatory role. Such cross-linking activates effector cells, stimulating the release of oxygen radicals, prostaglandins, and leukotrienes, which release is further potentiated by the actions of activated complement components.

Examples of Type II hypersensitivity-mediated conditions include hyperacute rejection of transplanted organs, autoimmune hemolytic and thrombocytopenic states, Goodpasture's syndrome (and associated glomerulonephritis and pulmonary hemorrhage), myasthenia gravis, pathologic sequellae associated with insulin-dependent diabetes melitus, and pemphigus vulgaris.

Type III hypersensitivity reactions involving circulating antigens can also result in the development of numerous pathologic conditions. These include glomerulonephritis (discussed in detail below), vasculitis (a potentially life-threatening inflammatory condition of large and/or small blood vessels), rheumatoid arthritis, dermatitis, and other disorders.

Other diseases associated with type III hypersensitivity reactions include autoimmune diseases such as systemic lupus erythematosis (SLE), many infectious diseases, neoplastic diseases, and a wide variety of other conditions (Dixon, et al. *Immune Complex Injury*, in Samter, (ed.) Immunological Diseases, 4th ed. Little Brown & Co. Boston, 1987).

II. Glomerulonephritis

The glomerulus is a key structural and functional element of the kidney. Each glomerulus is found as part of a larger structure that serves as the main functional unit of the kidney and is called a nephron. About a million nephrons are found in each kidney. Each glomerulus is a network of up to fifty parallel capillaries encased in a structure known as Bowman's capsule. The area inside Bowman's capsule that is not taken up by the glomerular capillaries is known as Bowman's space. The glomerulus functions as a filter, separating water and certain solutes from the proteins and cells of the blood into Bowman's space for further processing in the convoluted tubules, loop of Henle, and collecting duct of the nephron.

Glomerulonephritis (GN) is a disease of the kidney characterized by inflammation and resulting enlargement of the glomeruli that is typically due to immune complex formation. The accumulation of immune complexes in the glomeruli results in inflammatory responses, involving inter alia hypercellularity, that can cause total or partial blockage of the glomerulus through, among other factors, narrowing of capillary lumens. One result of this process is the inhibition of the normal filtration function of the glomerulus. Blockage may occur in large numbers of glomeruli, directly compromising kidney function and often causing the abnormal deposition of proteins in the walls of the capillaries making up the glomerulus. Such deposition can, in turn, cause damage to glomerular basement membranes. Those glomeruli that are not blocked develop increased permeability, allowing large amounts of protein to pass into the urine, a condition referred to as proteinuria.

In many cases of severe GN, pathological structures called crescents are formed within the Bowman's space, further impeding glomerular filtration. These structures can only be seen by microscopic examination of tissue samples obtained by biopsy or necropsy, and are thus not always observed in those patients in which they occur. Crescents are a manifestation of hypercellularity and are thought to arise from the extensive abnormal proliferation of parietal epithelial cells, the cells that form the inner lining of the Bowman's capsule. Clinical research has shown that there is a rough correlation between the percentage of glomeruli with crescents and the clinical severity of the disease, and thus the patient's prognosis. When present in large numbers, crescents are a poor prognostic sign.

Symptoms of GN include: proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria.

In 1990, over 210,000 patients in the United States required hemodialysis or transplantation for chronic renal failure at an annual cost in excess of 7 billion dollars, according to the United States Renal Data System (USRDS). The USRDS compiles data on kidney disease in the United States in conjunction with the National Institute of Diabetes and Digestive and Kidney Diseases, Division of Kidney, Urologic, and Hematologic Diseases, of the National Institutes of Health (NIDDKD). The USRDS estimates that the costs of treatment for renal failure are now increasing by 20 percent annually.

GN is the third leading cause of death in end-stage renal disease patients, exceeded only by diabetes and hypertension. As a result, there is a clear and long felt need in the medical community for effective treatments for this condition. Research aimed at the development of new treatments for GN is ongoing worldwide. In the United States, the NIDDKD, the National Kidney Foundation, and several other public and private organizations sponsor research in this area. The National Kidney Foundation alone supplies over two million dollars annually to fund the efforts of kidney researchers.

III. Current Treatments for GN

Corticosteroid administration, typically as high doses of "pulse" intravenous methylprednisolone or oral prednisone therapy, is currently considered the most effective pharmacologic agent available for the treatment of GN. Such steroid therapy is often administered in combination with cytotoxic general immunosuppressive agents such as azathioprine or cyclophosphamide. The overall immune suppression and resulting increased susceptibility to infection, along with other debilitating side effects associated with both steroid and cytotoxic drug administration, limit the effective use of these drugs.

Aspirin-like non-steroidal anti-inflammatory drugs (NSAIDs) have also been used to reduce the glomerular inflammation and enlargement of GN. These drugs are not routinely used for this purpose, however, probably because of their relatively weak anti-inflammatory effects and propensity to cause gastrointestinal and other side effects in many patients.

The administration of anticoagulants such as heparin or warfarin sodium, and antithrombotic agents such as cyproheptadine, dipyridamole, or sulfinpyrazone, has been used on the basis of evidence suggesting the involvement of the coagulation process in the genesis of glomerular crescents. However, objective evidence of benefit from such therapies in animals afflicted with experimentally induced crescentic GN has been inconsistent. Also, anticoagulants are dangerous drugs, as they can potentiate life-threatening bleeding episodes. They are especially hazardous in this regard in patients with advanced renal failure.

In addition to pharmacologic approaches, intensive plasma exchange (plasmapheresis) of 2 to 4 liters of plasma daily (or in some cases three times a week) can dramatically reduce high levels of circulating immune complexes when acute intervention in the inflammatory process is needed. Such treatment is expensive and requires that the patient be connected to the plasmapheresis machine for many hours each week. In addition, all procedures in which blood is removed from and returned to a patient are associated with an increased risk of infection. Nonetheless, plasma exchange is currently considered the most effective non-pharmacological treatment for removal of circulating immune complexes which can cause GN.

Circulating immune complex levels can also be decreased by eliminating or reducing the source of the antigen or antigens contained in the complexes by, for example, effective therapy of an underlying infection or change in an antibiotic. However, while such therapy is almost always a treatment of choice, great care must be taken since reduction of the antigen load alters the molar ratio of antigen to antibody involved in forming immune complexes and thus a dangerous temporary exacerbation of the inflammatory process may occur (see discussion below in Background Physiology & Pathology).

IV. Antibody Engineering

Native antibodies are multi-subunit animal protein molecules with highly specific antigen-binding properties. Animals make multiple classes of antibodies. There are five major classes (IgA, IgD, IgE, IgG and IgM) and a variety of subclasses. Native antibodies are made up of two or more heterodimeric subunits each containing one heavy (H) and one light (L) chain. The differences between antibody classes derive from their different H chains. H chains have a molecular weight of about 53 kDa, while L chains are about 23 kDa in mass.

Every individual native antibody has one type of L chain and one type of H chain, which are held together by disulfide bonds to form a heterodimeric subunit. Typically a native antibody (e.g., an IgG) has two such subunits, which are also held together by disulfide bonds. Within each chain, units of about 110 amino acid residues fold so as to form compact domains. Each domain is held together by a single intrachain disulfide bond. L chains have two domains, while H chains have four or five. Most H chains have a hinge region after the first (i.e., most amino-terminally located) two domains. The disulfide bonds linking together the heterodimeric subunits are located at the hinge regions. The hinge region is particularly sensitive to proteolytic cleavage, such proteolysis yielding two or three fragments (depending on the precise site of cleavage), a non-antigen binding fragment containing only H chain C regions (Fc) and one bivalent (Fab'2) or two monovalent (Fab) antigen binding fragments. The hinge region allows the antigen binding regions (each made up of a light chain and the first two domains of a heavy chain) to move freely relative to the rest of the native antibody, which includes the remaining heavy chain domains.

The first domain of each chain is highly variable in amino acid sequence, providing the vast spectrum of antibody binding specificities found in each individual. These are known as variable heavy (VH) and variable light (VL)

domains. The second and subsequent (if any) domains of each chain are relatively invariant in amino acid sequence. These are known as constant heavy (CH) and constant light (CL) domains.

Each variable region contains three loops of hypervariable sequence that provide a complementary structure to that of the antigen and are critical in determining the antigen binding specificity of the antibody, as they are the contact sites for binding to the antigen. These loops are known as complementarity determining regions, or CDRs. Each variable domain is made up of three CDRs embedded in four much less variable framework segments (FRs). Together, the sets of collinear CDRs and FRs are in large part responsible for determining the three dimensional conformation of the variable regions of antibody molecules.

CDRs and FRs are features that have been deduced from structural properties of antibody variable regions. Both amino acid sequence (primary structure) and three dimensional modeling (deduced secondary and tertiary structure) of antibody variable regions have been used by various researchers to define CDRs and, by default, FRs. While the positions of the CDRs are beyond question, not all workers in the art agree upon the precise locations of the boundaries of each CDR in VH or VL regions; there is no clear cut structural marker delineating CDR/FR boundaries.

Two definitions of CDR location are currently in general use in the art. These are the "sequence variability" definition of Kabat et al. ("Sequences of Proteins of Immunological Interest," 4th ed. Washington, D.C.: Public Health Service, N.I.H.) and the "structural variability" definition of Chothia and Lesk (J. Mol. Biol. 1987, 196:901). As used herein, the terms VL CDR1, VL CDR2, VL CDR3, VH CDR1, VH CDR2, and VH CDR3 refer minimally to the region of overlap between the regions designated for each CDR by each of these two definitions, and maximally to the total region spanned by the combination of the regions designated for each CDR by each of these two definitions.

One problem that antibody engineering attempts to address is the immune activity of a human patient that occurs in response to a native murine (or other non-human animal) antibody, typically a mAb, that is being administered to the patient for therapeutic purposes. This activity against murine antibodies is characterized by a human anti-mouse antibody (HAMA) response that can have deleterious effects on treatment efficacy and patient health. It has been found that almost all such human anti-non-human antibody ("HAMA type") activity is directed at the constant domains and at the FR regions of the variable domains of native non-human antibodies.

By manipulating the nucleic acid molecules encoding antibody H and L chains it is possible to incorporate non-human variable regions into antibodies otherwise made up of human constant regions. The resulting antibodies are referred to as "chimeric antibodies," and are typically less prone to eliciting HAMA type responses than are the non-human antibodies from which the variable regions are derived.

An even more effective approach to eliminating the potential of a non-human antibody to elicit a HAMA type response is to "humanize" it, i.e., to replace its non-human framework regions with human ones. One way of achieving such humanization involves the insertion of polynucleotide fragments encoding the non-human CDRs of the antibody to be humanized into a nucleic acid molecule encoding an otherwise human antibody (with human constant regions if desired) so as to replace the human CDRs and to use the resulting nucleic acid molecule to express the encoded "humanized" antibody.

Unfortunately, however, humanization of non-human antibodies has unpredictable effects on antibody antigen interactions, e.g., antigen binding properties. Some of this unpredictability stems from the properties of the CDRs. Certain CDRs may be more amenable to the construction of humanized antibodies that retain the properties of the non-human CDR donor antibody than others. While the CDRs are key to the antigen binding properties of an antibody, CDRs and FRs must interact appropriately if the antigen specificity of an antibody is to be retained following humanization. The effects of combination with particular human FRs on uncharacterized non-human CDRs cannot be reliably predicted by any known method. However, the successful humanization of an antibody provides information that, in general, facilitates the successful humanization of the CDRs of that antibody using other human or altered human FRs. In addition, approaches are available that facilitate tailoring human FRs to enhance the likelihood of successful humanization.

Other problems addressed by antibody engineering include efficient antibody production and alteration of antibody pharmacokinetics. Recombinant protein production is generally most efficiently carried out in bacterial hosts. The large size and multimeric nature of native antibodies makes their production in bacteria difficult. One approach to dealing with production problems is to use recombinant DNA methods to construct antibodies that have their H and L chains joined by a linker peptide to form a single chain (sc) antibody. As described below, there are several types of sc antibodies that can be constructed.

As is the case for humanization, the effects on antigen binding properties of constructing a particular type of sc antibody using H and L chains that have not been characterized with regard to their ability to function as part of an sc antibody cannot be reliably predicted by any known method. However, the successful construction of any one type of sc antibody from a particular native antibody provides information that, in general, facilitates the successful construction of other types of sc antibodies from that native antibody.

Single chain antibodies may include one each of only VH and VL domains, in which case they are referred to as scFv antibodies; they may include only one each of VH, VL, CH, and CL domains, in which case they are referred to as scFab antibodies; or they may contain all of the variable and constant regions of a native antibody, in which case they are referred to as full length sc antibodies.

The differing sizes of these antibodies imparts each with differing pharmacokinetic properties. In general, smaller proteins are cleared from the circulation more rapidly than larger proteins of the same general composition. Thus, full length sc antibodies and native antibodies generally have the longest duration of action, scFab antibodies have shorter durations of action, and scFv antibodies have even shorter durations of action. Of course, depending upon the illness being treated, longer or shorter acting therapeutic agents may be desired. For example, therapeutic agents for use in the prevention of immune and hemostatic disorders associated with extracorporeal circulation procedures (which are typically of brief duration) are preferably relatively short acting, while antibodies for the treatment of long term chronic conditions (such as inflammatory joint disease or GN) are preferably relatively long acting.

Detailed discussions of antibody engineering may be found in numerous recent publications including: Borrebaek, "Antibody Engineering, A Practical Guide," 1992, W.H. Freeman and Co. NY; and Borrebaek, "Antibody Engineering," 2nd ed. 1995, Oxford University Press, NY, Oxford.

SUMMARY OF THE INVENTION

In view of the foregoing, it is an object of the present invention to provide a new approach for reducing the glomerular inflammation and kidney dysfunction associated with GN.

The method of the invention involves the use of preparations containing antibodies to human complement component C5 as pharmaceutical agents. More particularly, the invention provides for the use of anti-C5 antibodies that bind to complement component C5 or active fragments thereof. Preferably, the antibodies block the generation and/or activity of complement components C5a and C5b. For most applications, the antibody is a monoclonal antibody.

In the preferred embodiments of the invention, the administration of the anti-C5 antibody preparation is started after the appearance of GN symptoms, e.g., after the appearance of proteinuria. Alternatively, the invention can be used prophylactically to treat patients who are at risk for an acute exacerbation of existing GN, e.g., patients experiencing a flare-up of symptoms of systemic lupus erythematosus or similar autoimmune diseases that have resulted in GN.

As shown in the examples presented below, anti-C5 antibodies administered subsequent to the onset of GN essentially eliminate glomerular inflammation/enlargement and reduce kidney dysfunction (see Examples 1 and 2).

Although not wishing to be bound by any particular theory of operation, it is believed that the anti-C5 antibodies have these and other therapeutic effects through their activity in blocking the generation or activity of the C5a and/or C5b active fragments of complement component C5. Through this blocking effect, the antibodies inhibit the proinflammatory (anaphylatoxic) effects of C5a and the generation of the C5b-9 membrane attack complex (MAC). Significantly, the blockage effected by the anti-C5 antibodies, since it occurs at the level of complement component C5, has the advantage of maintaining important opsonic, anti-infective, and immune complex clearance functions of the complement system mediated by, inter alia, complement component C3.

The invention additionally provides compositions comprising anti-C5 antibodies that block complement hemolytic activity and C5a generation. These antibodies are useful for the treatment of GN as well as a number of other conditions. These include treatment of immune and hemostatic dysfunctions associated with extracorporeal circulation (see copending U.S. patent application Ser. No. 08/217,391, now U.S. Pat. No. 5,853,722 which is incorporated herein by reference), treatment of inflammatory joint diseases (see copending U.S. patent application Ser. No. 08/311,489, which is incorporated herein by reference), and other complement associated conditions, particularly inflammatory diseases.

Although other antibodies can be used to treat GN in accordance with the present invention, the novel antibodies of the invention are preferred. Preferably, these novel antibodies bind to the alpha chain of C5, but do not exhibit substantial binding to the alpha chain cleavage product C5a (referred to hereinafter and in the claims as "free C5a"). Other preferred targets for antibody binding include fragments of the alpha chain of human C5 that are immunoreactive with the most preferred antibody of the invention, the 5G1.1 antibody discussed below. Such preferred targets include the 46 kDa acid hydrolysis fragment of C5 (the "5G46k" fragment), the 27 kDa tryptic digestion fragment of C5 (the "5G27k" fragment), the 325aa peptide spanning amino acid residues 725–1049 of SEQ ID NO:2 (the "5G325aa" peptide), the 200 amino acid peptide spanning amino acids residues 850 to 1049 of SEQ ID NO:2 (the "5G200aa" peptide)—as discussed below in Example 13.

The novel antibodies of the invention include antibodies that bind to an epitope within the amino acid sequence Val Ile Asp His Gln Gly Thr Lys Ser Ser Lys Cys Val Arg Gln Lys Val Glu Gly Ser Ser, (SEQ ID NO:1) hereinafter referred to as the KSSKC epitope. These novel antibodies that bind to the KSSKC epitope (SEQ ID NO:1) are hereinafter referred to as anti-KSSKC antibodies, and monoclonal antibodies binding to the KSSKC epitope are hereinafter referred to as anti-KSSKC mAbs.

The novel antibodies of the invention have many advantages over other anti-C5 antibodies, particularly with regard for their use as anti-inflammatory therapeutic agents. These include the ability to substantially block both complement hemolytic activity and the generation of the proinflammatory complement cleavage product C5a to substantially the same extent at the same concentration of antibody. Some of the preferred antibodies of the invention have the additional advantageous property of blocking the binding of C5 to C3 or C4.

Particularly preferred antibodies of the invention are monospecific native anti-KSSKC antibodies. The 5G1.1 native anti-KSSKC mAb has the distinct advantage of substantially blocking both complement hemolytic activity and the generation of C5a at a stoichiometric ratio of antibody to C5 that approaches the theoretical one to two (antibody to antigen) limit of binding that can be achieved by a bivalent antibody. This is a desirable property because it allows smaller doses of antibody to achieve therapeutic effects than would be required of otherwise similar antibodies that cannot function at such a ratio.

The invention further provides recombinant mAbs that are derivatives (including monovalent derivatives) of these native mAbs. These include anti-KSSKC recombinant mabs. Preferably the antibodies of the invention provide a level of blockade of both complement hemolytic activity and C5a generation (on a per mole of binding site basis) that is obtained when the antibody concentration is within an order of magnitude of that of the native mAbs. Particularly preferred anti-KSSKC recombinant mAbs provide a level of such blockade when the antibody concentration is no more than three fold that of the native mAbs of the invention.

The invention further provides nucleic acid sequences of polynucleotides encoding such recombinant anti-KSSKC mAbs, as well as amino acid sequences of the polypeptides encoded by these nucleic acid molecules of the invention.

The invention further provides CDR sequences that are useful in the construction of the humanized antibodies of the invention, as well as peptides and oligopeptides that are useful in the preparation and characterization of the antibodies of the invention.

Anti-C5 antibodies of the invention have activity in blocking the generation or activity of the C5a and/or C5b active fragments of complement component C5. Through this blocking effect, the antibodies inhibit the proinflammatory (anaphylatoxic) effects of C5a and the generation of the C5b-9 membrane attack complex (MAC). Significantly, the blockage effected by the anti-C5 antibodies, since it occurs at the level of complement component C5, has the advantage of maintaining important opsonic, anti-infective, and immune complex clearance functions of the complement system mediated by, inter alia, complement component C3.

The accompanying figures, which are incorporated in and constitute part of the specification, illustrate certain aspects

BRIEF DESCRIPTION OF THE DRAWINGS

FIG. 1A—uninduced untreated mouse. FIG. 1B—GN-induced PBS-(control)-treated mouse. FIG. 1C—GN-induced anti-C5 treated mouse. Magnification for each is the same, approximately 400×.

FIG. 2A—uninduced untreated mouse. FIG. 2B—GN-induced PBS-(control)-treated mouse. FIG. 2C—GN-induced anti-C5 treated mouse. Magnification for each is the same, approximately 200×.

FIG. 5A—uninduced untreated mouse. FIG. 5B—GN-induced PBS-(control)-treated mouse. FIG. 5C—GN-induced anti-C5 treated mouse. Magnification for each is the same, approximately 400×.

Figure 1A:
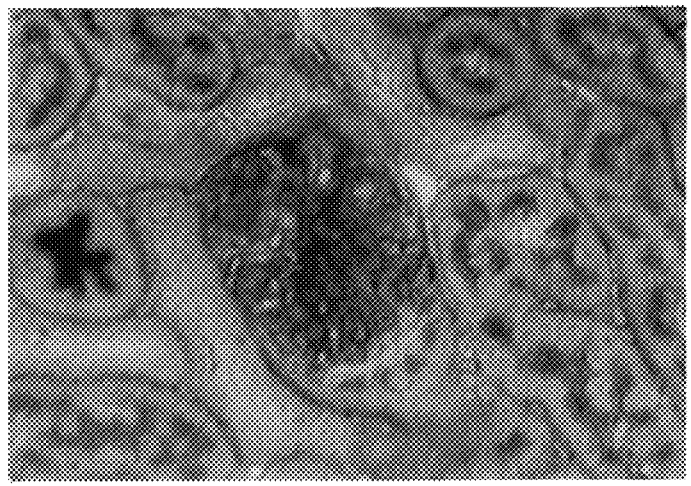
FIGS. 1A, 1B, and 1C—Photomicrographs of PAS stained sections of mouse kidneys.
Figure 1B:
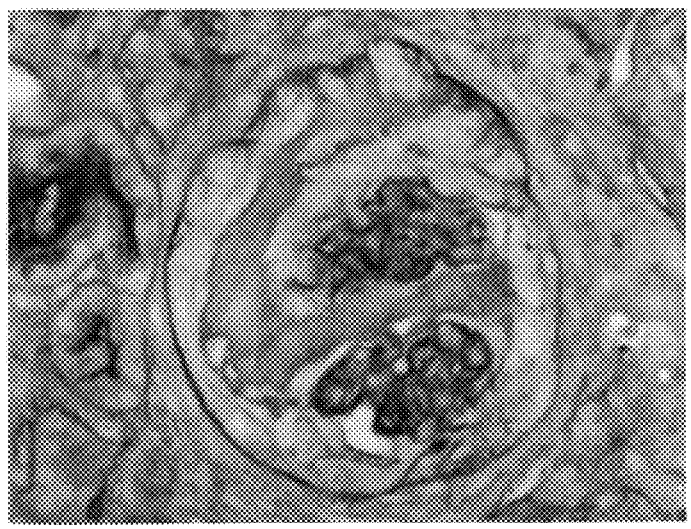
Figure 2A:
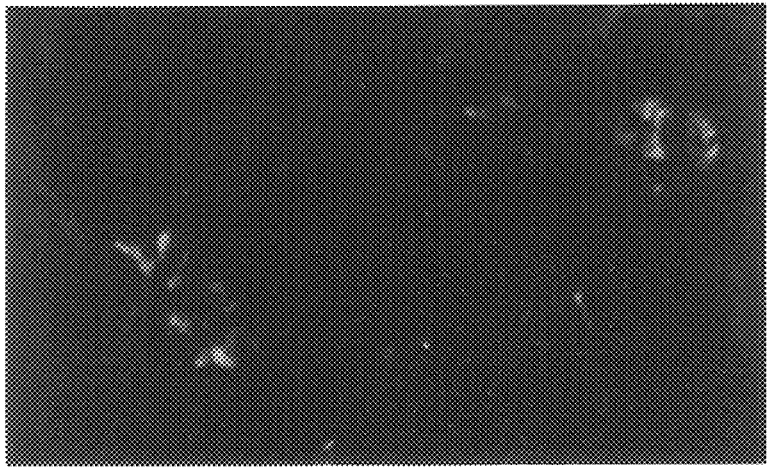
FIGS. 2A, 2B, and 2C—Photomicrographs of immunofluorescence stained sections of mouse kidneys.
Figure 2B:
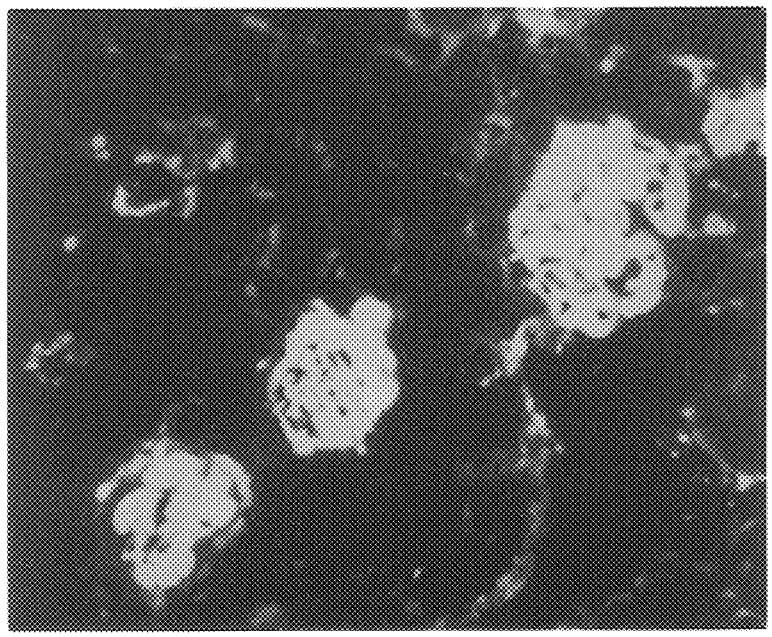
Figure 5A:
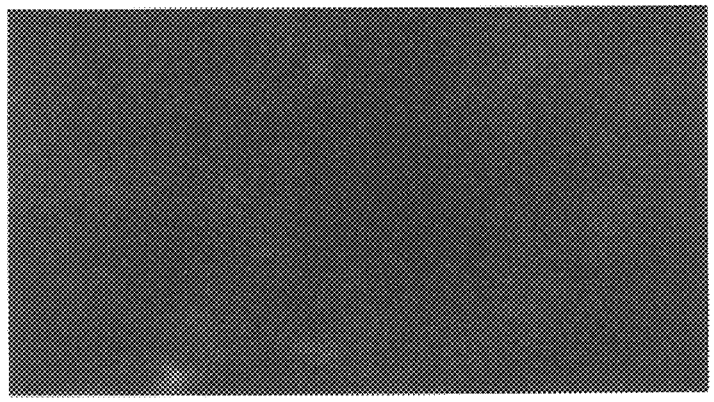
FIGS. 5A, 5B, and 5C—Immunofluorescence photomicrographs of kidney sections stained for mouse C3.
Figure 5B:

The immunofluorescent staining of FIGS. 2 and 5 is confined to the glomerular capillary network (tuft) and thus the enlargement of the glomerulus seen in FIG. 1B is not visible in FIGS. 2B and 5B.

Figure 8:
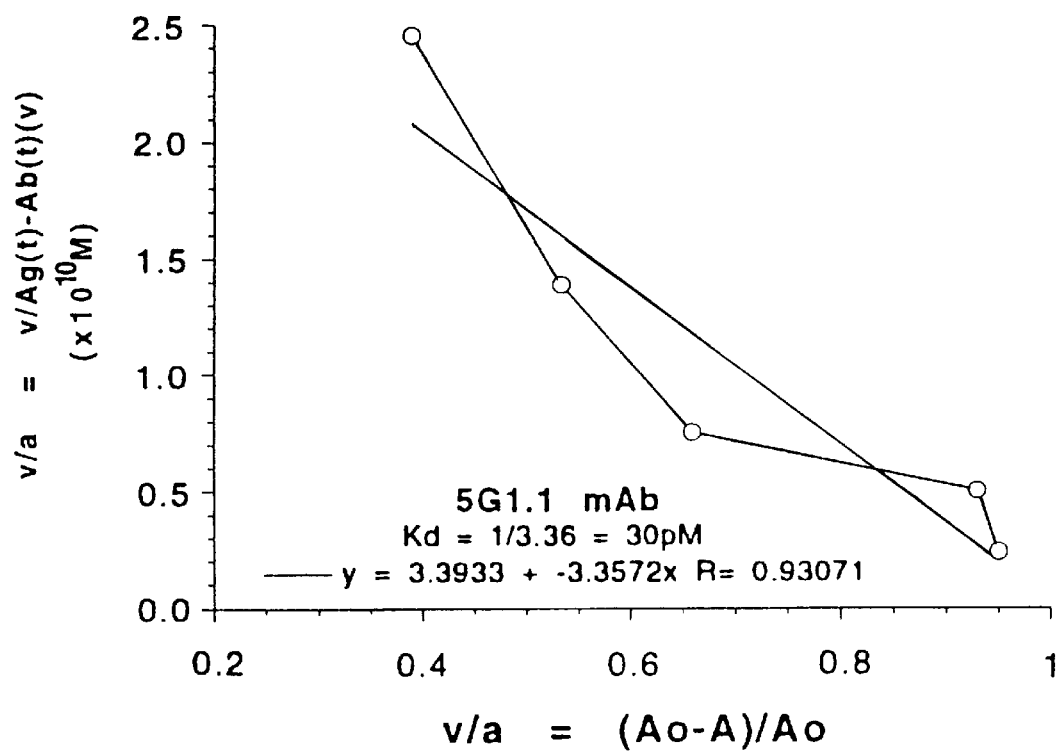

FIG. 8—Scatchard analysis of native 5G1.1 binding to C5.

Figure 9:
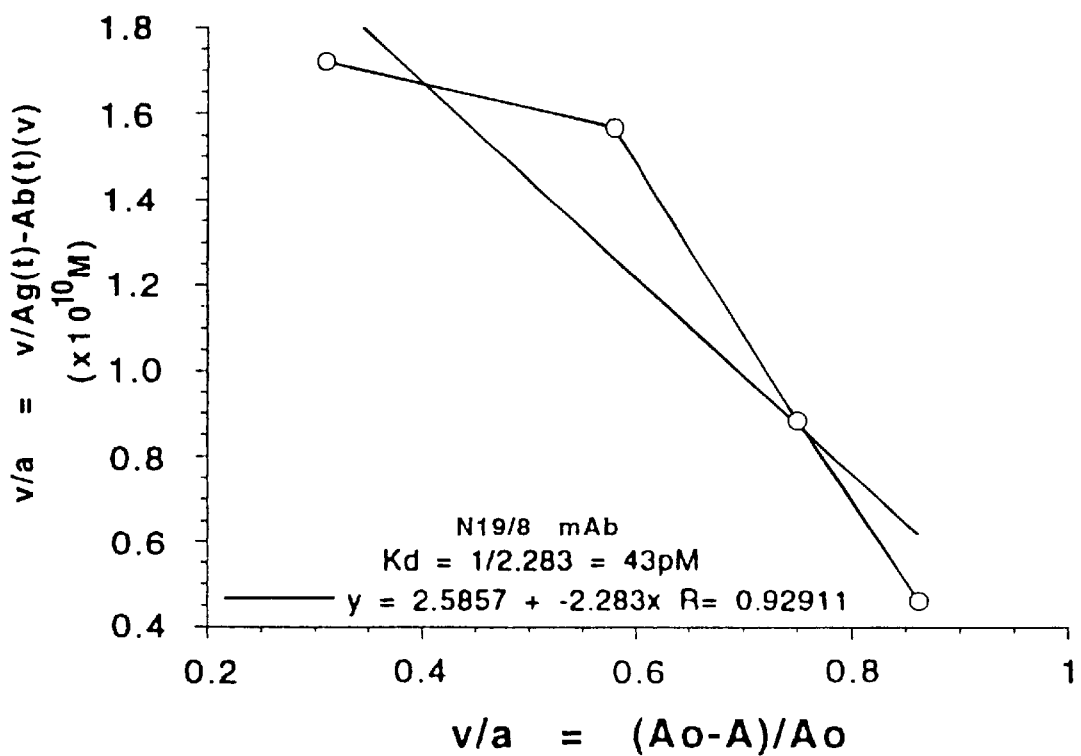

FIG. 9—Scatchard analysis of native N19/8 binding to C5.

Figure 10:
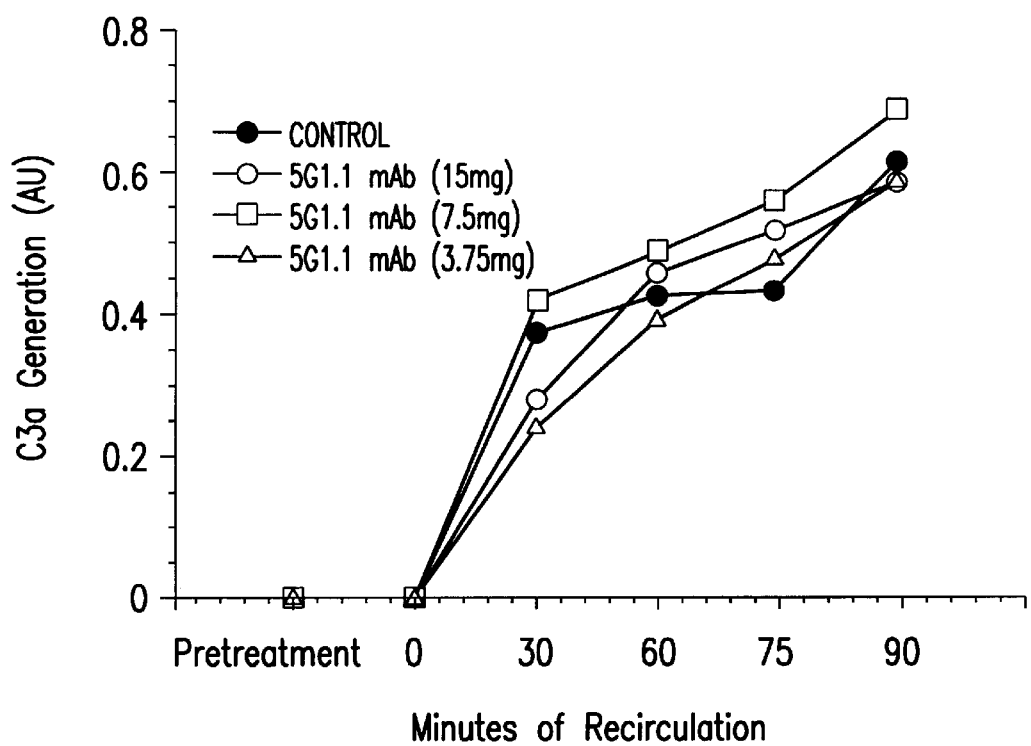

FIG. 10—C3a generation in samples of circulating human blood in the presence of native 5G1.1.

Figure 11:
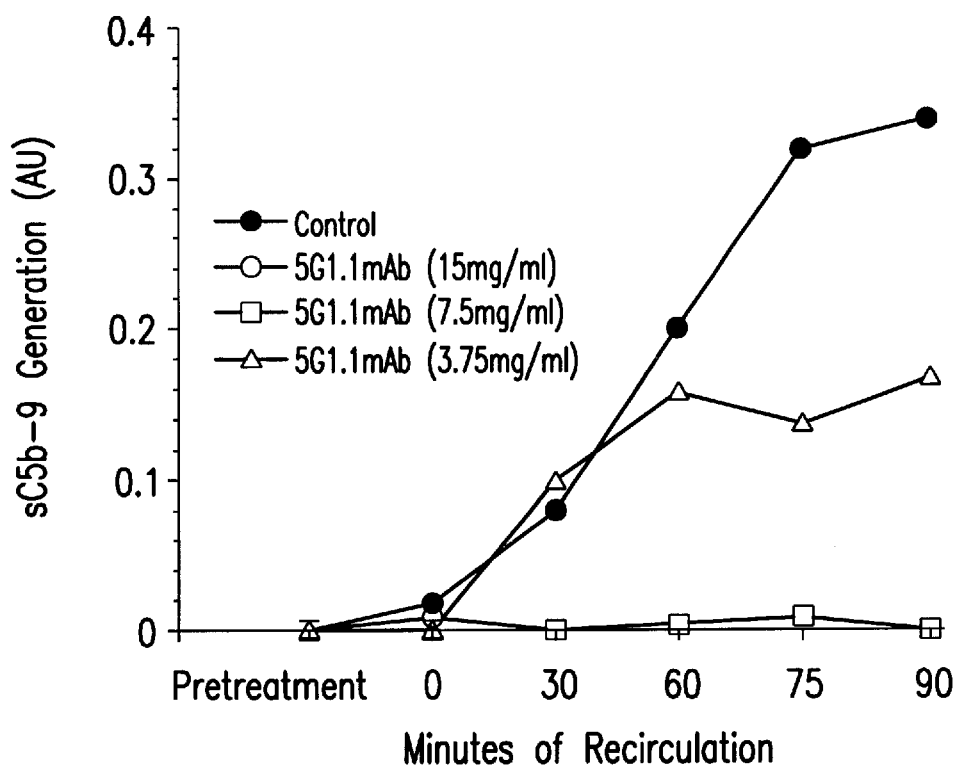

FIG. 11—sC5b-9 generation in samples of circulating human blood in the presence of native 5G1.1.

Figure 12:
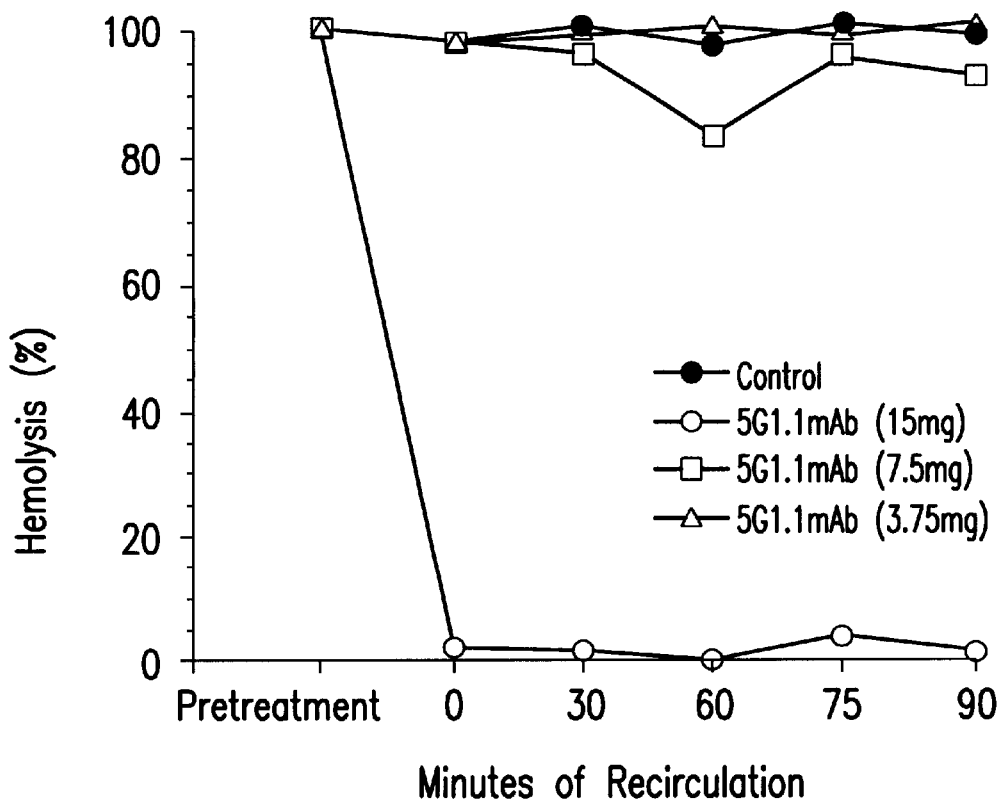

FIG. 12—Serum hemolytic activity of samples of circulating human blood in the presence of native 5G1.1.

Figure 13:
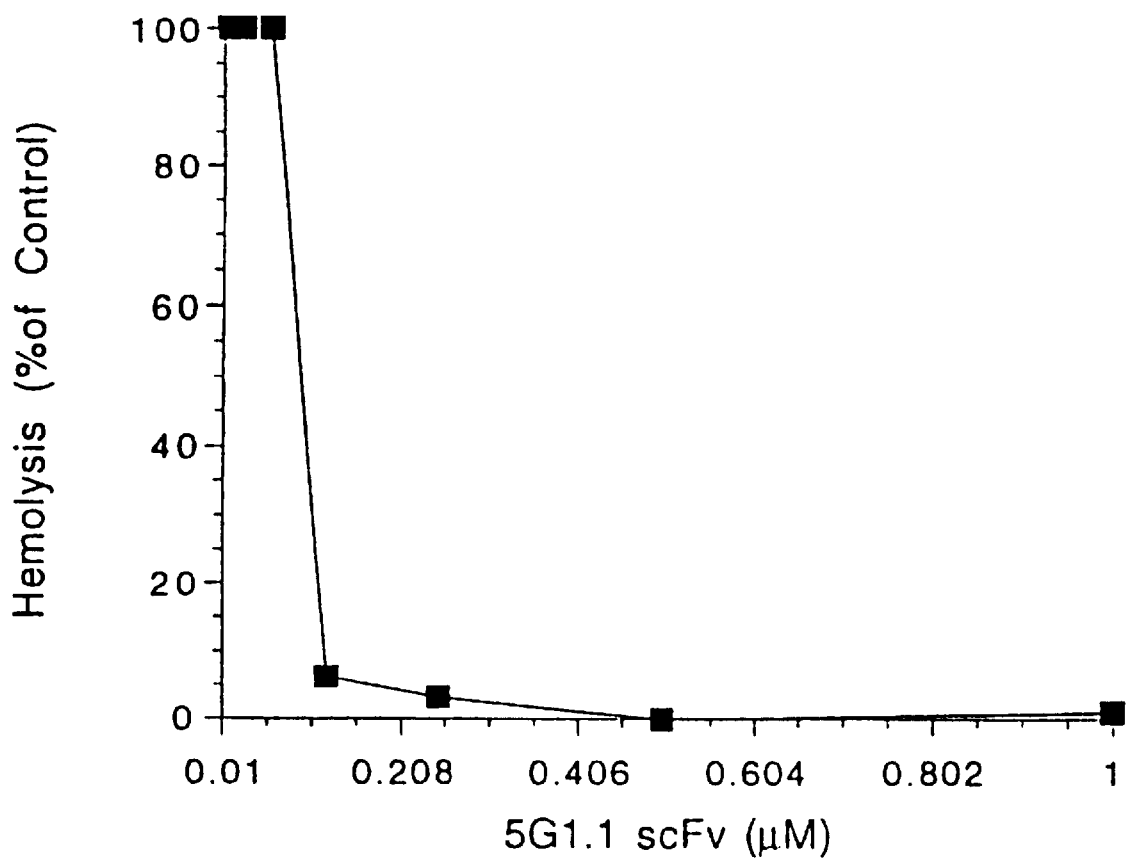

FIG. 13—Serum hemolytic activity in the presence of m5G1.1 scFv.

Figure 14:
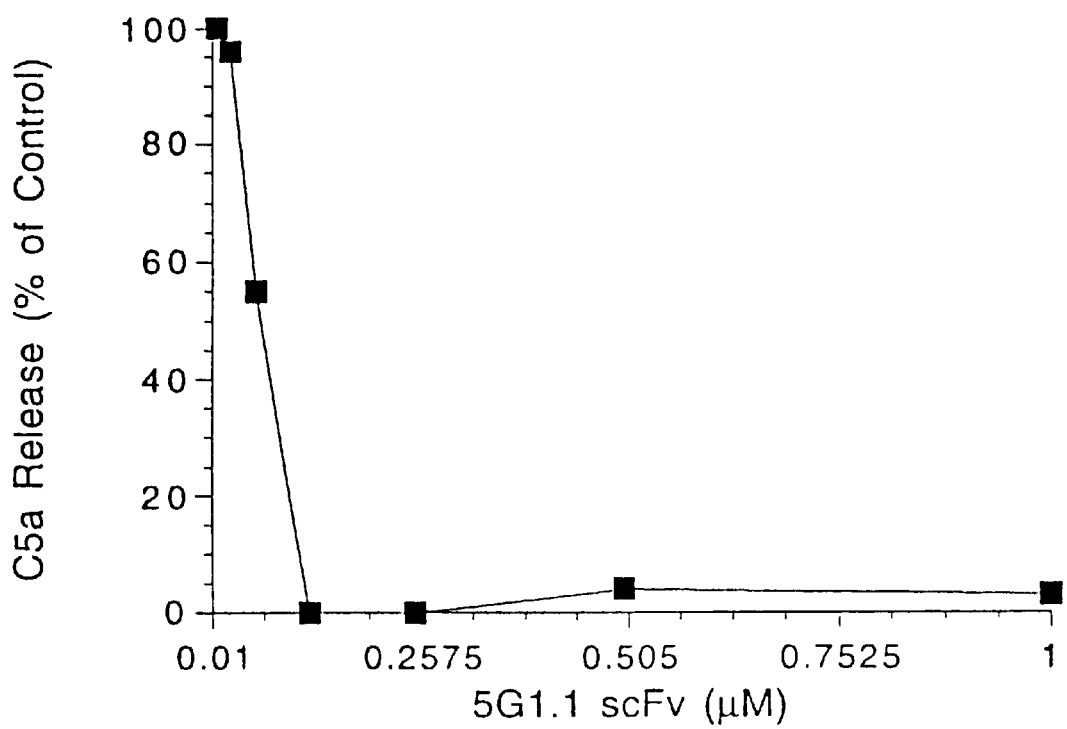

FIG. 14—C5a generation in the presence of m5G1.1 scFv.

Figure 15:
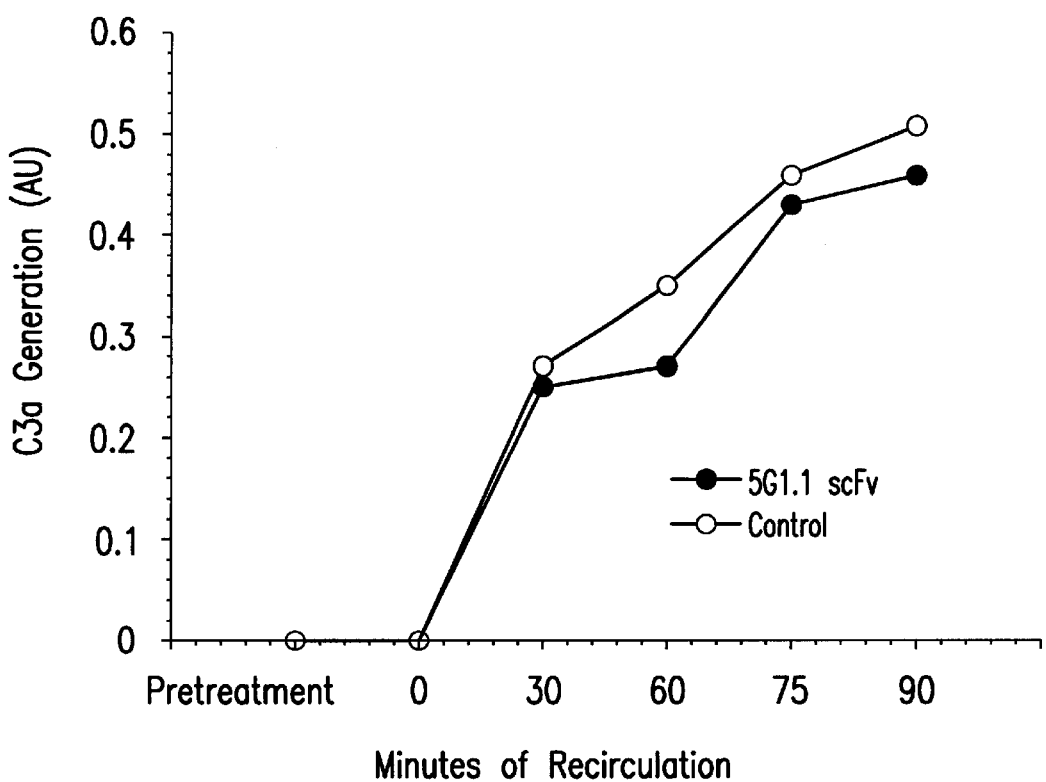

FIG. 15—C3a generation in samples of circulating human blood in the presence of m5G1.1 scFv.

Figure 16:
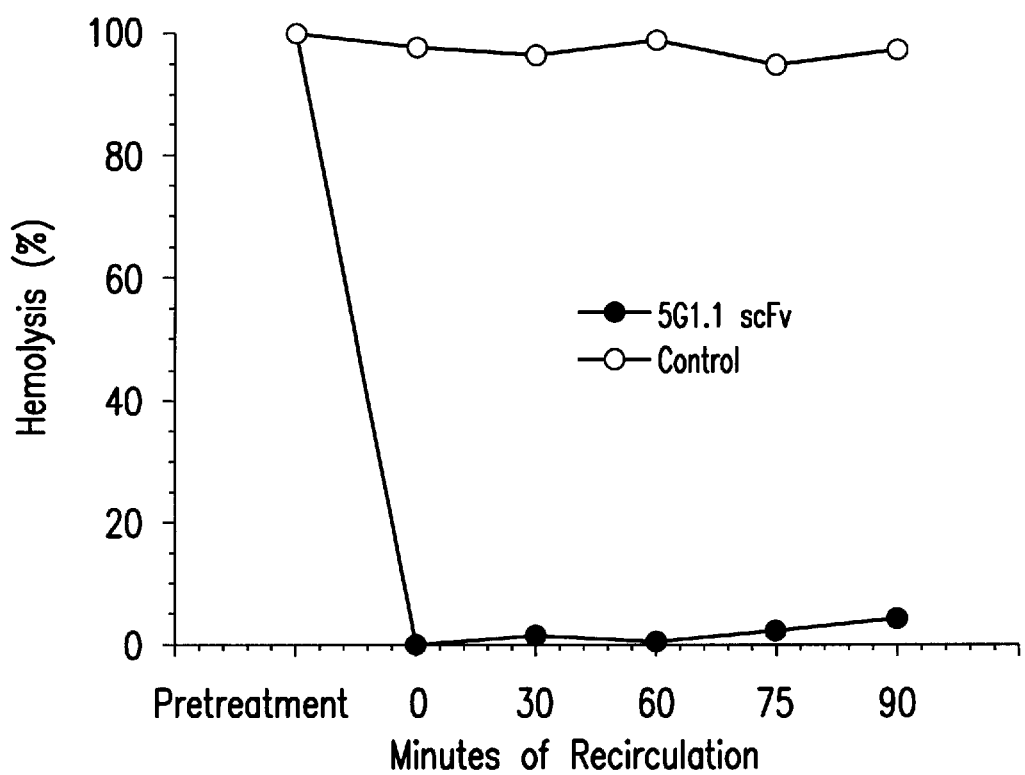

FIG. 16—Serum hemolytic activity of samples of circulating human blood in the presence of 5G1.1 scFv.

Figure 17:
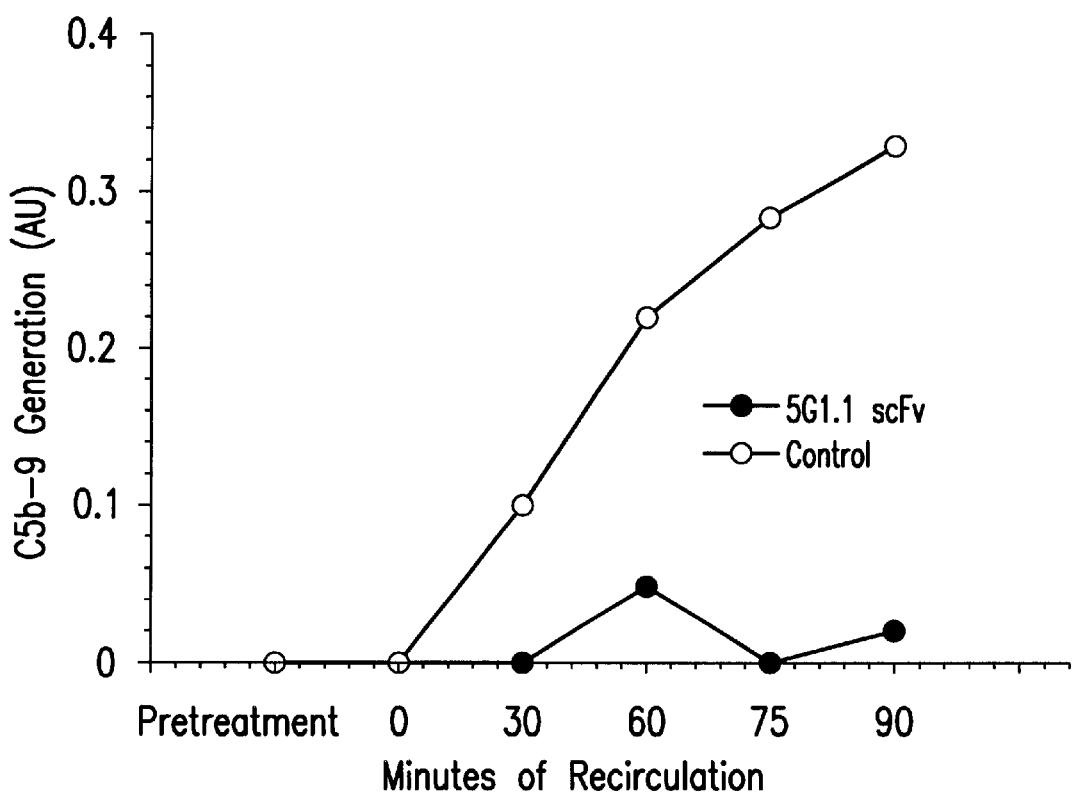

FIG. 17—sC5b-9 generation in samples of circulating human blood in the presence of m5G1.1 scFv.

FIG. 18—The light chain variable region of the antibody 5G1.1. Sequence derived from the 5' oligonucleotide primer used for PCR amplification of the variable region is shown in lower case. Amino acids are number according to Kabat et al., supra. Boxed amino acids correspond to peptide sequences obtained from the mature 5G1.1 light chain or from an endoproteinase Lys C peptide of 5G1.1. The complementarity determining region (CDR) residues according to the sequence variability definition and the structural variability definition are underlined and overlined, respectively.

FIG. 19—The heavy chain variable region of the antibody 5G1.1. Sequence derived from the 5' oligonucleotide primer used for PCR amplification of the variable region is shown in lower case. Amino acids are numbered using the scheme of Kabat et al. supra with +1 denoting the first amino acid of the processed mature variable region. Boxed amino acids correspond to peptide sequence obtained from the 5G1.1 heavy chain after treatment with pyroglutamate aminopeptidase. The complementarity determining region (CDR) residues according to the sequence variability definition or according to the structural variability definition are underlined and overlined, respectively.

BACKGROUND PHYSIOLOGY & PATHOLOGY

The discussion in this section is not limited to subject matter that qualifies as "prior art" against the present invention. Therefore, no admission of such prior art status shall be implied or inferred by reason of inclusion of particular subject matter in this discussion, and no declaration against the present inventors' interests shall be implied by reason of such inclusion.

I. Introduction

As described above, the present invention relates to therapeutic treatments for GN and other immune complex mediated diseases, as well as to the treatment of other complement mediated diseases and to the inhibition of complement component C5. To provide background for the description of the preferred embodiments and the examples presented below, we turn first to general discussions of the complement arm of the immune system, the pathophysiologic features of GN, and previous studies of the role of complement in GN pathogenesis.

General discussions of the complement system and GN can be found in, for example, Glassock and Brenner, 1994; Couser, 1993; Couser, 1992; Couser, et al, 1992; Rich, 1992; Glassock and Brenner, 1987; Robbins and Cotran, 1979; and Guyton, 1971.

II. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components, and while they differ in their initial steps, they converge and share the same "terminal complement" components (C5 through C9) responsible for the activation and destruction of target cells.

The classical complement pathway is typically initiated by antibody recognition of and binding to an antigenic site on a target cell. The alternative pathway is usually antibody independent, and can be initiated by certain molecules on pathogen surfaces. Both pathways converge at the point where complement component C3 is cleaved by an active protease (which is different in each pathway) to yield C3a and C3b. Other pathways activating complement attack can act later in the sequence of events leading to various aspects of complement function.

C3a is an anaphylatoxin (see discussion below). C3b binds to bacterial and other cells, as well as to certain viruses and immune complexes, and tags them for removal from the circulation. (C3b in this role is known as opsonin.) The opsonic function of C3b is considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to Neisseria infection, and then only somewhat more prone (Fearon, in *Intensive Review of Internal Medicine*, 2nd Ed. Fanta and Minaker, eds. Brigham and Women's and Beth Israel Hospitals, 1983).

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways (Wurzner, et al., *Complement Inflamm.* 8:328–340, 1991). This property of C3b is regulated by the serum protease Factor I, which acts on C3b to produce iC3b. While still functional as opsonin, iC3b cannot form an active C5 convertase.

C5 is a 190 kDa beta globulin found in normal serum at approximately 75 $\mu$g/ml (0.4 $\mu$M). C5 is glycosylated, with about 1.5–3 percent of its mass attributed to carbohydrate. Mature C5 is a heterodimer of a 999 amino acid 115 kDa alpha chain that is disulfide linked to a 656 amino acid 75 kDa beta chain. C5 is synthesized as a single chain precursor protein product of a single copy gene (Haviland et al. J. Immunol. 1991, 146:362–368). The cDNA sequence of the transcript of this gene predicts a secreted pro-C5 precursor of 1659 amino acids along with an 18 amino acid leader sequence (SEQ ID NO:2).

The pro-C5 precursor is cleaved after amino acid 655 and 659, to yield the beta chain as an amino terminal fragment (amino acid residues +1 to 655 of SEQ ID NO:2) and the alpha chain as a carboxyl terminal fragment (amino acid residues 660 to 1658 of SEQ ID NO:2), with four amino acids (amino acid residues 656–659 of SEQ ID NO:2) deleted between the two.

C5a is cleaved from the alpha chain of C5 by either alternative or classical C5 convertase as an amino terminal fragment comprising the first 74 amino acids of the alpha chain (i.e., amino acid residues 660–733 of SEQ ID NO:2). Approximately 20 percent of the 11 kDa mass of C5a is attributed to carbohydrate. The cleavage site for convertase action is at or immediately adjacent to amino acid residue 733 of SEQ ID NO:2. A compound that would bind at or adjacent to this cleavage site would have the potential to block access of the C5 convertase enzymes to the cleavage site and thereby act as a complement inhibitor.

C5 can also be activated by means other than C5 convertase activity. Limited trypsin digestion (Minta and Man, J. Immunol. 1977, 119:1597–1602; Wetsel and Kolb, J. Immunol. 1982, 128:2209–2216) and acid treatment (Yammamoto and Gewurz, J. Immunol. 1978, 120:2008; Damerau et al., Molec. Immunol. 1989, 26:1133–1142) can also cleave C5 and produce active C5b.

C5a is another anaphylatoxin (see discussion below). C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

III. Pathophysiology of GN

Although GN may accompany an extraordinary range of pathologic processes, in general it is encountered most commonly in the course of infectious diseases, in autoimmunity, and as a consequence of therapy for some other disease process. The causative mechanism for GN is typically the deposit of circulating immune complexes in the kidney. Factors involved in the pathogenesis of GN include the specific antigen and antibody involved and the inflammatory processes that occur as a consequence of immune complex deposition.

Antigens Involved in the Formation of Immune Complexes that Cause GN

Antigens involved in the development of GN can be broadly classified as endogenous, infectious, and iatrogenic (those encountered as a consequence of medical practice). In many cases the specific antigen is unknown, although the general class can usually be identified.

The best known example of the formation of endogenous immune complexes is the DNA anti-DNA complexes produced in connection with systemic lupus erythematosus (lupus, SLE). Other important sources of endogenous antigens include malignancies in which immune complex formation may contribute to the development of paraneoplastic syndromes.

Infections with organisms of many types, particularly chronic infections, are also associated with the development of immune complexes that can cause GN. Bacterial and fungal infections that can produce such complexes include infection with certain strains of streptococci, Pseudomonas, disseminated gonococcal infection, lepromatous leprosy, subacute bacterial endocarditis, bronchopulmonary aspergillosis, secondary syphilis, and chronic infections in patients with cystic fibrosis.

Viral diseases in which immune complex deposition may be a prominent feature include hepatitis B infection, dengue, infectious mononucleosis, and subacute sclerosing panencephalitis. GN is also a prominent feature of many parasitic infestations such as the GN seen in children with quartan malaria, as well as toxoplasmosis, trypanosomiasis, and schistosomiasis.

Iatrogenic antigens constitute a special class of exogenous antigens. These include those responsible for the prototype immune complex disease, serum sickness, which follows formation of immune complexes between heterologous serum constituents and autologous antibodies. Serum sickness was regularly seen earlier in this century when infectious diseases were frequently treated with heterologous antisera.

An iatrogenic disease essentially indistinguishable from classic serum sickness can occur as a consequence of high-dose antibiotic therapy. The serum sickness-like manifestations of immune responses to these drugs include GN and reflect the fact that certain drugs, particularly the β-lactam and sulfonamide antibiotics, are effective haptens that are capable of inducing antibody responses upon spontaneous conjugation to autologous proteins.

Factors Affecting Immune Complex Formation and Deposition

Features of both antigen and antibody determine the likelihood of pathologic immune complex formation and subsequent deposition in the kidney. Chief among these are the absolute concentrations of the reactants and their relative molar ratios.

Most antigens display multiple epitopes and typically stimulate a polyclonal antibody response. All naturally occurring antibody molecules are at least bivalent. These properties allow for the formation of an extensive antigen-antibody lattice, the size of which is determined largely by the affinity of the antibodies and the molar ratio of antigen to antibody.

In general, antibody responses begin under conditions in which antigen is present in excess to antibody, and this relative ratio changes as the antibody response increases in magnitude. Complexes formed initially are usually small and exhibit little or no pathogenic activity. In contrast, very large complexes are often formed as the amount of antigen becomes limiting, late in the course of an antibody response under conditions of antibody excess. Because these very large complexes are readily cleared by the reticuloendothelial system in the liver, they are also relatively nonpathogenic.

The formation of immune complexes that can cause GN is believed to occur during conditions of slight antigen excess or near the point of antibody-antigen equivalence, where lattice formation is maximal and lattice size is large, but not very large.

Several factors influence the speed and location of immune complex precipitation. Interactions between Fc regions of antibody molecules promote rapid precipitation of immune complexes. The role of Fc-Fc interactions in immune complex precipitation is illustrated by studies of the properties of F(ab')2 antibody fragments, which do not contain Fc regions. Although the valence of F(ab')2 fragments does not differ from that of most whole immunoglobulins, F(ab')2 antibody fragments form lattices more slowly.

Antigen charge plays a role in determining the tissue localization of sites of deposition of immune complex precipitates. Complexes with a substantial positive charge are preferentially attracted to the strong negative charge of basement membranes, particularly in the renal glomerulus.

Localized presence of antigen may largely account for certain cases of organ specific immune complex deposition. Diseases such as Goodpasture's syndrome (a rare form of GN) are typically not classified as immune complex diseases because the complexes are formed in situ in the kidney rather than being preformed in the circulation and then deposited. Once the immune complexes are formed, the subsequent inflammatory process is believed to be essentially the same as that seen following deposition of preformed complexes. However, the different mode of deposition distinguishes this syndrome from typical GN caused by circulating immune complexes.

Features of blood flow and vascular structure are also important in determining the localization of immune complex deposits. Chief among these is capillary permeability. Because their capillary endothelium is fenestrated, renal glomeruli are preferential sites for the deposition of immune complexes. Hemodynamic variables enhancing immune complex localization include turbulence of flow and increased blood pressure, both of which are present in the renal glomeruli.

Complement and Complement Receptors as Reaulators of Immune Complex Deposition

In addition to their proinflammatory functions, complement components can also inhibit immune complex deposition and resolubilize immune complex precipitates from sites of deposition. In addition, it is known that erythrocyte receptors for C3b, e.g., CR1, are important for reticuloendothelial clearance of opsonized circulating immune complexes.

Analysis of the clinical pattern of immune complex disease in patients with deficiencies of particular complement components provides information regarding the normal role of these components in the prevention of complex deposition. The incidence of immune complex disease in patients with deficiencies of Clq, Clr, Cls, C4, C2, or C3 varies from 60 to 90 percent, with the majority of these patients exhibiting a lupus-like syndrome. Immune complex disease is rarely associated with deficiencies of late-acting or alternative pathway components.

The binding of complement components to immune complexes prevents the formation of large antigen-antibody lattices and inhibits immune precipitation. This process requires activation via the classical pathway; serum that is deficient for Clq, C4, or C2 does not effectively inhibit lattice formation and complex precipitation. Classical pathway dependence may reflect the initial binding of Cl components, impeding the Fc-Fc interactions between IgG molecules that contribute to immune precipitation. This is followed by covalent binding of C3b to the complexes, which further inhibits immune precipitation and leads to solubilization of previously deposited complexes.

The solubilization process also depends upon activation of components of the alternative pathway. Consequently, by promoting clearance of immune complexes and inhibiting their deposition at sites of inflammation, complement components and their receptors serve as negative regulators of immune complex diseases that may retard disease development.

It should be noted that the present invention involves blocking the activities of complement component C5. The targeting of this component does not alter the functions of the early complement components, and thus does not compromise the negative regulatory effects on immune complex deposition of those early components.

Immune Complex-Mediated Inflammation

Basophils are important in the initiation of immune complex-mediated inflammatory responses, as capillary permeability is markedly increased by the action of vasoactive amines such as histamine and platelet-activating factor, which are released by these cells. Vascular permeability is also promoted by aggregation of platelets at sites of an inflammatory lesion, with the release of platelet-activating factor and the formation of microthrombi.

Basophil degranulation may reflect the effects of IgE antibodies, as well as the elaboration of the anaphylatoxin components of complement, C3a and C5a.

In addition to basophils and platelets, the primary cellular effectors of immune complex-mediated inflammation are polymorphonuclear leukocytes, monocytes, and macrophages.

IV. Previous Studies of the Role of Complement in GN Pathoaenesis

Extensive work has been performed in an attempt to understand the possible role of complement in the development of GN. This work has included studies of GN using a number of animal models by, among others, Unanue, et al., (1964); Cochrane, et al., (1965); Kniker, et al., (1965); Salant, et al., (1980); Groggel, et al., (1983); Falk and Jennette (1986); Jennette, et al., (1987); Passwell, et al., (1988); Schrijver, et al., (1988); Baker, et al., (1989); Schrijver, et al., (1990); Couser, et al., (1991); and Couser, et al., (1992).

These studies have shown that complement plays a role in GN pathogenesis. However, they have not established specific unequivocal roles for the various complement components. In particular, the relative roles of C3 and other anaphylatoxins compared to the roles of the terminal complement components in GN pathogenesis have not been unequivocally established. Also, some researchers have reported that complement depletion does not diminish glomerular injury. See Kniker, et al., (1965).

The foregoing work includes that of Falk and Jennette (1986), who reported results of experiments in which attempts were made to induce GN in mice having a genetic defect that resulted in a deficiency of complement component C5. The report concludes that C5 or some terminal complement component dependent on C5 plays a role in the pathogenesis of GN.

Significantly, with regard to the present invention, Falk and Jennette in no way disclose or suggest that an antibody to C5 can be used to treat GN. Indeed, it would be counterintuitive to use an antibody to treat disease which typically involves the formation and deposition of circulating antibody-antigen immune complexes. Plainly, the creation of more circulating immune complexes would seem to be the last way to go to solve a problem that can be caused by circulating immune complexes. Yet, as demonstrated by the surprising results presented below, anti-C5 antibodies have been found to effectively block GN, even though the creation of additional circulating immune complexes is inherent in their mode of action.

Baker et al. (1989), Couser et al. (1991), and Couser et al. (1992) (hereinafter referred to collectively as the "C6" work) discuss experiments in which high levels of an anti-C6 polyclonal antibody preparation were administered to rats, following which immune complexes were formed in situ in the rats' kidneys. Significantly, with regard to the present invention, the anti-C6 antibody preparation was not administered to animals with pre-existing kidney disease, i.e., it was not used as a therapeutic treatment. Moreover, the experimental protocol used in the C6 experiments did not involve circulating immune complexes, but rather involved complexes formed in situ. Accordingly, the experiments did not disclose or suggest the counterintuitive approach of the present invention wherein more circulating immune complexes are formed in the process of treating a disease state caused by circulating immune complexes.

Further, the anti-C6 antibody dosages used in the C6 work were too high for practical medical use. Specifically, these antibodies were used at a dosage of 1 gm/kg, a dosage which would correspond to 70 gm of antibody for a 70 kg (155 lb) individual. In contrast, the anti-C5 antibodies used in the practice of the present invention are used at concentrations at or below 0.1 gm/kg, i.e., a factor of at least ten times less than used in the C6 work. Indeed, as shown by the examples presented below, anti-C5 antibody dosages as low as 0.03 gm/kg, i.e., 33 times less than those used in the C6 work, have been found to achieve the therapeutic effects of the invention in treating GN. For a 70 kg individual, this antibody level corresponds to a dose of just 2.1 gms.

The novel anti-KSSKC antibodies of the invention allow the use of even lower dosage levels to treat GN and other inflammatory conditions. Based upon their level of activity in human blood, they are expected to provide complete complement inhibition at dosages below 0.005 g/kg, and to provide therapeutically effective complement inhibition at dosages below 0.003 g/kg. This 3 mg/kg dosage is one tenth the dosage discussed below in Examples 4 and 5 for the for the anti-C5 (beta chain specific) mAb N19/8. Some of the full length anti-KSSKC mabs of the invention will provide therapeutic benefits even at dosages below 0.0022 g/kg. This is the minimum dose providing complete complement inhibition as calculated from the data obtained using the anti-KSSKC 5G1.1 mAb in human blood in a CPB circuit, as discussed below in Example 9.

Accordingly, dosages of less than 0.005 g/kg are preferred, with dosages of below 0.003 g/kg being more preferred, and dosages below 0.0022 g/kg being particularly preferred. For a 70 kg individual, these antibody dosage levels correspond to a dose of less than 0.35 gms for the highest dosage of the preferred dosages, less than 0.21 gms for the more preferred dosage, and less than or equal to 0.15 gms for the most preferred dosage.

Of course, dosage levels of single chain and other recombinant mAbs of the invention must be adjusted according to their level of activity (e.g., their binding affinity, their ability to block C5 activation, and/or their ability to block complement hemolytic activity), their valency, and their molecular weight. For example, the humanized scFv anti-KSSKC mAbs of Example 11 are approximately 27 kDa, about one sixth the approximately 155 kDa mass of a native, full length IgG antibody. These antibodies completely block complement hemolytic activity and C5a generation at a ratio of 3:1, six fold greater than for native 5G1.1 (but only three fold greater when viewed in terms of numbers of antibody-antigen binding sites).

Thus, the number of molecules of each of these scFvs required to equal the effect of a single molecule of native 5G1.1 must be increased by a factor of six to adjust for the ratio at which blocking is complete. Since the mass of these molecules is approximately one sixth of the mass of native 5G1.1, dosages of the scFvs are in the same range as those for the native 5G1.1 mAb.

In addition to lowering dosage levels, the anti-C5 antibodies used in the practice of the present invention (i.e., in treating GN) achieve important therapeutic effects not achieved with the anti-C6 antibodies. Specifically, the control and test animals in the C6 work exhibited both hypercellularity and narrowing of capillary lumens. In direct contrast, no such hypercellularity or narrowing of capillary lumens was seen when diseased individuals were treated with anti-C5 antibodies (see FIG. 1).

Moreover, the anti-C5 antibodies used in the present invention achieve a reduction in glomerular enlargement, thus providing a clear demonstration of the unexpectedly powerful anti-inflammatory effects of the anti-C5 antibodies used in the practice of the invention. Nowhere in the C6 work is there any disclosure or suggestion of such a powerful anti-inflammatory effect.

V. Anti-C5 Monoclonal Antibodies that Block Complement Hemolytic Activity and Block the Generation of C5a Anti-C5 mabs that have the desirable ability to block complement hemolytic activity and to block the generation of C5a (and are thus preferred for use in the treatment of GN and other inflammatory conditions in accordance with the present invention) have been known in the art since at least 1982 (Moongkarndi et al. Immunobiol. 1982, 162:397; Moongkarndi et al. Immunobiol. 1983, 165:323). Antibodies known in the art that are immunoreactive against C5 or C5 fragments include antibodies against the C5 beta chain (Moongkarndi et al. Immunobiol. 1982, 162:397; Moongkarndi et al. Immunobiol. 1983, 165:323; Wurzner et al. 1991, supra; Mollnes et al. Scand. J. Immunol. 1988, 28:307–312); C5a (see for example, Ames et al. J. Immunol. 1994, 152:4572–4581, U.S. Pat. No. 4,686,100, and European patent publication No. 0 411 306); and antibodies against non-human C5 (see for example, Giclas et al. J. Immunol. Meth. 1987, 105:201–209). Significantly, none of these anti-C5 mAbs has the properties of the novel anti-C5 mabs of the invention, i.e., none of them binds to the C5 alpha chain but not to the C5 cleavage product C5a, none of them has the ability to substantially block both complement hemolytic activity and the generation of C5a to substantially the same extent at the same concentration of antibody. It is noteworthy that an scFv derivative of the N19/8 antibody of Wurzner et al. 1991, supra, has been prepared, and that the N19/8 scFv has 50% less inhibitory activity towards C5a generation than the native N19/8 antibody (see Example 15). This is in contrast to the 5G1.1 scFv, which retained substantially all of its inhibitory activity towards C5a generation (see Example 12).

While not wishing to be bound by any particular theory of operation, it is believed that these distinctions are due to the specific binding characteristics of the antibodies of the invention. Accordingly, antibodies that do not bind to sites within the alpha chain of C5, and antibodies that bind to the C5 cleavage product C5a (free C5a), are believed to lack the ability to substantially block both complement hemolytic activity and the generation of C5a to substantially the same extent at the same concentration of antibody.

DESCRIPTION OF THE PREFERRED EMBODIMENTS

As discussed above, the present invention relates to the use of anti-C5 antibodies in treating patients suffering from GN and other diseases, and to specific C5 antibodies and antibody preparations. Preferably, and when used to treat GN, the anti-C5 antibodies are used in an amount effective to substantially reduce (e.g., reduce by at least about 50%) the cell-lysing ability of complement present in the patient's blood (the "cell-lysing ability of complement present in the patient's blood" is also referred to herein as the "serum complement activity of the patient's blood"). Reduction of the cell-lysing ability of complement present in the patient's blood can be measured by methods well known in the art such as, for example, by the chicken erythrocyte hemolysis method described below under the heading "Cell Lysis Assays."

To achieve the desired reductions, the anti-C5 antibodies can be administered in a variety of unit dosage forms. The dose will vary according to the particular antibody. For example, different antibodies may have different masses and/or affinities, and thus require different dosage levels. Antibodies prepared as Fab' fragments will also require differing dosages than the equivalent intact immunoglobulins, as they are of considerably smaller mass than intact immunoglobulins, and thus require lower dosages to reach the same molar levels in the patient's blood.

The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, and preferably between about 5 mg per kg and about 50 mg per kg per patient per treatment. In terms of plasma concentrations, the antibody concentrations are preferably in the range from about 25 $\mu$g/ml to about 500 $\mu$g/ml.

Subject to the judgement of the physician, a typical therapeutic treatment includes a series of doses, which will usually be administered concurrently with the monitoring of clinical endpoints such as BUN levels, proteinuria levels, etc., with the dosage levels adjusted as needed to achieve the desired clinical outcome. Alternatively, levels of serum complement activity available in the patient's blood are monitored using the techniques set forth below under the heading "Cell Lysis Assays" to determine if additional doses or higher or lower dosage levels of antibodies are needed, with such doses being administered as required to maintain at least about a 50% reduction, and preferably about a 95% or greater reduction of serum complement activity. Other protocols can, of course, be used if desired as determined by the physician.

Administration of the anti-C5 antibodies will generally be performed by an intravascular route, e.g., via intravenous infusion by injection. Other routes of administration may be used if desired. Formulations suitable for injection are found in *Remington's Pharmaceutical Sciences*, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

The formulations of the invention can be distributed as articles of manufacture comprising packaging material and the anti-C5 antibodies. When prepared for use in the treatment of GN, the packaging material will include a label which indicates that the formulation is for use in the treatment of kidney disease and may specifically refer to nephritis or glomerulonephritis.

The anti-C5 antibody is preferably a monoclonal antibody, although polyclonal antibodies produced and screened by conventional techniques can also be used if desired. As discussed above, the anti-C5 antibodies must be effective in reducing the cell-lysing ability of complement present in human blood. As also discussed above, this property of the antibodies can be determined by methods well known in the art such as, for example, by the chicken erythrocyte hemolysis method described below under the heading "Cell Lysis Assays".

The anti-C5 antibodies used in the practice of the invention bind to C5 or fragments thereof, e.g., C5a or C5b. Preferably, the anti-C5 antibodies are immunoreactive against epitopes on the beta chain of purified human complement component C5 and are capable of blocking the conversion of C5 into C5a and C5b by C5 convertase. This capability can be measured using the techniques described in Wurzner, et al., *Complement Inflamm* 8:328–340, 1991. Preferably, the anti-C5 antibodies are used to treat GN in an amount effective to reduce the C5 convertase activity available in the patient's blood by at least about 50%.

In a particularly preferred embodiment of the invention, the anti-C5 antibodies are not immunoreactive against epitopes on the beta chain, but rather are immunoreactive against epitopes within the alpha chain of purified human complement component C5. In this embodiment the antibodies are also capable of blocking the conversion of C5 into C5a and C5b by C5 convertase. In an especially preferred example of this embodiment they can provide this blockade at substantially the same concentrations needed to block hemolytic activity.

Within the alpha chain, the most preferred antibodies bind to an amino-terminal region, however, they do not bind to free C5a. Particularly preferred targets for these antibodies within the alpha chain include the 5G46k fragment, the 5G27k fragment, the 5G325aa peptide, the 5G200aa peptide, or the KSSKC epitope. The scope of the invention also includes the 5G46k fragment, the 5G27k fragment, the 5G325aa peptide, the 5G200aa peptide, or the KSSKC epitope (SEQ ID NO:1) that are useful as immunogens and screening ligands for producing the antibodies of the invention.

Hybridomas producing monoclonal antibodies reactive with complement component C5 can be obtained according to the teachings of Sims, et al., U.S. Pat. No. 5,135,916. As discussed therein, antibodies are prepared using purified components of the complement membrane attack complex as immunogens. In accordance with the present invention, complement component C5 or C5b is preferably used as the immunogen. In accordance with a particularly preferred aspect of the present invention, the immunogen is the alpha chain of C5. Within the alpha chain, the most preferred immunogens include the 5G46k fragment, the 5G27k fragment, the 5G325aa peptide, or the 5G200aa peptide. A less preferred immunogen is the KSSKC epitope.

In accordance with the invention, the antibodies of the invention all share certain required functional properties. These are the ability to substantially inhibit complement hemolytic activity and to substantially inhibit the conversion of C5 to produce C5a. Preferably, but not requisitely, they provide these functions when used at a molar ratio of antibody to antigen (C5) of 3:1 or less.

A particularly preferred antibody of the invention is the 5G1.1 antibody (5G1.1, produced by the 5G1.1 hybridoma, ATCC designation HB-11625). Other particularly preferred antibodies of the present invention share the required functional properties discussed in the preceding paragraph and have any of the following characteristics:

(1) they compete with 5G1.1 for binding to portions of C5—the C5 alpha chain, the 5G46k fragment, the 5G27k fragment, the 5G325aa peptide (SEQ ID NO:1), the 5G200aa" peptide, or the KSSKC peptide—that are specifically immunoreactive with 5G1.1; and (2) they specifically bind to the C5 alpha chain, the 5G46k fragment, the 5G27k fragment, the 5G325aa peptide, the 5G200aa" peptide, and/or the KSSKC peptide (SEQ ID NO:1). Such specific binding, and competition for binding can be determined by various methods well known in the art, including the plasmon surface resonance method (Johne et al., J. Immunol. Meth. 1993, 160:191–198).

(3) they block the binding of C5 to either C3 or C4 (which are components of C5 convertase).

Also in accordance with the invention, the antibodies preferably should prevent the cleavage of C5 to form C5a and C5b, thus preventing the generation of the anaphylatoxic activity associated with C5a and preventing the assembly of the membrane attack complex associated with C5b. In a particularly preferred embodiment, these anti-C5 antibodies will not impair the opsonization function associated with the activation of complement component C3 by a C3 convertase. Plasma C3 convertase activity can be measured by assaying plasma for the presence of C3a as described below under the heading "Histology." Preferably, the anti-C5 antibody produces essentially no reduction in plasma C3a levels.

General methods for the immunization of animals (in this case with C5 or C5b or another preferred immunogen), isolation of polyclonal antibodies or antibody producing cells, fusion of such cells with immortal cells (e.g., myeloma cells) to generate Hybridomas secreting monoclonal antibodies, screening of hybridoma supernatants for reactivity of secreted monoclonal antibodies with a desired antigen (in this case C5 or C5b or another preferred immunogen), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies, A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz, et al., *Cellular Immunol.* 127:337–351, 1990; Wurzner, et al., *Complement Inflamm.* 8:328–340, 1991; and Mollnes, et al., *Scand. J. Immunol.* 28:307–312, 1988.

As used herein, the term "antibodies" refers to immunoglobulins produced in vivo, as well as those produced in vitro by a hybridoma, and antigen binding fragments (e.g., Fab' preparations) of such immunoglobulins, as well as to recombinantly expressed antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins. As used herein, "antibodies" also refers to antigen binding synthetic peptides comprising sequences derived from the sequences of immunoglobulin antigen binding domains. As used herein, the term "recombinant mAbs" refers to recombinantly expressed antigen binding proteins. As used herein, the term "antibody-antigen binding site" refers to an antigen binding site of an antibody comprising at least one CDR sequence.

Antibodies whose amino acid sequences are full length immunoglobulin sequences that have not been truncated (e.g., to produce an scFv or an Fab) or mutated (e.g., spliced to form a chimeric antibody or humanized) are referred to herein as "native" antibodies. Publications describing methods for the preparation of such antibodies, in addition to those listed immediately above, include: Reichmann, et al., *Nature*, 332:323–327, 1988; Winter and Milstein, *Nature*, 349:293–299, 1991; Clackson, et al., *Nature*, 352:624–628, 1991; Morrison, *Annu Rev Immunol*, 10:239–265, 1992; Haber, *Immunol Rev*, 130:189–212, 1992; and Rodrigues, et al., *J Immunol*, 151:6954–6961, 1993.

While treatment of GN in accordance with the process of the present invention may be carried out using polyclonal or monoclonal antibodies, monospecific antibodies are preferred. As used herein "monospecific antibodies" refer to antibodies that bind to a specific region of a particular antigen. All monoclonal antibodies are monospecific, but polyclonal antibodies are typically not monospecific.

As is known in the art, however, monospecific polyclonal antibodies may be prepared by various methods. For example, a peptide (e.g., an oligopeptide—as used hereinafter and in the claims, a polymer of 5 to 200 amino acids) may be used as an immunogen. Another procedure allowing the preparation of monospecific polyclonal antibodies is the use of antigen affinity purification techniques to isolate a monospecific antibody population from a polyclonal antibody mixture. In accordance with the present invention, peptides are preferred as immunogens for the production and as affinity ligands for the purification of monospecific polyclonal anti-KSSKC antibodies.

The native (i.e., non-engineered) monoclonal antibodies of the invention are preferably prepared by conventional means, with the 5G46k fragment, the 5G27k fragment, the 5G200aa peptide, the 5G325aa peptide, and/or the KSSKC peptide (SEQ ID NO:1) (e.g., immobilized on a polypropylene membrane as described below in Example 13) being used as screening ligand(s). This involves testing hybridoma supernatants for binding to each screening ligand.

In one preferred embodiment, the native mAbs of the invention are prepared using the alpha chain of human C5, or fragments thereof, as immunogen. Preferred fragments of the alpha chain of human C5 for this purpose include the 5G46k fragment, the 5G27k fragment, and/or the 5G200aa fragment. Although less preferred, the KSSKC peptide (SEQ ID NO:1) may also be used as an immunogen.

Another (albeit less preferred) immunogen and screening ligand for the preparation of antibodies within the scope of the novel antibodies of the present invention is the "cleavage site peptide," i.e., the peptide spanning amino acids 725 through 754 of SEQ ID NO:2 (the C5a cleavage site), as discussed below in Example 13.

In another preferred embodiment of the invention, the native mAbs of the invention are prepared in transgenic mice expressing human immunoglobulins (see, for example, Green et al., Nature Genet. 1994, 7:13–21). In this case, the same preferred immunogens and screening ligands are used as described for the preparation of other native mAbs.

In another preferred embodiment of the invention, the recombinant mAbs of the invention are prepared by screening phage display libraries expressing recombinant mab-encoding polynucleotides (preferably encoding human recombinant mabs). See, for example, Ames et al., 1994, supra; Smith and Scott, Meth. Enzymol. 1993, 217:228; Kay et al., Gene, 1993, 128:59–65. This screening is carried out with the screening ligands described above for the preparation of native mAbs. The recombinant mAbs of the invention are prepared by subcloning the recombinant mAb-encoding polynucleotides into a suitable expression vector, expressing them in a suitable host (as described below), and isolating the recombinant mAbs.

The present invention provides recombinant expression vectors which include the synthetic, genomic, or cDNA-derived nucleic acid fragments of the invention, i.e. polynucleotides encoding the mabs of the invention. The nucleotide sequence coding for any of the mAbs of the invention can be inserted into an appropriate expression vector, i.e., a vector that contains the necessary elements for the transcription and translation of the inserted protein-coding sequence. The necessary transcriptional and translational signals can also be supplied by the native or source gene and/or its flanking regions.

A variety of host vector systems may be utilized to express the recombinant expression vectors of the invention. These include, but are not limited to, mammalian cell systems infected with recombinant virus (e.g., vaccinia virus, adenovirus, retroviruses, etc.); mammalian cell systems transfected with recombinant plasmids; insect cell systems infected with recombinant virus (e.g., baculovirus); microorganisms such as yeast containing yeast expression vectors, or bacteria transformed with recombinant bacteriophage DNA, recombinant plasmid DNA, or cosmid DNA (see, for example, Goeddel, 1990).

Useful expression vectors for bacterial use can comprise a selectable marker and bacterial origin of replication derived from commercially available plasmids comprising genetic elements of the well-known cloning vector pBR322 (American Type Culture Collection-"ATCC"-, 10801 University Boulevard, Manassas, Va. 20110-2209, United States of America; ATCC Accession No. 37017). These pBR322 "backbone sections," or functionally equivalent sequences, are combined with an appropriate promoter and the structural gene to be expressed. Promoters commonly used in recombinant microbial expression vectors include, but are not limited to, the lactose promoter system (Chang, et al., Nature 275:615), the tryptophan (trp) promoter (Goeddel, et al., 1980, Gene Expression Technology, Volume 185. Academic Press, Inc., San Diego, Calif.) and the tac promoter, or a fusion between the tac and trp promoters referred to as the trc promoter (Maniatis, 1982, Molecular Cloning: A Laboratory Manual, Cold Spring Harbor Laboratory, Cold Spring Harbor, N.Y.). Particularly preferred promoters include the T7 promoter, which is used in conjunction with host cell expression of a T7 RNA polymerase (see Studier et al. 1990, Meth. Enzymol. 185:60–89), and the trc promoter, which is found in several commercially available vectors, as described below.

Preferred bacterial expression vectors include, but are not limited to, the pET vectors (see Studier et al. 1990, supra) and the Trc vectors. Many of the pET vectors are commercially available from Stratagene Cloning Systems (La Jolla, Calif.). A particularly preferred vector is the pET Trc SO5/NI vector described below (SEQ ID NO:18). A Trc vector, pTrc 99A, is available from Pharmacia. Other Trc vectors include the pSE vectors (Invitrogen, San Diego, Calif.).

Preferred bacteria for expression of recombinant mAbs include *Bacillus subtilis* and, most preferably, *Escherichia coli*. A particularly preferred strain of *E. coli* is strain W3110 (ATCC designation 27325). Under certain unusual conditions it may be necessary to use standard bacterial genetics methods to prepare derivative strains of W3110, for example, when a contaminating bacteriophage ("phage") is present in the laboratory where the bacterial manipulations are being carried out. Generally, and particularly for large scale preparation of the recombinant anti-KSSKC mAbs of the invention, it is preferred to use unmodified W3110, or another fully characterized strain.

In cases where phage contamination is a problem and disinfection is not practicable or desirable, it is preferred to identify the phage contaminant and to then use a fully characterized bacterial strain having a known mutation rendering the bacterium resistant to the phage. Preferably the mutation is a null mutant for the receptor for the phage. In some instances, however, the generation use of a relatively uncharacterized phage-resistant derivative strain may be acceptable, particularly in small scale experimental work. When such derivative strains are desired, they may be prepared using the methods described below in Example 11.

For most purposes the use of unmodified W3110 or another fully characterized bacterial strain is generally preferred. This is particularly true for the preparation of pharmaceutical agents comprising the recombinant anti-KSSKC mAbs of the invention. This is because of the problems, well known in the art, of using bacterial strains containing uncharacterized or partially characterized mutations for the production of ingredients of pharmaceutical agents.

The recombinant mAbs of the invention may also be expressed in fungal hosts, preferably yeast of the Saccharomyces genus such as S. cerevisiae. Fungi of other genera such as Aspergillus, Pichia or Kluyveromyces may also be employed. Fungal vectors will generally contain an origin of replication from the 2 µm yeast plasmid or another autonomously replicating sequence (ARS), a promoter, DNA encoding a mAb of the invention, sequences directing polyadenylation and transcription termination, and a selectable marker gene. Preferably, fungal vectors will include an origin of replication and selectable markers permitting transformation of both E. coli and fungi.

Suitable promoter systems in fungi include the promoters for metallothionein, 3-phosphoglycerate kinase, or other glycolytic enzymes such as enolase, hexokinase, pyruvate kinase, glucokinase, the glucose-repressible alcohol dehydrogenase promoter (ADH2), the constitutive promoter from the alcohol dehydrogenase gene, ADH1, and others. See, for example, Schena, et al. 1991 Meth. Enzymol. 194:389–398. Secretion signals, such as those directing the secretion of yeast alpha-factor or yeast invertase, can be incorporated into the fungal vector to promote secretion of a soluble recombinant mAb into the fungal growth medium. See Moir, et al., 1991, Meth. Enzymol. 194:491–507.

Preferred fungal expression vectors can be assembled using DNA sequences from pBR322 for selection and replication in bacteria, and fungal DNA sequences, including the ADH1 promoter and the alcohol dehydrogenase ADH1 termination sequence, as found in vector pAAH5 (Ammerer, 1983, Meth. Enzymol. 101:192). The ADH1 promoter is effective in yeast in that ADH1 mRNA is estimated to be 1–2% of total poly(A) RNA.

Various mammalian or insect cell culture systems can be employed to express recombinant mAbs. Suitable baculovirus systems for production of heterologous proteins in insect cells are reviewed by Luckow, et al., 1988. Examples of suitable mammalian host cell lines include the COS cell of monkey kidney origin, mouse L cells, murine C127 mammary epithelial cells, mouse Balb/3T3 cells, Chinese hamster ovary cells (CHO), human 293 EBNA and HeLa cells, myeloma, and baby hamster kidney (BHK) cells, with myeloma cells, CHO cells, and human 293 EBNA cells being particularly preferred.

Mammalian expression vectors may comprise non-transcribed elements such as origin of replication, a suitable promoter and enhancer linked to the recombinant mAb gene to be expressed, and other 5' or 3' flanking sequences such as ribosome binding sites, a polyadenylation sequence, splice donor and acceptor sites, and transcriptional termination sequences.

The transcriptional and translational control sequences in mammalian expression vector systems to be used in transforming vertebrate cells may be provided by viral sources. For example, commonly used promoters and enhancers are derived from Polyoma virus, Adenovirus, Simian Virus 40 (SV40), and human cytomegalovirus, including the cytomegalovirus immediate-early gene 1 promoter and enhancer (CMV).

Particularly preferred eukaryotic vectors for the expression of recombinant anti-KSSKC mAbs are pAPEX-1 (SEQ ID NO:3 and, more preferably, pAPEX-3p, SEQ ID NO:4. The vector pAPEX-1 is a derivative of the vector pcDNAI/Amp (Invitrogen) which was modified to increase protein expression levels. First, the 3'-untranslated SV40 small-t antigen intron was removed by deletion of a 601 base pair XbaI/HpaI fragment since this intron is susceptible to aberrant splicing into upstream coding regions (Evans and Scarpulla, 1989 Gene 84:135; Huang and Gorman, 1990, Molec. Cell Biol. 10:1805). Second, a chimeric adenovirus-immunoglobulin hybrid intron was introduced into the 5'-untranslated region by replacing a 484 base pair NdeI-NotI fragment with a corresponding 845 base pair NdeI-NotI fragment from the vector pRc/CMV7SB (Sato et al., 1994, J. Biol. Chem. 269:17267). Finally, to increase plasmid DNA yields from E. coli, the resulting CMV promoter expression cassette was shuttled into the vector pGEM-4Z (Promega Corp. Madison, Wis.).

The vector pAPEX-3 is a derivative of the vector pDR2 (Clontech Laboratories, Inc. Palo Alto, Calif.) in which the EBNA gene was first removed by deletion of a 2.4 kb ClaI/AccI fragment. The RSV promoter was then replaced with the CMV promoter and the adenovirus/immunoglobulin chimeric intron by exchanging a 450 bp MluI/BamHI fragment from pDR2 with a 1.0 kb MluI/BamHI fragment from the vector pAPEX-1. For construction of pAPEX-3P, a 1.7 kb BstBI/SwaI fragment containing the HSV tk promoter and hygromycin phosphotransferase (hyg) gene was removed from pAPEX-3 and replaced with a 1.1 kb SnaBI/NheI fragment containing the SV40 early promoter and puromycin acetyltransferase (pac) gene (Morgenstern and Land, 1990, Nucleic Acids Res. 18:3587–3596) plus a 137 bp XbaI/ClaI fragment containing an SV40 polyadenylation signal from the vector pAPEX-1.

A particularly preferred host cell for the expression of recombinant mAb-encoding inserts in the pAPEX vectors is the human 293 EBNA cell line (Invitrogen, San Diego, Calif.).

Another preferred eukaryotic vector for the expression of recombinant mAbs is pcDNAI/Amp (Invitrogen Corporation, San Diego, Calif.). The pcDNAI/Amp expression vector contains the human cytomegalovirus immediate-early gene I promoter and enhancer elements, the Simian Virus 40 (SV40) consensus intron donor and acceptor splice sequences, and the SV40 consensus polyadenylation signal. This vector also contains an SV40 origin of replication that allows for episomal amplification in cells (e.g., COS cells, MOP8 cells, etc.) transformed with SV40 large T antigen, and an ampicillin resistance gene for propagation and selection in bacterial hosts.

Purified recombinant mAbs are prepared by culturing suitable host/vector systems to express the recombinant mAb translation products of the nucleic acid molecules of the present invention, which are then purified from the culture media or cell extracts of the host system, e.g., the bacteria, insect cells, fungal, or mammalian cells. Fermentation of fungi or mammalian cells that express recombinant mAb proteins containing a histidine tag sequence (a sequence comprising a stretch of at least 5 histidine residues) as a secreted product greatly simplifies purification. Such a histidine tag sequence enables binding under specific conditions to metals such as nickel, and thereby to nickel (or other metal) columns for purification. Recombinant mAbs may also be purified by protein G affinity chromatography (Proudfoot et al., 1992, Protein Express. Purif. 3:368).

Additional preferred embodiments are numbered and set forth below as "favored embodiments."

FAVORED EMBODIMENTS

1. A method for the treatment of glomerulonephritis in a patient in need of such treatment comprising introducing an antibody that binds to complement component C5 into the patient's bloodstream in an amount effective to substantially reduce the cell-lysing ability of complement present in the patient's blood.

2. The method of favored embodiment 1 wherein the antibody reduces the conversion of complement component C5 into complement components C5a and C5b.

3. The method of favored embodiment 1 wherein the antibody binds to C5b.

4. The method of favored embodiment 1 wherein the antibody does not substantially inhibit formation of complement component C3b.

5. The method of favored embodiment 1 wherein the antibody is introduced into the patient's bloodstream in a dose that is not greater than 0.1 grams per kilogram.

6. An article of manufacture comprising packaging material and a pharmaceutical agent contained within said packaging material, wherein:
(a) said pharmaceutical agent comprises an antibody to complement component C5, said antibody being effective in substantially reducing the cell-lysing ability of complement present in the patient's blood; and
(b) said packaging material comprises a label which indicates that said pharmaceutical agent is for use in the treatment of kidney disease.

7. The article of manufacture of favored embodiment 6 wherein the label indicates that said pharmaceutical agent is for use in the treatment of nephritis.

8. The article of manufacture of favored embodiment 7 wherein the label indicates that said pharmaceutical agent is for use in the treatment of glomerulonephritis.

9. The article of manufacture of favored embodiment 6 wherein the pharmaceutical agent is to be used at a dosage level not greater than 0.1 grams per kilogram.

10. An antibody comprising at least one antibody-antigen binding site, said antibody exhibiting specific binding to human complement component C5, said specific binding being targeted to the alpha chain of human complement component C5, wherein the antibody inhibits complement activation in a human body fluid and does not specifically bind to the human complement activation product free C5a.

11. The antibody of favored embodiment 10 wherein the inhibition of complement activation in the human body fluid is measurable as a substantial increment of blockade of C5a generation and a substantial increment of blockade of complement hemolytic activity in the body fluid, said increment of blockade of C5a generation being substantially equal to said increment of blockade of complement hemolytic activity.

12. The antibody of favored embodiment 10 wherein, upon binding to human C5, the antibody substantially inhibits the ability of C5 to bind to human complement component C3.

13. The antibody of favored embodiment 10 wherein, upon binding to human C5, the antibody substantially inhibits the ability of C5 to bind to human complement component C4.

14. The antibody of favored embodiment 10 wherein the antibody binds specifically with a 5G46k fragment.

15. The antibody of favored embodiment 10 wherein the antibody binds specifically to a 5G27k fragment.

16. The antibody of favored embodiment 10 wherein the antibody binds specifically to a 5G325aa peptide.

17. The antibody of favored embodiment 10 wherein the antibody binds specifically to a 5G200aa peptide.

18. The antibody of favored embodiment 10 wherein the antibody binds specifically to a KSSKC peptide.

19. The antibody of favored embodiment 10 wherein the inhibition of complement activation in the human body fluid is measurable as a substantially complete blockade of C5a generation in the body fluid and a substantially complete blockade of complement hemolytic activity in the body fluid when the antibody is added to the body fluid at a concentration yielding a ratio equal to or less than 10 moles of antibody-antigen binding sites of the antibody to 1 mole of human C5 in the body fluid.

20. The antibody of favored embodiment 19 wherein the concentration yields a ratio equal to or less than 3 moles of antibody-antigen binding sites of the antibody to 1 mole of human C5 in the body fluid.

21. Hybridoma 5G1.1 having ATCC designation HB-11625.

22. An antibody produced by the hybridoma of favored embodiment 21.

23. An antibody that can compete with the antibody of favored embodiment 22 for binding to the alpha chain of human C5.

24. A nucleic acid molecule comprising a nucleotide sequence encoding an scFv polypeptide comprising an amino acid sequence corresponding to amino acid 1 through amino acid 248 of SEQ ID NO:7.

25. A nucleic acid molecule comprising a nucleotide sequence encoding a polypeptide comprising a variable light chain region amino acid sequence corresponding to amino acid 3 through amino acid 110 of SEQ ID NO:9.

26. A nucleic acid molecule comprising a nucleotide sequence encoding a polypeptide comprising a variable heavy chain region amino acid sequence corresponding to amino acid 1 through amino acid 122 of SEQ ID NO:10.

27. An isolated protein comprising:
(a) a first polypeptide region comprising a variable light chain region amino acid sequence corresponding to amino acid 3 through amino acid 110 of SEQ ID NO:9.; and
(b) a second polypeptide region comprising a variable heavy chain region amino acid sequence corresponding to amino acid 1 through amino acid 122 of SEQ ID NO:10.

28. An isolated polypeptide comprising an amino acid sequence encoded by the nucleic acid molecule of favored embodiment 24, favored embodiment 25, or favored embodiment 26, wherein the polypeptide is an antibody.

29. A nucleic acid vector comprising a first nucleic acid molecule covalently and operatively linked to a second nucleic acid molecule so that a host containing the vector expresses the polypeptide coded for by the first nucleic acid molecule, wherein the first nucleic acid molecule is the nucleic acid molecule of favored embodiment 24, favored embodiment 25, or favored embodiment 26.

30. A recombinant host cell containing the nucleic acid vector of favored embodiment 29.

31. A method for producing an isolated C5 antibody polypeptide comprising growing the recombinant host cell of favored embodiment 30 such that the polypeptide encoded by the first nucleic acid molecule of the vector is expressed by the host cell, and isolating the expressed polypeptide, wherein the expressed polypeptide is an anti-C5 antibody.

32. The isolated anti-C5 antibody of favored embodiment 31.

33. A nucleic acid molecule comprising a nucleotide sequence encoding an scFv comprising an amino acid sequence corresponding to amino acid 1 through amino acid 248 of SEQ ID NO:8.

34. A nucleic acid molecule comprising a nucleotide sequence encoding an scFv comprising an amino acid sequence corresponding to amino acid 1 through amino acid 248 of SEQ ID NO:17.

35. A nucleic acid molecule comprising a nucleotide sequence encoding a polypeptide comprising a variable light chain region amino acid sequence corresponding to amino acid 1 through amino acid 108 of SEQ ID NO:15.

36. A nucleic acid molecule comprising a nucleotide sequence encoding a polypeptide comprising a variable light chain region amino acid sequence corresponding to amino acid 3 through amino acid 110 of SEQ ID NO:14.

37. A nucleic acid molecule comprising a nucleotide sequence encoding a polypeptide comprising a variable heavy chain region amino acid sequence corresponding to amino acid 1 through amino acid 122 of SEQ ID NO:16.

38. A nucleic acid molecule comprising a nucleotide sequence encoding a polypeptide comprising a variable heavy chain region amino acid sequence corresponding to amino acid 1 through amino acid 122 of SEQ ID NO:12.

39. A nucleic acid molecule comprising a nucleotide sequence encoding a polypeptide comprising a variable heavy chain region amino acid sequence corresponding to amino acid 1 through amino acid 122 of SEQ ID NO:11.

40. An isolated protein comprising:
(a) a first polypeptide region comprising a variable light chain region amino acid sequence corresponding to amino acid 1 through amino acid 108 of SEQ ID NO:15; and
(b) a second polypeptide region comprising a variable heavy chain region amino acid sequence corresponding to amino acid 1 through amino acid 122 of SEQ ID NO:16.

41. An isolated protein comprising:
(a) a first polypeptide region comprising a variable light chain region amino acid sequence corresponding to amino acid 1 through amino acid 1 through amino acid 108 of SEQ ID NO:15; and
(b) a second polypeptide region comprising a variable heavy chain region amino acid sequence corresponding to amino acid 1 through amino acid 122 of SEQ ID NO:12.

42. An isolated protein comprising:
(a) a first polypeptide region comprising a variable light chain region amino acid sequence corresponding to amino acid 1 through amino acid 108 of SEQ ID NO:15; and
(b) a second polypeptide region comprising a variable heavy chain region amino acid sequence corresponding to amino acid 1 through amino acid 122 of SEQ ID NO:11.

43. An isolated protein comprising:
(a) a first polypeptide region comprising a variable light chain region amino acid sequence corresponding to amino acid 3 through amino acid 110 of SEQ ID NO:14; and
(b) a second polypeptide region comprising a variable heavy chain region amino acid sequence corresponding to amino acid 1 through amino acid 122 of SEQ ID NO:16.

44. An isolated protein comprising:
(a) a first polypeptide region comprising a variable light chain region amino acid sequence corresponding to amino acid 3 through amino acid 110 of SEQ ID NO:14; and
(b) a second polypeptide region comprising a variable heavy chain region amino acid sequence corresponding to amino acid 1 through amino acid 122 of SEQ ID NO:12.

45. An isolated protein comprising:
(a) a first polypeptide region comprising a variable light chain region amino acid sequence corresponding to amino acid 3 through amino acid 110 of SEQ ID NO:14; and
(b) a second polypeptide region comprising a variable heavy chain region amino acid sequence corresponding to amino acid 1 through amino acid 122 of SEQ ID NO:11.

46. An isolated protein comprising the amino acid sequence encoded by the nucleic acid molecule of favored embodiment 33, favored embodiment 34, favored embodiment 35, favored embodiment 36, favored embodiment 37, favored embodiment 38, or favored embodiment 39, wherein the isolated protein is an anti-C5 antibody.

47. A nucleic acid vector comprising a first nucleic acid molecule covalently and operatively linked to a second nucleic acid molecule so that a host containing the vector expresses the polypeptide coded for by the first nucleic acid molecule, wherein the first nucleic acid molecule is the nucleic acid molecule of favored embodiment 33, favored embodiment 34, favored embodiment 35, favored embodiment 36, favored embodiment 37, favored embodiment 38, or favored embodiment 39.

48. A recombinant host cell containing the nucleic acid vector of favored embodiment 47.

49. A method for producing an isolated anti-C5 antibody protein comprising growing the recombinant host cell of favored embodiment 48 such that a protein encoded by the nucleic acid molecule is expressed by the host cell, and isolating the expressed protein, wherein the expressed protein is an anti-C5 antibody.

50. The isolated anti-C5 antibody of favored embodiment 47.

51. An isolated nucleic acid molecule comprising:
(a) a nucleotide sequence encoding a variable light region CDR3 comprising an amino acid sequence corresponding to amino acid 93 through amino acid 98 of SEQ ID NO:7;
(b) a sequence complementary to (a); or
(c) both (a) and (b).

52. An isolated nucleic acid molecule comprising:
(a) a nucleotide sequence encoding a variable light region CDR3 comprising an amino acid sequence corresponding to amino acid 91 through amino acid 99 of SEQ ID NO:8;
(b) a sequence complementary to (a); or
(c) both (a) and (b).

53. An isolated nucleic acid molecule comprising:
(a) a nucleotide sequence encoding a variable heavy region CDR1 comprising an amino acid sequence corresponding to amino acid 156 through amino acid 159 of SEQ ID NO:7;
(b) a sequence complementary to (a); or
(c) both (a) and (b).

54. An isolated nucleic acid molecule comprising:
(a) a nucleotide sequence encoding a variable heavy region CDR1 comprising an amino acid sequence corresponding to amino acid 152 through amino acid 161 of SEQ ID NO:8;
(b) a sequence complementary to (a); or
(c) both (a) and (b).

55. An isolated nucleic acid molecule comprising:
(a) a nucleotide sequence encoding a variable heavy region CDR2 comprising an amino acid sequence corresponding to amino acid 179 through amino acid 182 of SEQ ID NO:7;

(b) a sequence complementary to (a); or (c) both (a) and (b).

56. An isolated nucleic acid molecule comprising:

(a) a nucleotide sequence encoding a variable heavy region CDR2 comprising an amino acid sequence corresponding to amino acid 176 through amino acid 186 of SEQ ID NO:8;

(b) a sequence complementary to (a); or (c) both (a) and (b).

57. An isolated nucleic acid molecule comprising:

(a) a nucleotide sequence encoding a variable heavy region CDR3 comprising an amino acid sequence corresponding to amino acid 226 through amino acid 236 of SEQ ID NO:7;

(b) a sequence complementary to (a); or (c) both (a) and (b).

58. An isolated nucleic acid molecule comprising:

(a) a nucleotide sequence encoding a variable heavy region CDR3 comprising an amino acid sequence corresponding to amino acid 225 through amino acid 237 of SEQ ID NO:8;

(b) a sequence complementary to (a); or (c) both (a) and (b).

59. An isolated nucleic acid molecule comprising:

(a) a nucleotide sequence encoding a variable light region CDR3 comprising an amino acid sequence corresponding to amino acid 91 through amino acid 99 of SEQ ID NO:8;

(b) a nucleotide sequence encoding a variable heavy region CDR1 comprising an amino acid sequence corresponding to amino acid 152 through amino acid 161 of SEQ ID NO:8;

(c) a nucleotide sequence encoding a variable heavy region CDR2 comprising an amino acid sequence corresponding to amino acid 176 through amino acid 186 of SEQ ID NO:8; and (d) a nucleotide sequence encoding a variable heavy region CDR3 comprising an amino acid sequence corresponding to amino acid 225 through amino acid 237 of SEQ ID NO:8.

60. An isolated nucleic acid molecule comprising:

(a) a nucleotide sequence encoding a variable light region CDR3 comprising an amino acid sequence corresponding to amino acid 91 through amino acid 99 of SEQ ID NO:8;

(b) a nucleotide sequence encoding a variable heavy region CDR1 comprising an amino acid sequence corresponding to amino acid 152 through amino acid 161 of SEQ ID NO:8;

(c) a nucleotide sequence encoding a variable heavy region CDR2 comprising an amino acid sequence corresponding to amino acid 176 through amino acid 192 of SEQ ID NO:8; and (d) a nucleotide sequence encoding a variable heavy region CDR3 comprising an amino acid sequence corresponding to amino acid 225 through amino acid 237 of SEQ ID NO:8.

61. An isolated nucleic acid molecule comprising:

(a) a nucleotide sequence encoding a variable light region CDR3 comprising an amino acid sequence corresponding to amino acid 91 through amino acid 99 of SEQ ID NO:8;

(b) a nucleotide sequence encoding a variable heavy region CDR1 comprising an amino acid sequence corresponding to amino acid 152 through amino acid 161 of SEQ ID NO:8;

(c) a nucleotide sequence encoding a variable heavy region CDR2 comprising an amino acid sequence corresponding to amino acid 179 through amino acid 182 of SEQ ID NO:7; and (d) a nucleotide sequence encoding a variable heavy region CDR3 comprising an amino acid sequence corresponding to amino acid 225 through amino acid 237 of SEQ ID NO:8.

62. An isolated protein comprising the amino acid sequence encoded by the nucleic acid molecule of favored embodiment 51, favored embodiment 52, favored embodiment 53, favored embodiment 54, favored embodiment 55, favored embodiment 56, favored embodiment 57, favored embodiment 58, favored embodiment 59, favored embodiment 60 or favored embodiment 87.

63. The isolated protein of favored embodiment 62 wherein the protein is an anti-C5 antibody.

64. A nucleic acid vector comprising a first nucleic acid molecule, said first nucleic acid molecule corresponding to the nucleic acid molecule of favored embodiment 51, favored embodiment 52, favored embodiment 53, favored embodiment 54, favored embodiment 55, favored embodiment 56, favored embodiment 57, favored embodiment 58, or favored embodiment 87 covalently and operatively linked to a second nucleic acid molecule so that a host containing the vector expresses the protein encoded by the first nucleic acid molecule.

65. A recombinant host cell containing the nucleic acid vector of favored embodiment 64.

66. A method for producing an anti-C5 antibody comprising growing the recombinant host cell of favored embodiment 65 so that the protein encoded by the nucleic acid molecule is expressed by the host cell, and isolating the expressed protein, wherein the expressed protein is an anti-C5 antibody.

67. The anti-C5 antibody of favored embodiment 66.

68. An isolated 5G46k fragment of human complement component C5.

69. An isolated 5G27k fragment of human complement component C5.

70. An isolated 5G325aa peptide.

71. An isolated 5G200aa peptide.

72. An isolated oligopeptide comprising an amino acid sequence corresponding to amino acid 8 through amino acid 12 of SEQ ID NO:1, i.e., Lys Ser Ser Lys Cys, or in single letter notation, KSSKC.

73. A method of inducing an animal to produce an anti-C5 antibody comprising repeatedly immunizing an animal with the isolated alpha chain of human C5.

74. A method of inducing an animal to produce an anti-C5 antibody comprising immunizing an animal with the isolated 5G46k fragment of favored embodiment 68.

75. A method of inducing an animal to produce an anti-C5 antibody comprising immunizing an animal with the isolated 5G27k fragment of favored embodiment 69.

76. A method of inducing an animal to produce an anti-C5 antibody comprising immunizing an animal with the isolated 5G325aa peptide of favored embodiment 70.

77. A method of inducing an animal to produce an anti-C5 antibody comprising immunizing an animal with the isolated 5G200aa peptide of favored embodiment 71.

78. A method of inducing an animal to produce an anti-C5 antibody comprising immunizing an animal with the isolated oligopeptide of favored embodiment 72.

79. A method of identifying an anti-C5 antibody comprising screening candidate antibodies with the isolated alpha chain of human C5.

80. A method of identifying an anti-C5 antibody comprising screening candidate antibodies with the isolated 5G46k fragment of favored embodiment 68.

81. A method of identifying an anti-C5 antibody comprising screening candidate antibodies with the isolated 5G27k fragment of favored embodiment 69.

82. A method of identifying an anti-C5 antibody comprising screening candidate antibodies with the isolated 5G325aa peptide of favored embodiment 70.

83. A method of identifying an anti-C5 antibody comprising screening candidate antibodies with the isolated 5G200aa peptide of favored embodiment 71.

84. A method of identifying an anti-C5 antibody comprising screening candidate antibodies with the isolated oligopeptide of favored embodiment 72.

85. A method of treating a patient in need of complement inhibition comprising administering the antibody of favored embodiment 10, favored embodiment 22, favored embodiment 23, favored embodiment 28, favored embodiment 32, favored embodiment 46, favored embodiment 50, favored embodiment 63, or favored embodiment 67 to the patient in an amount effective to substantially reduce hemolytic activity in a body fluid of the patient.

86. The antibody of favored embodiment 10 wherein the antibody is a recombinant antibody that comprises a human constant domain.

87. An isolated nucleic acid molecule comprising:
(a) a nucleotide sequence encoding a variable heavy region CDR2 comprising an amino acid sequence corresponding to amino acid 176 through amino acid 192 of SEQ ID NO:8;
(b) a sequence complementary to (a); or
(c) both (a) and (b).

88. An isolated nucleic acid molecule comprising:
(a) a nucleotide sequence encoding a variable heavy region CDR2 comprising an amino acid sequence corresponding to amino acid 176 through amino acid 192 of SEQ ID NO:8;
(b) a sequence complementary to (a); or
(c) both (a) and (b).

89. An isolated antibody comprising any one of the CDR regions of CO12, CO13, CO14, Co15, DO12b, DO12C, DO12D.

90. An isolated nucleic acid molecule encoding the antibody of favored embodiment 89.

EXAMPLES

Without intending to limit it in any manner, the present invention will be more fully described by the following examples. The methods and materials which are common to various of the examples are as follows.

Induction of GN in Mice

Four month old female B10.D2/nSnJ mice averaging approximately 25 gms each were obtained from the Jackson Laboratory, Bar Harbor, Me. Mice were injected with 0.1 mL daily (six days per week) of a 40 mg/mL solution of horse apoferritin (HAF), which was prepared by dilution of a saline solution of HAF (Sigma Chemical Company Catalog No. A-3641) with PBS.

Anti-C5 Monoclonal Antibodies

Monoclonal antibodies that bind to complement component C5 of the mouse were prepared by standard methods as an IgG fraction from supernatants of cultures of hybridoma BB5.1 (Frei, et al., 1987), which was obtained from Dr. Brigitta Stockinger of the National Institute for Medical Research, Mill Hill, London, England.

Histology

Kidneys were subjected to microscopic analysis using standard histochemical staining and immunofluorescence techniques. Periodic Acid Schiff (PAS) staining of 5 paraffin sections was by standard methods using a HARLECO PAS histochemical reaction set (EM Diagnostic Systems, Gibbstown, N.J., number 64945/93) according to the manufacturer's directions.

Immunofluorescence staining of $5\mu$ cryostat sections was carried out by standard methods using FITC conjugated sheep anti-mouse C3 (Biodesign International, Kennebunk, Me, Catalog No. W90280F) to detect murine complement component C3, or FITC conjugated goat anti-mouse IgG, IgA, and IgM (Zymed Laboratories, South San Francisco, Calif., Catalog No. 65-6411) to detect immune complexes.

Urine Assays

Protein and glucose levels were determined by spotting urine samples on CHEMSTRIP 2GP dipsticks (Boehringer Mannheim Diagnostics, Indianapolis, Ind., Catalog No. 200743). The detection areas of these strips change color when exposed to urine containing protein or glucose; a lack of color change indicates no detectable protein or glucose is present. The level of analyte in the urine being tested is read out by matching changed colors with color charts supplied by the manufacturer. The urine protein chart shows colors corresponding to trace, 30, 100, and 500 mg/dL.

Cell Lysis Assays

The cell-lysing ability of complement in blood can be determined using hemolytic assays that are performed as follows: Chicken erythrocytes are washed well in GVBS (Rollins, et al., J Immunol 144:3478–3483, 1990, Sigma Chemical Co. St. Louis, Mo., catalog No. G-6514) and resuspended to $2 \times 10^8$/mL in GVBS. Anti-chicken erythrocyte antibody (IgG fraction of anti-chicken-RBC antiserum, Intercell Technologies, Hopewell, N.J.) is added to the cells at a final concentration of 25 $\mu$g/mL and the cells are incubated for 15 min. at 23° C. The cells are washed 2× with GVBS and $5 \times 10^6$ cells are resuspended to 30 $\mu$L in GVBS. A 100 $\mu$L volume of serum test solution is then added to yield a final reaction mixture volume of 130 $\mu$L. As used herein, reference to the serum percentage and/or serum input in these assays indicates the percent serum in the 100 $\mu$L volume of serum test solution.

For assays of mouse serum activity, the 100 $\mu$L volume of serum test solution contained 50 $\mu$L of diluted (in GVBS) mouse serum and 50 $\mu$L of human C5 deficient serum (Quidel Corporation, San Diego, Calif.). For assays of human serum activity, the serum test solution may contain up to 100% human plasma or serum, with hybridoma supernatants and/or GVBS being added to yield the 100 $\mu$L volume. For the assays used to screen hybridoma supernatants discussed below in Example 7, each 100 $\mu$L volume of serum test solution contained 50 $\mu$L of hybridoma supernatant and 50 $\mu$L of a 10% solution of human serum in GVBS, yielding a 5% human serum input.

After incubation for 30 min. at 37° C., percent hemolysis was calculated relative to a fully lysed control sample. Hemolysis was determined by spinning the cells down and measuring released hemoglobin in the supernatant as the optical density at 415 nm.

A 50% reduction in hemolysis after treatment with the anti-C5 antibodies used in the practice of the invention means that the percent hemolysis after treatment is one half of the percent hemolysis before treatment.

Example 1

Anti-C5 Antibodies Inhibit Glomerular Inflammation and Enlargement

This example illustrates that anti-C5 antibodies will inhibit glomerular inflammation and enlargement.

The protocol for these experiments was as follows. GN-induced mice were treated with anti-C5 antibodies or with PBS as a control after 2 weeks of GN induction. Each mouse received 750 µg of anti-C5 monoclonal antibodies in PBS (30 mg/kg in a 25 gm mouse) or an equal volume of PBS alone. The amount injected was from 0.25 to 0.365 mL (the concentration of antibodies in PBS varied), which was administered by intraperitoneal injection once a day, six days a week. After an additional 2 weeks of induction and treatment, the animals were sacrificed and kidneys were harvested and prepared for histological examination as described above. Kidneys were also obtained from age-matched uninduced and untreated control mice.

Figure 1C:
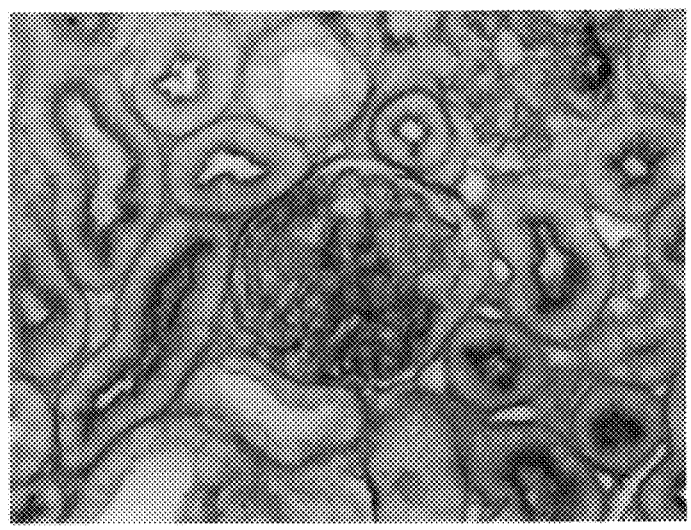

FIG. 1 shows sections of mouse kidneys with a single glomerulus located centrally amidst surrounding interstitium and cross sections of convoluted tubules in each section. As can be seen therein, the kidneys of the GN-induced, PBS-treated mice (FIG. 1B) developed severe crescentic glomerular pathology, including inflammatory glomerular hypercellularity, apparent basement membrane thickening, and glomerular enlargement, while the glomeruli of the GN-induced, anti-C5-treated animals (FIG. 1C) were essentially indistinguishable from the glomeruli of the normal healthy kidneys of the uninduced untreated mice (FIG. 1A).

Note that in the glomeruli with severe crescentic pathology, the size of the glomerular capillary network (glomerular tuft) is not enlarged, but shows signs of compression by a crescentic-shaped proliferation of epithelial cells and PAS-positive material, and the Bowman's capsule is dramatically enlarged. Also note that in the section of diseased glomerulus shown in FIG. 1B, the capillary network is split in half by a projection of the hypercellular crescentic mass.

The non-inflamed glomerulus of the uninduced untreated mouse shown in FIG. 1A is approximately 100µ in diameter; the inflamed glomerulus of the GN-induced, PBS treated mouse shown in FIG. 1B is approximately 175µ in diameter; the non-inflamed glomerulus of the GN-induced, anti-C5-treated mouse shown in FIG. 1C is approximately 90µ in diameter.

Example 2

Anti-C5 Antibodies Prevent/Reduce Proteinuria Associated with GN

This example demonstrates that treatment with anti-C5 antibodies results in the prevention/reduction of kidney damage as evidenced by the lack of significant amounts of protein in the urine (i.e. the presence of less than 100 mg/dL of protein in the urine).

The protocol for the experiments of this example was the same as that used in the experiments of Example 1. Five PBS-treated, GN-induced mice, 6 anti-C5-treated, GN-induced mice, and 4 age-matched untreated uninduced mice were used in this study. A first set of urine samples was analyzed prior to treatment after the initial 2 week induction period. A second set of urine samples was analyzed after the 2 week treatment period. None of the untreated uninduced control animals had detectable protein in their urine at either of these timepoints.

The results obtained with the GN-induced mice are set forth in Table 1. As shown therein, at the end of the 2 week PBS treatment period, 4 out of the 5 PBS treated (control) animals developed significant proteinuria, i.e., at least 100 mg/dL of protein in the urine. The fifth animal (mouse D in Table 1) did not have detectable protein in the urine at either timepoint but, unlike the other mice in the study, was found to have very high levels of glucose in the urine after the 2 week PBS treatment period, suggesting that this animal was physiologically compromised.

In the anti-C5-treated, GN-induced group, the one mouse that developed significant proteinuria at the end of the initial 2 week induction period (mouse 6 in Table 1) improved by the end of the 2 week antibody treatment period. In addition, in contrast to the development of significant proteinuria in 4 out of 5 PBS-treated, GN-induced mice, none of the anti-C5-treated, GN-induced mice exhibited significant proteinuria at the end of the 2 week antibody treatment period.

Example 3

Anti-C5 Antibodies do not Inhibit Glomerular Immune Complex Deposition

This example demonstrates that anti-C5 antibodies used in the practice of the invention achieve their therapeutic effects even though immune complexes are deposited in the glomeruli of treated animals at equivalent levels to those seen in the glomeruli of PBS-treated animals. The example further illustrates that the mechanism of operation of the anti-C5 antibodies is not through the inhibition of immune complex deposition in the glomerulus.

The protocol used in the experiments of this example was the same as that used in the experiments of Example 1. Immunofluorescence staining as described above was performed on sections from the same kidneys harvested in Example 1.

Figure 2C:
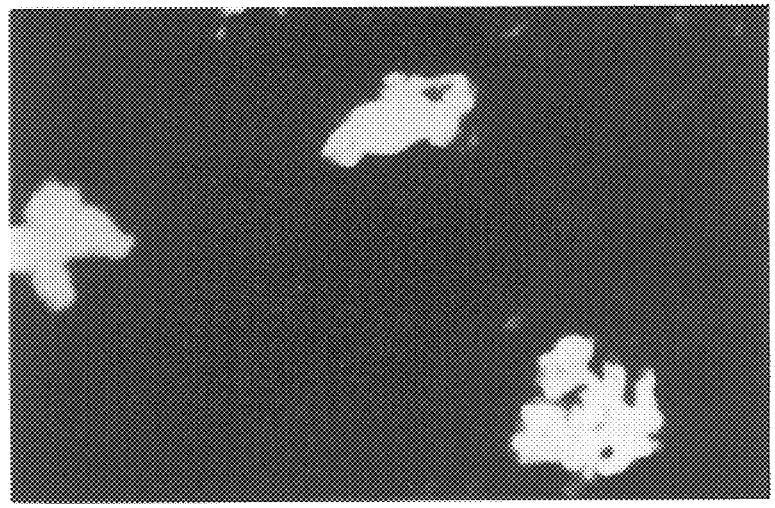

The results are shown in FIG. 2. As can be seen in this figure, equivalent amounts of immune complexes were deposited in the glomeruli of the kidneys of both the PBS-treated, GN-induced mice (FIG. 2B) and the anti-C5-treated, GN-induced mice (FIG. 2C), but not in the untreated uninduced controls (FIG. 2A). Kidneys of GN-induced mice harvested after the 2 week induction period, but before treatment, showed immune complex deposits in the glomeruli, but at lower levels (as indicated by lower fluorescence intensity) than in the kidney sections shown in FIG. 2B and FIG. 2C.

Example 4

Anti-C5 Antibodies Inhibit C5b-9 Generation

This example demonstrates that the anti-C5 antibodies used in the practice of the invention inhibit C5b-9 generation. C5b-9 generation was assayed in 2 ways: (1) by testing the cell-lysing (hemolytic) ability of blood samples, and (2) by measuring levels of soluble C5b-9 in blood samples.

Figure 3:
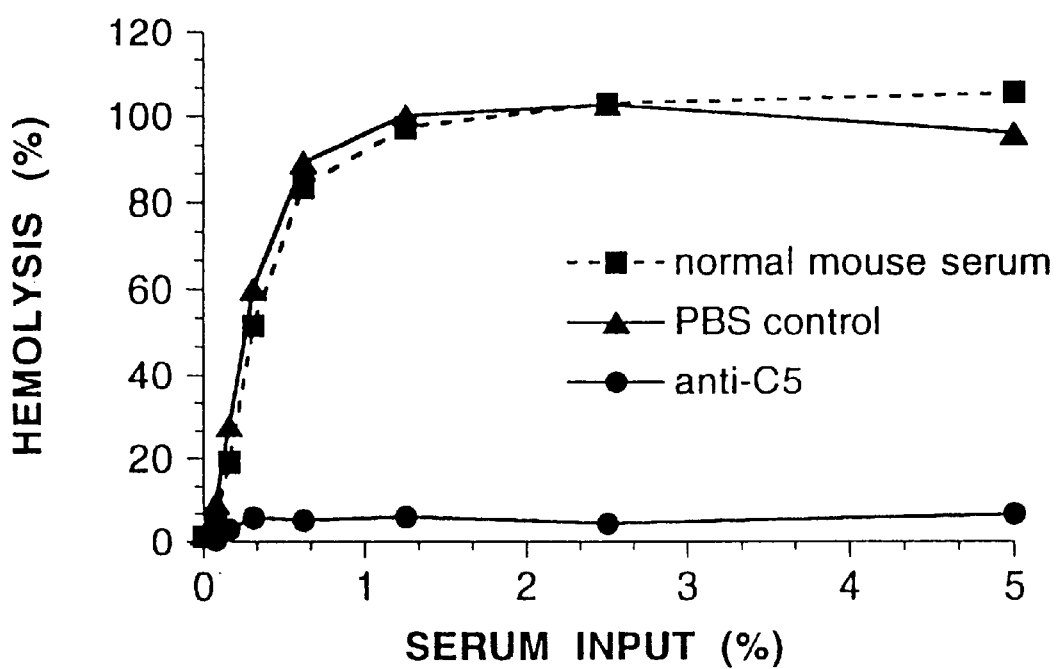
FIG. 3—Results of hemolytic (cell lysis) assays of serum from GN-induced animals treated with either anti-C5 antibodies in PBS ("Anti-C5") or PBS alone ("PBS control"). Also shown are the results of assays performed with normal serum.

FIG. 3 shows the results of cell lysis assays performed as described above, with mouse serum added to the percentage indicated on the X axis ("serum input %"). In these assays, serum from GN-induced animals treated with either anti-C5 antibodies in PBS or PBS alone (see above) was assayed at the end of the two week treatment period. Serum from normal, uninduced, uninjected mice ("normal mouse serum") obtained from Sigma Chemical Company (St. Louis, Mo., Catalog No. S-3269) was also assayed as an additional control. These results indicate that the anti-C5 monoclonal antibody administered to mice at a dosage of 30 mg/Kg completely blocked the cell lysing ability of mouse blood at serum input levels 4-fold higher than the levels of normal serum that produce maximum hemolysis in the assay.

The effects of an anti-C5 monoclonal antibody raised to human C5 was evaluated in circulating human blood. Hybridoma N19/8 (Wurzner, et al., 1991) was obtained from Dr. Otto Götze, Department of Immunology, University of Göttingen, FRG. The C5 monoclonal antibody was prepared following immunization of mice with purified human C5 protein as described in Wurzner, et al., (1991). The hybridoma was propagated in mice, and the monoclonal antibody recovered and purified as an IgG fraction from mouse ascites fluid (*Antibodies, A Laboratory Manual*, Cold Spring Harbor Laboratory, New York, 1988; *Current Protocols In Immunology*, John Wiley & Sons, New York, 1992).

To carry out these experiments, as well as others described below in Examples 5 and 6, 300 mL of whole human blood was drawn from a healthy human donor and additionally a 1 mL sample was removed as a control sample for later analysis. The blood was diluted to 600 mL by the addition of Ringer's lactate solution containing 10 U/mL heparin. The anti-C5 mAb (30 mg in sterile PBS) was added to the diluted blood to a final concentration of 50 µg/mL (results using test samples obtained in this way are labeled "+anti-C5 sample" in FIG. 4 and FIG. 6). In a control experiment, an equal volume of sterile PBS was added to diluted blood (results using control samples obtained in this way are labeled "−anti-C5 sample" in FIG. 4 and FIG. 6).

The blood was then used to prime the extracorporeal circuit of a COBE CML EXCEL membrane oxygenator cardiopulmonary bypass (CPB) machine (Cobe BCT, Inc., Lakewood, Colo.) and circulation through the circuit was started. The circuit was cooled to 28° C. and circulated for 60 minutes. The circuit was then warmed to 37° C. and circulated for an additional 30 minutes, after which time the experiment was terminated. Mechanical circulation of blood in this fashion activates the complement cascade. Samples were taken at several time points.

Figure 4:
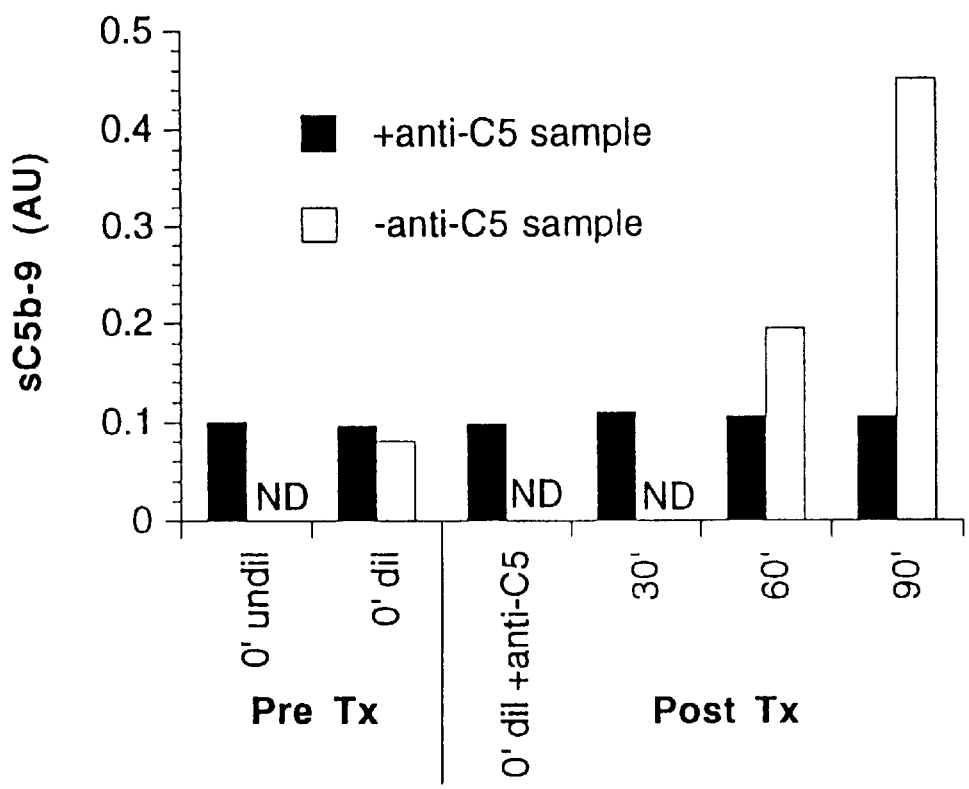
FIG. 4—Results of soluble C5b-9 ("sC5b-9") assays. "ND" indicates not determined.
Figure 6:
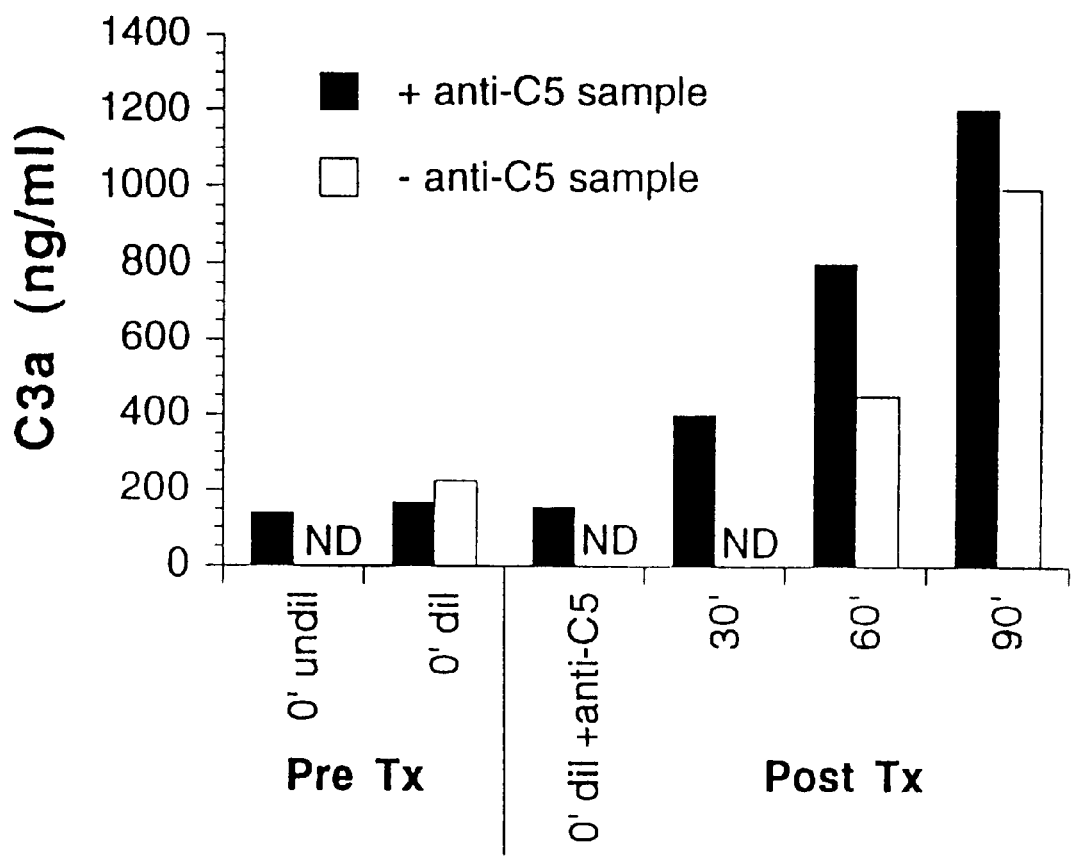
FIG. 6—Results of C3a assays of samples of circulating human blood. "ND" indicates not determined.

At each time point an aliquot of blood was taken, and subaliquots were centrifuged to remove all cells and the remaining plasma diluted 1:1 in QUIDEL sample preservation solution (Quidel Corporation, San Diego, Calif.) and stored at −80° C. for subsequent evaluation of soluble C5b-9 (sC5b-9) generation. Diluted subaliquots of plasma were also frozen for evaluation of C3a generation (see Example 5, below). Undiluted subaliquots of plasma were frozen at −80° C. for analysis in hemolytic assays to evaluate the pharmacokinetics of the effects of the anti-C5 antibodies on the cell lysing ability of complement present in the blood (see Example 6, below). These experiments are also discussed in copending U.S. patent application Ser. No. 08/217,391, filed Mar. 23, 1994, now U.S. Pat. No. 5,853,722.

sC5b-9 assays were performed before the addition of the antibody or the commencement of the CPB circuit (labeled "Pre Tx" in FIG. 4 and FIG. 6) using undiluted blood (i.e. blood from the 1 mL sample taken before the blood was diluted with Ringer's lactate solution—labeled "undil" in FIG. 4 and FIG. 6) and Ringer's lactate solution diluted blood (labeled "dil" in FIG. 4 and FIG. 6). Samples of Ringer's lactate solution diluted blood to which the antibody had been added (labeled "Post Tx" in FIG. 4 and FIG. 6) were assayed at the times indicated after starting the CPB circuit.

As can be seen in FIG. 4, while sC5b-9 levels were more than 4-fold higher in untreated samples after 90 minutes of circulation than before circulation, the anti-C5 antibody completely inhibited C5b-9 generation throughout the 90 minute time course of circulation so that sC5b-9 levels during circulation were essentially equivalent to control, uncirculated samples, at all timepoints.

Example 5

Anti-C5 Antibodies do not Inhibit C3 Deposition or Activation

This example demonstrates that treatment with anti-C5 antibodies does not result in the inhibition of the activation of complement component C3 or in the deposition of C3 or its activated fragments in glomeruli.

Figure 5C:

The deposition of C3, or the fragments generated by its activation (e.g., C3a and C3b), in the glomeruli of GN-induced and GN-uninduced mice was visualized by immunofluorescence staining with a FITC-conjugated sheep anti-mouse C3 antibody preparation using standard methods, as described above. As can be seen in FIG. 5, kidneys of the PBS-treated (FIG. 5B) and the anti-C5 antibody-treated (FIG. 5C) GN-induced mice had roughly equivalent levels of C3 immunoreactive material in the glomeruli, while the uninduced untreated control mice had only traces of C3 immunoreactive material in their kidneys (FIG. 5A).

Note that the print shown in FIG. 5A was overexposed compared to those of FIG. 5B and FIG. 5C to show the very slight levels of reactivity present in normal uninduced kidneys. Kidneys of GN-induced mice harvested after the 2 week induction period, but before treatment, showed C3 immunoreactive materials in the glomeruli, but at lower levels (as indicated by lower fluorescence intensity) than in the kidney sections shown in FIG. 5B and FIG. 5C.

Anti-human C5 antibodies were also tested for possible inhibition of C3 activation in human blood prepared and circulated as described above in Example 4. Activation of complement component C3 was indicated by the presence in the blood of the C3 activation product C3a. C3a assays were performed as follows.

The plasma samples that had previously been diluted in QUIDEL sample preservation solution and frozen (see Example 4) were assayed for the presence of C3a by using the QUIDEL C3A EIA kit (Quidel Corporation, San Diego, Calif.) according to the manufacturer's specifications. Concentrations of C3a in the samples is expressed as ng/well as determined by comparison to a standard curve generated from samples containing known amounts of human C3a.

As seen in FIG. 6, the addition of the anti-C5 mAb had no inhibitory effect on the production of C3a during the circulation of human blood in this experiment.

Example 6

Pharmacokinetics of Anti-C5 Antibodies

The in vivo duration of action of mAb BB5.1, and a Fab' fragment of mAb BB5.1 (prepared by standard methods) was determined in normal female BALB/cByJ mice (averaging approximately 20 gms each) which were obtained from the Jackson Laboratory, Bar Harbor, Me. The mice were given a single intravenous injection (at 35 mg/kg body weight) of the mAB or the Fab' fragment of the mAb (or an equal volume of PBS as a control). Blood samples were collected from the retroorbital plexus at 1, 4, 24, 96, and 144 hours after administration of PBS; 4, 16, and 24 hours after administration of the Fab' fragment of mAb BB5.1; and 4, 24, 48, 72, 96, and 144 hours after administration of intact mAb BB5.1.

Figure 7A:
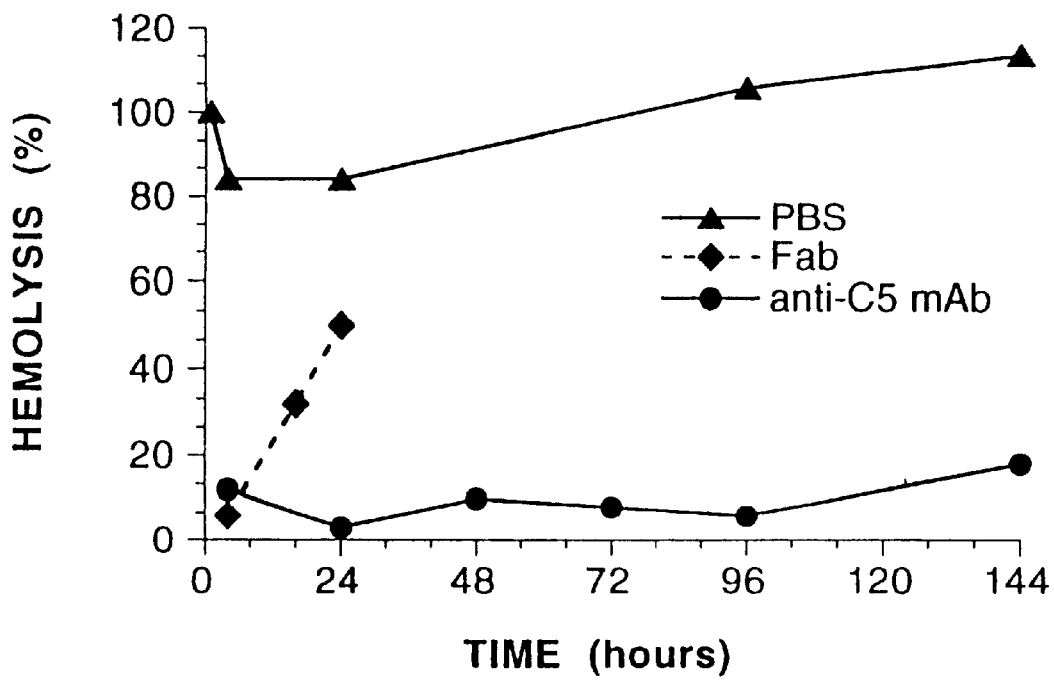
FIGS. 7A and 7B—Pharmacokinetic analyses of the reduction of the cell lysis ability of mouse (FIG. 7A) or human (FIG. 7B) blood after treatment with anti-C5 antibodies.

FIG. 7A shows the time course of inhibition of the cell-lysing ability of complement in mouse blood (determined, by testing serum obtained from the blood and diluted to 2.5%, as described above) after the in vivo administration of the mAb, the Fab' fragment, or the PBS. As shown in the figure, the mAb almost completely inhibited the hemolytic activity of the blood throughout the 6 day test period. The Fab', however, had a half-life of approximately 24 hours.

In addition to the above experiments, at the end of the 6 day testing period all of the mice were sacrificed. Kidneys, lungs, and livers were harvested and examined by gross inspection, as well as by microscopic examination of stained sections. All of the organs of the anti-C5 antibody treated animals appeared the same as those taken from PBS control treated animals. The overall appearance of the test and control mice was also indistinguishable prior to necropsy.

Figure 7B:
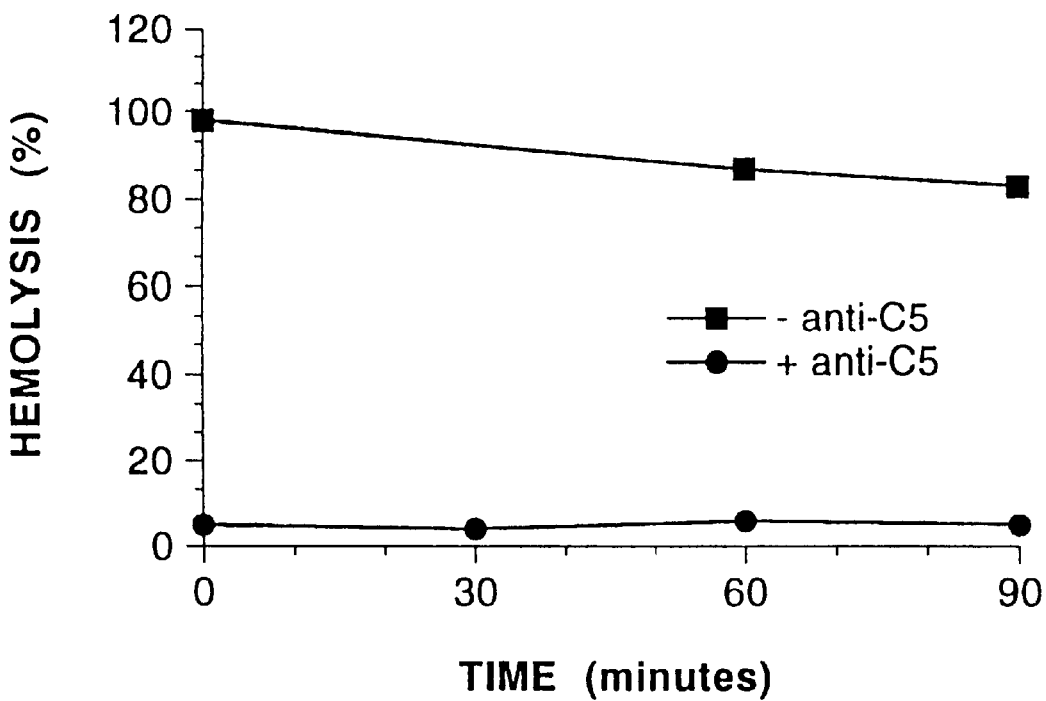

Anti-human C5 antibodies were also tested for pharmacokinetic properties in circulating human blood as described above in Example 4. As described therein, the hemolysis inhibiting effects of an anti-human C5 monoclonal antibody were assayed over a 90 minute period of circulation. The results of these assays are charted in FIG. 7B, and show that the N19/8 anti-C5 mAb essentially completely inhibited the cell lysing ability of the human blood during the entire 90 minute period of circulation.

The results of these experiments demonstrate that the anti-C5 antibodies will survive in the bloodstream for a substantial period of time, thus making periodic administration practical.

Example 7

Preparation of Anti-C5 Monoclonal Antibodies

A monoclonal antibody suitable for use in the practice of the present invention was prepared in accordance with the teachings of Sims, et al., U.S. Pat. No. 5,135,916, as follows.

Balb/c mice were immunized three times by intraperitoneal injection with human C5 protein (Quidel Corporation, San Diego, Calif., Cat # A403). The first injection contained 100 μg of C5 protein in a complete Freund's adjuvant emulsion, the second immunization contained 100 μg of C5 protein in an incomplete Freund's adjuvant emulsion, and the third immunization was 100 μg of protein in PBS. The mice were injected at roughly 2 month intervals.

Fusions of splenocytes to myeloma cells to generate hybridomas were performed essentially as described in Current Protocols in Immunology (John Wiley & Sons, New York, 1992, pages 2.5.1 to 2.5.17). One day prior to fusion the mice were boosted IV with 100 μg of C5 protein. On the day of fusion, the immunized mice were sacrificed and spleens was harvested. SP2/0-AG14 myeloma cells (ATCC CRL#1581) were used as the fusion partner. SP2/0-AG14 cultures were split on the day before the fusion to induce active cell division. A ratio of 1:10 (myeloma cells:splenocytes) was used in the fusions.

The cells were fused using PEG 1450 in PBS without calcium (Sigma Chemical Company, St. Louis, Mo., Catalog No. P-7181) and plated at 1–2.5×10$^5$ cells per well. Selection in EX-CELL 300 medium (JRH Biosciences, Lexena, Kans., Catalog No. 14337-78P) supplemented with 10% heat inactivated fetal bovine serum (FBS); glutamine, penicillin and streptomycin (GPS); and HAT (Sigma Chemical Company, St. Louis, Mo., Catalog No. H-0262) was started the following day. The fusions were then fed every other day with fresh FBS, GPS, and HAT supplemented medium. Cell death could be seen as early as 2 days and viable cell clusters could be seen as early as 5 days after initiating selection. After two weeks of selection in HAT, surviving hybridomas chosen for further study were transferred to EX-CELL 300 medium supplemented with FBS, GPS, and HT (Sigma Chemical Company, St. Louis, Mo., Catalog No. H-0137) for 1 week and then cultured in EX-CELL 300 medium supplemented with FBS and GPS.

Hybridomas were screened for reactivity to C5 and inhibition of complement-mediated hemolysis 10–14 days after fusion, and were carried at least until the screening results were analyzed. The screen for inhibition of hemolysis was the chicken erythrocyte lysis assay described above. The screen for C5 reactivity was an ELISA, which was carried out using the following protocol:

A 50 μL aliquot of a 2 μg/mL solution of C5 (Quidel Corporation, San Diego, Calif.) in sodium carbonate/bicarbonate buffer, pH 9.5, was incubated overnight at 4° C. in each test well of a 96 well plate (NUNC-IMMUNO F96 POLYSORP, A/S Nunc, Roskilde, Denmark). The wells were then subjected to a wash step. (Each wash step consisted of three washes with TBST.) Next, test wells were blocked with 200 μL of blocking solution, 1% BSA in TBS (BSA/TBS) for 1 hour at 37° C. After an additional wash step, a 50 μL aliquot of hybridoma supernatant was incubated in each test well for 1 hour at 37° C. with a subsequent wash step. As a secondary (detection) antibody, 50 μL of a 1:2000 dilution of horseradish peroxidase (HRP) conjugated goat anti-mouse IgG in BSA/TBS, was incubated in each test well for 1 hour at 37° C., followed by a wash step. Following the manufacturer's procedures, 10 mg of O-phenylenediamine (Sigma Chemical Company, St. Louis, Mo., Catalog No. P-8287) was dissolved in 25 mLs of phosphate-citrate buffer (Sigma Chemical Company, St. Louis, Mo., Catalog No. P-4922), and 50 μL of this substrate solution was added to each well to allow detection of peroxidase activity. Finally, to stop the peroxidase detection reaction, a 50 μL aliquot of 3N hydrochloric acid was added to each well. The presence of antibodies reactive with C5 in the hybridoma supernatants was read out by a spectrophotometric OD determination at 490 nm.

The supernatant from a hybridoma designated as 5G1.1 tested positive by ELISA and substantially reduced the cell-lysing ability of complement present in normal human blood in the chicken erythrocyte hemolysis assay. Further analyses revealed that the 5G1.1 antibody reduces the cell-lysing ability of complement present in normal human blood so efficiently that, even when present at roughly one-half the molar concentration of human C5 in the hemolytic assay, it can almost completely neutralize serum hemolytic activity.

Immunoblot analysis was undertaken to further characterize the 5G1.1 mAb. Human C5 (Quidel Corporation, San Diego, Calif., Catalog No. A403) was subjected to polyacrylamide gel electrophoresis under reducing conditions, transferred to a nitrocellulose membrane, and probed with the 5G1.1 mAb as a purified IgG preparation. Two bands were immunoreactive with the 5G1.1 mAb at apparent molecular weights corresponding to those of the alpha and beta chains of the human C5 protein. The two 5G1.1 immunoreactive bands seen on this Western blot were subsequently found to result from the binding of the 5G1.1 antibody to the 115 kDa C5 alpha chain and to a large fragment of the alpha chain that had the same apparent molecular weight (approximately 75 kDa) as the beta chain of C5 and was present in the C5 preparations used for the experiment.

Assays were performed to determine the relative activity of the N19/8 mAb discussed in Examples 4 and 5 with the 5G1.1 mAb in functional hemolytic assays and to assess whether these mAbs blocked the cleavage of C5 to yield C5a. To this end, the N19/8 and 5G1.1 mAbs were directly compared in human complement hemolytic and C5a release assays.

Hemolytic assays performed in the presence of 20% v/v human serum revealed that the 5G1.1 mAb effectively blocked serum hemolytic activity at a final concentration of 6.25 µg/ml (0.5/1 molar ratio of 5G1.1/C5) whereas the N19/8 mAb blocked at a higher concentration of 25.0 µg/ml (2.0/1 molar ratio of N19/8/C5). When the supernatants from these assays were tested for the presence of C5a, the 5G1.1 mAb was found to have effectively inhibited C5a generation at doses identical to those required for the blockade of C5b-9 mediated hemolytic activity.

In contrast, the N19/8 mAb was 10 fold less effective in blocking the release of C5a in these assays when compared to the 5G1.1 mAb. Furthermore, the ability of the N19/8 mAb to block complement mediated hemolysis was not equivalent to its capacity to block C5a generation in that a dose of 25 µg/ml of N19/8 completely blocked hemolysis while only reducing C5a generation by 37%.

Hybridoma 5G1.1 was deposited with the American Type Culture Collection, 10801 University Boulevard, Manassas, Va. 20110-2209, United States of America, on Apr. 27, 1994, and has been assigned the designation HB-11625. This deposit were made under the Budapest Treaty on the International Recognition of the Deposit of Micro-organisms for the Purposes of Patent Procedure (1977).

Example 8

Determination of the Affinity Constants ($K_D$) for the Anti-human C5 Monoclonal Antibodies 5G1.1 and N19/8

The procedure utilized to determine the dissociation constant ($K_D$) of antibody-antigen equilibria in solution was that described by Friguet et al., J. Immunol. Meth. 1985, 77:305–319. This method was used to determine the $K_D$ for the anti-human C5 monoclonal antibodies N19/8 and 5G1.1. The monoclonal antibodies were incubated with the antigen (C5) in solution until the equilibrium was reached. The proportion of antibody that remains unbound (free) at equilibrium was measured using a conventional Enzyme Linked Immunosorbant Assay (ELISA). The experimental values of $K_D$ obtained by this method have been shown to be equivalent to those obtained by other methods (immunoprecipitation of the radiolabeled antigen and fluorescence transfer). This method offers the advantage of dealing with unmodified antigen.

FIGS. 8 and 9 show the Scatchard plots of the binding of the anti-human C5 monoclonal antibodies 5G1.1 and N19/8 to human C5 as measured by ELISA. In each graph (v) represents the fraction of bound antibody and (a) represents the concentration of free antigen at equilibrium. The calculated $K_D$ for the 5G1.1 mAb was 30 pM while the calculated $K_D$ for the N19/8 mAb was 43 pM. These results indicate that the $K_D$ for the 5G1.1 and N19/8 mab's are similar, and therefore the functional disparity between the two antibodies cannot be explained simply by the differences in affinity for the C5 antigen.

Example 9

Effect of 5G1.1 mAb on Complement Activation During CPB

Experiments involving recirculation of human blood in an CPB circuit, as described above in Examples 4 and 5, were carried out using three doses of the 5G1.1 mAb (15 mg, 7.5 mg, 3.75 mg) as well as controls in the absence of the 5G1.1 mAb. In five such control experiments performed in this series, C3a FIG. 10) and sC5b-9 (FIG. 11) levels increased during the first 30 min and continued to rise throughout the entire experiment. Addition of the 5G1.1 mAb to the CPB circuit had no effect on the generation of C3a in these experiments.

Conversely, addition of the two highest doses (15 mg and 7.5 mg) of the 5G1.1 mab completely blocked the generation of sC5b-9 in these experiments while the lowest dose (3.75 mg) only partially blocked sC5b-9 generation. Hemolytic assays performed on serum samples drawn throughout the time course of these experiments revealed that total serum complement activity was not affected in control experiments (FIG. 12). In contrast, the highest dose of the 5G1.1 mAb (15 mg) completely blocked complement hemolytic activity, while the two lower doses (7.5 mg and 3.75 mg), failed to block hemolytic activity.

These results show that the 7.5 mg dose effectively blocked C5b-9 generation in the CPB circuit but failed to block C5b-9-mediated hemolytic activity, suggesting that hemolytic assays alone may not accurately reflect the complement activation that occurs during CPB. These results further indicate that the 5G1.1 mAb can completely block complement activation in human blood, as measured by either criterion, at a dosage of 15 mg/500 ml, a dose that is approximately equivalent to a dose of 150 mg for a 70 kg patient.

Example 10

Cloning of Anti-C5 Recombinant Anti-KSSKC Variable Region Genes Amino Acid Sequencing To determine the N-terminal amino acid sequence of the 5G1.1 mAb, a 12% acrylamide gel (37.5:1 acrylamide/N, N'-methylene-bisacrylamide) was prepared and pre-electrophoresed for 45 minutes at 10 mA using 1× pre-electrophoresis buffer (123 mM bis-Tris, pH 6.6, with the cathode buffer reservoir supplemented with 1 mM reduced glutathione). The following day, the pre-electrophoresis buffer in the cathode reservoir was replaced with cathode reservoir buffer (44 mM N-tris-(hydroxymethyl)methyl-2-aminoethanesulfonic acid, 113 mM bis-Tris, 0.1% (w/v) sodium dodecyl sulfate (SDS), 0.067% (w/v) thioglycolic acid) and the pre-electrophoresis buffer in the anode reservoir was replaced with anode reservoir buffer (63 mM bis-Tris, pH 5.9).

75 µg 5G1.1 monoclonal antibody was added to Laemmli sample buffer (30 mM Tris-HCl pH 6.8, 3% (w/v) SDS, 10 mM EDTA, 0.02% (w/v) bromophenol blue, 5% (v/v) glycerol, 2.5% (v/v) beta-mercaptoethanol) and electrophoresed at 10 mA until the bromophenol blue tracking dye reached the bottom of the gel. The protein was transferred to a PROBLOTT membrane (Applied Biosystems, Foster City, Calif.) using 1× transfer buffer (10 mM cyclohexylamino-propane sulfonic acid, 0.05% (w/v) dithiothreitol, 15% (v/v) methanol) at 50 V for one hour.

Protein bands were localized by staining with 0.2% Ponceau S (in 3% trichloroacetic acid, 3% sulfosalicylic acid) followed by destaining with water. Bands were excised and subjected to amino acid sequence analysis using Edman chemistry performed on a pulsed liquid protein sequencer (ABI model 477A), with the PTH amino acids thereby obtained being analyzed with an on-line microbore HPLC system (ABI model 120A).

To deblock the amino terminus of the 5G1.1 heavy chain, 10 mg 5G1.1 monoclonal antibody was exchanged into reducing buffer (5 M guanidine-HCl, 50 mM Tris-HCl, 10 mM dithiothreitol, pH 8.5) using a PD-10 column (Pharmacia, Piscataway, N.J.). After a one hour incubation at room temperature, 50 mM iodoacetamide was added and the incubation allowed to continue for 30 minutes. The carbamidomethylated light and heavy chains thus obtained were separated by size exclusion chromatography on a SUPEROSE 12 (Pharmacia) column equilibrated with 5 M guanidine-HCl, 50 mM Tris-HCl pH 8.5. The carbamidomethylated heavy chain was exchanged into 50 mM sodium phosphate, pH 7.0 using a PD-10 column, subjected to digestion with pyroglutamate aminopeptidase (PanVera, Madison, Wis.; 0.5 mU per nmol of heavy chain protein), and sequenced as described above.

For determination of internal amino acid sequence, the carbamidomethylated 5G1.1 light chain was exchanged into 2 M urea, 25 mM Tris-HCl, 1 mM EDTA, pH 8.0 and incubated with endoproteinase Lys-C (Promega, Madison, Wis.; protease:protein ratio of 1:40) at 37° C. overnight. The digested material was run on a C18 reversed phase HPLC column (Beckman Instruments, Fullerton, Calif.) and eluted using a linear 0–50% acetonitrile gradient in 0.1% trifluoroacetic acid. Peaks were subjected to amino acid sequence analysis as described above.

PCR Cloning

Cloning of the 5G1.1 variable heavy region was performed using a set of commercially available primers (Mouse Ig-PRIMER SET, catalogue number 69831-1, Novagen, Madison, Wis.). Total RNA was isolated from 5G1.1 hybridoma cells using the acid/guanidinium thiocyanate technique (Chomczynski and Sacchi, Anal. Biochem. 1987, 162:156–159). For first strand cDNA synthesis, ten micrograms total RNA were denatured at 65° C. for 5 min., chilled on ice, and added to a 100 μl reaction containing 10 mM Tris pH 8.3, 50 mM KCl, 1.5 mM MgCl$_2$, 10 mM dithiothreitol, 250 μM each dNTP, 20 units AMV reverse transcriptase (Seikagaku America, Rockville, Md.), and 10 pmole of the appropriate 3' primer (as described in the Ig-PRIMER SET kit protocol). After incubation at 37° C. for one hour, five microliters of the cDNA synthesis reaction were added to a 100 microliter PCR reaction containing: 10 mM Tris-HCl pH 9.0 at 25° C., 50 mM KCl, 1.5 mM MgCl$_2$, 0.1% (w/v) gelatin, 1.0% (v/v) Triton X-100, 200 μM each dNTP, 2.5 U AMPLITAQ DNA polymerase (Perkin-Elmer-Cetus, Norwalk, Conn.) and 25 pmoles of the appropriate 5' and 3' primers (as described in the Ig-PRIMER SET kit protocol). The reaction conditions were 1 minute at 95° C., 1 minute at 42° C., and 1 minute at 72° C. for 30 cycles, followed by a final extension at 72° C. for 10 minutes.

PCR products having the expected size (approximately 450 bp) were cloned into the vector PCRII (Invitrogen, San Diego, Calif.) using a T/A cloning kit (Invitrogen). DNA sequence analysis of cloned DNA fragments was performed by the dideoxy chain-termination method using doublestranded plasmid DNA as a template. A unique heavy chain variable region was isolated by this procedure, with the resulting clones designated p5G1.1 VH 2-1-3. Several clones obtained from independent replicate PCR reactions were sequenced to detect any mutations introduced during the PCR amplification of this variable region.

To clone the 5G1.1 light chain variable region, PCR primers were designed by using the UWGCG program TFASTA (University of Wisconsin, Madison, Wis.) to search the GenBank rodent subdirectory with the 19mer query amino acid sequence Ile Gln Met Thr Gln Ser Pro Ala Ser Leu Ser Ala Ser Val Gly Glu Thr Val Thr, that was obtained by amino acid sequencing as described above. An exact match to this sequence was located in the murine germline gene encoding the v-kappa k2 variable region (Seidman et al. Proc. Natl. Acad. Sci. USA 1978 75:3881–3885). The DNA sequence of this germline gene was used to design the oligonucleotide UDEC690 (SEQ ID NO:5) for use as a variable region 5'-primer. A murine kappa gene constant region primer, UDEC395 (SEQ ID NO:6) was also synthesized and used in this reaction. Cloning of the 5G1.1 variable light region was performed using the UDEC690 variable region 5'-primer and the UDEC395 murine kappa gene constant region primer.

PolyA mRNA was isolated from hybridoma 5G1.1. The acid/guanidinium thiocyanate procedure (Chomczynski and Sacchi, supra) was used to isolate total RNA, and was followed by oligo(dT)-cellulose chromatography of 1 mg of total RNA. For first strand cDNA synthesis, one microliter of the 25 microliters of oligo(dT)-cellulose eluate (containing approximately 2 micrograms of purified 5G1.1 mRNA) was denatured at 65° C. for 5 min., chilled on ice, and incubated in extension buffer (10 mM Tris pH 8.3, 50 mM KCl, 1 mM dithiothreitol, 240 μM each dNTP) containing 100 nM UDEC395 (SEQ ID NO:6) and 25 units AMV reverse transcriptase (Seikagaku America, Rockville, Md.) at 42° C. for one hour. Five microliters of the completed first strand reaction was subjected to PCR amplification using amplification buffer supplemented with 2.5 units AMPLITAQ DNA polymerase (Perkin Elmer, Foster City, Calif.) and 500 nM each of primer UDEC690 (SEQ ID NO:5) and UDEC395 (SEQ ID NO:6). Amplification was performed using 30 cycles each consisting of 1 minute at 95° C., 1 minute at 52° C., and 1 minute at 72° C., followed by a single ten minute incubation at 72° C.

The resulting PCR product was purified using GENECLEAN according to the manufacturer's directions (Bio 101, La Jolla, Calif.), digested with Sse8387 I and Hind III, gel purified, and ligated into the vector Bluescript II SK$^+$ (Stratagene, La Jolla, Calif.). Ligated plasmids were transformed into the bacterial strain DH10B by electroporation.

Plasmid DNA was purified from cultures of transformed bacteria by conventional methods including column chromatography using a QUIAGEN-TIP-500 column according to the manufacturer's directions (Quiagen, Chatsworth, Calif.) and sequenced by the Sanger dideoxy chain termination method using SEQUENASE enzyme (U.S. Biochemical, Cleveland, Ohio). Clones obtained from a second independent PCR reaction verified that no mutations were introduced during the amplification process. The resulting plasmid containing the cloned variable region was designated SK (+) 690/395. This light chain encoding insert in this plasmid coded for both the N-terminal and internal light chain sequences determined by amino acid sequencing of 5G1.1, as described above.

Example 11

Construction and Expression of Recombinant mAbs

Recombinant DNA constructions encoding the recombinant mAbs comprising the 5G1.1 CDRs are prepared by conventional recombinant DNA methods including restriction fragment subcloning and overlapping PCR procedures. The resulting recombinant mAb-encoding DNAs include:

(1) one encoding a non-humanized (murine) scFv designated 5G1.1M1scFv (SEQ ID NO:7), wherein CDR L1 is amino acid residues 28–34 of SEQ ID NO:7, CDR L2 is amino acid residues 52–54 of SEQ ID NO:7, CDR L3 is amino acid residues 93–98 of SEQ ID NO:7, CDR H1 is amino acid residues 156–159 of SEQ ID NO:7, CDR H2 is amino acid residues 179–183 of SEQ ID NO:7, and CDR H3 is amino acid residues 226–236 of SEQ ID NO:7;

(2) one encoding a humanized (CDR grafted) scFv designated 5G1.1 scFv CB (SEQ ID NO:8), wherein CDR L1 is amino acid residues 26–36 of SEQ ID NO:8, CDR L2 is amino acid residues 52–58 of SEQ ID NO:8, CDR L3 is amino acid residues 91–99 of SEQ ID NO:8, CDR H1 is amino acid residues 152–161 of SEQ ID NO:8, CDR H2 is amino acid residues 176–192 of SEQ ID NO:8, H3 is amino acid residues 225–237 of SEQ ID NO:8;

(3) one encoding a chimeric light chain (which can form the light chain portion of an Fab) designated 5G1.1M1 VL HuK (SEQ ID NO:9);

(4) one encoding a chimeric Fd (the heavy chain portion of an Fab) designated 5G1.1M1 VH HuG1 (SEQ ID NO:10);

(5) one encoding a humanized (CDR grafted and framework sequence altered) Fd designated 5G1.1 VH+IGHRL (SEQ ID NO:11), wherein CDR H1 is amino acid residues 26–35 of SEQ ID NO:11, CDR H2 is amino acid residues 50–60 of SEQ ID NO:11, and CDR H3 is amino acid residues 99–111 of SEQ ID NO:11;

(6) one encoding a humanized (CDR grafted, not framework altered) Fd designated 5G1.1 VH+IGHRLC (SEQ ID NO:12), CDR H1 is amino acid residues 26–35 of SEQ ID NO:12, CDR H2 is amino acid residues 50–66 of SEQ ID NO:12, and CDR H3 is amino acid residues 99–111 of SEQ ID NO:12;

(7) one encoding a humanized (CDR grafted and framework sequence altered) light chain designated 5G1.1 VL+KLV56 (SEQ ID NO:13), wherein CDR L1 is amino acid residues 26–36 of SEQ ID NO:13, CDR L2 is amino acid residues 52–58 of SEQ ID NO:13, and CDR L3 is amino acid residues 91–99 of SEQ ID NO:13;

(8) one encoding a humanized (CDR grafted, not framework altered) light chain designated 5G1.1 VL+KLV56B (SEQ ID NO:14), wherein CDR L1 is amino acid residues 26–36 of SEQ ID NO:14, CDR L2 is amino acid residues 52–58 of SEQ ID NO:14, and CDR L3 is amino acid residues 91–99 of SEQ ID NO:14;

(9) one encoding a humanized (CDR grafted, not framework altered) light chain designated 5G1.1 VL+012 (SEQ ID NO:15), wherein CDR L1 is amino acid residues 24–34 of SEQ ID NO:15, CDR L2 is amino acid residues 50–56 of SEQ ID NO:15, and CDR L3 is amino acid residues 89–97 of SEQ ID NO:15; and

(10) one encoding a humanized (CDR grafted, not framework altered) Fd designated 5G1.1 VH+IGHRLD (SEQ ID NO:16), wherein CDR H1 is amino acid residues 26–35 of SEQ ID NO:16, CDR H2 is amino acid residues 50–60 of SEQ ID NO:16, and CDR H3 is amino acid residues 99–111 of SEQ ID NO:16.

(11) one encoding a humanized (CDR grafted) scFv designated 5G1.1 scFv DO12 (SEQ ID NO:17), wherein CDR L1 is amino acid residues 26–36 of SEQ ID NO:17, CDR L2 is amino acid residues 52–58 of SEQ ID NO:17, CDR L3 is amino acid residues 91–99 of SEQ ID NO:17, CDR H1 is amino acid residues 152–161 of SEQ ID NO:17, CDR H2 is amino acid residues 176–186 of SEQ ID NO:17, and CDR H3 is amino acid residues 225–237 of SEQ ID NO:17;

(12) one encoding a humanized (CDR grafted and framework sequence altered) scFv designated 5G1.1 scFv CO12 (SEQ ID NO:20), wherein CDR L1 is amino acid residues 26–36 of SEQ ID NO:20, CDR L2 is amino acid residues 52–58 of SEQ ID NO:20, CDR L3 is amino acid residues 91–99 of SEQ ID NO:20, CDR H1 is amino acid residues 152–161 of SEQ ID NO:20, CDR H2 is amino acid residues 176–192 of SEQ ID NO:20, H3 is amino acid residues 225–237 of SEQ ID NO:20;

(13) one encoding a humanized (CDR grafted) scFv designated 5G1.1 scFv DO12B (SEQ ID NO:21), wherein CDR L1 is amino acid residues 26–36 of SEQ ID NO:21, CDR L2 is amino acid residues 52–58 of SEQ ID NO:21, CDR L3 is amino acid residues 91–99 of SEQ ID NO:21, CDR H1 is amino acid residues 152–161 of SEQ ID NO:21, CDR H2 is amino acid residues 176–192 of SEQ ID NO:21, H3 is amino acid residues 225–237 of SEQ ID NO:21;

(14) one encoding a humanized (CDR grafted) scFv designated 5G1.1 scFv DO12C (SEQ ID NO:22), wherein CDR L1 is amino acid residues 26–36 of SEQ ID NO:22, CDR L2 is amino acid residues 52–58 of SEQ ID NO:22, CDR L3 is amino acid residues 91–99 of SEQ ID NO:22, CDR H1 is amino acid residues 152–161 of SEQ ID NO:22, CDR H2 is amino acid residues 176–192 of SEQ ID NO:22, H3 is amino acid residues 225–237 of SEQ ID NO:22;

(15) one encoding a humanized (CDR grafted) scFv designated 5G1.1 scFv DO12D (SEQ ID NO:23), wherein CDR L1 is amino acid residues 26–36 of SEQ ID NO:23, CDR L2 is amino acid residues 52–58 of SEQ ID NO:23, CDR L3 is amino acid residues 91–99 of SEQ ID NO:23, CDR H1 is amino acid residues 152–161 of SEQ ID NO:23, CDR H2 is amino acid residues 176–192 of SEQ ID NO:23, H3 is amino acid residues 225–237 of SEQ ID NO:23;

(16) one encoding a humanized (CDR grafted and framework sequence altered) scFv designated 5G1.1 scFv CO13 (SEQ ID NO:24), wherein CDR L1 is amino acid residues 26–36 of SEQ ID NO:24, CDR L2 is amino acid residues 52–58 of SEQ ID NO:24, CDR L3 is amino acid residues 91–99 of SEQ ID NO:24, CDR H1 is amino acid residues 152–161 of SEQ ID NO:24, CDR H2 is amino acid residues 176–192 of SEQ ID NO:24, H3 is amino acid residues 225–237 of SEQ ID NO:24;

(17) one encoding a humanized (CDR grafted and framework sequence altered) scFv designated 5G1.1 scFv C014 (SEQ ID NO:25), wherein CDR L1 is amino acid residues 26–36 of SEQ ID NO:25, CDR L2 is amino acid residues 52–58 of SEQ ID NO:25, CDR L3 is amino acid residues 91–99 of SEQ ID NO:25, CDR H1 is amino acid residues 152–161 of SEQ ID NO:25, CDR H2 is amino acid residues 176–192 of SEQ ID NO:25, H3 is amino acid residues 225–237 of SEQ ID NO:25;

(18) one encoding a humanized (CDR grafted and framework sequence altered) scFv designated 5G1.1 scFv CO15 (SEQ ID NO:26), wherein CDR L1 is amino acid residues 26–36 of SEQ ID NO:26, CDR L2 is amino acid residues 52–58 of SEQ ID NO:26, CDR L3 is amino acid residues 91–99 of SEQ ID NO:26, CDR H1 is amino acid residues 152–161 of SEQ ID NO:26, CDR H2 is amino acid residues 176–192 of SEQ ID NO:26, H3 is amino acid residues 225–237 of SEQ ID NO:26;

In accordance with the invention, one each of the various L1, L2 and L3 CDRs discussed in (1) to (18) above may be combined with any of the other light chain CDRs so as to make a set of 3 light chain CDRs comprising one L1, one L2, and one L3 CDR, as part of a recombinant antibody or synthetic peptide antibody (i.e., a synthetic peptide with the sequence of a recombinant peptide of the invention). Furthermore, the framework regions (i.e., the regions not included in the CDRs as described for each) of each of (1) to (18) above may be interchanged with homologous framework regions of the other recombinant antibody molecules of (1) to (18) to produce other antibodies of the invention.

In accordance with the invention, one each of the various H1, H2 and H3 CDRs discussed in (1) to (18) above may be combined with any of the other light chain CDRs so as to make a set of 3 light chain CDRs comprising one H1, one H2, and one H3 CDR, as part of a recombinant antibody or synthetic peptide antibody (i.e., a synthetic peptide with the sequence of a recombinant peptide of the invention).

In accordance with the invention, matched pairs of the variable regions (e.g., a VL and a VH region) of the various antibody molecules, Fds, and light chains described above may be combined with constant region domains by recombinant DNA or other methods known in the art to form full length antibodies of the invention. Particularly preferred constant regions for this purpose are IgG constant regions, which may be unaltered, or constructed of a mixture of constant domains from IgGs of various subtypes, e.g., IgG1 and IgG 4.

Matched pairs of the Fd and light chain encoding DNAs described immediately above—i.e. (3) and (4), (5) and (7), (6) and (8), and (6) and (9)—were subcloned together into the APEX-3P vector, essentially as described below in Example 15 for N19/8. The scFv constructs of (1) and (2) were subcloned into pET Trc SO5/NI using conventional techniques.

Plasmids so obtained were introduced by into the bacterial strain ME2 (pET plasmids) by conventional electroporation, or into human 293 EBNA cells (APEX plasmids) by lipofection using 2–3 microliters of TRANSFECTAM reagent (Promega, Madison, Wis.) per microgram of DNA according to the manufacturer's directions. Bacterial strains ME1 and ME2 are derivatives of *Escherichia coli* strain W3110 (ATCC designation 27325) prepared as follows.

Preparation of W3110 Derivatives ME1 and ME2

The non-humanized, non-chimeric murine 5G1.1-scFv "m5G1.1-scFv"—made up of light chain (3) and Fd (4)— was expressed in a derivative of *E. coli* K12 strain W3110. This derivative was prepared by inactivating an uncharacterized gene to provide protection against infections by a lytic bacteriophage. *E. coli* strain W3110 is a particularly preferred strain because it is fully characterized and is commonly used for recombinant DNA product fermentations.

A single colony of *E. coli* strain W3110 was grown overnight in L medium at 30° C. The cells were collected by centrifugation and resuspended in 10 mM $MgSO_4$. A total of 0.1 ml of the culture was added to 2.5 ml 0.7% L soft agar at 45° C. and quickly poured on an L plate. Fifty microliter aliquots of a plaque purified phage lysate, undiluted, diluted $10^{-2}$ and diluted $10^{-4}$, were spotted onto the agar surface. Phage lysates had previously been filtered through 0.45 µm membranes and stored in sterile tubes with a drop of chloroform at 4° C. The spots were allowed to dry on the soft agar surface and incubated overnight at 37° C.

The next day L plates were spread with $10^9$ phage PFU and allowed to dry. Using a sterile, flat toothpick, cells from isolated colonies growing in the zones of phage lysis on the spot plates were streaked for single colonies on the plates spread with $10^9$ phage PFU and incubated overnight at 37° C. Single colonies were rechecked for phage resistance by cross-streaking after single colony purification. The cross streak test for phage sensitivity was performed as follows. Fifty µl of phage ($10^8$ pfu/ml) was spread in a vertical line in the left hand portion of the plate using a Pasteur pipette. Additional phage were tested parallel to the first and to the right. The plate was allowed to dry, and strains to be checked for sensitivity or resistance were spread perpendicular to and across the lines of all phages in a single swath from the left to the right. Resistant strains grow in the area of the phage streaks while sensitive strains lyse.

The phage resistant mutant strain ME1 was tested for phage production after overnight growth in L medium and treatment with the DNA damaging agent, mitomycin C. The strain failed to produce viable phage utilizing a standard plaque assay and *E. coli* W3110 as the phage sensitive indicator strain. These results suggest that strain ME1 does not harbor a resident prophage.

Strain ME2 was constructed by site specific integration of the lambdaDE3 prophage (Studier et al. 1990, Meth. Enzymol. 185:60–89) into the ME1 chromosome. Expression of the T7 RNA polymerase, directed by the prophage, allows expression of target genes cloned into pET vectors (Studier et al., supra) under the control of the T7 promoter in the lysogenized host. Lysogenization was accomplished in a three way infection with lambdaDE3, the lambda helper phage, lambdaB10 and the selection phage, lambdaB482 (Studier et al., supra).

lambdaDE3 (imm2l) was constructed by Studier and colleagues (1990, Meth. Enzymol. 185:60–89) by inserting the T7 RNA polymerase gene behind the *E. coli* lacUV5 promoter into the BamHI cloning site of lambdaD69 (imm21). Since cloning into the BamHI site of lambdaD69 interrupts the integrase gene, lambdaDE3 cannot integrate or excise from the chromosome by itself. The helper phage lambdaB10 provides the integrase function that lambdaDE3 lacks but cannot form a lysogen by itself. The selection phage, lambdaB482, lyses any lambdaDE3 host range mutants that otherwise would be among the surviving cells, but it can neither integrate into susceptible cells nor lyse lambdaDE3 lysogens since it has the same immunity region as lambdaDE3 (imm21).

Lysoaenization Protocol

Strain ME1 was grown in L medium supplemented with 0.2% maltose and 10 MM $MgSO_4$ at 37° C. to a density of approximately $10^8$ cells/ml. One µl of ME1 cells were incubated with $2 \times 10^8$ plaque forming units (pfu) of lambdaDE3 and $10^8$ pfu of lambdaB10 and lambdaB482. The host/phage mixture was incubated at 37° C. for 20 min to allow phage adsorption to ME1 cells. Several dilutions of the cell/phage suspension were spread on L plates to produce plates containing approximately 30–200 candidate lysogens as isolated colonies. The plates were inverted and incubated at 37° C. overnight. Several isolated colonies were screened for the acquisition of the lambdaDE3 prophage as described below.

Verification of lambdaDE3 Lysogens lambdaDE3 lysogen candidates were tested for their ability to support the growth of the T7 phage 4107, a T7 phage deletion mutant that is completely defective unless active T7

RNA polymerase is provided in trans. Only lambdaDE3 lysogens will support the normal growth of the phage in the presence of IPTG (isopropyl-beta-thiogalactopyranoside). The T7 phage produces very large plaques on lambdaDE3 lysogens in the presence of IPTG, while very small plaques are observed in the absence of inducer. The size of the plaque in the absence of IPTG is an indication of the basal level of T7 RNA polymerase expression in the lysogen. Putative lambdaDE3 lysogens were grown in L broth supplemented with 0.2 % maltose and 10 mM MgSO$_4$ at 37° C. to a cell density of approximately 10$^8$ cells/ml. A total of 0.5 ml of cells was centrifuged and the pellet was resuspended in 0.2 ml of a T7 phage lysate containing 2×10$^4$ pfu. The phage was allowed to adsorb for 30 min at 37° C. One-half of suspension (0.1 ml) was added to 3.0 ml of molten top agarose at 47° C. and poured onto L plates. The remaining aliquot of cell/phage suspension was poured onto an L plate supplemented with 0.4 mM IPTG to check for induction of T7 RNA polymerase. The plates were inverted and incubated at 37° C. overnight.

Strains were also tested for the presence of the lambdaDE3 lysogen by demonstrating that each strain was resistant to infection by the phage lambdaB482, which is in the same immunity group (imm21), by the cross streak method described above. A lysogen was chosen with a low basal expression level for protein production from pET vectors. The resulting strain, designated ME2, is phage resistant and overexpresses T7 RNA polymerase in the presence of IPTG.

Purification of Humanized 5G1.1-scFv from *E. coli*

The humanized 5G1.1-scFv (h5G1.1-scFv) cDNA construct was cloned into the bacterial expression plasmid pET Trc SO5/NI (SEQ ID NO:18) and transformed into *E. coli* strain ME1. The resulting strain expressing h5G1.1 scFv was grown at 37° C. in 2 liter Applikon glass vessel fermentors containing Terrific Broth (1.2 % (w/v) bacto-tryptone, 2.4% (w/v) bacto-yeast extract, 0.4% (v/v) glycerol, 90 mM KPO$_4$, pH 7.0) supplemented with 100 µg/ml ampicillin. The production of recombinant scFv was induced by the addition of 1 mM IPTG when the O.D.$_{550}$ of the culture reached 10. After an additional 3 h incubation at 37° C., the cells were harvested by centrifugation and the cell pellets stored at −80° C.

Cells were resuspended in 1 mM EDTA, pH 5.0 at 10 ml per gram weight and lysed by a single pass through a microfluidizer (Model M110T, Microfluidics Corp., Newton, Mass.). After centrifugation at 17,500×g for 15 min, the resulting inclusion body pellet was washed by resuspension in 20 mM Tris-HCl pH 8.0, 1 mM EDTA, 100 mM NaCl, 0.15% (w/v) deoxycholate at 10 ml per gram inclusion body using a Tekmar POLYTRON. The inclusion bodies were again pelleted by centrifugation at 17,500×g for 15 min and resuspended in 20 mM Tris-HCl pH 9.0, 8 M urea at 10 ml per g. After stirring for 1 h, the sample was centrifuged at 14,000×g for 30 min to pellet remaining insoluble material.

The extract supernatant was diluted 10-fold with 20 mM Tris-HCL pH 9.0, 7 M urea, 50 µM cupric sulfate and allowed to stir for at least 16 hours at 4° C. to refold the scFv. After addition of BIOCRYL BPA-1000 (TosoHaas, Montgomeryville, Pa.) as a flocculating agent at 3 µl per ml, the sample was centrifuged at 15,000×g for 10 minutes to remove insoluble material. The refolding mixture was exchanged into 20 mM Tris, pH 9.0, 1 mM EDTA by diafiltration and concentrated by ultrafiltration using a stirred cell fitted with a YM10 membrane (Amicon, Beverly, Mass.).

In subsequent experiments, other refolding conditions were tested. Thawed bacterial cells were resuspended with a POLYTRON homogenizer in 1 mM EDTA at 2.5 mL per gram of cells, passed through the MICROFLUIDIZER at 18,000 psi, and centrifuged at 10,000 RPM for 15 min in a Beckman JA-10 rotor, the resulting pellet was washed by resuspension in 20 mM Tris-HCl pH 8.0, 1 mM EDTA, 100 mM NaCl, 0.15% (w/v) deoxycholate at 10 ml per gram inclusion body using a Tekmar POLYTRON. The inclusion bodies were again pelleted by centrifugation. The pellet from this centrifugation was resuspended with a POLYTRON homogenizer in 8M urea, 20 mM Tris pH9 at 10 mL per gram of pellet. After stirring for 1 hour at 4 degrees C., the resuspended pellet was diluted with 9 volumes of 7M urea, 20 mM Tris pH9. Cupric sulfate was then added to various final concentrations (0, 5, 10, 20, 25, 30, 40, 50, 100, 150, and 200 µM) before incubation overnight at 4 degrees C. with stirring. The use of 5 µM copper was found to give the highest levels of refolding of the humanized 5G1.1-scFv as assessed by analytical HPLC.

In the initial experiments, the properly refolded scFv was then separated from aggregated material and contaminating proteins by anion exchange chromatography using Q SEPHAROSE FAST FLOW (Pharmacia, Piscataway, N.J.). Bound scFv was eluted with 20 mM Tris-HCL pH 9.0, 1 mM EDTA containing a linear NaCl gradient (0 to 0.5 M). The fractions containing the scFv were combined, concentrated by ultrafiltration using a stirred cell fitted with a YM10 membrane, and applied to a SEPHACRYL S200 HR 26/100 gel filtration column (Pharmacia) equilibrated in 20 mM Tris-HCL pH 9.0, 1 mM EDTA, 150 mM NaCl. Fractions containing the scFv were combined, exchanged into phosphate-buffered saline by diafiltration, concentrated by ultrafiltration, filtered through a 0.22 µm MILLEX-GV filter (Millipore, Bedford, Mass.), and stored at 4° C.

Subsequent experiments have indicated that cation exchange chromatography (e.g., using POROS HS resin—PerSeptive Biosystems, Cambridge, Mass.) should give better yields than the Q Sepharose Fast Flow anion exchange chromatography step described in the preceding paragraph. In addition, it would be preferable to carry out the final gel filtration chromatography in a buffer that is more pharmaceutically acceptable than the Tris buffer described. A buffer such as PBS would be preferred if it does not interfere with the efficacy of the gel filtration chromatographic separation. This would reduce any trace amounts of Tris remaining in the preparation after diafiltration, and might eliminate the need for the diafiltration step.

Purification of m5G1.1-scFv from *E. coli*

Frozen bacterial cell paste was thawed and resuspended in 2.5 ml of 1 MM EDTA (pH 5) per gram of cell paste. This suspension of cells was lysed by passage through a MICROFLUIDIZER (Microfluidics) with the interaction chamber in line and a backpressure of approximately 18000 psi. The cell lysate was then centrifuged at 10,000 rpm in a JA-10 centrifuge rotor at 4° C. for 15 min. The supernatant was decanted and discarded.

The pellet was resuspended in 10 ml of 20 mM Tris, pH 8.0, 100 mM NaCl, 0.15% sodium deoxycholate per gram of pellet. This suspension was centrifuged as above for 10 min. Again the supernatant was decanted and discarded. This detergent washed pellet was then resuspended in 10 ml of 8 M urea, 20 mM Tris-HCl, pH 9 (1 mM EDTA may also be added to this buffer, but has the effect of increasing the time required to achieve a particular level of refolding). The suspension was stirred at 4° C. for 1 hr. and was then diluted 10 fold with 7 M urea, 20 mM Tris-HCl, pH 9 and stirred at 4° C. CUSO$_4$ was then added to a final concentration of 50 µM and stirring was continued overnight at 4° C.

The majority of contaminating proteins (including incorrectly folded versions of m5G1.1 scFv) were then removed by precipitation by diluting (with stirring) the refolded sample five fold with buffer such that the final concentrations after dilution were 1.4 M urea, 25 mM NaCl, 1 mM EDTA, and 20 mM sodium acetate at 4° C. The pH of the dilution buffer when prepared at room temperature was pH 5.0. Prior to dilution the pH of the dilution buffer is determined at 4° C. After the dilution the pH of the sample was greater than pH 5.5. The pH of the sample was then adjusted with 6. N HCl to the initial pH 5.0 of the buffer at 4° C. The solution immediately became cloudy and it was left stirring at 4–8° C. for 0.5 to 24 hours.

The precipitate was removed by filtering the sample through a 300 kDa cut-off ultrafiltration membrane (Millipore Corporation, Bedford, Mass.). The permeate was collected and concentrated 5 fold using a 10 kDa cutoff ultrafiltration membrane (Millipore). This concentrated retentate was then diluted 2 fold with 20 mM sodium acetate, 1 mM EDTA, pH 5.0 in order to lower the NaCl concentration to 12.5 mM.

The diluted retentate was then loaded at 4° C. onto a SP SEPHAROSE FF column (Pharmacia) equilibrated in 0.7 M urea, 1 mM EDTA, 10 mM NaCl, 20 mM sodium acetate, pH 5.0, at a linear flowrate of 5 cm/min. Bed height was equal to or greater than 3.5 cm. Following loading the column was washed with 40 column volumes (CV) of equilibration buffer. The column was then washed with 20 CV of 20 mM sodium acetate, pH 5.0, 1 mM EDTA. The bound scFv was then eluted using 20 mM sodium citrate, pH 5.8, 1 mM EDTA. A single peak was collected in approximately 4 column volumes.

The SP SEPHAROSE eluate was then adjusted to 20 mM Tris-HCL by addition of 1 M Tris-HCL, pH 8. The pH of the sample was adjusted to 8.0 by addition of 1 N NaOH. This sample was loaded onto a Q SEPHAROSE FF column (Pharmacia) equilibrated in 20 mM Tris-HCL, pH 8.0, 1 mM EDTA at room temperature at a flowrate of 5 cm/min. The flow through fraction containing the scFv was collected.

The Q SEPHAROSE flow through fraction was then adjusted to 150 mM NaCl and concentrated to 10 mg of scFv per ml using a 10 kDa cutoff ultrafiltration membrane. This concentrated sample was then loaded onto a SEPHACRYL S200 column equilibrated in phosphate buffered saline, pH 7.4 and eluted at 0.4 cm/min. The fractions were analyzed by SDS-PAGE and silver staining. Peak fractions were combined after discarding the front and back shoulder fractions that contained the majority of contaminants.

Example 12

Functional Analysis of the m5G1.1 scFv

Titration of the m5G1.1 scFv in hemolytic assays revealed that the m5G1.1 scFv inhibited human complement-mediated lysis in a dose dependent fashion (FIG. 13). Direct comparison of the efficacy of the m5G1.1 scFv to the 5G1.1 mAb and Fab demonstrated that the m5G1.1 scFv completely blocked C5b-9-mediated hemolysis in 20% human serum at 0.15 µM while the 5G1.1 mAb and Fab blocked at 0.06–0.08 µM. Analysis of C5a generation in these assays revealed similar results in that the 5G1.1 scfv completely blocked C5a generation at 0.15 µM while the 5G1.1 mAb and Fab blocked at 0.06–0.08 µM (FIG. 14). Taken together these experiments indicated that unlike N19/8, which lost half of its effectiveness at blocking C5a generation upon being engineered as an scFv (SEQ ID NO:19), the 5G1.1 murine scFv retained the capacity to block the generation of both C5a and C5b-9.

Additionally, these data demonstrate that the m5G1.1 scFv retained similar activity to that of the parent molecule (the native murine 5G1.1 mAb) in that the molar concentration of 5G1.1 murine scFv required to completely block C5a and C5b-9 (0.15 µM) was within two-fold of that required for the 5G1.1 mAb and Fab (0.06–0.08 µM).

In order to determine whether the m5G1.1 scFv retained the capacity to block the activation of complement in the ex vivo model of cardiopulmonary bypass, 4.5 mg of the purified bacterially produced 5G1.1 murine scFv was added to the CPB circuit and complement activation was monitored. In control experiments, both C3a and C5b-9 levels increased throughout the time course of the experiment. In a single experiment, addition of 4.5 mg of the m5G1.1 scFv to the CPB circuit had no effect on the generation of C3a (FIG. 15). Conversely, complement hemolytic activity as well as the generation of sC5b-9 was completely blocked in this experiment (FIG. 16 and FIG. 17).

Example 13

Characterization of the Epitope Recognized by 5G1.1

Tryptic digestion: Twenty micrograms of purified human C5 (Advanced Technologies, San Diego, Calif.) was subjected to enzymatic digestion with 1 µg of TPCK-treated trypsin (Worthington Biochemical Corp., Freehold, N.J.). The digestion was allowed to continue for 3 minutes, after which time it was stopped by the addition of 20 µg soy bean trypsin inhibitor (Worthington). The reaction was then denatured and reduced by the addition of protein sample buffer and immediately boiled for 5 min. The digested fragments were size fractionated through a SDS-PAGE on a 12 % gel. The gel was then electroblotted in transfer buffer (20% (v/v) methanol, 25 mM Tris-base pH 8.0, and 192 mM glycine) to nitrocellulose (Bio-Rad Laboratories, Hercules, Calif.) and subjected to ECL western blot analysis using either 5G1.1 or a C5a specific monoclonal antibody (G25/2, obtained from Dr. Otto Götze, Department of Immunology, University of Göttingen, Germany).

The filters were incubated twice for 30 minutes each in blocking solution (500 mM NaCl, 5 mM Tris p-H 7.4, 10% (v/v) nonfat dry milk, and 0.2% (v/v) TWEEN-20). The filters were then changed to fresh blocking solution (20 ml) containing the primary antibody and incubated for 40 minutes on a rocking platform. The filters were rinsed briefly with washing solution (500 mM NaCl, 35 mM Tris pH7.4, 0.1% SDS, 1% NP40, and 0.5% deoxycholic acid) to remove any milk, and then fresh wash solution was added and incubated for two 20 minute intervals on an orbiting shaker. The filters were rinsed briefly with 10 to 20 mls of secondary antibody solution (500 mM NaCl, 5 mM Tris pH 7.4, 10% (v/v) Nonfat dry milk, 0.2% (v/v) TWEEN-20, and 1% NP-40) and then incubated with fresh secondary antibody solution containing a 1:2000 dilution of HRP conjugated goat anti-mouse for 20 minutes on a rocking platform. The filters were then washed as described above, incubated in ECL reagent (Amersham Corp., Arlington Heights, Ill.) for 1 minute and then exposed to ECL HYPERFILM (Amersham).

Acid Hydrolysis: Twenty micrograms of purified human C5 (Advanced Technologies) was subjected to hydrolysis in 1N acetic acid. The 20 µg of human C5 (1 µg/µl) was added to 20 µl of 2N acetic acid and incubated for 10 min at 100° C. The sample was denatured and reduced with protein sample buffer, also at 100° C., for 5 minutes. The acid was neutralized by dropwise addition of a saturated tris base solution until the sample turned blue. The cleavage products were then size fractionated by SDS-PAGE and western blotted as described above. For N-terminal sequencing, the gel fractionated acid hydrolysate was transferred to PVDF membrane. N-terminal sequence was obtained by excising the 46 kDa acid hydrolysis fragment band from a PVDF membrane and subjecting it to amino acid sequence analysis as discussed above in Example 10.

Deglycosylation: Reduced and denatured acid hydrolyzed or tryptic fragments of human C5 were subjected to deglycosylation with N-Glycosidase F (Peptide-N-Glycosidase F, Boehringer Mannheim Corp., Indianapolis, Ind.) according to the manufacture's directions.

Results: Acid hydrolysis of human C5 yielded a fragment with an apparent molecular weight by SDS-PAGE of 46 kDa that was immunoreactive for both the anti-C5a mAb G25/2 and the anti-C5 alpha chain mAb 5G1.1. Western blots probed with both antibodies simultaneously, as well as silver stain SDS-PAGE analysis, confirmed the presence of a single 46 kDa fragment that was immunoreactive with both antibodies. The presence of a single immunoreactive fragment containing binding sites for both 5G1.1 and G25/2 strongly suggested that the 5G1.1 epitope was contained within approximately the first 46 kDa of the N-terminus of the alpha chain of C5.

As discussed above in the description of the complement system under the heading "Background Physiology & Pathology," a compound (e.g., an antibody) that binds to a site at or immediately adjacent to the C5a cleavage site would have the potential to act as a terminal complement inhibitor. The potential inhibitory activity of antibodies binding to this site led to the expectation that the C5 alpha chain-binding 5G1.1 antibody would bind to an epitope at or near the C5a cleavage site. The finding that 5G1.1 bound to the 46 kDa acid hydrolysis fragment of C5 lent support to this expectation.

Western blot analysis of the tryptic digestion products identified one proteolytic fragment migrating at approximately 27 kDa that was immunoreactive with 5G1.1. Likewise, one immunoreactive proteolytic fragment migrating at approximately 29 kDa was observed following western blot analysis with the anti-C5a mAb G25/2. Experiments in which a blot was simultaneously probed with both 5G1.1 and G25/2 demonstrated that each band was distinct and that their apparent differential mobility was not a gel anomaly. This was surprising, because the 5G1.1 mAb was thought likely to bind to the C5 convertase cleavage site. 5G1.1 was thus expected to be immunoreactive with any fragment of C5 of over 12 kDa that exhibited immunoreactivity with G25/2. Such a fragment would contain enough of the extreme amino terminus of the C5 alpha chain to bind specifically to the anti-C5a mAb, and enough beyond that to encompass a region including and extending beyond the C5 convertase cleavage site.

The immunoreactivity of G25/2 with the 29 kDa fragment indicated that that fragment contains the N-terminal region of the alpha chain of C5 that is cleaved off to yield C5a. Furthermore, because 5G1.1 was not immunoreactive with this band, the 5G1.1 epitope was not likely to be contained within approximately the first 29 kDa of the N-terminus of the alpha chain of C5, and therefore could not be located near the C5 convertase cleavage site.

These tryptic digestion and acid hydrolysis mapping data suggested that the 5G1.1 epitope was contained within a region starting about 29 kDa (including post-translational modifications) from the N-terminus of the alpha chain of C5 and continuing 17 kDa in a C-terminal direction, i.e., ending 46 kDa from the N-terminus, a surprising finding in view of the expectation, discussed above, that the antibody would bind at or immediately adjacent to the point at which C5a is cleaved off of the C5 alpha chain, i.e., at or immediately adjacent to amino acid residue 733 of SEQ ID NO:2.

Post-translational modifications can alter the mobility of proteins during SDS-PAGE electrophoresis. One such modification is the addition of carbohydrate via N-linked glycosylation. As discussed above under the heading "Background Physiology & Pathology", C5 is glycosylated, as is C5a. C5a is glycosylated at an asparagine residue corresponding to amino acid number 723 of the full length pro-C5 precursor of human C5 (SEQ ID NO:2).

Computer analysis of the human C5 alpha chain suggests potential N-linked glycosylation sites at positions corresponding to amino acid numbers 893, 1097, and 1612 of SEQ ID NO:2. In order to determine the contribution of carbohydrate to the electrophoretic mobility of both the tryptic and acid fragments, enzymatic deglycosylation of the fragments was performed and followed by western blot analysis. It was determined that each tryptic fragment lost approximately 3 kDa in apparent molecular weight while the acid fragment lost approximately 6 kDa.

This result was interpreted as indicating that the tryptic fragments were each glycosylated at a single site and that the 46 kDa acid fragment was glycosylated at two sites (one of which was the known glycosylation site in C5a referred to above). The diminished mobility observed following deglycosylation agrees with the computed prediction of a second N-linked glycosylation site within the first 233 amino acids of the C5 alpha chain.

N-terminal sequence analysis determined that the first four amino acids of the 46 kDa fragment generated by 1N acetic acid treatment was Thr Leu Gln Lys. This sequence is found only once in the full length human pro-C5 precursor molecule—at a position corresponding to amino acids 660 through 663 of SEQ ID NO:2. This four amino acid sequence also corresponds to the sequence of the amino-terminus of the alpha chain of human C5 and, thus to the amino-terminus of human C5a.

In order to more precisely map the binding site of 5G1.1, overlapping peptide analysis was performed. The sequence predicted to be contained within the 17 kDa section of human C5 described above (SEQ ID NO:2; amino acids 893 through 1019) together with an extension of 43 amino acids towards the N-terminus and 30 amino acids towards the C-terminus (a total of 200 amino acids) was synthesized as a series of 88 overlapping peptides by solid phase synthesis on polypropylene filters (Research Genetics Inc., Huntsville, Ala.).

The 43 and 30 amino acid extensions were added to allow for possible inaccuracies in the prediction of the span of this 17 kDa region. Such inaccuracies are likely due to the uncertainty of the specific extent of glycosylation of each of the various regions of C5a, as well as to the aberrant gel mobility that is commonly seen when highly charged polypeptides (such as the 5G46k fragment and the 5G27k fragment) are analyzed by SDS-PAGE. As discussed above in the Summary of the Invention, a 200 amino acid peptide corresponding to the region covered by these overlapping peptides is referred to herein as the "5G200aa" peptide.

Because of the expectation that the 5G1.1 antibody would bind at the C5a cleavage site, an additional set of 8 overlapping peptides was synthesized that spanned a 30 amino acid section spanning the C5a cleavage site (amino acids 725 through 754 of SEQ ID NO:2). A peptide having the sequence of this 30 amino acid section is referred to herein as the "cleavage site peptide". A 325aa peptide spanning amino acid residues 725–1049 of SEQ ID NO:2 (this peptide spans the region covered by the cleavage site peptide and the 5G200aa peptide) is referred to herein as the "5G325aa" peptide.

These filters were probed with 5G1.1 as described above for ECL western blot analysis, and a set of 4 overlapping peptides spanning the region corresponding to amino acid residues 3–19 of the KSSKC peptide (SEQ ID NO:1) each gave a positive signal indicative of monoclonal antibody binding, while peptides corresponding to the C5a cleavage site did not bind to the 5G1.1 antibody.

Example 14

C3/C4 Binding Assay

C3 and C4 are both key components of classical C5 convertase, and C3 is also a key component of alternative C5 convertase. These C5 convertases are required for the conversion of C5 to active C5a and C5b. The ability to block C5 binding to C3 and C4 is thus a desirable property for an antibody to be used in treatment of complement mediated diseases in accordance with the present invention.

96 well microtiter plates were coated with 501 μ/well, 10 μg/ml of either purified human C3 or C4 (Quidel) for 1 hour at 37° C. The plates were then blocked with 200 μl/well of TBS containing 1% BSA for 1 hour at room temperature. After three washes in TBS 0.1% BSA, purified human C5 (Quidel, 20 μg/ml in TBS 1% BSA) was added to the plates in the presence (20 μg/ml) or absence of a 5G1.1 Fab (derived from 5G1.1 by conventional papain digestion) and allowed to incubate for 1 hour at 37° C. After three washes in TBS/0.1% BSA, a monoclonal antibody directed against the C5 beta chain (N19/8, 5 μg/ml) was added to the wells to detect C5 bound to either C3 or C4. After three final washes in TBS/0.1% BSA, the plate was developed using a horseradish peroxidase-conjugated secondary antibody and the appropriate substrate.

The results of these assays showed that the 5G1.1 mAb inhibited the binding of purified human C5 to either C3 or C4 by at least 60% to 90%. As used herein and in the claims, such a 60% to 90% reduction in C3 or C4 binding is a "substantial reduction" in C3 or C4 binding.

Example 15

Construction and Functional Analysis of N19/8 Chimeric Fab

The heavy chain and light chain variable regions from the hybridoma N19-8 were cloned by PCR using the Ig-Prime System (Novagen) as described by the manufacturer. Clones from multiple independent PCR reactions were sequenced to detect mutations introduced during the PCR amplification. An N19-8 VL/human kappa constant region chimeric cDNA was created by using a plasmid containing the N19-8 light chain variable region and the plasmid pHuCK (Hieter et al., 1980 Cell, 22:197–207) as templates in an overlapping PCR reaction.

Similarly, an N19-8 VH/human IgG1 Fd chimeric cDNA was created using a plasmid containing the N19-8 heavy chain variable region and a plasmid containing the human IgG1 gene (obtained from Ilan R. Kirsch, National Cancer Institute, Bethesda, Md.) as templates. This Fd construct contained the first nine amino acids of the IgG1 hinge region, including the cysteine residue which normally forms a disulfide bond with the terminal cysteine residue of the kappa light chain.

The resulting chimeric cDNAs were separately cloned into the APEX-1 vector using appropriate flanking restriction enzyme sites introduced during the PCR amplification procedure and sequenced. A fragment containing the promoter, intron, and cDNA insert from one of these APEX vectors was subsequently subcloned into the polylinker of the other to produce a single vector directing the expression of both the light chain and Fd. The tandem expression cassette from this APEX-1 vector was subsequently subcloned into APEX-3P, which was transfected into 293 EBNA cells for expression of the chimeric Fab.

When tested for the ability to block complement hemolytic activity and C5a generation, the chimeric N19/8 Fab retained the ability to block hemolytic activity, but lost 50% of its C5a generation blocking capacity.

Throughout this application various publications and patent disclosures are referred to. The teachings and disclosures thereof, in their entireties, are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

REFERENCES

Baker, et al., 1989, *American Journal of Pathology*. 135, pp. 185–194.

Clackson, et al., 1991, *Nature*. 352, pp. 624–628.

Cochrane, et al., 1965, *Journal of Experimental Medicine*. 122, pp. 99–116.

Coligan, et al., eds. 1992, *Current Protocols in Immunology*. John Wiley & Sons, New York.

Couser, et al., 1985, *Kidney International*. 28, pp. 897–890.

Couser, et al., 1991, *Journal of the American Society of Nephrology*. 2, pp. 894–901.

Couser, 1992, in *Cecil Textbook of Medicine*. 19th Ed. (Wyngaarden, Smith, and Bennett, eds.) W.B. Saunders Co., Philadelphia, Pa., Ch. 79, pp. 551–568.

Couser, et al., 1992, *Nephrology Dialysis Transplantation*. Suppl. 1, pp. 25–30.

Couser, 1993, *Kidney International*. 44, Suppl. 42, pp. S19–S26.

Falk and Jennette, 1986, *Kidney International*. 30, pp. 678–686.

Fearon, 1983, in *Intensive Review of Internal Medicine, 2nd Ed.*; Fanta and Minaker, eds. Brigham and Women's and Beth Israel Hospitals, pp. 204–210.

Floege, et al., 1992, *Laboratory Investigation*. 67, pp. 486–497.

Frei, et al., 1987, *Molecular and Cellular Probes*. 1, pp. 141–149.

Glassock and Brenner, 1987, in *Harrison's Principles of Internal Medicine*, 11th Ed. (Braunwald, Isselbacher, Petersdorf, Wilson, Martin, and Fauci, eds.) McGraw-Hill Book Co., New York, N.Y., Ch. 222 & 223, pp. 1170–1189.

Glassock and Brenner, 1994, in *Harrison's Principles of Internal Medicine*, 13th Ed. (Isselbacher, Braunwald, Wilson, Martin, Fauci, and Kasper, eds.) McGraw-Hill, Inc., New York, N.Y., pp. 1292–1313.

Grogel, et al., 1983, *Journal of Clinical Investigations.* 72, pp. 1948–1957.

Guyton, 1971, *Textbook of Medical Physiology, 4th Ed.* W.B. Saunders Co., Ch. 34 & 38, pp. 393–405 & pp. 442–454.

Haber, 1992, *Immunology Review.* 130, pp. 189–212.

Harlow and Lane, 1988, *Antibodies, A Laboratory Manual,* Cold Spring Harbor Laboratory, New York.

Jennette, et al., 1987, *American Journal of Pathology.* 127, pp. 499–506.

Knicker and Cochrane, 1965, *Journal of Experimental Medicine.* 122, pp. 83–98.

Liddell and Cryer, 1991, *A Practical Guide to Monoclonal Antibodies,* John Wiley & Sons, Chichester, West Sussex, England.

Mollnes, et al., 1988, *Scandinavian Journal of Immunology.* 28, pp. 307–312.

Montz, et al., 1990, *Cellular Immunology.* 127, pp. 337–351.

Morrison, et al., 1992, *Annual Review of Immunology.* 10, pp. 239–265.

Passwell, et al., 1988, *The American Society for Clinical Investigation, Inc.* 82, pp. 1676–1684.

Reichmann, et al., 1988, *Nature.* 332, pp. 323–327. *Remington's Pharmaceutical Sciences.* 17th Ed. 1985, Mack Publishing Company, Philadelphia, Pa.

Rich, 1992, in *Cecil Textbook of Medicine, 19th Ed.* (Wyngaarden, Smith, and Bennett, eds.) W.B. Saunders Co., Philadelphia, Pa., Ch. 249, pp. 1467–1470.

Robbins and Cotran, 1979, *Pathologic Basis of Disease.* 2nd ed. W.B. Saunders Co., Philadelphia, Pa,, pp. 1128–1129.

Rodrigues, et al., 1993, *Journal of Immunology.* 151, pp. 6954–6961.

Salant, et al., 1980, *Journal of Clinical Investigations.* 66, pp. 1339–1350.

Schrijver, et al., 1988, *Laboratory Investigation.* 59, pp. 484–491.

Schrijver, et al., 1990, *Kidney International.* 38, pp. 86–95.

Unanue and Dixon, 1964, *Journal of Experimental Medicine.* 119, pp. 965–982.

Winter and Milstein, 1991, *Nature.* 349, 293–299.

Wurzner, et al., 1991, *Complement Inflammation.* 8, 328–340.

TABLE 1

Prevention/Reduction of Proteinuria by Treatment With Anti-C5 Antibodies

|  | Before Treatment Urine Protein (mg/dL) | After Treatment Urine Protein (mg/dL) |
|---|---|---|
| PBS Control | | |
| mouse A | none | 100 |
| mouse B | none | 500 |
| mouse C | none | 500 |
| mouse D* | trace | trace |
| mouse E | 100 | 100 |
| Anti-C5 Treated | | |
| mouse 1 | none | none |
| mouse 2 | none | 30 |
| mouse 3 | 30 | trace |
| mouse 4 | 30 | 30 |
| mouse 5 | 30 | 30 |
| mouse 6 | 100 | 30 |

*Mouse D had more than 500 mg/dL urine glucose after treatment

---

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH:  21 amino acids
      (B) TYPE:  Amino Acid
      (C) STRANDEDNESS:  Single
      (D) TOPOLOGY:  Linear (ii) MOLECULE TYPE:
      (A) DESCRIPTION:  KSSKC peptide (iii) HYPOTHETICAL:  No (iv) ANTI-SENSE:  No (xi) SEQUENCE DESCRIPTION:  SEQ ID NO:1:

Val Ile Asp His Gln Gly Thr Lys Ser Ser
5                   10

Lys Cys Val Arg Gln Lys Val Glu Gly Ser Ser
15                  20

(2) INFORMATION FOR SEQ ID NO:2:

(i) SEQUENCE CHARACTERISTICS:
      (A) LENGTH:  1676 Amino Acids
      (B) TYPE:  Amino Acid

```
        (C) STRANDEDNESS: Single
        (D) TOPOLOGY: Linear (ii) MOLECULE TYPE:
        (A) DESCRIPTION: Pro-C5 Polytpeptide (iii) HYPOTHETICAL: No (iv) ANTI-SENSE: No (vi) ORIGINAL SOURCE:
        (A) ORGANISM: Homo sapiens (x) PUBLICATION INFORMATION:
        (A) AUTHORS:  Haviland, D.L.
                      Haviland, J.C.
                      Fleischer, D.T.
                      Hunt, A.
                      Wetsel, R.A.
        (B) TITLE: Complete cDNA Sequence of Human
            Complement Pro-C5
        (C) JOURNAL: Journal of Immunology
        (D) VOLUME: 146
        (F) PAGES: 362-368
        (G) DATE: 1991

(xi) SEQUENCE DESCRIPTION: SEQ ID NO:2:

Met Gly Leu Leu Gly Ile Leu Cys Phe Leu
-15               -10

Ile Phe Leu Gly Lys Thr Trp Gly Gln Glu Gln Thr Tyr Val
-5               -1            5

Ile Ser Ala Pro Lys Ile Phe Arg Val Gly Ala Ser Glu Asn
10              15                  20

Ile Val Ile Gln Val Tyr Gly Tyr Thr Glu Ala Phe Asp Ala
25              30

Thr Ile Ser Ile Lys Ser Tyr Pro Asp Lys Lys Phe Ser Tyr
35              40                  45

Ser Ser Gly His Val His Leu Ser Ser Glu Asn Lys Phe Gln
50              55                  60

Asn Ser Ala Ile Leu Thr Ile Gln Pro Lys Gln Leu Pro Gly
65              70                  75

Gly Gln Asn Pro Val Ser Tyr Val Tyr Leu Glu Val Val Ser
80              85                  90

Lys His Phe Ser Lys Ser Lys Arg Met Pro Ile Thr Tyr Asp
95              100

Asn Gly Phe Leu Phe Ile His Thr Asp Lys Pro Val Tyr Thr
105             110                 115

Pro Asp Gln Ser Val Lys Val Arg Val Tyr Ser Leu Asn Asp
120             125                 130

Asp Leu Lys Pro Ala Lys Arg Glu Thr Val Leu Thr Phe Ile
135             140                 145

Asp Pro Glu Gly Ser Glu Val Asp Met Val Glu Ile Asp
150             155                 160

His Ile Gly Ile Ile Ser Phe Pro Asp Phe Lys Ile Pro Ser
165             170

Asn Pro Arg Tyr Gly Met Trp Thr Ile Lys Ala Lys Tyr Lys
175             180                 185

Glu Asp Phe Ser Thr Thr Gly Thr Ala Tyr Phe Glu Val Lys
190             195                 200

Glu Tyr Val Leu Pro His Phe Ser Val Ser Ile Glu Pro Glu
205             210                 215
```

-continued

```
Tyr Asn Phe Ile Gly Tyr Lys Asn Phe Lys Asn Phe Glu Ile
220                 225                 230

Thr Ile Lys Ala Arg Tyr Phe Tyr Asn Lys Val Val Thr Glu
235                 240

Ala Asp Val Tyr Ile Thr Phe Gly Ile Arg Glu Asp Leu Lys
245                 250                 255

Asp Asp Gln Lys Glu Met Met Gln Thr Ala Met Gln Asn Thr
260                 265                 270

Met Leu Ile Asn Gly Ile Ala Gln Val Thr Phe Asp Ser Glu
275                 280                 285

Thr Ala Val Lys Glu Leu Ser Tyr Tyr Ser Leu Glu Asp Leu
290                 295                 300

Asn Asn Lys Tyr Leu Tyr Ile Ala Val Thr Val Ile Glu Ser
305                 310

Thr Gly Gly Phe Ser Glu Glu Ala Glu Ile Pro Gly Ile Lys
315                 320                 325

Tyr Val Leu Ser Pro Tyr Lys Leu Asn Leu Val Ala Thr Pro
330                 335                 340

Leu Phe Leu Lys Pro Gly Ile Pro Tyr Pro Ile Lys Val Gln
345                 350                 355

Val Lys Asp Ser Leu Asp Gln Leu Val Gly Gly Val Pro Val
360                 365                 370

Ile Leu Asn Ala Gln Thr Ile Asp Val Asn Gln Glu Thr Ser
375                 380

Asp Leu Asp Pro Ser Lys Ser Val Thr Arg Val Asp Asp Gly
385                 390                 395

Val Ala Ser Phe Val Leu Asn Leu Pro Ser Gly Val Thr Val
400                 405                 410

Leu Glu Phe Asn Val Lys Thr Asp Ala Pro Asp Leu Pro Glu
415                 420                 425

Glu Asn Gln Ala Arg Glu Gly Tyr Arg Ala Ile Ala Tyr Ser
430                 435                 440

Ser Leu Ser Gln Ser Tyr Leu Tyr Ile Asp Trp Thr Asp Asn
445                 450

His Lys Ala Leu Leu Val Gly Glu His Leu Asn Ile Ile Val
455                 460                 465

Thr Pro Lys Ser Pro Tyr Ile Asp Lys Ile Thr His Tyr Asn
470                 475                 480

Tyr Leu Ile Leu Ser Lys Gly Lys Ile Ile His Phe Gly Thr
485                 490                 495

Arg Glu Lys Phe Ser Asp Ala Ser Tyr Gln Ser Ile Asn Ile
500                 505                 510

Pro Val Thr Gln Asn Met Val Pro Ser Ser Arg Leu Leu Val
515                 520

Tyr Tyr Ile Val Thr Gly Glu Gln Thr Ala Glu Leu Val Ser
525                 530                 535

Asp Ser Val Trp Leu Asn Ile Glu Glu Lys Cys Gly Asn Gln
540                 545                 550

Leu Gln Val His Leu Ser Pro Asp Ala Asp Ala Tyr Ser Pro
555                 560                 565

Gly Gln Thr Val Ser Leu Asn Met Ala Thr Gly Met Asp Ser
570                 575                 580
```

-continued

```
Trp Val Ala Leu Ala Ala Val Asp Ser Ala Val Tyr Gly Val
585                 590
Gln Arg Gly Ala Lys Lys Pro Leu Glu Arg Val Phe Gln Phe
595                 600                 605
Leu Glu Lys Ser Asp Leu Gly Cys Gly Ala Gly Gly Gly Leu
610                 615                 620
Asn Asn Ala Asn Val Phe His Leu Ala Gly Leu Thr Phe Leu
625                 630                 635
Thr Asn Ala Asn Ala Asp Asp Ser Gln Glu Asn Asp Glu Pro
640                 645                 650
Cys Lys Glu Ile Leu Arg Pro Arg Arg Thr Leu Gln Lys Lys
655                 660
Ile Glu Glu Ile Ala Ala Lys Tyr Lys His Ser Val Val Lys
665                 670                 675
Lys Cys Cys Tyr Asp Gly Ala Cys Val Asn Asn Asp Glu Thr
680                 685                 690
Cys Glu Gln Arg Ala Ala Arg Ile Ser Leu Gly Pro Arg Cys
695                 700                 705
Ile Lys Ala Phe Thr Glu Cys Cys Val Val Ala Ser Gln Leu
710                 715                 720
Arg Ala Asn Ile Ser His Lys Asp Met Gln Leu Gly Arg Leu
725                 730
His Met Lys Thr Leu Leu Pro Val Ser Lys Pro Glu Ile Arg
735                 740                 745
Ser Tyr Phe Pro Glu Ser Trp Leu Trp Glu Val His Leu Val
750                 755                 760
Pro Arg Arg Lys Gln Leu Gln Phe Ala Leu Pro Asp Ser Leu
765                 770                 775
Thr Thr Trp Glu Ile Gln Gly Ile Gly Ile Ser Asn Thr Gly
780                 785                 790
Ile Cys Val Ala Asp Thr Val Lys Ala Lys Val Phe Lys Asp
795                 800
Val Phe Leu Glu Met Asn Ile Pro Tyr Ser Val Val Arg Gly
805                 810                 815
Glu Gln Ile Gln Leu Lys Gly Thr Val Tyr Asn Tyr Arg Thr
820                 825                 830
Ser Gly Met Gln Phe Cys Val Lys Met Ser Ala Val Glu Gly
835                 840                 845
Ile Cys Thr Ser Glu Ser Pro Val Ile Asp His Gln Gly Thr
850                 855                 860
Lys Ser Ser Lys Cys Val Arg Gln Lys Val Glu Gly Ser Ser
865                 870
Ser His Leu Val Thr Phe Thr Val Leu Pro Leu Glu Ile Gly
875                 880                 885
Leu His Asn Ile Asn Phe Ser Leu Glu Thr Trp Phe Gly Lys
890                 895                 900
Glu Ile Leu Val Lys Thr Leu Arg Val Val Pro Glu Gly Val
905                 910                 915
Lys Arg Glu Ser Tyr Ser Gly Val Thr Leu Asp Pro Arg Gly
920                 925                 930
Ile Tyr Gly Thr Ile Ser Arg Arg Lys Glu Phe Pro Tyr Arg
935                 940
```

-continued

```
Ile Pro Leu Asp Leu Val Pro Lys Thr Glu Ile Lys Arg Ile
945                 950                 955

Leu Ser Val Lys Gly Leu Leu Val Gly Glu Ile Leu Ser Ala
960                 965                 970

Val Leu Ser Gln Glu Gly Ile Asn Ile Leu Thr His Leu Pro
975                 980                 985

Lys Gly Ser Ala Glu Ala Glu Leu Met Ser Val Val Pro Val
990                 995                 1000

Phe Tyr Val Phe His Tyr Leu Glu Thr Gly Asn His Trp Asn
1005                1010

Ile Phe His Ser Asp Pro Leu Ile Glu Lys Gln Lys Leu Lys
1015                1020                1025

Lys Lys Leu Lys Glu Gly Met Leu Ser Ile Met Ser Tyr Arg
1030                1035                1040

Asn Ala Asp Tyr Ser Tyr Ser Val Trp Lys Gly Gly Ser Ala
1045                1050                1055

Ser Thr Trp Leu Thr Ala Phe Ala Leu Arg Val Leu Gly Gln
1060                1065                1070

Val Asn Lys Tyr Val Glu Gln Asn Gln Asn Ser Ile Cys Asn
1075                1080

Ser Leu Leu Trp Leu Val Glu Asn Tyr Gln Leu Asp Asn Gly
1085                1090                1095

Ser Phe Lys Glu Asn Ser Gln Tyr Gln Pro Ile Lys Leu Gln
1100                1105                1110

Gly Thr Leu Pro Val Glu Ala Arg Glu Asn Ser Leu Tyr Leu
1115                1120                1125

Thr Ala Phe Thr Val Ile Gly Ile Arg Lys Ala Phe Asp Ile
1130                1135                1140

Cys Pro Leu Val Lys Ile Asp Thr Ala Leu Ile Lys Ala Asp
1145                1150

Asn Phe Leu Leu Glu Asn Thr Leu Pro Ala Gln Ser Thr Phe
1155                1160                1165

Thr Leu Ala Ile Ser Ala Tyr Ala Leu Ser Leu Gly Asp Lys
1170                1175                1180

Thr His Pro Gln Phe Arg Ser Ile Val Ser Ala Leu Lys Arg
1185                1190                1195

Glu Ala Leu Val Lys Gly Asn Pro Pro Ile Tyr Arg Phe Trp
1200                1205                1210

Lys Asp Asn Leu Gln His Lys Asp Ser Ser Val Pro Asn Thr
1215                1220

Gly Thr Ala Arg Met Val Glu Thr Thr Ala Tyr Ala Leu Leu
1225                1230                1235

Thr Ser Leu Asn Leu Lys Asp Ile Asn Tyr Val Asn Pro Val
1240                1245                1250

Ile Lys Trp Leu Ser Glu Glu Gln Arg Tyr Gly Gly Gly Phe
1255                1260                1265

Tyr Ser Thr Gln Asp Thr Ile Asn Ala Ile Glu Gly Leu Thr
1270                1275                1280

Glu Tyr Ser Leu Leu Val Lys Gln Leu Arg Leu Ser Met Asp
1285                1290

Ile Asp Val Ser Tyr Lys His Lys Gly Ala Leu His Asn Tyr
1295                1300                1305
```

-continued

```
Lys Met Thr Asp Lys Asn Phe Leu Gly Arg Pro Val Glu Val
1310            1315                1320

Leu Leu Asn Asp Asp Leu Ile Val Ser Thr Gly Phe Gly Ser
1325            1330                1335

Gly Leu Ala Thr Val His Val Thr Thr Val Val His Lys Thr
1340            1345                1350

Ser Thr Ser Glu Glu Val Cys Ser Phe Tyr Leu Lys Ile Asp
1355            1360

Thr Gln Asp Ile Glu Ala Ser His Tyr Arg Gly Tyr Gly Asn
1365            1370                1375

Ser Asp Tyr Lys Arg Ile Val Ala Cys Ala Ser Tyr Lys Pro
1380            1385                1390

Ser Arg Glu Glu Ser Ser Ser Gly Ser Ser His Ala Val Met
1395            1400                1405

Asp Ile Ser Leu Pro Thr Gly Ile Ser Ala Asn Glu Glu Asp
1410            1415                1420

Leu Lys Ala Leu Val Glu Gly Val Asp Gln Leu Phe Thr Asp
1425            1430

Tyr Gln Ile Lys Asp Gly His Val Ile Leu Gln Leu Asn Ser
1435            1440                1445

Ile Pro Ser Ser Asp Phe Leu Cys Val Arg Phe Arg Ile Phe
1450            1455                1460

Glu Leu Phe Glu Val Gly Phe Leu Ser Pro Ala Thr Phe Thr
1465            1470                1475

Val Tyr Glu Tyr His Arg Pro Asp Lys Gln Cys Thr Met Phe
1480            1485                1490

Tyr Ser Thr Ser Asn Ile Lys Ile Gln Lys Val Cys Glu Gly
1495            1500

Ala Ala Cys Lys Cys Val Glu Ala Asp Cys Gly Gln Met Gln
1505            1510                1515

Glu Glu Leu Asp Leu Thr Ile Ser Ala Glu Thr Arg Lys Gln
1520            1525                1530

Thr Ala Cys Lys Pro Glu Ile Ala Tyr Ala Tyr Lys Val Ser
1535            1540                1545

Ile Thr Ser Ile Thr Val Glu Asn Val Phe Val Lys Tyr Lys
1550            1555                1560

Ala Thr Leu Leu Asp Ile Tyr Lys Thr Gly Glu Ala Val Ala
1565            1570

Glu Lys Asp Ser Glu Ile Thr Phe Ile Lys Lys Val Thr Cys
1575            1580                1585

Thr Asn Ala Glu Leu Val Lys Gly Arg Gln Tyr Leu Ile Met
1590            1595                1600

Gly Lys Glu Ala Leu Gln Ile Lys Tyr Asn Phe Ser Phe Arg
1605            1610                1615

Tyr Ile Tyr Pro Leu Asp Ser Leu Thr Trp Ile Glu Tyr Trp
1620            1625                1630

Pro Arg Asp Thr Thr Cys Ser Ser Cys Gln Ala Phe Leu Ala
1635            1640

Asn Leu Asp Glu Phe Ala Glu Asp Ile Phe Leu Asn Gly Cys
1645            1650                1655
```

(2) INFORMATION FOR SEQ ID NO:3:

(i) SEQUENCE CHARACTERISTICS:
        (A) LENGTH: 4059 base pairs
        (B) TYPE: Nucleic Acid
        (C) STRANDEDNESS: Double
        (D) TOPOLOGY: Circular (ii) MOLECULE TYPE: Other nucleic acid
        (A) DESCRIPTION: Apex-1 Eukaryotic
            Expression Vector (xi) SEQUENCE DESCRIPTION: SEQ ID NO:3:

```
ACGCGTTGAC ATTGATTATT GACTAGTTAT TAATAGTAAT CAATTACGGG         50
GTCATTAGTT CATAGCCCAT ATATGGAGTT CCGCGTTACA TAACTTACGG        100
TAAATGGCCC CGCCTGGCTG ACCGCCCAAC GACCCCCGCC CATTGACGTC        150
AATAATGACG TATGTTCCCA TAGTAACGCC AATAGGGACT TTCCATTGAC        200
GTCAATGGGT GGACTATTTA CGGTAAACTG CCCACTTGGC AGTACATCAA        250
GTGTATCATA TGCCAAGTAC GCCCCCTATT GACGTCAATG ACGGTAAATG        300
GCCCGCCTGG CATTATGCCC AGTACATGAC CTTATGGGAC TTTCCTACTT        350
GGCAGTACAT CTACGTATTA GTCATCGCTA TTACCATGGT GATGCGGTTT        400
TGGCAGTACA TCAATGGGCG TGGATAGCGG TTTGACTCAC GGGGATTTCC        450
AAGTCTCCAC CCCATTGACG TCAATGGGAG TTTGTTTTGG CACCAAAATC        500
AACGGGACTT TCCAAAATGT CGTAACAACT CCGCCCCATT GACGCAAATG        550
GGCGGTAGGC GTGTACGGTG GGAGGTCTAT ATAAGCAGAG CTCGTTTAGT        600
GAACCGTCAG AATTCTGTTG GGCTCGCGGT TGATTACAAA CTCTTCGCGG        650
TCTTTCCAGT ACTCTTGGAT CGGAAACCCG TCGGCCTCCG AACGGTACTC        700
CGCCACCGAG GGACCTGAGC GAGTCCGCAT CGACCGGATC GGAAAACCTC        750
TCGACTGTTG GGGTGAGTAC TCCCTCTCAA AAGCGGGCAT GACTTCTGCG        800
CTAAGATTGT CAGTTTCCAA AAACGAGGAG GATTTGATAT TCACCTGGCC        850
CGCGGTGATG CCTTTGAGGG TGGCCGCGTC CATCTGGTCA GAAAAGACAA        900
TCTTTTTGTT GTCAAGCTTG AGGTGTGGCA GGCTTGAGAT CTGGCCATAC        950
ACTTGAGTGA CAATGACATC CACTTTGCCT TTCTCTCCAC AGGTGTCCAC       1000
TCCCAGGTCC AACTGCAGGT CGACCGGCTT GGTACCGAGC TCGGATCCAC       1050
TAGTAACGGC CGCCAGTGTG CTGGAATTCT GCAGATATCC ATCACACTGG       1100
CGGCCGCTCG AGCATGCATC TAGAACTTGT TTATTGCAGC TTATAATGGT       1150
TACAAATAAA GCAATAGCAT CACAAATTTC ACAAATAAAG CATTTTTTTC       1200
ACTGCATTCT AGTTGTGGTT TGTCCAAACT CATCAATGTA TCTTATCATG       1250
TCTGGATCGA TCCCGCCATG GTATCAACGC CATATTTCTA TTTACAGTAG       1300
GGACCTCTTC GTTGTGTAGG TACCGCTGTA TTCCTAGGGA AATAGTAGAG       1350
GCACCTTGAA CTGTCTGCAT CAGCCATATA GCCCCGCTG TTCGACTTAC        1400
AAACACAGGC ACAGTACTGA CAAACCCATA CACCTCCTCT GAAATACCCA       1450
TAGTTGCTAG GGCTGTCTCC GAACTCATTA CACCCTCCAA AGTCAGAGCT       1500
GTAATTTCGC CATCAAGGGC AGCGAGGGCT CTCCAGATAA AAATAGCTTC       1550
TGCCGAGAGT CCCGTAAGGG TAGACACTTC AGCTAATCCC TCGATGAGGT       1600
CTACTAGAAT AGTCAGTGCG GCTCCCATTT TGAAAATTCA CTTACTTGAT       1650
```

| | |
|---|---|
| CAGCTTCAGA AGATGGCGGA GGGCCTCCAA CACAGTAATT TTCCTCCCGA | 1700 |
| CTCTTAAAAT AGAAAATGTC AAGTCAGTTA AGCAGGAAGT GGACTAACTG | 1750 |
| ACGCAGCTGG CCGTGCGACA TCCTCTTTTA ATTAGTTGCT AGGCAACGCC | 1800 |
| CTCCAGAGGG CGTGTGGTTT TGCAAGAGGA AGCAAAAGCC TCTCCACCCA | 1850 |
| GGCCTAGAAT GTTTCCACCC AATCATTACT ATGACAACAG CTGTTTTTTT | 1900 |
| TAGTATTAAG CAGAGGCCGG GGACCCCTGG GCCCGCTTAC TCTGGAGAAA | 1950 |
| AAGAAGAGAG GCATTGTAGA GGCTTCCAGA GGCAACTTGT CAAAACAGGA | 2000 |
| CTGCTTCTAT TTCTGTCACA CTGTCTGGCC CTGTCACAAG GTCCAGCACC | 2050 |
| TCCATACCCC CTTTAATAAG CAGTTTGGGA ACGGGTGCGG GTCTTACTCC | 2100 |
| GCCCATCCCG CCCCTAACTC CGCCCAGTTC CGCCCATTCT CCGCCCCATG | 2150 |
| GCTGACTAAT TTTTTTTATT TATGCAGAGG CCGAGGCCGC CTCGGCCTCT | 2200 |
| GAGCTATTCC AGAAGTAGTG AGGAGGCTTT TTTGGAGGCC TAGGCTTTTG | 2250 |
| CAAAAAGGAG CTCCCAGCAA AAGGCCAGGA ACCGTAAAAA GGCCGCGTTG | 2300 |
| CTGGCGTTTT TCCATAGGCT CCGCCCCCCT GACGAGCATC ACAAAAATCG | 2350 |
| ACGCTCAAGT CAGAGGTGGC GAAACCCGAC AGGACTATAA AGATACCAGG | 2400 |
| CGTTTCCCCC TGGAAGCTCC CTCGTGCGCT CTCCTGTTCC GACCCTGCCG | 2450 |
| CTTACCGGAT ACCTGTCCGC CTTTCTCCCT TCGGGAAGCG TGGCGCTTTC | 2500 |
| TCAATGCTCA CGCTGTAGGT ATCTCAGTTC GGTGTAGGTC GTTCGCTCCA | 2550 |
| AGCTGGGCTG TGTGCACGAA CCCCCCGTTC AGCCCGACCG CTGCGCCTTA | 2600 |
| TCCGGTAACT ATCGTCTTGA GTCCAACCCG GTAAGACACG ACTTATCGCC | 2650 |
| ACTGGCAGCA GCCACTGGTA ACAGGATTAG CAGAGCGAGG TATGTAGGCG | 2700 |
| GTGCTACAGA GTTCTTGAAG TGGTGGCCTA ACTACGGCTA CACTAGAAGG | 2750 |
| ACAGTATTTG GTATCTGCGC TCTGCTGAAG CCAGTTACCT TCGGAAAAAG | 2800 |
| AGTTGGTAGC TCTTGATCCG GCAAACAAAC CACCGCTGGT AGCGGTGGTT | 2850 |
| TTTTTGTTTG CAAGCAGCAG ATTACGCGCA GAAAAAAAGG ATCTCAAGAA | 2900 |
| GATCCTTTGA TCTTTTCTAC GGGGTCTGAC GCTCAGTGGA ACGAAAACTC | 2950 |
| ACGTTAAGGG ATTTTGGTCA TGAGATTATC AAAAAGGATC TTCACCTAGA | 3000 |
| TCCTTTTAAA TTAAAAATGA AGTTTTAAAT CAATCTAAAG TATATATGAG | 3050 |
| TAAACTTGGT CTGACAGTTA CCAATGCTTA ATCAGTGAGG CACCTATCTC | 3100 |
| AGCGATCTGT CTATTTCGTT CATCCATAGT TGCCTGACTC CCCGTCGTGT | 3150 |
| AGATAACTAC GATACGGGAG GGCTTACCAT CTGGCCCCAG TGCTGCAATG | 3200 |
| ATACCGCGAG ACCCACGCTC ACCGGCTCCA GATTTATCAG CAATAAACCA | 3250 |
| GCCAGCCGGA AGGGCCGAGC GCAGAAGTGG TCCTGCAACT TTATCCGCCT | 3300 |
| CCATCCAGTC TATTAATTGT TGCCGGGAAG CTAGAGTAAG TAGTTCGCCA | 3350 |
| GTTAATAGTT TGCGCAACGT TGTTGCCATT GCTACAGGCA TCGTGGTGTC | 3400 |
| ACGCTCGTCG TTTGGTATGG CTTCATTCAG CTCCGGTTCC CAACGATCAA | 3450 |
| GGCGAGTTAC ATGATCCCCC ATGTTGTGCA AAAAAGCGGT TAGCTCCTTC | 3500 |
| GGTCCTCCGA TCGTTGTCAG AAGTAAGTTG GCCGCAGTGT TATCACTCAT | 3550 |
| GGTTATGGCA GCACTGCATA ATTCTCTTAC TGTCATGCCA TCCGTAAGAT | 3600 |
| GCTTTTCTGT GACTGGTGAG TACTCAACCA AGTCATTCTG AGAATAGTGT | 3650 |

-continued

| | |
|---|---|
| ATGCGGCGAC CGAGTTGCTC TTGCCCGGCG TCAATACGGG ATAATACCGC | 3700 |
| GCCACATAGC AGAACTTTAA AAGTGCTCAT CATTGGAAAA CGTTCTTCGG | 3750 |
| GGCGAAAACT CTCAAGGATC TTACCGCTGT TGAGATCCAG TTCGATGTAA | 3800 |
| CCCACTCGTG CACCCAACTG ATCTTCAGCA TCTTTTACTT TCACCAGCGT | 3850 |
| TTCTGGGTGA GCAAAAACAG GAAGGCAAAA TGCCGCAAAA AAGGGAATAA | 3900 |
| GGGCGACACG GAAATGTTGA ATACTCATAC TCTTCCTTTT TCAATATTAT | 3950 |
| TGAAGCATTT ATCAGGGTTA TTGTCTCATG AGCGGATACA TATTTGAATG | 4000 |
| TATTTAGAAA AATAAACAAA TAGGGGTTCC GCGCACATTT CCCCGAAAAG | 4050 |
| TGCCACCTG | 4059 |

(2) INFORMATION FOR SEQ ID NO:4:

(i) SEQUENCE CHARACTERISTICS:
        (A) LENGTH: 8540 base pairs
        (B) TYPE: Nucleic Acid
        (C) STRANDEDNESS: Double
        (D) TOPOLOGY: Circular (ii) MOLECULE TYPE: Other nucleic acid
        (A) DESCRIPTION: Apex-3P Eukaryotic
           Expression Vector (xi) SEQUENCE DESCRIPTION: SEQ ID NO:4:

| | |
|---|---|
| GTGACCAATA CAAAACAAAA GCGCCCCTCG TACCAGCGAA GAAGGGGCAG | 50 |
| AGATGCCGTA GTCAGGTTTA GTTCGTCCGG CGGCGGGGGA TCTGTATGGT | 100 |
| GCACTCTCAG TACAATCTGC TCTGATGCCG CATAGTTAAG CCAGTATCTG | 150 |
| CTCCCTGCTT GTGTGTTGGA GGTCGCTGAG TAGTGCGCGA GCAAAATTTA | 200 |
| AGCTACAACA AGGCAAGGCT TGACCGACAA TTGCATGAAG AATCTGCTTA | 250 |
| GGGTTAGGCG TTTTGCGCTG CTTCGCGATG TACGGGCCAG ATATACGCGT | 300 |
| TGACATTGAT TATTGACTAG TTATTAATAG TAATCAATTA CGGGGTCATT | 350 |
| AGTTCATAGC CCATATATGG AGTTCCGCGT TACATAACTT ACGGTAAATG | 400 |
| GCCCGCCTGG CTGACCGCCC AACGACCCCC GCCCATTGAC GTCAATAATG | 450 |
| ACGTATGTTC CCATAGTAAC GCCAATAGGG ACTTTCCATT GACGTCAATG | 500 |
| GGTGGACTAT TTACGGTAAA CTGCCCACTT GGCAGTACAT CAAGTGTATC | 550 |
| ATATGCCAAG TACGCCCCCT ATTGACGTCA ATGACGGTAA ATGGCCCGCC | 600 |
| TGGCATTATG CCCAGTACAT GACCTTATGG GACTTTCCTA CTTGGCAGTA | 650 |
| CATCTACGTA TTAGTCATCG CTATTACCAT GGTGATGCGG TTTTGGCAGT | 700 |
| ACATCAATGG GCGTGGATAG CGGTTTGACT CACGGGGATT TCCAAGTCTC | 750 |
| CACCCCATTG ACGTCAATGG GAGTTTGTTT TGGCACCAAA ATCAACGGGA | 800 |
| CTTTCCAAAA TGTCGTAACA ACTCCGCCCC ATTGACGCAA ATGGGCGGTA | 850 |
| GGCGTGTACG GTGGGAGGTC TATATAAGCA GAGCTCGTTT AGTGAACCGT | 900 |
| CAGAATTCTG TTGGGCTCGC GGTTGATTAC AAACTCTTCG CGGTCTTTCC | 950 |
| AGTACTCTTG GATCGGAAAC CCGTCGGCCT CCGAACGGTA CTCCGCCACC | 1000 |
| GAGGGACCTG AGCGAGTCCG CATCGACCGG ATCGGAAAAC CTCTCGACTG | 1050 |
| TTGGGGTGAG TACTCCCTCT CAAAAGCGGG CATGACTTCT GCGCTAAGAT | 1100 |
| TGTCAGTTTC CAAAAACGAG GAGGATTTGA TATTCACCTG GCCCGCGGTG | 1150 |
| ATGCCTTTGA GGGTGGCCGC GTCCATCTGG TCAGAAAAGA CAATCTTTTT | 1200 |

-continued

| | |
|---|---|
| GTTGTCAAGC TTGAGGTGTG GCAGGCTTGA GATCTGGCCA TACACTTGAG | 1250 |
| TGACAATGAC ATCCACTTTG CCTTTCTCTC CACAGGTGTC CACTCCCAGG | 1300 |
| TCCAACTGCA GGTCGACCGG CTTGGTACCG AGCTCGGATC CTCTAGAGTC | 1350 |
| GACCTGCAGG CATGCAAGCT TGGCACTGGC CGTCGTTTTA CAACGTCGTG | 1400 |
| ACTGGGAAAA CCCTGGCGTT ACCCAACTTA ATCGCCTTGC AGCACATCCC | 1450 |
| CCTTTCGCCA GCTGGCGTAA TAGCGAAGAG GCCCGCACCG ATCCAGACAT | 1500 |
| GATAAGATAC ATTGATGAGT TTGGACAAAC CACAACTAGA ATGCAGTGAA | 1550 |
| AAAAATGCTT TATTTGTGAA ATTTGTGATG CTATTGCTTT ATTTGTAACC | 1600 |
| ATTATAAGCT GCAATAAACA AGTTAACAAC AACAATTGCA TTCATTTTAT | 1650 |
| GTTTCAGGTT CAGGGGAGG TGTGGGAGGT TTTTTAAAGC AAGTAAAACC | 1700 |
| TCTACAAATG TGGTATGGCT GATTATGATC CCCAGGAAGC TCCTCTGTGT | 1750 |
| CCTCATAAAC CCTAACCTCC TCTACTTGAG AGGACATTCC AATCATAGGC | 1800 |
| TGCCCATCCA CCCTCTGTGT CCTCCTGTTA ATTAGGTCAC TTAACAAAAA | 1850 |
| GGAAATTGGG TAGGGGTTTT TCACAGACCG CTTTCTAAGG GTAATTTTAA | 1900 |
| AATATCTGGG AAGTCCCTTC CACTGCTGTG TTCCAGAAGT GTTGGTAAAC | 1950 |
| AGCCCACAAA TGTCAACAGC AGAAACATAC AAGCTGTCAG CTTTGCACAA | 2000 |
| GGGCCCAACA CCCTGCTCAT CAAGAAGCAC TGTGGTTGCT GTGTTAGTAA | 2050 |
| TGTGCAAAAC AGGAGGCACA TTTTCCCCAC CTGTGTAGGT TCCAAAATAT | 2100 |
| CTAGTGTTTT CATTTTTACT TGGATCAGGA ACCCAGCACT CCACTGGATA | 2150 |
| AGCATTATCC TTATCCAAAA CAGCCTTGTG GTCAGTGTTC ATCTGCTGAC | 2200 |
| TGTCAACTGT AGCATTTTTT GGGGTTACAG TTTGAGCAGG ATATTTGGTC | 2250 |
| CTGTAGTTTG CTAACACACC CTGCAGCTCC AAAGGTTCCC CACCAACAGC | 2300 |
| AAAAAAATGA AAATTTGACC CTTGAATGGG TTTTCCAGCA CCATTTTCAT | 2350 |
| GAGTTTTTTG TGTCCCTGAA TGCAAGTTTA ACATAGCAGT TACCCCAATA | 2400 |
| ACCTCAGTTT TAACAGTAAC AGCTTCCCAC ATCAAAATAT TTCCACAGGT | 2450 |
| TAAGTCCTCA TTTGTAGAAT TCGCCAGCAC AGTGGTCGAC CCTGTGGATG | 2500 |
| TGTGTCACTT AGGGTGTGGA AAGTCCCCAG GCTCCCCAGC AGGCAGAAGT | 2550 |
| ATGCAAAGCA TGCATCTCAA TTAGTCAGCA ACCAGGTGTG GAAAGTCCCC | 2600 |
| AGGCTCCCCA GCAGGCAGAA GTATGCAAAG CATGCATCTC AATTAGTCAG | 2650 |
| CAACCATAGT CCCGCCCCTA ACTCCGCCCA TCCCGCCCCT AACTCCGCCC | 2700 |
| AGTTCCGCCC ATTCTCCGCC CCATGGCTGA CTAATTTTTT TTATTTATGC | 2750 |
| AGAGGCCGAG GCCGCCTCGG CCTCTGAGCT ATTCCAGAAG TAGTGAGGAG | 2800 |
| GCTTTTTTGG AGGCCTAGGC TTTTGCAAAA GCTTACCATG ACCGAGTACA | 2850 |
| AGCCCACGGT GCGCCTCGCC ACCCGCGACG ACGTCCCCCG GCCGTACGC | 2900 |
| ACCCTCGCCG CCGCGTTCGC CGACTACCCC GCCACGCGCC ACACCGTCGA | 2950 |
| CCCGGACCGC CACATCGAGC GGGTCACCGA GCTGCAAGAA CTCTTCCTCA | 3000 |
| CGCGCGTCGG GCTCGACATC GGCAAGGTGT GGGTCGCGGA CGACGGCGCC | 3050 |
| GCGGTGGCGG TCTGGACCAC GCCGGAGAGC GTCGAAGCGG GGGCGGTGTT | 3100 |
| CGCCGAGATC GGCCCGCGCA TGGCCGAGTT GAGCGGTTCC CGGCTGGCCG | 3150 |
| CGCAGCAACA GATGGAAGGC CTCCTGGCGC CGCACCGGCC CAAGGAGCCC | 3200 |

| | |
|---|---|
| GCGTGGTTCC TGGCCACCGT CGGCGTCTCG CCCGACCACC AGGGCAAGGG | 3250 |
| TCTGGGCAGC GCCGTCGTGC TCCCCGGAGT GGAGGCGGCC GAGCGCGCCG | 3300 |
| GGGTGCCCGC CTTCCTGGAG ACCTCCGCGC CCCGCAACCT CCCCTTCTAC | 3350 |
| GAGCGGCTCG GCTTCACCGT CACCGCCGAC GTCGAGTGCC CGAAGGACCG | 3400 |
| CGCGACCTGG TGCATGACCC GCAAGCCCGG TGCCTGACGC CCGCCCCACG | 3450 |
| ACCCGCAGCG CCCGACCGAA AGGAGCGCAC GACCCCATGC ATCGATAAAA | 3500 |
| TAAAAGATTT TATTTAGTCT CCAGAAAAAG GGGGAATGA AAGACCCCAC | 3550 |
| CTGTAGGTTT GGCAAGCTAG AACTTGTTTA TTGCAGCTTA TAATGGTTAC | 3600 |
| AAATAAAGCA ATAGCATCAC AAATTTCACA AATAAAGCAT TTTTTTCACT | 3650 |
| GCATTCTAGT TGTGGTTTGT CCAAACTCAT CAATGTATCT TATCATGTCT | 3700 |
| GGATCGATCC CGCCATGGTA TCAACGCCAT ATTTCTATTT ACAGTAGGGA | 3750 |
| CCTCTTCGTT GTGTAGGTAC CCCGGGTTCG AAATCGAATT CGCCAATGAC | 3800 |
| AAGACGCTGG GCGGGGTTTG TGTCATCATA GAACTAAAGA CATGCAAATA | 3850 |
| TATTTCTTCC GGGGACACCG CCAGCAAACG CGAGCAACGG GCCACGGGGA | 3900 |
| TGAAGCAGCC CGGCGGCACC TCGCTAACGG ATTCACCACT CCAAGAATTG | 3950 |
| GAGCCAATCA ATTCTTGCGG AGAACTGTGA ATGCGCAAAC CAACCCTTGG | 4000 |
| CAGAACATAT CCATCGCGTC CGCCATCTCC AGCAGCCGCA CGCGGCGCAT | 4050 |
| CTCGGGGCCG ACGCGCTGGG CTACGTCTTG CTGGCGTTCG CGACGCGAGG | 4100 |
| CTGGATGGCC TTCCCCATTA TGATTCTTCT CGCTTCCGGC GGCATCGGGA | 4150 |
| TGCCCGCGTT GCAGGCCATG CTGTCCAGGC AGGTAGATGA CGACCATCAG | 4200 |
| GGACAGCTTC AAGGATCGCT CGCGGCTCTT ACCAGCGCCA GCAAAAGGCC | 4250 |
| AGGAACCGTA AAAAGGCCGC GTTGCTGGCG TTTTTCCATA GGCTCCGCCC | 4300 |
| CCCTGACGAG CATCACAAAA ATCGACGCTC AAGTCAGAGG TGGCGAAACC | 4350 |
| CGACAGGACT ATAAAGATAC CAGGCGTTTC CCCCTGGAAG CTCCCTCGTG | 4400 |
| CGCTCTCCTG TTCCGACCCT GCCGCTTACC GGATACCTGT CCGCCTTTCT | 4450 |
| CCCTTCGGGA AGCGTGGCGC TTTCTCATAG CTCACGCTGT AGGTATCTCA | 4500 |
| GTTCGGTGTA GGTCGTTCGC TCCAAGCTGG GCTGTGTGCA CGAACCCCCC | 4550 |
| GTTCAGCCCG ACCGCTGCGC CTTATCCGGT AACTATCGTC TTGAGTCCAA | 4600 |
| CCCGGTAAGA CACGACTTAT CGCCACTGGC AGCAGCCACT GGTAACAGGA | 4650 |
| TTAGCAGAGC GAGGTATGTA GGCGGTGCTA CAGAGTTCTT GAAGTGGTGG | 4700 |
| CCTAACTACG GCTACACTAG AAGGACAGTA TTTGGTATCT GCGCTCTGCT | 4750 |
| GAAGCCAGTT ACCTTCGGAA AAAGAGTTGG TAGCTCTTGA TCCGGCAAAC | 4800 |
| AAACCACCGC TGGTAGCGGT GGTTTTTTTG TTTGCAAGCA GCAGATTACG | 4850 |
| CGCAGAAAAA AAGGATCTCA AGAAGATCCT TTGATCTTTT CTACGGGGTC | 4900 |
| TGACGCTCAG TGGAACGAAA ACTCACGTTA AGGGATTTTG GTCATGAGAT | 4950 |
| TATCAAAAAG GATCTTCACC TAGATCCTTT TAAATTAAAA ATGAAGTTTT | 5000 |
| AAATCAATCT AAAGTATATA TGAGTAAACT TGGTCTGACA GTTACCAATG | 5050 |
| CTTAATCAGT GAGGCACCTA TCTCAGCGAT CTGTCTATTT CGTTCATCCA | 5100 |
| TAGTTGCCTG ACTCCCCGTC GTGTAGATAA CTACGATACG GGAGGGCTTA | 5150 |
| CCATCTGGCC CCAGTGCTGC AATGATACCG CGAGACCCAC GCTCACCGGC | 5200 |

```
TCCAGATTTA TCAGCAATAA ACCAGCCAGC CGGAAGGGCC GAGCGCAGAA         5250

GTGGTCCTGC AACTTTATCC GCCTCCATCC AGTCTATTAA TTGTTGCCGG         5300

GAAGCTAGAG TAAGTAGTTC GCCAGTTAAT AGTTTGCGCA ACGTTGTTGC         5350

CATTGCTGCA GGCATCGTGG TGTCACGCTC GTCGTTTGGT ATGGCTTCAT         5400

TCAGCTCCGG TTCCCAACGA TCAAGGCGAG TTACATGATC CCCCATGTTG         5450

TGCAAAAAAG CGGTTAGCTC CTTCGGTCCT CCGATCGTTG TCAGAAGTAA         5500

GTTGGCCGCA GTGTTATCAC TCATGGTTAT GGCAGCACTG CATAATTCTC         5550

TTACTGTCAT GCCATCCGTA AGATGCTTTT CTGTGACTGG TGAGTACTCA         5600

ACCAAGTCAT TCTGAGAATA GTGTATGCGG CGACCGAGTT GCTCTTGCCC         5650

GGCGTCAACA CGGGATAATA CCGCGCCACA TAGCAGAACT TTAAAAGTGC         5700

TCATCATTGG AAAACGTTCT TCGGGGCGAA AACTCTCAAG GATCTTACCG         5750

CTGTTGAGAT CCAGTTCGAT GTAACCCACT CGTGCACCCA ACTGATCTTC         5800

AGCATCTTTT ACTTTCACCA GCGTTTCTGG GTGAGCAAAA ACAGGAAGGC         5850

AAAATGCCGC AAAAAAGGGA ATAAGGGCGA CACGGAAATG TTGAATACTC         5900

ATACTCTTCC TTTTTCAATA TTATTGAAGC ATTTATCAGG GTTATTGTCT         5950

CATGAGCGGA TACATATTTG AATGTATTTA GAAAAATAAA CAAATAGGGG         6000

TTCCGCGCAC ATTTCCCCGA AAAGTGCCAC CTGACGTCTA AGAAACCATT         6050

ATTATCATGA CATTAACCTA TAAAAATAGG CGTATCACGA GGCCCTTTCG         6100

TCTTCAAGAA TTCTCATGTT TGACAGCTTA TCGTAGACAT CATGCGTGCT         6150

GTTGGTGTAT TTCTGGCCAT CTGTCTTGTC ACCATTTTCG TCCTCCCAAC         6200

ATGGGGCAAT TGGGCATACC CATGTTGTCA CGTCACTCAG CTCCGCGCTC         6250

AACACCTTCT CGCGTTGGAA AACATTAGCG ACATTTACCT GGTGAGCAAT         6300

CAGACATGCG ACGGCTTTAG CCTGGCCTCC TTAAATTCAC CTAAGAATGG         6350

GAGCAACCAG CAGGAAAAGG ACAAGCAGCG AAAATTCACG CCCCCTTGGG         6400

AGGTGGCGGC ATATGCAAAG GATAGCACTC CCACTCTACT ACTGGGTATC         6450

ATATGCTGAC TGTATATGCA TGAGGATAGC ATATGCTACC CGGATACAGA         6500

TTAGGATAGC ATATACTACC CAGATATAGA TTAGGATAGC ATATGCTACC         6550

CAGATATAGA TTAGGATAGC CTATGCTACC CAGATATAAA TTAGGATAGC         6600

ATATACTACC CAGATATAGA TTAGGATAGC ATATGCTACC CAGATATAGA         6650

TTAGGATAGC CTATGCTACC CAGATATAGA TTAGGATAGC ATATGCTACC         6700

CAGATATAGA TTAGGATAGC ATATGCTATC CAGATATTTG GGTAGTATAT         6750

GCTACCCAGA TATAAATTAG GATAGCATAT ACTACCCTAA TCTCTATTAG         6800

GATAGCATAT GCTACCCGGA TACAGATTAG GATAGCATAT ACTACCCAGA         6850

TATAGATTAG GATAGCATAT GCTACCCAGA TATAGATTAG GATAGCCTAT         6900

GCTACCCAGA TATAAATTAG GATAGCATAT ACTACCCAGA TATAGATTAG         6950

GATAGCATAT GCTACCCAGA TATAGATTAG GATAGCCTAT GCTACCCAGA         7000

TATAGATTAG GATAGCATAT GCTATCCAGA TATTTGGGTA GTATATGCTA         7050

CCCATGGCAA CATTAGCCCA CCGTGCTCTC AGCGACCTCG TGAATATGAG         7100

GACCAACAAC CCTGTGCTTG GCGCTCAGGC GCAAGTGTGT GTAATTTGTC         7150

CTCCAGATCG CAGCAATCGC GCCCCTATCT TGGCCCGCCC ACCTACTTAT         7200
```

-continued

| | |
|---|---|
| GCAGGTATTC CCCGGGGTGC CATTAGTGGT TTTGTGGGCA AGTGGTTTGA | 7250 |
| CCGCAGTGGT TAGCGGGGTT ACAATCAGCC AAGTTATTAC ACCCTTATTT | 7300 |
| TACAGTCCAA AACCGCAGGG CGGCGTGTGG GGGCTGACGC GTGCCCCCAC | 7350 |
| TCCACAATTT CAAAAAAAAG AGTGGCCACT TGTCTTTGTT TATGGGCCCC | 7400 |
| ATTGGCGTGG AGCCCCGTTT AATTTTCGGG GGTGTTAGAG ACAACCAGTG | 7450 |
| GAGTCCGCTG CTGTCGGCGT CCACTCTCTT TCCCCTTGTT ACAAATAGAG | 7500 |
| TGTAACAACA TGGTTCACCT GTCTTGGTCC CTGCCTGGGA CACATCTTAA | 7550 |
| TAACCCCAGT ATCATATTGC ACTAGGATTA TGTGTTGCCC ATAGCCATAA | 7600 |
| ATTCGTGTGA GATGGACATC CAGTCTTTAC GGCTTGTCCC CACCCCATGG | 7650 |
| ATTTCTATTG TTAAAGATAT TCAGAATGTT TCATTCCTAC ACTAGTATTT | 7700 |
| ATTGCCCAAG GGGTTTGTGA GGGTTATATT GGTGTCATAG CACAATGCCA | 7750 |
| CCACTGAACC CCCCGTCCAA ATTTTATTCT GGGGGCGTCA CCTGAAACCT | 7800 |
| TGTTTTCGAG CACCTCACAT ACACCTTACT GTTCACAACT CAGCAGTTAT | 7850 |
| TCTATTAGCT AAACGAAGGA GAATGAAGAA GCAGGCGAAG ATTCAGGAGA | 7900 |
| GTTCACTGCC CGCTCCTTGA TCTTCAGCCA CTGCCCTTGT GACTAAAATG | 7950 |
| GTTCACTACC CTCGTGGAAT CCTGACCCCA TGTAAATAAA ACCGTGACAG | 8000 |
| CTCATGGGGT GGGAGATATC GCTGTTCCTT AGGACCCTTT TACTAACCCT | 8050 |
| AATTCGATAG CATATGCTTC CCGTTGGGTA ACATATGCTA TTGAATTAGG | 8100 |
| GTTAGTCTGG ATAGTATATA CTACTACCCG GGAAGCATAT GCTACCCGTT | 8150 |
| TAGGGTTAAC AAGGGGGCCT TATAAACACT ATTGCTAATG CCCTCTTGAG | 8200 |
| GGTCCGCTTA TCGGTAGCTA CACAGGCCCC TCTGATTGAC GTTGGTGTAG | 8250 |
| CCTCCCGTAG TCTTCCTGGG CCCCTGGGAG GTACATGTCC CCCAGCATTG | 8300 |
| GTGTAAGAGC TTCAGCCAAG AGTTACACAT AAAGGCAATG TTGTGTTGCA | 8350 |
| GTCCACAGAC TGCAAAGTCT GCTCCAGGAT GAAAGCCACT CAGTGTTGGC | 8400 |
| AAATGTGCAC ATCCATTTAT AAGGATGTCA ACTACAGTCA GAGAACCCCT | 8450 |
| TTGTGTTTGG TCCCCCCCCG TGTCACATGT GGAACAGGGC CCAGTTGGCA | 8500 |
| AGTTGTACCA ACCAACTGAA GGGATTACAT GCACTGCCCC | 8540 |

(2) INFORMATION FOR SEQ ID NO:5:

(i) SEQUENCE CHARACTERISTICS:
        (A) LENGTH: 30 bases
        (B) TYPE: Nucleic Acid
        (C) STRANDEDNESS: Single
        (D) TOPOLOGY: Linear (ii) MOLECULE TYPE: Other nucleic acid
        (A) DESCRIPTION: Oligonucleotide primer UDEC690

(iii) HYPOTHETICAL: No (iv) ANTI-SENSE: No (xi) SEQUENCE DESCRIPTION: SEQ ID NO:5:

| | |
|---|---|
| CGCCTGCAGG ACATCCAGAT GACTCAGTCT | 30 |

(2) INFORMATION FOR SEQ ID NO:6:

(i) SEQUENCE CHARACTERISTICS:
        (A) LENGTH: 30 bases
        (B) TYPE: Nucleic Acid

```
        (C) STRANDEDNESS: Single
        (D) TOPOLOGY: Linear (ii) MOLECULE TYPE: Other nucleic acid
        (A) DESCRIPTION: Oligonucleotide primer UDEC395

(iii) HYPOTHETICAL: No (iv) ANTI-SENSE: Yes (xi) SEQUENCE DESCRIPTION: SEQ ID NO:6:

CCCAAGCTTA CTGGATGGTG GGAAGATGGA                                30

(2) INFORMATION FOR SEQ ID NO:7:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1M1 scFv (murine)

(xi) SEQUENCE DESCRIPTION: SEQ ID NO:7:

ATG GCC GAC ATC CAG ATG ACT CAG TCT CCA                         30
Met Ala Asp Ile Gln Met Thr Gln Ser Pro
1               5                   10

GCT TCA CTG TCT GCA TCT GTG GGA GAA ACT                         60
Ala Ser Leu Ser Ala Ser Val Gly Glu Thr
15                  20

GTC ACC ATC ACA TGT GGA GCA AGT GAG AAT                         90
Val Thr Ile Thr Cys Gly Ala Ser Glu Asn
25                  30

ATT TAC GGT GCT TTA AAT TGG TAT CAG CGG                         120
Ile Tyr Gly Ala Leu Asn Trp Tyr Gln Arg
35                  40

AAA CAG GGA AAA TCT CCT CAG CTC CTG ATC                         150
Lys Gln Gly Lys Ser Pro Gln Leu Leu Ile
45                  50

TAT GGT GCA ACC AAC TTG GCA GAT GGC ATG                         180
Tyr Gly Ala Thr Asn Leu Ala Asp Gly Met
55                  60

TCA TCG AGG TTC AGT GGC AGT GGA TCT GGT                         210
Ser Ser Arg Phe Ser Gly Ser Gly Ser Gly
65                  70

AGA CAG TAT TAT CTC AAG ATC AGT AGC CTG                         240
Arg Gln Tyr Tyr Leu Lys Ile Ser Ser Leu
75                  80

CAT CCT GAC GAT GTT GCA ACG TAT TAC TGT                         270
His Pro Asp Asp Val Ala Thr Tyr Tyr Cys
85                  90

CAA AAT GTG TTA AAT ACT CCT CTC ACG TTC                         300
Gln Asn Val Leu Asn Thr Pro Leu Thr Phe
95                  100

GGT GCT GGG ACC AAG TTG GAG CTG AAA CGG                         330
Gly Ala Gly Thr Lys Leu Glu Leu Lys Arg
105                 110

ACC GGA GGT GGC GGG TCG GGT GGC GGG GGA                         360
Thr Gly Gly Gly Gly Ser Gly Gly Gly Gly
115                 120

TCG GGT GGC GGA GGG TCG CAG GTT CAG CTG                         390
Ser Gly Gly Gly Gly Ser Gln Val Gln Leu
125                 130
```

-continued

```
CAG CAG TCT GGA GCC GAG CTG ATG AAG CCT                        420
Gln Gln Ser Gly Ala Glu Leu Met Lys Pro
135                 140

GGG GCC TCA GTG AAG ATG TCC TGC AAG GCT                        450
Gly Ala Ser Val Lys Met Ser Cys Lys Ala
145                 150

ACT GGC TAC ATA TTC AGT AAC TAC TGG ATA                        480
Thr Gly Tyr Ile Phe Ser Asn Tyr Trp Ile
155                 160

CAG TGG ATA AAG CAG AGG CCT GGA CAT GGC                        510
Gln Trp Ile Lys Gln Arg Pro Gly His Gly
165                 170

CTT GAG TGG ATT GGT GAG ATT TTA CCT GGA                        540
Leu Glu Trp Ile Gly Glu Ile Leu Pro Gly
175                 180

AGT GGT TCT ACT GAG TAC ACT GAG AAC TTC                        570
Ser Gly Ser Thr Glu Tyr Thr Glu Asn Phe
185                 190

AAG GAC AAG GCC GCA TTC ACT GCA GAT ACA                        600
Lys Asp Lys Ala Ala Phe Thr Ala Asp Thr
195                 200

TCC TCC AAC ACA GCC TAC ATG CAA CTC AGC                        630
Ser Ser Asn Thr Ala Tyr Met Gln Leu Ser
205                 210

AGC CTG ACA TCA GAG GAC TCT GCC GTC TAT                        660
Ser Leu Thr Ser Glu Asp Ser Ala Val Tyr
215                 220

TAC TGT GCA AGA TAT TTC TTC GGT AGT AGC                        690
Tyr Cys Ala Arg Tyr Phe Phe Gly Ser Ser
225                 230

CCC AAC TGG TAC TTC GAT GTC TGG GGC GCA                        720
Pro Asn Trp Tyr Phe Asp Val Trp Gly Ala
235                 240

GGG ACC ACG GTC ACC GTC TCC TCA TGA                            747
Gly Thr Thr Val Thr Val Ser Ser
245
```

(2) INFORMATION FOR SEQ ID NO:8:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 scFv CB (humanized)

(xi) SEQUENCE DESCRIPTION: SEQ ID NO:8:

```
ATG GCC GAT ATC CAG ATG ACC CAG TCC CCG                         30
Met Ala Asp Ile Gln Met Thr Gln Ser Pro
1                   5                   10

TCC TCC CTG TCC GCC TCT GTG GGC GAT AGG                         60
Ser Ser Leu Ser Ala Ser Val Gly Asp Arg
15                  20

GTC ACC ATC ACC TGC GGC GCC AGC GAA AAC                         90
Val Thr Ile Thr Cys Gly Ala Ser Glu Asn
25                  30

ATC TAT GGC GCG CTG AAC TGG TAT CAA CGT                        120
Ile Tyr Gly Ala Leu Asn Trp Tyr Gln Arg
35                  40
```

```
AAA CCT GGG AAA GCT CCG AAG CTT CTG ATT                           150
Lys Pro Gly Lys Ala Pro Lys Leu Leu Ile
 45              50

TAC GGT GCG ACG AAC CTG GCA GAT GGA GTC                           180
Tyr Gly Ala Thr Asn Leu Ala Asp Gly Val
 55              60

CCT TCT CGC TTC TCT GGA TCC GGC TCC GGA                           210
Pro Ser Arg Phe Ser Gly Ser Gly Ser Gly
 65              70

ACG GAT TTC ACT CTG ACC ATC AGC AGT CTG                           240
Thr Asp Phe Thr Leu Thr Ile Ser Ser Leu
 75              80

CAG CCT GAA GAC TTC GCT ACG TAT TAC TGT                           270
Gln Pro Glu Asp Phe Ala Thr Tyr Tyr Cys
 85              90

CAG AAC GTT TTA AAT ACT CCG TTG ACT TTC                           300
Gln Asn Val Leu Asn Thr Pro Leu Thr Phe
 95             100

GGA CAG GGT ACC AAG GTG GAA ATA AAA CGT                           330
Gly Gln Gly Thr Lys Val Glu Ile Lys Arg
105             110

ACT GGC GGT GGT GGT TCT GGT GGC GGT GGA                           360
Thr Gly Gly Gly Gly Ser Gly Gly Gly Gly
115             120

TCT GGT GGT GGC GGT TCT CAA GTC CAA CTG                           390
Ser Gly Gly Gly Gly Ser Gln Val Gln Leu
125             130

GTG CAA TCC GGC GCC GAG GTC AAG AAG CCA                           420
Val Gln Ser Gly Ala Glu Val Lys Lys Pro
135             140

GGG GCC TCA GTC AAA GTG TCC TGT AAA GCT                           450
Gly Ala Ser Val Lys Val Ser Cys Lys Ala
145             150

AGC GGC TAT ATT TTT TCT AAT TAT TGG ATT                           480
Ser Gly Tyr Ile Phe Ser Asn Tyr Trp Ile
155             160

CAA TGG GTG CGT CAG GCC CCC GGG CAG GGC                           510
Gln Trp Val Arg Gln Ala Pro Gly Gln Gly
165             170

CTG GAA TGG ATG GGT GAG ATC TTA CCG GGC                           540
Leu Glu Trp Met Gly Glu Ile Leu Pro Gly
175             180

TCT GGT AGC ACC GAA TAT ACC GAA AAT TTT                           570
Ser Gly Ser Thr Glu Tyr Thr Glu Asn Phe
185             190

AAA GAC CGT GTT ACT ATG ACG CGT GAC ACT                           600
Lys Asp Arg Val Thr Met Thr Arg Asp Thr
195             200

TCG ACT AGT ACA GTA TAC ATG GAG CTC TCC                           630
Ser Thr Ser Thr Val Tyr Met Glu Leu Ser
205             210

AGC CTG CGA TCG GAG GAC ACG GCC GTC TAT                           660
Ser Leu Arg Ser Glu Asp Thr Ala Val Tyr
215             220

TAT TGC GCG CGT TAT TTT TTT GGT TCT AGC                           690
Tyr Cys Ala Arg Tyr Phe Phe Gly Ser Ser
225             230

CCG AAT TGG TAT TTT GAT GTT TGG GGT CAA                           720
Pro Asn Trp Tyr Phe Asp Val Trp Gly Gln
235             240
```

```
GGA ACC CTG GTC ACT GTC TCG AGC TGA                              747
Gly Thr Leu Val Thr Val Ser Ser
245

(2) INFORMATION FOR SEQ ID NO:9:

(i) SEQUENCE CHARACTERISTICS:
        (A) LENGTH: 726 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1M1 VL HuK (chimeric light chain)

(xi) SEQUENCE DESCRIPTION: SEQ ID NO:9:

ATG GGA ATC CAA GGA GGG TCT GTC CTG TTC                           30
Met Gly Ile Gln Gly Gly Ser Val Leu Phe
-25             -20

GGG CTG CTG CTC GTC CTG GCT GTC TTC TGC                           60
Gly Leu Leu Leu Val Leu Ala Val Phe Cys
-15             -10

CAT TCA GGT CAT AGC CTG CAG GAC ATC CAG                           90
His Ser Gly His Ser Leu Gln Asp Ile Gln
-5               1               5

ATG ACT CAG TCT CCA GCT TCA CTG TCT GCA                          120
Met Thr Gln Ser Pro Ala Ser Leu Ser Ala
10              15

TCT GTG GGA GAA ACT GTC ACC ATC ACA TGT                          150
Ser Val Gly Glu Thr Val Thr Ile Thr Cys
20              25

GGA GCA AGT GAG AAT ATT TAC GGT GCT TTA                          180
Gly Ala Ser Glu Asn Ile Tyr Gly Ala Leu
30              35

AAT TGG TAT CAG CGG AAA CAG GGA AAA TCT                          210
Asn Trp Tyr Gln Arg Lys Gln Gly Lys Ser
40              45

CCT CAG CTC CTG ATC TAT GGT GCA ACC AAC                          240
Pro Gln Leu Leu Ile Tyr Gly Ala Thr Asn
50              55

TTG GCA GAT GGC ATG TCA TCG AGG TTC AGT                          270
Leu Ala Asp Gly Met Ser Ser Arg Phe Ser
60              65

GGC AGT GGA TCT GGT AGA CAG TAT TAT CTC                          300
Gly Ser Gly Ser Gly Arg Gln Tyr Tyr Leu
70              75

AAG ATC AGT AGC CTG CAT CCT GAC GAT GTT                          330
Lys Ile Ser Ser Leu His Pro Asp Asp Val
80              85

GCA ACG TAT TAC TGT CAA AAT GTG TTA AAT                          360
Ala Thr Tyr Tyr Cys Gln Asn Val Leu Asn
90              95

ACT CCT CTC ACG TTC GGT GCT GGG ACC AAG                          390
Thr Pro Leu Thr Phe Gly Ala Gly Thr Lys
100             105

TTG GAG CTG AAA CGA ACT GTG GCT GCA CCA                          420
Leu Glu Leu Lys Arg Thr Val Ala Ala Pro
110             115

TCT GTC TTC ATC TTC CCG CCA TCT GAT GAG                          450
Ser Val Phe Ile Phe Pro Pro Ser Asp Glu
120             125
```

```
CAG TTG AAA TCT GGA ACT GCC TCT GTT GTG                              480
Gln Leu Lys Ser Gly Thr Ala Ser Val Val
130                 135

TGC CTG CTG AAT AAC TTC TAT CCC AGA GAG                              510
Cys Leu Leu Asn Asn Phe Tyr Pro Arg Glu
140                 145

GCC AAA GTA CAG TGG AAG GTG GAT AAC GCC                              540
Ala Lys Val Gln Trp Lys Val Asp Asn Ala
150                 155

CTC CAA TCG GGT AAC TCC CAG GAG AGT GTC                              570
Leu Gln Ser Gly Asn Ser Gln Glu Ser Val
160                 165

ACA GAG CAG GAC AGC AAG GAC AGC ACC TAC                              600
Thr Glu Gln Asp Ser Lys Asp Ser Thr Tyr
170                 175

AGC CTC AGC AGC ACC CTG ACG CTG AGC AAA                              630
Ser Leu Ser Ser Thr Leu Thr Leu Ser Lys
180                 185

GCA GAC TAC GAG AAA CAC AAA GTC TAC GCC                              660
Ala Asp Tyr Glu Lys His Lys Val Tyr Ala
190                 195

TGC GAA GTC ACC CAT CAG GGC CTG AGC TCG                              690
Cys Glu Val Thr His Gln Gly Leu Ser Ser
200                 205

CCC GTC ACA AAG AGC TTC AAC AGG GGA GAG                              720
Pro Val Thr Lys Ser Phe Asn Arg Gly Glu
210                 215

TGT TAG                                                              726
Cys (2) INFORMATION FOR SEQ ID NO:10:

(i) SEQUENCE CHARACTERISTICS:
        (A) LENGTH: 750 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1M1 VH +HuG1 (chimeric Fd)

(xi) SEQUENCE DESCRIPTION: SEQ ID NO:10:

ATG AAA TGG AGC TGG GTT ATT CTC TTC CTC                               30
Met Lys Trp Ser Trp Val Ile Leu Phe Leu
-15                 -10

CTG TCA GTA ACT GCA GGT GTC CAC TCC CAG                               60
Leu Ser Val Thr Ala Gly Val His Ser Gln
-5                  1

GTT CAG CTG CAG CAG TCT GGA GCT GAG CTG                               90
Val Gln Leu Gln Gln Ser Gly Ala Glu Leu
5                   10

ATG AAG CCT GGG GCC TCA GTG AAG ATG TCC                              120
Met Lys Pro Gly Ala Ser Val Lys Met Ser
15                  20

TGC AAG GCT ACT GGC TAC ATA TTC AGT AAC                              150
Cys Lys Ala Thr Gly Tyr Ile Phe Ser Asn
25                  30

TAC TGG ATA CAG TGG ATA AAG CAG AGG CCT                              180
Tyr Trp Ile Gln Trp Ile Lys Gln Arg Pro
35                  40

GGA CAT GGC CTT GAG TGG ATT GGT GAG ATT                              210
Gly His Gly Leu Glu Trp Ile Gly Glu Ile
45                  50
```

```
TTA CCT GGA AGT GGT TCT ACT GAG TAC ACT                              240
Leu Pro Gly Ser Gly Ser Thr Glu Tyr Thr
 55                  60

GAG AAC TTC AAG GAC AAG GCC GCA TTC ACT                              270
Glu Asn Phe Lys Asp Lys Ala Ala Phe Thr
 65                  70

GCA GAT ACA TCC TCC AAC ACA GCC TAC ATG                              300
Ala Asp Thr Ser Ser Asn Thr Ala Tyr Met
 75                  80

CAA CTC AGC AGC CTG ACA TCA GAG GAC TCT                              330
Gln Leu Ser Ser Leu Thr Ser Glu Asp Ser
 85                  90

GCC GTC TAT TAC TGT GCA AGA TAT TTC TTC                              360
Ala Val Tyr Tyr Cys Ala Arg Tyr Phe Phe
 95                 100

GGT AGT AGC CCC AAC TGG TAC TTC GAT GTC                              390
Gly Ser Ser Pro Asn Trp Tyr Phe Asp Val
105                 110

TGG GGC GCA GGG ACC ACG GTC ACC GTC TCC                              420
Trp Gly Ala Gly Thr Thr Val Thr Val Ser
115                 120

TCA GCC TCC ACC AAG GGC CCA TCG GTC TTC                              450
Ser Ala Ser Thr Lys Gly Pro Ser Val Phe
125                 130

CCC CTG GCG CCC TCC TCC AAG AGC ACC TCT                              480
Pro Leu Ala Pro Ser Ser Lys Ser Thr Ser
135                 140

GGG GGC ACA GCG GCC CTG GGC TGC CTG GTC                              510
Gly Gly Thr Ala Ala Leu Gly Cys Leu Val
145                 150

AAG GAC TAC TTC CCC GAA CCG GTG ACG GTG                              540
Lys Asp Tyr Phe Pro Glu Pro Val Thr Val
155                 160

TCG TGG AAC TCA GGC GCC CTG ACC AGC GGC                              570
Ser Trp Asn Ser Gly Ala Leu Thr Ser Gly
165                 170

GTG CAC ACC TTC CCG GCT GTC CTA CAG TCC                              600
Val His Thr Phe Pro Ala Val Leu Gln Ser
175                 180

TCA GGA CTC TAC TCC CTC AGC AGC GTG GTG                              630
Ser Gly Leu Tyr Ser Leu Ser Ser Val Val
185                 190

ACC GTG CCC TCC AGC AGC TTG GGC ACC CAG                              660
Thr Val Pro Ser Ser Ser Leu Gly Thr Gln
195                 200

ACC TAC ATC TGC AAC GTG AAT CAC AAG CCC                              690
Thr Tyr Ile Cys Asn Val Asn His Lys Pro
205                 210

AGC AAC ACC AAG GTG GAC AAG AAA GTT GAG                              720
Ser Asn Thr Lys Val Asp Lys Lys Val Glu
215                 220

CCC AAA TCT TGT GAC AAA ACT CAC ACA TAA                              750
Pro Lys Ser Cys Asp Lys Thr His Thr
225
```

(2) INFORMATION FOR SEQ ID NO:11:

(i) SEQUENCE CHARACTERISTICS:
        (A) LENGTH: 750 base pairs
        (B) TYPE: Nucleic Acid
        (C) STRANDEDNESS: Double
        (D) TOPOLOGY: linear (ii) MOLECULE TYPE: Other nucleic acid
    (A) DESCRIPTION:5G1.1 VH + IGHRL (Humanized Fd)

(xi) SEQUENCE DESCRIPTION: SEQ ID NO:11:

| | | |
|---|---|---|
| ATG AAG TGG AGC TGG GTT ATT CTC TTC CTC<br>Met Lys Trp Ser Trp Val Ile Leu Phe Leu<br>-15                    -10 | | 30 |
| CTG TCA GTA ACT GCC GGC GTC CAC TCC CAA<br>Leu Ser Val Thr Ala Gly Val His Ser Gln<br>-5                       1 | | 60 |
| GTC CAA CTG GTG CAA TCC GGC GCC GAG GTC<br>Val Gln Leu Val Gln Ser Gly Ala Glu Val<br>5                       10 | | 90 |
| AAG AAG CCA GGG GCC TCA GTC AAA GTG TCC<br>Lys Lys Pro Gly Ala Ser Val Lys Val Ser<br>15                      20 | | 120 |
| TGT AAA GCT AGC GGC TAT ATT TTT TCT AAT<br>Cys Lys Ala Ser Gly Tyr Ile Phe Ser Asn<br>25                      30 | | 150 |
| TAT TGG ATT CAA TGG GTG CGT CAG GCC CCC<br>Tyr Trp Ile Gln Trp Val Arg Gln Ala Pro<br>35                      40 | | 180 |
| GGG CAG GGC CTG GAA TGG ATG GGT GAG ATC<br>Gly Gln Gly Leu Glu Trp Met Gly Glu Ile<br>45                      50 | | 210 |
| TTA CCG GGC TCT GGT AGC ACC GAA TAT GCC<br>Leu Pro Gly Ser Gly Ser Thr Glu Tyr Ala<br>55                      60 | | 240 |
| CAA AAA TTC CAG GGC CGT GTT ACT ATG ACT<br>Gln Lys Phe Gln Gly Arg Val Thr Met Thr<br>65                      70 | | 270 |
| GCG GAC ACT TCG ACT AGT ACA GCC TAC ATG<br>Ala Asp Thr Ser Thr Ser Thr Ala Tyr Met<br>75                      80 | | 300 |
| GAG CTC TCC AGC CTG CGA TCG GAG GAC ACG<br>Glu Leu Ser Ser Leu Arg Ser Glu Asp Thr<br>85                      90 | | 330 |
| GCC GTC TAT TAT TGC GCG CGT TAT TTT TTT<br>Ala Val Tyr Tyr Cys Ala Arg Tyr Phe Phe<br>95                     100 | | 360 |
| GGT TCT AGC CCG AAT TGG TAT TTT GAT GTT<br>Gly Ser Ser Pro Asn Trp Tyr Phe Asp Val<br>105                    110 | | 390 |
| TGG GGT CAA GGA ACC CTG GTC ACT GTC TCG<br>Trp Gly Gln Gly Thr Leu Val Thr Val Ser<br>115                    120 | | 420 |
| AGC GCC TCC ACC AAG GGC CCA TCG GTC TTC<br>Ser Ala Ser Thr Lys Gly Pro Ser Val Phe<br>125                    130 | | 450 |
| CCC CTG GCG CCC TCC TCC AAG AGC ACC TCT<br>Pro Leu Ala Pro Ser Ser Lys Ser Thr Ser<br>135                    140 | | 480 |
| GGG GGC ACA GCG GCC CTG GGC TGC CTG GTC<br>Gly Gly Thr Ala Ala Leu Gly Cys Leu Val<br>145                    150 | | 510 |
| AAG GAC TAC TTC CCC GAA CCG GTG ACG GTG<br>Lys Asp Tyr Phe Pro Glu Pro Val Thr Val<br>155                    160 | | 540 |

```
TCG TGG AAC TCA GGC GCC CTG ACC AGC GGC                                570
Ser Trp Asn Ser Gly Ala Leu Thr Ser Gly
165                 170

GTG CAC ACC TTC CCG GCT GTC CTA CAG TCC                                600
Val His Thr Phe Pro Ala Val Leu Gln Ser
175                 180

TCA GGA CTC TAC TCC CTC AGC AGC GTG GTG                                630
Ser Gly Leu Tyr Ser Leu Ser Ser Val Val
185                 190

ACC GTG CCC TCC AGC AGC TTG GGC ACC CAG                                660
Thr Val Pro Ser Ser Ser Leu Gly Thr Gln
195                 200

ACC TAC ATC TGC AAC GTG AAT CAC AAG CCC                                690
Thr Tyr Ile Cys Asn Val Asn His Lys Pro
205                 210

AGC AAC ACC AAG GTG GAC AAG AAA GTT GAG                                720
Ser Asn Thr Lys Val Asp Lys Lys Val Glu
215                 220

CCC AAA TCT TGT GAC AAA ACT CAC ACA TAA                                750
Pro Lys Ser Cys Asp Lys Thr His Thr
225                 230
```

(2) INFORMATION FOR SEQ ID NO:12:

(i) SEQUENCE CHARACTERISTICS:
        (A) LENGTH: 750 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 VH + IGHRLC (Humanized Fd)

(xi) SEQUENCE DESCRIPTION: SEQ ID NO:12:

```
ATG AAG TGG AGC TGG GTT ATT CTC TTC CTC                                30
Met Lys Trp Ser Trp Val Ile Leu Phe Leu
-15                 -10

CTG TCA GTA ACT GCC GGC GTC CAC TCC CAA                                60
Leu Ser Val Thr Ala Gly Val His Ser Gln
-5                  1

GTC CAA CTG GTG CAA TCC GGC GCC GAG GTC                                90
Val Gln Leu Val Gln Ser Gly Ala Glu Val
5                   10

AAG AAG CCA GGG GCC TCA GTC AAA GTG TCC                                120
Lys Lys Pro Gly Ala Ser Val Lys Val Ser
15                  20

TGT AAA GCT AGC GGC TAT ATT TTT TCT AAT                                150
Cys Lys Ala Ser Gly Tyr Ile Phe Ser Asn
25                  30

TAT TGG ATT CAA TGG GTG CGT CAG GCC CCC                                180
Tyr Trp Ile Gln Trp Val Arg Gln Ala Pro
35                  40

GGG CAG GGC CTG GAA TGG ATG GGT GAG ATC                                210
Gly Gln Gly Leu Glu Trp Met Gly Glu Ile
45                  50

TTA CCG GGC TCT GGT AGC ACC GAA TAT ACC                                240
Leu Pro Gly Ser Gly Ser Thr Glu Tyr Thr
55                  60

GAA AAT TTT AAA GAC CGT GTT ACT ATG ACG                                270
Glu Asn Phe Lys Asp Arg Val Thr Met Thr
65                  70
```

```
CGT GAC ACT TCG ACT AGT ACA GTA TAC ATG                           300
Arg Asp Thr Ser Thr Ser Thr Val Tyr Met
75                  80

GAG CTC TCC AGC CTG CGA TCG GAG GAC ACG                           330
Glu Leu Ser Ser Leu Arg Ser Glu Asp Thr
85                  90

GCC GTC TAT TAT TGC GCG CGT TAT TTT TTT                           360
Ala Val Tyr Tyr Cys Ala Arg Tyr Phe Phe
95                 100

GGT TCT AGC CCG AAT TGG TAT TTT GAT GTT                           390
Gly Ser Ser Pro Asn Trp Tyr Phe Asp Val
105                 110

TGG GGT CAA GGA ACC CTG GTC ACT GTC TCG                           420
Trp Gly Gln Gly Thr Leu Val Thr Val Ser
115                 120

AGC GCC TCC ACC AAG GGC CCA TCG GTC TTC                           450
Ser Ala Ser Thr Lys Gly Pro Ser Val Phe
125                 130

CCC CTG GCG CCC TCC TCC AAG AGC ACC TCT                           480
Pro Leu Ala Pro Ser Ser Lys Ser Thr Ser
135                 140

GGG GGC ACA GCG GCC CTG GGC TGC CTG GTC                           510
Gly Gly Thr Ala Ala Leu Gly Cys Leu Val
145                 150

AAG GAC TAC TTC CCC GAA CCG GTG ACG GTG                           540
Lys Asp Tyr Phe Pro Glu Pro Val Thr Val
155                 160

TCG TGG AAC TCA GGC GCC CTG ACC AGC GGC                           570
Ser Trp Asn Ser Gly Ala Leu Thr Ser Gly
165                 170

GTG CAC ACC TTC CCG GCT GTC CTA CAG TCC                           600
Val His Thr Phe Pro Ala Val Leu Gln Ser
175                 180

TCA GGA CTC TAC TCC CTC AGC AGC GTG GTG                           630
Ser Gly Leu Tyr Ser Leu Ser Ser Val Val
185                 190

ACC GTG CCC TCC AGC AGC TTG GGC ACC CAG                           660
Thr Val Pro Ser Ser Ser Leu Gly Thr Gln
195                 200

ACC TAC ATC TGC AAC GTG AAT CAC AAG CCC                           690
Thr Tyr Ile Cys Asn Val Asn His Lys Pro
205                 210

AGC AAC ACC AAG GTG GAC AAG AAA GTT GAG                           720
Ser Asn Thr Lys Val Asp Lys Lys Val Glu
215                 220

CCC AAA TCT TGT GAC AAA ACT CAC ACA TAA                           750
Pro Lys Ser Cys Asp Lys Thr His Thr
225                 230
```

(2) INFORMATION FOR SEQ ID NO:13:

(i) SEQUENCE CHARACTERISTICS:
        (A) LENGTH: 726 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 VL +KLV56
        (Humanized light chain)

(xi) SEQUENCE DESCRIPTION: SEQ ID NO:13:

| | | | | | | | | | |
|---|---|---|---|---|---|---|---|---|---|
| ATG | GGA | ATC | CAA | GGA | GGG | TCT | GTC | CTG | TTC | 30
| Met | Gly | Ile | Gln | Gly | Gly | Ser | Val | Leu | Phe |
| -25 | | | | -20 | | | | | |

| | | | | | | | | | |
|---|---|---|---|---|---|---|---|---|---|
| GGG | CTG | CTG | CTC | GTC | CTG | GCT | GTC | TTC | TGC | 60
| Gly | Leu | Leu | Leu | Val | Leu | Ala | Val | Phe | Cys |
| -15 | | | | -10 | | | | | |

| | | | | | | | | | |
|---|---|---|---|---|---|---|---|---|---|
| CAT | TCA | GGT | CAT | AGC | CTG | CAG | GAT | ATC | CAG | 90
| His | Ser | Gly | His | Ser | Leu | Gln | Asp | Ile | Gln |
| -5 | | | | 1 | | | | 5 | |

| | | | | | | | | | |
|---|---|---|---|---|---|---|---|---|---|
| ATG | ACC | CAG | TCC | CCG | TCC | TCC | CTG | TCC | GCC | 120
| Met | Thr | Gln | Ser | Pro | Ser | Ser | Leu | Ser | Ala |
| 10 | | | | 15 | | | | | |

| | | | | | | | | | |
|---|---|---|---|---|---|---|---|---|---|
| TCT | GTG | GGC | GAT | AGG | GTC | ACC | ATC | ACC | TGC | 150
| Ser | Val | Gly | Asp | Arg | Val | Thr | Ile | Thr | Cys |
| 20 | | | | 25 | | | | | |

| | | | | | | | | | |
|---|---|---|---|---|---|---|---|---|---|
| GGC | GCC | AGC | GAA | AAC | ATC | TAT | GGC | GCG | CTG | 180
| Gly | Ala | Ser | Glu | Asn | Ile | Tyr | Gly | Ala | Leu |
| 30 | | | | 35 | | | | | |

| | | | | | | | | | |
|---|---|---|---|---|---|---|---|---|---|
| AAC | TGG | TAT | CAA | CGT | AAA | CCT | GGG | AAA | GCT | 210
| Asn | Trp | Tyr | Gln | Arg | Lys | Pro | Gly | Lys | Ala |
| 40 | | | | 45 | | | | | |

| | | | | | | | | | |
|---|---|---|---|---|---|---|---|---|---|
| CCG | AAG | CTT | CTG | ATT | TAC | GGT | GCG | ACG | AAC | 240
| Pro | Lys | Leu | Leu | Ile | Tyr | Gly | Ala | Thr | Asn |
| 50 | | | | 55 | | | | | |

| | | | | | | | | | |
|---|---|---|---|---|---|---|---|---|---|
| CTG | GCA | GAT | GGA | GTC | CCT | TCT | CGC | TTC | TCT | 270
| Leu | Ala | Asp | Gly | Val | Pro | Ser | Arg | Phe | Ser |
| 60 | | | | 65 | | | | | |

| | | | | | | | | | |
|---|---|---|---|---|---|---|---|---|---|
| GGA | TCC | GGC | TCC | GGA | ACG | GAT | TAC | ACT | CTG | 300
| Gly | Ser | Gly | Ser | Gly | Thr | Asp | Tyr | Thr | Leu |
| 70 | | | | 75 | | | | | |

| | | | | | | | | | |
|---|---|---|---|---|---|---|---|---|---|
| ACC | ATC | AGC | AGT | CTG | CAA | CCT | GAG | GAC | TTC | 330
| Thr | Ile | Ser | Ser | Leu | Gln | Pro | Glu | Asp | Phe |
| 80 | | | | 85 | | | | | |

| | | | | | | | | | |
|---|---|---|---|---|---|---|---|---|---|
| GCT | ACG | TAT | TAC | TGT | CAG | AAC | GTT | TTA | AAT | 360
| Ala | Thr | Tyr | Tyr | Cys | Gln | Asn | Val | Leu | Asn |
| 90 | | | | 95 | | | | | |

| | | | | | | | | | |
|---|---|---|---|---|---|---|---|---|---|
| ACT | CCG | TTG | ACT | TTC | GGA | CAG | GGT | ACC | AAG | 390
| Thr | Pro | Leu | Thr | Phe | Gly | Gln | Gly | Thr | Lys |
| 100 | | | | 105 | | | | | |

| | | | | | | | | | |
|---|---|---|---|---|---|---|---|---|---|
| GTG | GAA | ATA | AAA | CGA | ACT | GTG | GCT | GCA | CCA | 420
| Val | Glu | Ile | Lys | Arg | Thr | Val | Ala | Ala | Pro |
| 110 | | | | 115 | | | | | |

| | | | | | | | | | |
|---|---|---|---|---|---|---|---|---|---|
| TCT | GTC | TTC | ATC | TTC | CCG | CCA | TCT | GAT | GAG | 450
| Ser | Val | Phe | Ile | Phe | Pro | Pro | Ser | Asp | Glu |
| 120 | | | | 125 | | | | | |

| | | | | | | | | | |
|---|---|---|---|---|---|---|---|---|---|
| CAG | TTG | AAA | TCT | GGA | ACT | GCC | TCT | GTT | GTG | 480
| Gln | Leu | Lys | Ser | Gly | Thr | Ala | Ser | Val | Val |
| 130 | | | | 135 | | | | | |

| | | | | | | | | | |
|---|---|---|---|---|---|---|---|---|---|
| TGC | CTG | CTG | AAT | AAC | TTC | TAT | CCC | AGA | GAG | 510
| Cys | Leu | Leu | Asn | Asn | Phe | Tyr | Pro | Arg | Glu |
| 140 | | | | 145 | | | | | |

| | | | | | | | | | |
|---|---|---|---|---|---|---|---|---|---|
| GCC | AAA | GTA | CAG | TGG | AAG | GTG | GAT | AAC | GCC | 540
| Ala | Lys | Val | Gln | Trp | Lys | Val | Asp | Asn | Ala |
| 150 | | | | 155 | | | | | |

| | | | | | | | | | |
|---|---|---|---|---|---|---|---|---|---|
| CTC | CAA | TCG | GGT | AAC | TCC | CAG | GAG | AGT | GTC | 570
| Leu | Gln | Ser | Gly | Asn | Ser | Gln | Glu | Ser | Val |
| 160 | | | | 165 | | | | | |

```
ACA GAG CAG GAC AGC AAG GAC AGC ACC TAC                          600
Thr Glu Gln Asp Ser Lys Asp Ser Thr Tyr
170                 175

AGC CTC AGC AGC ACC CTG ACG CTG AGC AAA                          630
Ser Leu Ser Ser Thr Leu Thr Leu Ser Lys
180                 185

GCA GAC TAC GAG AAA CAC AAA GTC TAC GCC                          660
Ala Asp Tyr Glu Lys His Lys Val Tyr Ala
190                 195

TGC GAA GTC ACC CAT CAG GGC CTG AGC TCG                          690
Cys Glu Val Thr His Gln Gly Leu Ser Ser
200                 205

CCC GTC ACA AAG AGC TTC AAC AGG GGA GAG                          720
Pro Val Thr Lys Ser Phe Asn Arg Gly Glu
210                 215

TGT TAG                                                          726
Cys (2) INFORMATION FOR SEQ ID NO:14:

(i) SEQUENCE CHARACTERISTICS:
        (A) LENGTH:  726 base pairs
        (B) TYPE:  Nucleic Acid
        (C) STRANDEDNESS:  Double
        (D) TOPOLOGY:  linear (ii) MOLECULE TYPE:  Other nucleic acid
        (A) DESCRIPTION:5G1.1 VL +KLV56B
            (Humanized light chain)

(xi) SEQUENCE DESCRIPTION:  SEQ ID NO:14:

ATG GGA ATC CAA GGA GGG TCT GTC CTG TTC                          30
Met Gly Ile Gln Gly Gly Ser Val Leu Phe
-25                 -20

GGG CTG CTG CTC GTC CTG GCT GTC TTC TGC                          60
Gly Leu Leu Leu Val Leu Ala Val Phe Cys
-15                 -10

CAT TCA GGT CAT AGC CTG CAG GAT ATC CAG                          90
His Ser Gly His Ser Leu Gln Asp Ile Gln
-5                   1                   5

ATG ACC CAG TCC CCG TCC TCC CTG TCC GCC                         120
Met Thr Gln Ser Pro Ser Ser Leu Ser Ala
10                  15

TCT GTG GGC GAT AGG GTC ACC ATC ACC TGC                         150
Ser Val Gly Asp Arg Val Thr Ile Thr Cys
20                  25

GGC GCC AGC GAA AAC ATC TAT GGC GCG CTG                         180
Gly Ala Ser Glu Asn Ile Tyr Gly Ala Leu
30                  35

AAC TGG TAT CAA CGT AAA CCT GGG AAA GCT                         210
Asn Trp Tyr Gln Arg Lys Pro Gly Lys Ala
40                  45

CCG AAG CTT CTG ATT TAC GGT GCG ACG AAC                         240
Pro Lys Leu Leu Ile Tyr Gly Ala Thr Asn
50                  55

CTG GCA GAT GGA GTC CCT TCT CGC TTC TCT                         270
Leu Ala Asp Gly Val Pro Ser Arg Phe Ser
60                  65

GGA TCC GGC TCC GGA ACG GAT TTC ACT CTG                         300
Gly Ser Gly Ser Gly Thr Asp Phe Thr Leu
70                  75
```

-continued

```
ACC ATC AGC AGT CTG CAG CCT GAA GAC TTC                              330
Thr Ile Ser Ser Leu Gln Pro Glu Asp Phe
 80                  85

GCT ACG TAT TAC TGT CAG AAC GTT TTA AAT                              360
Ala Thr Tyr Tyr Cys Gln Asn Val Leu Asn
 90                  95

ACT CCG TTG ACT TTC GGA CAG GGT ACC AAG                              390
Thr Pro Leu Thr Phe Gly Gln Gly Thr Lys
100                 105

GTG GAA ATA AAA CGA ACT GTG GCT GCA CCA                              420
Val Glu Ile Lys Arg Thr Val Ala Ala Pro
110                 115

TCT GTC TTC ATC TTC CCG CCA TCT GAT GAG                              450
Ser Val Phe Ile Phe Pro Pro Ser Asp Glu
120                 125

CAG TTG AAA TCT GGA ACT GCC TCT GTT GTG                              480
Gln Leu Lys Ser Gly Thr Ala Ser Val Val
130                 135

TGC CTG CTG AAT AAC TTC TAT CCC AGA GAG                              510
Cys Leu Leu Asn Asn Phe Tyr Pro Arg Glu
140                 145

GCC AAA GTA CAG TGG AAG GTG GAT AAC GCC                              540
Ala Lys Val Gln Trp Lys Val Asp Asn Ala
150                 155

CTC CAA TCG GGT AAC TCC CAG GAG AGT GTC                              570
Leu Gln Ser Gly Asn Ser Gln Glu Ser Val
160                 165

ACA GAG CAG GAC AGC AAG GAC AGC ACC TAC                              600
Thr Glu Gln Asp Ser Lys Asp Ser Thr Tyr
170                 175

AGC CTC AGC AGC ACC CTG ACG CTG AGC AAA                              630
Ser Leu Ser Ser Thr Leu Thr Leu Ser Lys
180                 185

GCA GAC TAC GAG AAA CAC AAA GTC TAC GCC                              660
Ala Asp Tyr Glu Lys His Lys Val Tyr Ala
190                 195

TGC GAA GTC ACC CAT CAG GGC CTG AGC TCG                              690
Cys Glu Val Thr His Gln Gly Leu Ser Ser
200                 205

CCC GTC ACA AAG AGC TTC AAC AGG GGA GAG                              720
Pro Val Thr Lys Ser Phe Asn Arg Gly Glu
210                 215

TGT TAG                                                              726
Cys
```

(2) INFORMATION FOR SEQ ID NO:15:

(i) SEQUENCE CHARACTERISTICS:
        (A) LENGTH: 711 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 VL + O12
        (Humanized light chain)

(xi) SEQUENCE DESCRIPTION: SEQ ID NO:15:

```
ATG GAC ATG AGG GTC CCC GCT CAG CTC CTG                               30
Met Asp Met Arg Val Pro Ala Gln Leu Leu
-20                 -15
```

```
GGG CTC CTG CTA CTC TGG CTC CGA GGT GCC                              60
Gly Leu Leu Leu Leu Trp Leu Arg Gly Ala
-10                 -5

AGA TGT GAT ATC CAG ATG ACC CAG TCC CCG                              90
Arg Cys Asp Ile Gln Met Thr Gln Ser Pro
 1               5

TCC TCC CTG TCC GCC TCT GTG GGC GAT AGG                             120
Ser Ser Leu Ser Ala Ser Val Gly Asp Arg
10              15

GTC ACC ATC ACC TGC GGC GCC AGC GAA AAC                             150
Val Thr Ile Thr Cys Gly Ala Ser Glu Asn
20              25

ATC TAT GGC GCG CTG AAC TGG TAT CAA CAG                             180
Ile Tyr Gly Ala Leu Asn Trp Tyr Gln Gln
30              35

AAA CCC GGG AAA GCT CCG AAG CTT CTG ATT                             210
Lys Pro Gly Lys Ala Pro Lys Leu Leu Ile
40              45

TAC GGT GCG ACG AAC CTG GCA GAT GGA GTC                             240
Tyr Gly Ala Thr Asn Leu Ala Asp Gly Val
50              55

CCT TCT CGC TTC TCT GGA TCC GGC TCC GGA                             270
Pro Ser Arg Phe Ser Gly Ser Gly Ser Gly
60              65

ACG GAT TTC ACT CTG ACC ATC AGC AGT CTG                             300
Thr Asp Phe Thr Leu Thr Ile Ser Ser Leu
70              75

CAG CCT GAA GAC TTC GCT ACG TAT TAC TGT                             330
Gln Pro Glu Asp Phe Ala Thr Tyr Tyr Cys
80              85

CAG AAC GTT TTA AAT ACT CCG TTG ACT TTC                             360
Gln Asn Val Leu Asn Thr Pro Leu Thr Phe
90              95

GGA CAG GGT ACC AAG GTG GAA ATA AAA CGA                             390
Gly Gln Gly Thr Lys Val Glu Ile Lys Arg
100             105

ACT GTG GCT GCA CCA TCT GTC TTC ATC TTC                             420
Thr Val Ala Ala Pro Ser Val Phe Ile Phe
110             115

CCG CCA TCT GAT GAG CAG TTG AAA TCT GGA                             450
Pro Pro Ser Asp Glu Gln Leu Lys Ser Gly
120             125

ACT GCC TCT GTT GTG TGC CTG CTG AAT AAC                             480
Thr Ala Ser Val Val Cys Leu Leu Asn Asn
130             135

TTC TAT CCC AGA GAG GCC AAA GTA CAG TGG                             510
Phe Tyr Pro Arg Glu Ala Lys Val Gln Trp
140             145

AAG GTG GAT AAC GCC CTC CAA TCG GGT AAC                             540
Lys Val Asp Asn Ala Leu Gln Ser Gly Asn
150             155

TCC CAG GAG AGT GTC ACA GAG CAG GAC AGC                             570
Ser Gln Glu Ser Val Thr Glu Gln Asp Ser
160             165

AAG GAC AGC ACC TAC AGC CTC AGC AGC ACC                             600
Lys Asp Ser Thr Tyr Ser Leu Ser Ser Thr
170             175

CTG ACG CTG AGC AAA GCA GAC TAC GAG AAA                             630
Leu Thr Leu Ser Lys Ala Asp Tyr Glu Lys
180             185
```

```
CAC AAA GTC TAC GCC TGC GAA GTC ACC CAT                              660
His Lys Val Tyr Ala Cys Glu Val Thr His
190                     195

CAG GGC CTG AGC TCG CCC GTC ACA AAG AGC                              690
Gln Gly Leu Ser Ser Pro Val Thr Lys Ser
200                     205

TTC AAC AGG GGA GAG TGT TAG                                          711
Phe Asn Arg Gly Glu Cys
210
```

(2) INFORMATION FOR SEQ ID NO:16:

(i) SEQUENCE CHARACTERISTICS:
        (A) LENGTH: 750 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 VH + IGHRLD
        (Humanized Fd)

(xi) SEQUENCE DESCRIPTION: SEQ ID NO:16:

```
ATG AAG TGG AGC TGG GTT ATT CTC TTC CTC                              30
Met Lys Trp Ser Trp Val Ile Leu Phe Leu
-15                     -10

CTG TCA GTA ACT GCC GGC GTC CAC TCC CAA                              60
Leu Ser Val Thr Ala Gly Val His Ser Gln
-5                      1

GTC CAA CTG GTG CAA TCC GGC GCC GAG GTC                              90
Val Gln Leu Val Gln Ser Gly Ala Glu Val
5                       10

AAG AAG CCA GGG GCC TCA GTC AAA GTG TCC                              120
Lys Lys Pro Gly Ala Ser Val Lys Val Ser
15                      20

TGT AAA GCT AGC GGC TAT ATT TTT TCT AAT                              150
Cys Lys Ala Ser Gly Tyr Ile Phe Ser Asn
25                      30

TAT TGG ATT CAA TGG GTG CGT CAG GCC CCC                              180
Tyr Trp Ile Gln Trp Val Arg Gln Ala Pro
35                      40

GGG CAG GGC CTG GAA TGG ATG GGT GAG ATC                              210
Gly Gln Gly Leu Glu Trp Met Gly Glu Ile
45                      50

TTA CCG GGC TCT GGT AGC ACC GAA TAT GCC                              240
Leu Pro Gly Ser Gly Ser Thr Glu Tyr Ala
55                      60

CAA AAA TTC CAG GGC CGT GTT ACT ATG ACT                              270
Gln Lys Phe Gln Gly Arg Val Thr Met Thr
65                      70

CGT GAC ACT TCG ACT AGT ACA GTA TAC ATG                              300
Arg Asp Thr Ser Thr Ser Thr Val Tyr Met
75                      80

GAG CTC TCC AGC CTG CGA TCG GAG GAC ACG                              330
Glu Leu Ser Ser Leu Arg Ser Glu Asp Thr
85                      90

GCC GTC TAT TAT TGC GCG CGT TAT TTT TTT                              360
Ala Val Tyr Tyr Cys Ala Arg Tyr Phe Phe
95                      100

GGT TCT AGC CCG AAT TGG TAT TTT GAT GTT                              390
Gly Ser Ser Pro Asn Trp Tyr Phe Asp Val
105                     110
```

```
TGG GGT CAA GGA ACC CTG GTC ACT GTC TCG                          420
Trp Gly Gln Gly Thr Leu Val Thr Val Ser
115                 120

AGC GCC TCC ACC AAG GGC CCA TCG GTC TTC                          450
Ser Ala Ser Thr Lys Gly Pro Ser Val Phe
125                 130

CCC CTG GCG CCC TCC TCC AAG AGC ACC TCT                          480
Pro Leu Ala Pro Ser Ser Lys Ser Thr Ser
135                 140

GGG GGC ACA GCG GCC CTG GGC TGC CTG GTC                          510
Gly Gly Thr Ala Ala Leu Gly Cys Leu Val
145                 150

AAG GAC TAC TTC CCC GAA CCG GTG ACG GTG                          540
Lys Asp Tyr Phe Pro Glu Pro Val Thr Val
155                 160

TCG TGG AAC TCA GGC GCC CTG ACC AGC GGC                          570
Ser Trp Asn Ser Gly Ala Leu Thr Ser Gly
165                 170

GTG CAC ACC TTC CCG GCT GTC CTA CAG TCC                          600
Val His Thr Phe Pro Ala Val Leu Gln Ser
175                 180

TCA GGA CTC TAC TCC CTC AGC AGC GTG GTG                          630
Ser Gly Leu Tyr Ser Leu Ser Ser Val Val
185                 190

ACC GTG CCC TCC AGC AGC TTG GGC ACC CAG                          660
Thr Val Pro Ser Ser Ser Leu Gly Thr Gln
195                 200

ACC TAC ATC TGC AAC GTG AAT CAC AAG CCC                          690
Thr Tyr Ile Cys Asn Val Asn His Lys Pro
205                 210

AGC AAC ACC AAG GTG GAC AAG AAA GTT GAG                          720
Ser Asn Thr Lys Val Asp Lys Lys Val Glu
215                 220

CCC AAA TCT TGT GAC AAA ACT CAC ACA TAA                          750
Pro Lys Ser Cys Asp Lys Thr His Thr
225                 230
```

(2) INFORMATION FOR SEQ ID NO:17:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 scFv DO12
        (Humanized scFv)

(xi) SEQUENCE DESCRIPTION: SEQ ID NO:17:

```
ATG GCC GAT ATC CAG ATG ACC CAG TCC CCG                           30
Met Ala Asp Ile Gln Met Thr Gln Ser Pro
1                   5                  10

TCC TCC CTG TCC GCC TCT GTG GGC GAT AGG                           60
Ser Ser Leu Ser Ala Ser Val Gly Asp Arg
15                  20

GTC ACC ATC ACC TGC GGC GCC AGC GAA AAC                           90
Val Thr Ile Thr Cys Gly Ala Ser Glu Asn
25                  30

ATC TAT GGC GCG CTG AAC TGG TAT CAA CAG                          120
Ile Tyr Gly Ala Leu Asn Trp Tyr Gln Gln
35                  40
```

|                                                                 |     |
| --------------------------------------------------------------- | --- |
| AAA CCT GGG AAA GCT CCG AAG CTT CTG ATT<br>Lys Pro Gly Lys Ala Pro Lys Leu Leu Ile<br>45                  50 | 150 |
| TAC GGT GCG ACG AAC CTG GCA GAT GGA GTC<br>Tyr Gly Ala Thr Asn Leu Ala Asp Gly Val<br>55                  60 | 180 |
| CCT TCT CGC TTC TCT GGA TCC GGC TCC GGA<br>Pro Ser Arg Phe Ser Gly Ser Gly Ser Gly<br>65                  70 | 210 |
| ACG GAT TTC ACT CTG ACC ATC AGC AGT CTG<br>Thr Asp Phe Thr Leu Thr Ile Ser Ser Leu<br>75                  80 | 240 |
| CAG CCT GAA GAC TTC GCT ACG TAT TAC TGT<br>Gln Pro Glu Asp Phe Ala Thr Tyr Tyr Cys<br>85                  90 | 270 |
| CAG AAC GTT TTA AAT ACT CCG TTG ACT TTC<br>Gln Asn Val Leu Asn Thr Pro Leu Thr Phe<br>95                  100 | 300 |
| GGA CAG GGT ACC AAG GTG GAA ATA AAA CGT<br>Gly Gln Gly Thr Lys Val Glu Ile Lys Arg<br>105                 110 | 330 |
| ACT GGC GGT GGT GGT TCT GGT GGC GGT GGA<br>Thr Gly Gly Gly Gly Ser Gly Gly Gly Gly<br>115                 120 | 360 |
| TCT GGT GGT GGC GGT TCT CAA GTC CAA CTG<br>Ser Gly Gly Gly Gly Ser Gln Val Gln Leu<br>125                 130 | 390 |
| GTG CAA TCC GGC GCC GAG GTC AAG AAG CCA<br>Val Gln Ser Gly Ala Glu Val Lys Lys Pro<br>135                 140 | 420 |
| GGG GCC TCA GTC AAA GTG TCC TGT AAA GCT<br>Gly Ala Ser Val Lys Val Ser Cys Lys Ala<br>145                 150 | 450 |
| AGC GGC TAT ATT TTT TCT AAT TAT TGG ATT<br>Ser Gly Tyr Ile Phe Ser Asn Tyr Trp Ile<br>155                 160 | 480 |
| CAA TGG GTG CGT CAG GCC CCC GGG CAG GGC<br>Gln Trp Val Arg Gln Ala Pro Gly Gln Gly<br>165                 170 | 510 |
| CTG GAA TGG ATG GGT GAG ATC TTA CCG GGC<br>Leu Glu Trp Met Gly Glu Ile Leu Pro Gly<br>175                 180 | 540 |
| TCT GGT AGC ACC GAA TAT GCC CAA AAA TTC<br>Ser Gly Ser Thr Glu Tyr Ala Gln Lys Phe<br>185                 190 | 570 |
| CAG GGC CGT GTT ACT ATG ACG CGT GAC ACT<br>Gln Gly Arg Val Thr Met Thr Arg Asp Thr<br>195                 200 | 600 |
| TCG ACT AGT ACA GTA TAC ATG GAG CTC TCC<br>Ser Thr Ser Thr Val Tyr Met Glu Leu Ser<br>205                 210 | 630 |
| AGC CTG CGA TCG GAG GAC ACG GCC GTC TAT<br>Ser Leu Arg Ser Glu Asp Thr Ala Val Tyr<br>215                 220 | 660 |
| TAT TGC GCG CGT TAT TTT TTT GGT TCT AGC<br>Tyr Cys Ala Arg Tyr Phe Phe Gly Ser Ser<br>225                 230 | 690 |
| CCG AAT TGG TAT TTT GAT GTT TGG GGT CAA<br>Pro Asn Trp Tyr Phe Asp Val Trp Gly Gln<br>235                 240 | 720 |

```
GGA ACC CTG GTC ACT GTC TCG AGC TGA                              747
Gly Thr Leu Val Thr Val Ser Ser
245
```

(2) INFORMATION FOR SEQ ID NO:18:

(i) SEQUENCE CHARACTERISTICS:
        (A) LENGTH: 5248 base pairs
        (B) TYPE: Nucleic Acid
        (C) STRANDEDNESS: Double
        (D) TOPOLOGY: Circular (ii) MOLECULE TYPE: Other nucleic acid
        (A) DESCRIPTION: pET Trc SO5/NI
            prokaryotic expression vector (xi) SEQUENCE DESCRIPTION: SEQ ID NO:18:

```
TGGCGAATGG GACGCGCCCT GTAGCGGCGC ATTAAGCGCG GCGGGTGTGG           50

TGGTTACGCG CAGCGTGACC GCTACACTTG CCAGCGCCCT AGCGCCCGCT          100

CCTTTCGCTT TCTTCCCTTC CTTTCTCGCC ACGTTCGCCG GCTTTCCCCG          150

TCAAGCTCTA AATCGGGGGC TCCCTTTAGG GTTCCGATTT AGTGCTTTAC          200

GGCACCTCGA CCCCAAAAAA CTTGATTAGG GTGATGGTTC ACGTAGTGGG          250

CCATCGCCCT GATAGACGGT TTTTCGCCCT TTGACGTTGG AGTCCACGTT          300

CTTTAATAGT GGACTCTTGT TCCAAACTGG AACAACACTC AACCCTATCT          350

CGGTCTATTC TTTTGATTTA TAAGGGATTT TGCCGATTTC GGCCTATTGG          400

TTAAAAAATG AGCTGATTTA ACAAAAATTT AACGCGAATT TTAACAAAAT          450

ATTAACGTTT ACAATTTCAG GTGGCACTTT TCGGGGAAAT GTGCGCGGAA          500

CCCCTATTTG TTTATTTTTC TAAATACATT CAAATATGTA TCCGCTCATG          550

AGACAATAAC CCTGATAAAT GCTTCAATAA TATTGAAAAA GGAAGAGTAT          600

GAGTATTCAA CATTTCCGTG TCGCCCTTAT TCCCTTTTTT GCGGCATTTT          650

GCCTTCCTGT TTTTGCTCAC CCAGAAACGC TGGTGAAAGT AAAAGATGCT          700

GAAGATCAGT TGGGTGCACG AGTGGGTTAC ATCGAACTGG ATCTCAACAG          750

CGGTAAGATC CTTGAGAGTT TTCGCCCCGA AGAACGTTTT CCAATGATGA          800

GCACTTTTAA AGTTCTGCTA TGTGGCGCGG TATTATCCCG TATTGACGCC          850

GGGCAAGAGC AACTCGGTCG CCGCATACAC TATTCTCAGA ATGACTTGGT          900

TGAGTACTCA CCAGTCACAG AAAAGCATCT TACGGATGGC ATGACAGTAA          950

GAGAATTATG CAGTGCTGCC ATAACCATGA GTGATAACAC TGCGGCCAAC         1000

TTACTTCTGA CAACGATCGG AGGACCGAAG GAGCTAACCG CTTTTTTGCA         1050

CAACATGGGG GATCATGTAA CTCGCCTTGA TCGTTGGGAA CCGGAGCTGA         1100

ATGAAGCCAT ACCAAACGAC GAGCGTGACA CCACGATGCC TGCAGCAATG         1150

GCAACAACGT TGCGCAAACT ATTAACTGGC GAACTACTTA CTCTAGCTTC         1200

CCGGCAACAA TTAATAGACT GGATGGAGGC GGATAAAGTT GCAGGACCAC         1250

TTCTGCGCTC GGCCCTTCCG GCTGGCTGGT TTATTGCTGA TAAATCTGGA         1300

GCCGGTGAGC GTGGGTCTCG CGGTATCATT GCAGCACTGG GGCCAGATGG         1350

TAAGCCCTCC CGTATCGTAG TTATCTACAC GACGGGGAGT CAGGCAACTA         1400

TGGATGAACG AAATAGACAG ATCGCTGAGA TAGGTGCCTC ACTGATTAAG         1450

CATTGGTAAC TGTCAGACCA AGTTTACTCA TATATACTTT AGATTGATTT         1500

AAAACTTCAT TTTTAATTTA AAAGGATCTA GGTGAAGATC CTTTTTGATA         1550
```

-continued

| | |
|---|---|
| ATCTCATGAC CAAAATCCCT TAACGTGAGT TTTCGTTCCA CTGAGCGTCA | 1600 |
| GACCCCGTAG AAAAGATCAA AGGATCTTCT TGAGATCCTT TTTTTCTGCG | 1650 |
| CGTAATCTGC TGCTTGCAAA CAAAAAAACC ACCGCTACCA GCGGTGGTTT | 1700 |
| GTTTGCCGGA TCAAGAGCTA CCAACTCTTT TTCCGAAGGT AACTGGCTTC | 1750 |
| AGCAGAGCGC AGATACCAAA TACTGTCCTT CTAGTGTAGC CGTAGTTAGG | 1800 |
| CCACCACTTC AAGAACTCTG TAGCACCGCC TACATACCTC GCTCTGCTAA | 1850 |
| TCCTGTTACC AGTGGCTGCT GCCAGTGGCG ATAAGTCGTG TCTTACCGGG | 1900 |
| TTGGACTCAA GACGATAGTT ACCGGATAAG GCGCAGCGGT CGGGCTGAAC | 1950 |
| GGGGGGTTCG TGCACACAGC CCAGCTTGGA GCGAACGACC TACACCGAAC | 2000 |
| TGAGATACCT ACAGCGTGAG CTATGAGAAA GCGCCACGCT TCCCGAAGGG | 2050 |
| AGAAAGGCGG ACAGGTATCC GGTAAGCGGC AGGGTCGGAA CAGGAGAGCG | 2100 |
| CACGAGGGAG CTTCCAGGGG GAAACGCCTG GTATCTTTAT AGTCCTGTCG | 2150 |
| GGTTTCGCCA CCTCTGACTT GAGCGTCGAT TTTTGTGATG CTCGTCAGGG | 2200 |
| GGGCGGAGCC TATGGAAAAA CGCCAGCAAC GCGGCCTTTT TACGGTTCCT | 2250 |
| GGCCTTTTGC TGGCCTTTTG CTCACATGTT CTTTCCTGCG TTATCCCCTG | 2300 |
| ATTCTGTGGA TAACCGTATT ACCGCCTTTG AGTGAGCTGA TACCGCTCGC | 2350 |
| CGCAGCCGAA CGACCGAGCG CAGCGAGTCA GTGAGCGAGG AAGCGGAAGA | 2400 |
| GCGCCTGATG CGGTATTTTC TCCTTACGCA TCTGTGCGGT ATTTCACACC | 2450 |
| GCATATATGG TGCACTCTCA GTACAATCTG CTCTGATGCC GCATAGTTAA | 2500 |
| GCCAGTATAC ACTCCGCTAT CGCTACGTGA CTGGGTCATG GCTGCGCCCC | 2550 |
| GACACCCGCC AACACCCGCT GACGCGCCCT GACGGGCTTG TCTGCTCCCG | 2600 |
| GCATCCGCTT ACAGACAAGC TGTGACCGTC TCCGGGAGCT GCATGTGTCA | 2650 |
| GAGGTTTTCA CCGTCATCAC CGAAACGCGC GAGGCAGCTG CGGTAAAGCT | 2700 |
| CATCAGCGTG GTCGTGAAGC GATTCACAGA TGTCTGCCTG TTCATCCGCG | 2750 |
| TCCAGCTCGT TGAGTTTCTC CAGAAGCGTT AATGTCTGGC TTCTGATAAA | 2800 |
| GCGGGCCATG TTAAGGGCGG TTTTTTCCTG TTTGGTCACT GATGCCTCCG | 2850 |
| TGTAAGGGGG ATTTCTGTTC ATGGGGGTAA TGATACCGAT GAAACGAGAG | 2900 |
| AGGATGCTCA CGATACGGGT TACTGATGAT GAACATGCCC GGTTACTGGA | 2950 |
| ACGTTGTGAG GGTAAACAAC TGGCGGTATG GATGCGGCGG GACCAGAGAA | 3000 |
| AAATCACTCA GGGTCAATGC CAGCGCTTCG TTAATACAGA TGTAGGTGTT | 3050 |
| CCACAGGGTA GCCAGCAGCA TCCTGCGATG CAGATCCGGA ACATAATGGT | 3100 |
| GCAGGGCGCT GACTTCCGCG TTTCCAGACT TTACGAAACA CGGAAACCGA | 3150 |
| AGACCATTCA TGTTGTTGCT CAGGTCGCAG ACGTTTTGCA GCAGCAGTCG | 3200 |
| CTTCACGTTC GCTCGCGTAT CGGTGATTCA TTCTGCTAAC CAGTAAGGCA | 3250 |
| ACCCCGCCAG CCTAGCCGGG TCCTCAACGA CAGGAGCACG ATCATGCGCA | 3300 |
| CCCGTGGGGC CGCCATGCCG GCGATAATGG CCTGCTTCTC GCCGAAACGT | 3350 |
| TTGGTGGCGG GACCAGTGAC GAAGGCTTGA GCGAGGGCGT GCAAGATTCC | 3400 |
| GAATACCGCA AGCGACAGGC CGATCATCGT CGCGCTCCAG CGAAAGCGGT | 3450 |
| CCTCGCCGAA AATGACCCAG AGCGCTGCCG GCACCTGTCC TACGAGTTGC | 3500 |
| ATGATAAAGA AGACAGTCAT AAGTGCGGCG ACGATAGTCA TGCCCCGCGC | 3550 |

| | |
|---|---|
| CCACCGGAAG GAGCTGACTG GGTTGAAGGC TCTCAAGGGC ATCGGTCGAG | 3600 |
| ATCCCGGTGC CTAATGAGTG AGCTAACTTA CATTAATTGC GTTGCGCTCA | 3650 |
| CTGCCCGCTT TCCAGTCGGG AAACCTGTCG TGCCAGCTGC ATTAATGAAT | 3700 |
| CGGCCAACGC GCGGGGAGAG GCGGTTTGCG TATTGGGCGC CAGGGTGGTT | 3750 |
| TTTCTTTTCA CCAGTGAGAC GGGCAACAGC TGATTGCCCT TCACCGCCTG | 3800 |
| GCCCTGAGAG AGTTGCAGCA AGCGGTCCAC GCTGGTTTGC CCCAGCAGGC | 3850 |
| GAAAATCCTG TTTGATGGTG GTTAACGGCG GGATATAACA TGAGCTGTCT | 3900 |
| TCGGTATCGT CGTATCCCAC TACCGAGATA TCCGCACCAA CGCGCAGCCC | 3950 |
| GGACTCGGTA ATGGCGCGCA TTGCGCCCAG CGCCATCTGA TCGTTGGCAA | 4000 |
| CCAGCATCGC AGTGGGAACG ATGCCCTCAT TCAGCATTTG CATGGTTTGT | 4050 |
| TGAAAACCGG ACATGGCACT CCAGTCGCCT TCCCGTTCCG CTATCGGCTG | 4100 |
| AATTTGATTG CGAGTGAGAT ATTTATGCCA GCCAGCCAGA CGCAGACGCG | 4150 |
| CCGAGACAGA ACTTAATGGG CCCGCTAACA GCGCGATTTG CTGGTGACCC | 4200 |
| AATGCGACCA GATGCTCCAC GCCCAGTCGC GTACCGTCTT CATGGGAGAA | 4250 |
| AATAATACTG TTGATGGGTG TCTGGTCAGA GACATCAAGA AATAACGCCG | 4300 |
| GAACATTAGT GCAGGCAGCT TCCACAGCAA TGGCATCCTG GTCATCCAGC | 4350 |
| GGATAGTTAA TGATCAGCCC ACTGACGCGT TGCGCGAGAA GATTGTGCAC | 4400 |
| CGCCGCTTTA CAGGCTTCGA CGCCGCTTCG TTCTACCATC GACACCACCA | 4450 |
| CGCTGGCACC CAGTTGATCG GCGCGAGATT TAATCGCCGC GACAATTTGC | 4500 |
| GACGGCGCGT GCAGGGCCAG ACTGGAGGTG GCAACGCCAA TCAGCAACGA | 4550 |
| CTGTTTGCCC GCCAGTTGTT GTGCCACGCG GTTGGGAATG TAATTCAGCT | 4600 |
| CCGCCATCGC CGCTTCCACT TTTTCCCGCG TTTTCGCAGA AACGTGGCTG | 4650 |
| GCCTGGTTCA CCACGCGGGA AACGGTCTGA TAAGAGACAC CGGCATACTC | 4700 |
| TGCGACATCG TATAACGTTA CTGGTTTCAC ATTCACCACC CTGAATTGAC | 4750 |
| TCTCTTCCGG GCGCTATCAT GCCATACCGC GAAAGGTTTT GCGCCATTCG | 4800 |
| ATGGTGTCCG GATCTCGAC GCTCTCCCTT ATGCGACTCC TGCATTAGGA | 4850 |
| AGCAGCCCAG TAGTAGGTTG AGGCCGTTGA GCACCGCCGC CGCAAGGAAT | 4900 |
| GGTGCATGCG GTACCAGCTG TTGACAATTA ATCATCCGGC TCGTATAATA | 4950 |
| GTACTGTGTG GAATTGTGAG CGCTCACAAT TCCACACATC TAGAAATAAT | 5000 |
| TTTGTTTAAC TTTAAGAAGG AGATATACCA TGGAGATCTG GATCCATCGA | 5050 |
| TGAATTCGAG CTCCGTCGAC AAGCTTGCGG CCGCACTCGA GCACCACCAC | 5100 |
| CACCACCACT GAGATCCGGC TGCTAACAAA GCCCGAAAGG AAGCTGAGTT | 5150 |
| GGCTGCTGCC ACCGCTGAGC AATAACTAGC ATAACCCCTT GGGGCCTCTA | 5200 |
| AACGGGTCTT GAGGGGTTTT TTGCTGAAAG GAGGAACTAT ATCCGGAT | 5248 |

(2) INFORMATION FOR SEQ ID NO:19:

(i) SEQUENCE CHARACTERISTICS:
        (A) LENGTH: 783 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION: N19/8 scFv (His Tagged)

(xi) SEQUENCE DESCRIPTION: SEQ ID NO:19:

```
ATG GCC AAT ATT GTG CTG ACC CAA TCT CCA                          30
Met Ala Asn Ile Val Leu Thr Gln Ser Pro
1               5                   10

GCT TCT TTG GCT GTG TCT CTA GGG CAG AGG                          60
Ala Ser Leu Ala Val Ser Leu Gly Gln Arg
        15                  20

GCC ACC ATA TCC TGC AGA GCC AGT GAA AGT                          90
Ala Thr Ile Ser Cys Arg Ala Ser Glu Ser
25                  30

GTT GAT AGT TAT GAC AAT AGT TTT ATG CAC                         120
Val Asp Ser Tyr Asp Asn Ser Phe Met His
35                  40

TGG TAC CAG CAG AAA CCA GGA CAG CCA CCC                         150
Trp Tyr Gln Gln Lys Pro Gly Gln Pro Pro
45                  50

AAA CTC CTC ATC TTT CTT GCA TCC AAC CTA                         180
Lys Leu Leu Ile Phe Leu Ala Ser Asn Leu
55                  60

GAA TCT GGG GTC CCT GCC AGG TTC AGT GGC                         210
Glu Ser Gly Val Pro Ala Arg Phe Ser Gly
65                  70

AGT GGG TCT AGG ACA GAC TTC ACC CTC ACC                         240
Ser Gly Ser Arg Thr Asp Phe Thr Leu Thr
75                  80

ATT GAT CCT GTG GAG GCT GAT GAT GCT GCA                         270
Ile Asp Pro Val Glu Ala Asp Asp Ala Ala
85                  90

ACC TAT TAC TGT CAG CAA AAT AAT GAG GTT                         300
Thr Tyr Tyr Cys Gln Gln Asn Asn Glu Val
95                  100

CCG AAC ACG TTC GGA GGG GGG ACC AAG CTG                         330
Pro Asn Thr Phe Gly Gly Gly Thr Lys Leu
105                 110

GAA ATA AAA CGG ACC GGA GGT GGC GGG TCG                         360
Glu Ile Lys Arg Thr Gly Gly Gly Gly Ser
115                 120

GGT GGC GGG GGA TCG GGT GGC GGA GGG TCG                         390
Gly Gly Gly Gly Ser Gly Gly Gly Gly Ser
125                 130

GAC GTC AAG CTC GTG GAG TCT GGG GGA GAC                         420
Asp Val Lys Leu Val Glu Ser Gly Gly Asp
135                 140

TTA GTG AAG CTT GGA GGG TCC CTG AAA CTC                         450
Leu Val Lys Leu Gly Gly Ser Leu Lys Leu
145                 150

TCC TGT GCA GCC TCT GGA TTC ACC TTC AGT                         480
Ser Cys Ala Ala Ser Gly Phe Thr Phe Ser
155                 160

AGC TAT TAT ATG TCT TGG GTT CGC CAG ATT                         510
Ser Tyr Tyr Met Ser Trp Val Arg Gln Ile
165                 170

TCA GAG AAG AGG CTG GAG TTG GTC GCA GCC                         540
Ser Glu Lys Arg Leu Glu Leu Val Ala Ala
175                 180

ATT AAT AGT AAT GGT GAT AGC ACC TAC TAT                         570
Ile Asn Ser Asn Gly Asp Ser Thr Tyr Tyr
185                 190
```

```
CCA GAC ACT GTG AAG GGC CGA TTC ACC ATC                              600
Pro Asp Thr Val Lys Gly Arg Phe Thr Ile
195                 200

TCC AGA GAC AAT GCC AAG AGC ACC CTG GAT                              630
Ser Arg Asp Asn Ala Lys Ser Thr Leu Asp
205                 210

CTG CAA ATG AGC AGT CTG AAG TCT GAG GAC                              660
Leu Gln Met Ser Ser Leu Lys Ser Glu Asp
215                 220

ACA GCC TTG TAT TTC TGT GTA AGA GAG ACT                              690
Thr Ala Leu Tyr Phe Cys Val Arg Glu Thr
225                 230

TAT TAC TAC GGG ATT AGT CCC GTC TTC GAT                              720
Tyr Tyr Tyr Gly Ile Ser Pro Val Phe Asp
235                 240

GTC TGG GGC ACA GGG ACC ACG GTC ACC GTC                              750
Val Trp Gly Thr Gly Thr Thr Val Thr Val
245                 250

TCC TCA CTC GAG CAC CAC CAC CAC CAC CAC                              780
Ser Ser Leu Glu His His His His His His
255                 260

TGA                                                                  783
```

(2) INFORMATION FOR SEQ ID NO:20:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 scFv C012 (humanized)

(xi) SEQUENCE DESCRIPTION: SEQ ID NO:20:

```
ATG GCC GAT ATC CAG ATG ACC CAG TCC CCG                               30
Met Ala Asp Ile Gln Met Thr Gln Ser Pro
1               5                   10

TCC TCC CTG TCC GCC TCT GTG GGC GAT AGG                               60
Ser Ser Leu Ser Ala Ser Val Gly Asp Arg
15                  20

GTC ACC ATC ACC TGC GGC GCC AGC GAA AAC                               90
Val Thr Ile Thr Cys Gly Ala Ser Glu Asn
25                  30

ATC TAT GGC GCG CTG AAC TGG TAT CAA CAG                              120
Ile Tyr Gly Ala Leu Asn Trp Tyr Gln Gln
35                  40

AAA CCC GGG AAA GCT CCG AAG CTT CTG ATT                              150
Lys Pro Gly Lys Ala Pro Lys Leu Leu Ile
45                  50

TAC GGT GCG ACG AAC CTG GCA GAT GGA GTC                              180
Tyr Gly Ala Thr Asn Leu Ala Asp Gly Val
55                  60

CCT TCT CGC TTC TCT GGA TCC GGC TCC GGA                              210
Pro Ser Arg Phe Ser Gly Ser Gly Ser Gly
65                  70

ACG GAT TTC ACT CTG ACC ATC AGC AGT CTG                              240
Thr Asp Phe Thr Leu Thr Ile Ser Ser Leu
75                  80

CAG CCT GAA GAC TTC GCT ACG TAT TAC TGT                              270
Gln Pro Glu Asp Phe Ala Thr Tyr Tyr Cys
85                  90
```

```
CAG AAC GTT TTA AAT ACT CCG TTG ACT TTC                                    300
Gln Asn Val Leu Asn Thr Pro Leu Thr Phe
 95                 100
GGA CAG GGT ACC AAG GTG GAA ATA AAA CGT                                    330
Gly Gln Gly Thr Lys Val Glu Ile Lys Arg
105                 110
ACT GGC GGT GGT GGT TCT GGT GGC GGT GGA                                    360
Thr Gly Gly Gly Gly Ser Gly Gly Gly Gly
115                 120
TCT GGT GGT GGC GGT TCT CAA GTC CAA CTG                                    390
Ser Gly Gly Gly Gly Ser Gln Val Gln Leu
125                 130
GTG CAA TCC GGC GCC GAG GTC AAG AAG CCA                                    420
Val Gln Ser Gly Ala Glu Val Lys Lys Pro
135                 140
GGG GCC TCA GTC AAA GTG TCC TGT AAA GCT                                    450
Gly Ala Ser Val Lys Val Ser Cys Lys Ala
145                 150
AGC GGC TAT ATT TTT TCT AAT TAT TGG ATT                                    480
Ser Gly Tyr Ile Phe Ser Asn Tyr Trp Ile
155                 160
CAA TGG GTG CGT CAG GCC CCC GGG CAG GGC                                    510
Gln Trp Val Arg Gln Ala Pro Gly Gln Gly
165                 170
CTG GAA TGG ATG GGT GAG ATC TTA CCG GGC                                    540
Leu Glu Trp Met Gly Glu Ile Leu Pro Gly
175                 180
TCT GGT AGC ACC GAA TAT ACC GAA AAT TTT                                    570
Ser Gly Ser Thr Glu Tyr Thr Glu Asn Phe
185                 190
AAA GAC CGT GTT ACT ATG ACG CGT GAC ACT                                    600
Lys Asp Arg Val Thr Met Thr Arg Asp Thr
195                 200
TCG ACT AGT ACA GTA TAC ATG GAG CTC TCC                                    630
Ser Thr Ser Thr Val Tyr Met Glu Leu Ser
205                 210
AGC CTG CGA TCG GAG GAC ACG GCC GTC TAT                                    660
Ser Leu Arg Ser Glu Asp Thr Ala Val Tyr
215                 220
TAT TGC GCG CGT TAT TTT TTT GGT TCT AGC                                    690
Tyr Cys Ala Arg Tyr Phe Phe Gly Ser Ser
225                 230
CCG AAT TGG TAT TTT GAT GTT TGG GGT CAA                                    720
Pro Asn Trp Tyr Phe Asp Val Trp Gly Gln
235                 240
GGA ACC CTG GTC ACT GTC TCG AGC TGA                                        747
Gly Thr Leu Val Thr Val Ser Ser
245
```

(2) INFORMATION FOR SEQ ID NO:21:

(i) SEQUENCE CHARACTERISTICS:
        (A) LENGTH:   747 base pairs
        (B) TYPE:  Nucleic Acid
        (C) STRANDEDNESS:  Double
        (D) TOPOLOGY:  linear (ii) MOLECULE TYPE:  Other nucleic acid
        (A) DESCRIPTION:5G1.1 scFv DO12B
        (Humanized scFv)

(xi) SEQUENCE DESCRIPTION: SEQ ID NO:21:

```
ATG GCC GAT ATC CAG ATG ACC CAG TCC CCG                          30
Met Ala Asp Ile Gln Met Thr Gln Ser Pro
1               5                   10

TCC TCC CTG TCC GCC TCT GTG GGC GAT AGG                          60
Ser Ser Leu Ser Ala Ser Val Gly Asp Arg
15                  20

GTC ACC ATC ACC TGC CGT GCT AGC GAA AAC                          90
Val Thr Ile Thr Cys Arg Ala Ser Glu Asn
25                  30

ATC TAT GGC GCG CTG AAC TGG TAT CAA CAG                         120
Ile Tyr Gly Ala Leu Asn Trp Tyr Gln Gln
35                  40

AAA CCT GGG AAA GCT CCG AAG CTT CTG ATT                         150
Lys Pro Gly Lys Ala Pro Lys Leu Leu Ile
45                  50

TAC GGT GCG ACG AAC CTG GCA GAT GGA GTC                         180
Tyr Gly Ala Thr Asn Leu Ala Asp Gly Val
55                  60

CCT TCT CGC TTC TCT GGA TCC GGC TCC GGA                         210
Pro Ser Arg Phe Ser Gly Ser Gly Ser Gly
65                  70

ACG GAT TTC ACT CTG ACC ATC AGC AGT CTG                         240
Thr Asp Phe Thr Leu Thr Ile Ser Ser Leu
75                  80

CAG CCT GAA GAC TTC GCT ACG TAT TAC TGT                         270
Gln Pro Glu Asp Phe Ala Thr Tyr Tyr Cys
85                  90

CAG AAC GTT TTA AAT ACT CCG TTG ACT TTC                         300
Gln Asn Val Leu Asn Thr Pro Leu Thr Phe
95                  100

GGA CAG GGT ACC AAG GTG GAA ATA AAA CGT                         330
Gly Gln Gly Thr Lys Val Glu Ile Lys Arg
105                 110

ACT GGC GGT GGT GGT TCT GGT GGC GGT GGA                         360
Thr Gly Gly Gly Gly Ser Gly Gly Gly Gly
115                 120

TCT GGT GGT GGC GGT TCT CAA GTC CAA CTG                         390
Ser Gly Gly Gly Gly Ser Gln Val Gln Leu
125                 130

GTG CAA TCC GGC GCC GAG GTC AAG AAG CCA                         420
Val Gln Ser Gly Ala Glu Val Lys Lys Pro
135                 140

GGG GCC TCA GTC AAA GTG TCC TGT AAA GCT                         450
Gly Ala Ser Val Lys Val Ser Cys Lys Ala
145                 150

AGC GGC TAT ATT TTT TCT AAT TAT TGG ATT                         480
Ser Gly Tyr Ile Phe Ser Asn Tyr Trp Ile
155                 160

CAA TGG GTG CGT CAG GCC CCC GGG CAG GGC                         510
Gln Trp Val Arg Gln Ala Pro Gly Gln Gly
165                 170

CTG GAA TGG ATG GGT GAG ATC TTA CCG GGC                         540
Leu Glu Trp Met Gly Glu Ile Leu Pro Gly
175                 180

TCT GGT AGC ACC GAA TAT GCC CAA AAA TTC                         570
Ser Gly Ser Thr Glu Tyr Ala Gln Lys Phe
185                 190
```

```
CAG GGC CGT GTT ACT ATG ACG CGT GAC ACT                    600
Gln Gly Arg Val Thr Met Thr Arg Asp Thr
195                     200

TCG ACT AGT ACA GTA TAC ATG GAG CTC TCC                    630
Ser Thr Ser Thr Val Tyr Met Glu Leu Ser
205                     210

AGC CTG CGA TCG GAG GAC ACG GCC GTC TAT                    660
Ser Leu Arg Ser Glu Asp Thr Ala Val Tyr
215                     220

TAT TGC GCG CGT TAT TTT TTT GGT TCT AGC                    690
Tyr Cys Ala Arg Tyr Phe Phe Gly Ser Ser
225                     230

CCG AAT TGG TAT TTT GAT GTT TGG GGT CAA                    720
Pro Asn Trp Tyr Phe Asp Val Trp Gly Gln
235                     240

GGA ACC CTG GTC ACT GTC TCG AGC TGA                        747
Gly Thr Leu Val Thr Val Ser Ser
245
```

(2) INFORMATION FOR SEQ ID NO:22:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 scFv DO12C
        (Humanized scFv)

(xi) SEQUENCE DESCRIPTION: SEQ ID NO:22:

```
ATG GCC GAT ATC CAG ATG ACC CAG TCC CCG                     30
Met Ala Asp Ile Gln Met Thr Gln Ser Pro
1               5                   10

TCC TCC CTG TCC GCC TCT GTG GGC GAT AGG                     60
Ser Ser Leu Ser Ala Ser Val Gly Asp Arg
15                      20

GTC ACC ATC ACC TGC GGC GCC AGC GAA AAC                     90
Val Thr Ile Thr Cys Gly Ala Ser Glu Asn
25                      30

ATC TAT GGC GCG CTG AAC TGG TAT CAA CAG                    120
Ile Tyr Gly Ala Leu Asn Trp Tyr Gln Gln
35                      40

AAA CCT GGG AAA GCT CCG AAG CTT CTG ATT                    150
Lys Pro Gly Lys Ala Pro Lys Leu Leu Ile
45                      50

TAC GGT GCG ACG AGC CTG CAG TCT GGA GTC                    180
Tyr Gly Ala Thr Ser Leu Gln Ser Gly Val
55                      60

CCT TCT CGC TTC TCT GGA TCC GGC TCC GGA                    210
Pro Ser Arg Phe Ser Gly Ser Gly Ser Gly
65                      70

ACG GAT TTC ACT CTG ACC ATC AGC AGT CTG                    240
Thr Asp Phe Thr Leu Thr Ile Ser Ser Leu
75                      80

CAG CCT GAA GAC TTC GCT ACG TAT TAC TGT                    270
Gln Pro Glu Asp Phe Ala Thr Tyr Tyr Cys
85                      90

CAG AAC GTT TTA AAT ACT CCG TTG ACT TTC                    300
Gln Asn Val Leu Asn Thr Pro Leu Thr Phe
95                      100
```

```
GGA CAG GGT ACC AAG GTG GAA ATA AAA CGT                              330
Gly Gln Gly Thr Lys Val Glu Ile Lys Arg
105                 110

ACT GGC GGT GGT GGT TCT GGT GGC GGT GGA                              360
Thr Gly Gly Gly Gly Ser Gly Gly Gly Gly
115                 120

TCT GGT GGT GGC GGT TCT CAA GTC CAA CTG                              390
Ser Gly Gly Gly Gly Ser Gln Val Gln Leu
125                 130

GTG CAA TCC GGC GCC GAG GTC AAG AAG CCA                              420
Val Gln Ser Gly Ala Glu Val Lys Lys Pro
135                 140

GGG GCC TCA GTC AAA GTG TCC TGT AAA GCT                              450
Gly Ala Ser Val Lys Val Ser Cys Lys Ala
145                 150

AGC GGC TAT ATT TTT TCT AAT TAT TGG ATT                              480
Ser Gly Tyr Ile Phe Ser Asn Tyr Trp Ile
155                 160

CAA TGG GTG CGT CAG GCC CCC GGG CAG GGC                              510
Gln Trp Val Arg Gln Ala Pro Gly Gln Gly
165                 170

CTG GAA TGG ATG GGT GAG ATC TTA CCG GGC                              540
Leu Glu Trp Met Gly Glu Ile Leu Pro Gly
175                 180

TCT GGT AGC ACC GAA TAT GCC CAA AAA TTC                              570
Ser Gly Ser Thr Glu Tyr Ala Gln Lys Phe
185                 190

CAG GGC CGT GTT ACT ATG ACG CGT GAC ACT                              600
Gln Gly Arg Val Thr Met Thr Arg Asp Thr
195                 200

TCG ACT AGT ACA GTA TAC ATG GAG CTC TCC                              630
Ser Thr Ser Thr Val Tyr Met Glu Leu Ser
205                 210

AGC CTG CGA TCG GAG GAC ACG GCC GTC TAT                              660
Ser Leu Arg Ser Glu Asp Thr Ala Val Tyr
215                 220

TAT TGC GCG CGT TAT TTT TTT GGT TCT AGC                              690
Tyr Cys Ala Arg Tyr Phe Phe Gly Ser Ser
225                 230

CCG AAT TGG TAT TTT GAT GTT TGG GGT CAA                              720
Pro Asn Trp Tyr Phe Asp Val Trp Gly Gln
235                 240

GGA ACC CTG GTC ACT GTC TCG AGC TGA                                  747
Gly Thr Leu Val Thr Val Ser Ser
245
```

(2) INFORMATION FOR SEQ ID NO:23:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 scFv DO12D
        (Humanized scFv)

(xi) SEQUENCE DESCRIPTION: SEQ ID NO:23:

```
ATG GCC GAT ATC CAG ATG ACC CAG TCC CCG                               30
Met Ala Asp Ile Gln Met Thr Gln Ser Pro
1               5                   10
```

-continued

| | |
|---|---|
| TCC TCC CTG TCC GCC TCT GTG GGC GAT AGG<br>Ser Ser Leu Ser Ala Ser Val Gly Asp Arg<br>15                           20 | 60 |
| GTC ACC ATC ACC TGC CGT GCT AGC GAA AAC<br>Val Thr Ile Thr Cys Arg Ala Ser Glu Asn<br>25                           30 | 90 |
| ATC TAT GGC GCG CTG AAC TGG TAT CAA CAG<br>Ile Tyr Gly Ala Leu Asn Trp Tyr Gln Gln<br>35                           40 | 120 |
| AAA CCT GGG AAA GCT CCG AAG CTT CTG ATT<br>Lys Pro Gly Lys Ala Pro Lys Leu Leu Ile<br>45                           50 | 150 |
| TAC GGT GCG ACG AGC CTG CAG TCT GGA GTC<br>Tyr Gly Ala Thr Ser Leu Gln Ser Gly Val<br>55                           60 | 180 |
| CCT TCT CGC TTC TCT GGA TCC GGC TCC GGA<br>Pro Ser Arg Phe Ser Gly Ser Gly Ser Gly<br>65                           70 | 210 |
| ACG GAT TTC ACT CTG ACC ATC AGC AGT CTG<br>Thr Asp Phe Thr Leu Thr Ile Ser Ser Leu<br>75                           80 | 240 |
| CAG CCT GAA GAC TTC GCT ACG TAT TAC TGT<br>Gln Pro Glu Asp Phe Ala Thr Tyr Tyr Cys<br>85                           90 | 270 |
| CAG AAC GTT TTA AAT ACT CCG TTG ACT TTC<br>Gln Asn Val Leu Asn Thr Pro Leu Thr Phe<br>95                       100 | 300 |
| GGA CAG GGT ACC AAG GTG GAA ATA AAA CGT<br>Gly Gln Gly Thr Lys Val Glu Ile Lys Arg<br>105                    110 | 330 |
| ACT GGC GGT GGT GGT TCT GGT GGC GGT GGA<br>Thr Gly Gly Gly Gly Ser Gly Gly Gly Gly<br>115                    120 | 360 |
| TCT GGT GGT GGC GGT TCT CAA GTC CAA CTG<br>Ser Gly Gly Gly Gly Ser Gln Val Gln Leu<br>125                    130 | 390 |
| GTG CAA TCC GGC GCC GAG GTC AAG AAG CCA<br>Val Gln Ser Gly Ala Glu Val Lys Lys Pro<br>135                    140 | 420 |
| GGG GCC TCA GTC AAA GTG TCC TGT AAA GCT<br>Gly Ala Ser Val Lys Val Ser Cys Lys Ala<br>145                    150 | 450 |
| AGC GGC TAT ATT TTT TCT AAT TAT TGG ATT<br>Ser Gly Tyr Ile Phe Ser Asn Tyr Trp Ile<br>155                    160 | 480 |
| CAA TGG GTG CGT CAG GCC CCC GGG CAG GGC<br>Gln Trp Val Arg Gln Ala Pro Gly Gln Gly<br>165                    170 | 510 |
| CTG GAA TGG ATG GGT GAG ATC TTA CCG GGC<br>Leu Glu Trp Met Gly Glu Ile Leu Pro Gly<br>175                    180 | 540 |
| TCT GGT AGC ACC GAA TAT GCC CAA AAA TTC<br>Ser Gly Ser Thr Glu Tyr Ala Gln Lys Phe<br>185                    190 | 570 |
| CAG GGC CGT GTT ACT ATG ACG CGT GAC ACT<br>Gln Gly Arg Val Thr Met Thr Arg Asp Thr<br>195                    200 | 600 |
| TCG ACT AGT ACA GTA TAC ATG GAG CTC TCC<br>Ser Thr Ser Thr Val Tyr Met Glu Leu Ser<br>205                    210 | 630 |

```
AGC CTG CGA TCG GAG GAC ACG GCC GTC TAT                                660
Ser Leu Arg Ser Glu Asp Thr Ala Val Tyr
215                     220

TAT TGC GCG CGT TAT TTT TTT GGT TCT AGC                                690
Tyr Cys Ala Arg Tyr Phe Phe Gly Ser Ser
225                     230

CCG AAT TGG TAT TTT GAT GTT TGG GGT CAA                                720
Pro Asn Trp Tyr Phe Asp Val Trp Gly Gln
235                     240

GGA ACC CTG GTC ACT GTC TCG AGC TGA                                    747
Gly Thr Leu Val Thr Val Ser Ser
245
```

(2) INFORMATION FOR SEQ ID NO:24:

(i) SEQUENCE CHARACTERISTICS:
        (A) LENGTH: 747 base pairs
        (B) TYPE: Nucleic Acid
        (C) STRANDEDNESS: Double
        (D) TOPOLOGY: linear (ii) MOLECULE TYPE: Other nucleic acid
        (A) DESCRIPTION:5G1.1 scFv C013 (humanized)

(xi) SEQUENCE DESCRIPTION: SEQ ID NO:24:

```
ATG GCC GAT ATC CAG ATG ACC CAG TCC CCG                                30
Met Ala Asp Ile Gln Met Thr Gln Ser Pro
1               5                   10

TCC TCC CTG TCC GCC TCT GTG GGC GAT AGG                                60
Ser Ser Leu Ser Ala Ser Val Gly Asp Arg
15                      20

GTC ACC ATC ACC TGC CGT GCT AGC GAA AAC                                90
Val Thr Ile Thr Cys Arg Ala Ser Glu Asn
25                      30

ATC TAT GGC GCG CTG AAC TGG TAT CAA CAG                                120
Ile Tyr Gly Ala Leu Asn Trp Tyr Gln Gln
35                      40

AAA CCC GGG AAA GCT CCG AAG CTT CTG ATT                                150
Lys Pro Gly Lys Ala Pro Lys Leu Leu Ile
45                      50

TAC GGT GCG ACG AAC CTG GCA GAT GGA GTC                                180
Tyr Gly Ala Thr Asn Leu Ala Asp Gly Val
55                      60

CCT TCT CGC TTC TCT GGA TCC GGC TCC GGA                                210
Pro Ser Arg Phe Ser Gly Ser Gly Ser Gly
65                      70

ACG GAT TTC ACT CTG ACC ATC AGC AGT CTG                                240
Thr Asp Phe Thr Leu Thr Ile Ser Ser Leu
75                      80

CAG CCT GAA GAC TTC GCT ACG TAT TAC TGT                                270
Gln Pro Glu Asp Phe Ala Thr Tyr Tyr Cys
85                      90

CAG AAC GTT TTA AAT ACT CCG TTG ACT TTC                                300
Gln Asn Val Leu Asn Thr Pro Leu Thr Phe
95                      100

GGA CAG GGT ACC AAG GTG GAA ATA AAA CGT                                330
Gly Gln Gly Thr Lys Val Glu Ile Lys Arg
105                     110

ACT GGC GGT GGT GGT TCT GGT GGC GGT GGA                                360
Thr Gly Gly Gly Gly Ser Gly Gly Gly Gly
115                     120
```

```
TCT GGT GGT GGC GGT TCT CAA GTC CAA CTG                                390
Ser Gly Gly Gly Gly Ser Gln Val Gln Leu
125                 130

GTG CAA TCC GGC GCC GAG GTC AAG AAG CCA                                420
Val Gln Ser Gly Ala Glu Val Lys Lys Pro
135                 140

GGG GCC TCA GTC AAA GTG TCC TGT AAA GCT                                450
Gly Ala Ser Val Lys Val Ser Cys Lys Ala
145                 150

AGC GGC TAT ATT TTT TCT AAT TAT TGG ATT                                480
Ser Gly Tyr Ile Phe Ser Asn Tyr Trp Ile
155                 160

CAA TGG GTG CGT CAG GCC CCC GGG CAG GGC                                510
Gln Trp Val Arg Gln Ala Pro Gly Gln Gly
165                 170

CTG GAA TGG ATG GGT GAG ATC TTA CCG GGC                                540
Leu Glu Trp Met Gly Glu Ile Leu Pro Gly
175                 180

TCT GGT AGC ACC GAA TAT ACC GAA AAT TTT                                570
Ser Gly Ser Thr Glu Tyr Thr Glu Asn Phe
185                 190

AAA GAC CGT GTT ACT ATG ACG CGT GAC ACT                                600
Lys Asp Arg Val Thr Met Thr Arg Asp Thr
195                 200

TCG ACT AGT ACA GTA TAC ATG GAG CTC TCC                                630
Ser Thr Ser Thr Val Tyr Met Glu Leu Ser
205                 210

AGC CTG CGA TCG GAG GAC ACG GCC GTC TAT                                660
Ser Leu Arg Ser Glu Asp Thr Ala Val Tyr
215                 220

TAT TGC GCG CGT TAT TTT TTT GGT TCT AGC                                690
Tyr Cys Ala Arg Tyr Phe Phe Gly Ser Ser
225                 230

CCG AAT TGG TAT TTT GAT GTT TGG GGT CAA                                720
Pro Asn Trp Tyr Phe Asp Val Trp Gly Gln
235                 240

GGA ACC CTG GTC ACT GTC TCG AGC TGA                                    747
Gly Thr Leu Val Thr Val Ser Ser
245

(2) INFORMATION FOR SEQ ID NO:25:

(i) SEQUENCE CHARACTERISTICS:
        (A) LENGTH:  747 base pairs
        (B) TYPE:  Nucleic Acid
        (C) STRANDEDNESS:  Double
        (D) TOPOLOGY:  linear (ii) MOLECULE TYPE:  Other nucleic acid
        (A) DESCRIPTION:5G1.1 scFv C014 (humanized)

(xi) SEQUENCE DESCRIPTION:  SEQ ID NO:25:

ATG GCC GAT ATC CAG ATG ACC CAG TCC CCG                                 30
Met Ala Asp Ile Gln Met Thr Gln Ser Pro
1               5                   10

TCC TCC CTG TCC GCC TCT GTG GGC GAT AGG                                 60
Ser Ser Leu Ser Ala Ser Val Gly Asp Arg
15                  20

GTC ACC ATC ACC TGC GGC GCC AGC GAA AAC                                 90
Val Thr Ile Thr Cys Gly Ala Ser Glu Asn
25                  30
```

```
ATC TAT GGC GCG CTG AAC TGG TAT CAA CAG                    120
Ile Tyr Gly Ala Leu Asn Trp Tyr Gln Gln
 35                      40

AAA CCC GGG AAA GCT CCG AAG CTT CTG ATT                    150
Lys Pro Gly Lys Ala Pro Lys Leu Leu Ile
 45                      50

TAC GGT GCG ACG AGC CTG CAG TCT GGA GTC                    180
Tyr Gly Ala Thr Ser Leu Gln Ser Gly Val
 55                      60

CCT TCT CGC TTC TCT GGA TCC GGC TCC GGA                    210
Pro Ser Arg Phe Ser Gly Ser Gly Ser Gly
 65                      70

ACG GAT TTC ACT CTG ACC ATC AGC AGT CTG                    240
Thr Asp Phe Thr Leu Thr Ile Ser Ser Leu
 75                      80

CAG CCT GAA GAC TTC GCT ACG TAT TAC TGT                    270
Gln Pro Glu Asp Phe Ala Thr Tyr Tyr Cys
 85                      90

CAG AAC GTT TTA AAT ACT CCG TTG ACT TTC                    300
Gln Asn Val Leu Asn Thr Pro Leu Thr Phe
 95                     100

GGA CAG GGT ACC AAG GTG GAA ATA AAA CGT                    330
Gly Gln Gly Thr Lys Val Glu Ile Lys Arg
105                     110

ACT GGC GGT GGT GGT TCT GGT GGC GGT GGA                    360
Thr Gly Gly Gly Gly Ser Gly Gly Gly Gly
115                     120

TCT GGT GGT GGC GGT TCT CAA GTC CAA CTG                    390
Ser Gly Gly Gly Gly Ser Gln Val Gln Leu
125                     130

GTG CAA TCC GGC GCC GAG GTC AAG AAG CCA                    420
Val Gln Ser Gly Ala Glu Val Lys Lys Pro
135                     140

GGG GCC TCA GTC AAA GTG TCC TGT AAA GCT                    450
Gly Ala Ser Val Lys Val Ser Cys Lys Ala
145                     150

AGC GGC TAT ATT TTT TCT AAT TAT TGG ATT                    480
Ser Gly Tyr Ile Phe Ser Asn Tyr Trp Ile
155                     160

CAA TGG GTG CGT CAG GCC CCC GGG CAG GGC                    510
Gln Trp Val Arg Gln Ala Pro Gly Gln Gly
165                     170

CTG GAA TGG ATG GGT GAG ATC TTA CCG GGC                    540
Leu Glu Trp Met Gly Glu Ile Leu Pro Gly
175                     180

TCT GGT AGC ACC GAA TAT ACC GAA AAT TTT                    570
Ser Gly Ser Thr Glu Tyr Thr Glu Asn Phe
185                     190

AAA GAC CGT GTT ACT ATG ACG CGT GAC ACT                    600
Lys Asp Arg Val Thr Met Thr Arg Asp Thr
195                     200

TCG ACT AGT ACA GTA TAC ATG GAG CTC TCC                    630
Ser Thr Ser Thr Val Tyr Met Glu Leu Ser
205                     210

AGC CTG CGA TCG GAG GAC ACG GCC GTC TAT                    660
Ser Leu Arg Ser Glu Asp Thr Ala Val Tyr
215                     220

TAT TGC GCG CGT TAT TTT TTT GGT TCT AGC                    690
Tyr Cys Ala Arg Tyr Phe Phe Gly Ser Ser
225                     230
```

```
CCG AAT TGG TAT TTT GAT GTT TGG GGT CAA                              720
Pro Asn Trp Tyr Phe Asp Val Trp Gly Gln
235                 240

GGA ACC CTG GTC ACT GTC TCG AGC TGA                                  747
Gly Thr Leu Val Thr Val Ser Ser
245

(2) INFORMATION FOR SEQ ID NO:26:

(i) SEQUENCE CHARACTERISTICS:
        (A) LENGTH:   747 base pairs
        (B) TYPE:  Nucleic Acid
        (C) STRANDEDNESS:  Double
        (D) TOPOLOGY:  linear (ii) MOLECULE TYPE:  Other nucleic acid
        (A) DESCRIPTION:5G1.1 scFv C015 (humanized)

(xi) SEQUENCE DESCRIPTION:  SEQ ID NO:26:

ATG GCC GAT ATC CAG ATG ACC CAG TCC CCG                               30
Met Ala Asp Ile Gln Met Thr Gln Ser Pro
1               5                   10

TCC TCC CTG TCC GCC TCT GTG GGC GAT AGG                               60
Ser Ser Leu Ser Ala Ser Val Gly Asp Arg
15                  20

GTC ACC ATC ACC TGC CGT GCT AGC GAA AAC                               90
Val Thr Ile Thr Cys Arg Ala Ser Glu Asn
25                  30

ATC TAT GGC GCG CTG AAC TGG TAT CAA CAG                              120
Ile Tyr Gly Ala Leu Asn Trp Tyr Gln Gln
35                  40

AAA CCC GGG AAA GCT CCG AAG CTT CTG ATT                              150
Lys Pro Gly Lys Ala Pro Lys Leu Leu Ile
45                  50

TAC GGT GCG ACG AGC CTG CAG TCT GGA GTC                              180
Tyr Gly Ala Thr Ser Leu Gln Ser Gly Val
55                  60

CCT TCT CGC TTC TCT GGA TCC GGC TCC GGA                              210
Pro Ser Arg Phe Ser Gly Ser Gly Ser Gly
65                  70

ACG GAT TTC ACT CTG ACC ATC AGC AGT CTG                              240
Thr Asp Phe Thr Leu Thr Ile Ser Ser Leu
75                  80

CAG CCT GAA GAC TTC GCT ACG TAT TAC TGT                              270
Gln Pro Glu Asp Phe Ala Thr Tyr Tyr Cys
85                  90

CAG AAC GTT TTA AAT ACT CCG TTG ACT TTC                              300
Gln Asn Val Leu Asn Thr Pro Leu Thr Phe
95                  100

GGA CAG GGT ACC AAG GTG GAA ATA AAA CGT                              330
Gly Gln Gly Thr Lys Val Glu Ile Lys Arg
105                 110

ACT GGC GGT GGT GGT TCT GGT GGC GGT GGA                              360
Thr Gly Gly Gly Gly Ser Gly Gly Gly Gly
115                 120

TCT GGT GGT GGC GGT TCT CAA GTC CAA CTG                              390
Ser Gly Gly Gly Gly Ser Gln Val Gln Leu
125                 130

GTG CAA TCC GGC GCC GAG GTC AAG AAG CCA                              420
Val Gln Ser Gly Ala Glu Val Lys Lys Pro
135                 140
```

-continued

| | |
|---|---|
| GGG GCC TCA GTC AAA GTG TCC TGT AAA GCT<br>Gly Ala Ser Val Lys Val Ser Cys Lys Ala<br>145             150 | 450 |
| AGC GGC TAT ATT TTT TCT AAT TAT TGG ATT<br>Ser Gly Tyr Ile Phe Ser Asn Tyr Trp Ile<br>155             160 | 480 |
| CAA TGG GTG CGT CAG GCC CCC GGG CAG GGC<br>Gln Trp Val Arg Gln Ala Pro Gly Gln Gly<br>165             170 | 510 |
| CTG GAA TGG ATG GGT GAG ATC TTA CCG GGC<br>Leu Glu Trp Met Gly Glu Ile Leu Pro Gly<br>175             180 | 540 |
| TCT GGT AGC ACC GAA TAT ACC GAA AAT TTT<br>Ser Gly Ser Thr Glu Tyr Thr Glu Asn Phe<br>185             190 | 570 |
| AAA GAC CGT GTT ACT ATG ACG CGT GAC ACT<br>Lys Asp Arg Val Thr Met Thr Arg Asp Thr<br>195             200 | 600 |
| TCG ACT AGT ACA GTA TAC ATG GAG CTC TCC<br>Ser Thr Ser Thr Val Tyr Met Glu Leu Ser<br>205             210 | 630 |
| AGC CTG CGA TCG GAG GAC ACG GCC GTC TAT<br>Ser Leu Arg Ser Glu Asp Thr Ala Val Tyr<br>215             220 | 660 |
| TAT TGC GCG CGT TAT TTT TTT GGT TCT AGC<br>Tyr Cys Ala Arg Tyr Phe Phe Gly Ser Ser<br>225             230 | 690 |
| CCG AAT TGG TAT TTT GAT GTT TGG GGT CAA<br>Pro Asn Trp Tyr Phe Asp Val Trp Gly Gln<br>235             240 | 720 |
| GGA ACC CTG GTC ACT GTC TCG AGC TGA<br>Gly Thr Leu Val Thr Val Ser Ser<br>245 | 747 |

What is claimed is:

1. An antibody comprising at least one antibody-antigen binding site, said antibody exhibiting specific binding to human complement component C5, said specific binding being targeted to the alpha chain of human complement component C5, wherein the antibody 1) inhibits complement activation in a human body fluid, 2) inhibits the binding of purified human complement component C5 to either human complement component C3 or human complement component C4, and 3) does not specifically bind to the human complement activation product free C5a.

2. The antibody of claim 1 wherein the inhibition of complement activation in the human body fluid is measurable as an increment of blockade of C5a generation and an increment of blockade of complement hemolytic activity in the body fluid, said increment of blockade of C5a generation being substantially equal to said increment of blockade of complement hemolytic activity.

3. The antibody of claim 1 wherein, upon binding to human C5, there is a 60% to 90% reduction in the ability of C5 to bind to human complement component C3.

4. The antibody of claim 1 wherein, upon binding to human C5, there is a 60% to 90% reduction in the ability of C5 to bind to human complement component C4.

5. The antibody of claim 1 wherein the antibody binds specifically to an isolated oligopeptide comprising an amino acid sequence corresponding to amino acid 8 through amino acid 12 of SEQ ID NO:1.

6. The antibody of claim 1 wherein the inhibition of complement activation in the human body fluid is measurable as a substantially complete blockade of C5a generation in the body fluid and a substantially complete blockade of complement hemolytic activity in the body fluid when the antibody is added to the body fluid at a concentration yielding a ratio equal to or less than 10 moles of antibody-antigen binding sites of the antibody to 1 mole of human C5 in the body fluid.

7. The antibody of claim 1 wherein the antibody is a humanized antibody.

8. The antibody of claim 1 wherein the antibody is an scFv.

9. The antibody of claim 1, wherein, when administered to a human patient via intravenous infusion, the antibody provides complete complement inhibition at dosages below 0.005 g/kg.

10. The antibody of claim 1, wherein, when administered to a human patient via intravenous infusion, the antibody provides therapeutic benefits at dosages below 0.0022 g/kg.

11. The antibody of claim 10, wherein the antibody is administered in association with an extracorporeal circulation procedure.

12. The antibody of claim 1 wherein the inhibition of complement activation in the human body fluid is measurable as a substantially complete blockade of C5a generation in the body fluid and a substantially complete blockade of complement hemolytic activity in the body fluid when the antibody is added to the body fluid at a concentration yielding a ratio equal to or less than 3 moles of antibody-antigen binding sites of the antibody to 1 mole of human C5 in the body fluid.

13. The antibody of claim 1, wherein, when administered to a human patient via intravenous infusion, the antibody provides therapeutically effective complement inhibition at dosages below 0.003 g/kg.

14. A sterile non-pyrogenic therapeutic agent comprising the antibody of claim 1 in a formulation suitable for administration to a human.

15. The therapeutic agent of claim 14 wherein the antibody is a humanized immunoglobulin.

16. The therapeutic agent of claim 14 wherein the antibody is an scFv.

17. The therapeutic agent of claim 14 wherein the antibody is made up of two or more heterodimeric subunits each containing one heavy and one light chain.

18. Antibody 5G1.1 scFv CB (humanized) having the amino acid sequence encoded by the nucleic acid sequence of SEQ ID NO:8.

19. An isolated antigen binding protein comprising:
   1) a variable light region CDR1 comprising an amino acid sequence corresponding to amino acid residues 26–36 of SEQ ID NO:8,
   2) a variable light region CDR2 comprising an amino acid sequence corresponding to amino acid residues 52–58 of SEQ ID NO:8,
   3) a variable light region CDR3 comprising an amino acid sequence corresponding to amino acid residues 91 through amino acid 99 of SEQ ID NO:8,
   4) a variable heavy region CDR1 comprising an amino acid sequence corresponding to amino acid residues 152 through amino acid 161 of SEQ ID NO:8,
   5) a variable heavy region CDR2 comprising an amino acid sequence corresponding to amino acid residues 176 through amino acid 192 of SEQ ID NO:8,
   6) a variable heavy region CDR3 comprising an amino acid sequence corresponding to amino acid residues 225 through amino acid 237 of SEQ ID NO:8, said protein exhibiting specific binding to human complement component C5, said specific binding being targeted to the alpha chain of human complement component C5, wherein the protein inhibits complement activation in a human body fluid and does not specifically bind to the human complement activation product free C5a.

20. A nucleic acid molecule comprising a nucleotide sequence encoding a polypeptide comprising a variable heavy chain region amino acid sequence corresponding to amino acid 1 through amino acid 122 of SEQ ID NO: 12.

21. Hybridoma 5G1.1 having ATCC designation HB-11625.

22. An antibody produced by the hybridoma of claim 21.

23. An antibody comprising at least one antibody-antigen binding site, said antibody exhibiting specific binding to human complement component C5, said specific binding being targeted to the alpha chain of human complement component C5, wherein:
   (A) the antibody inhibits (i) C5b-9-mediated hemolysis and (ii) C5a generation in a fluid comprising human serum; and
   (B) the antibody does not specifically bind to the human complement activation product free C5a.

* * * * *

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Title page, and Column 1, lines 1-3,</u>
Delete the title "C5-SPECIFIC ANTIBODIES FOR THE TREATMENT OF INFLAMMATORY DISEASES" and insert therefor -- ANTIBODIES TO HUMAN COMPLEMENT COMPONENT C5 --.

<u>Column 19,</u>
Line 54, delete "(SEQ ID NO:1)".
Line 55, following "KSSKC peptide", insert -- (SEQ ID NO:1) --.

<u>Column 55,</u>
Please delete lines 50-53, and insert therefor:

```
    Val Ile Asp His Gln Gly Thr Lys Ser Ser
                     5                  10

Lys Cys Val Arg Gln Lys Val Glu Gly Ser Ser
                    15                  20
```

<u>Column 57,</u>
Please delete lines 22-37, and insert therefor:

```
                Met Gly Leu Leu Gly Ile Leu Cys Phe Leu
                            -15                 -10

Ile Phe Leu Gly Lys Thr Trp Gly Gln Glu Gln Thr Tyr Val
                 -5                  -1                  5

Ile Ser Ala Pro Lys Ile Phe Arg Val Gly Ala Ser Glu Asn
                 10                  15                  20

Ile Val Ile Gln Val Tyr Gly Tyr Thr Glu Ala Phe Asp Ala
                     25                  30

Thr Ile Ser Ile Lys Ser Tyr Pro Asp Lys Lys Phe Ser Tyr
    35                   40                  45

Ser Ser Gly His Val His Leu Ser Ser Glu Asn Lys Phe Gln
        50                      55                  60

Asn Ser Ala Ile Leu Thr Ile Gln Pro Lys Gln Leu Pro Gly
                65                  70                  75

Gly Gln Asn Pro Val Ser Tyr Val Tyr Leu Glu Val Val Ser
                    80                  85                  90
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 57,</u>
Please delete lines 38-55, and insert therefor:

```
Lys His Phe Ser Lys Ser Lys Arg Met Pro Ile Thr Tyr Asp
                95                  100

Asn Gly Phe Leu Phe Ile His Thr Asp Lys Pro Val Tyr Thr
105                 110                 115

Pro Asp Gln Ser Val Lys Val Arg Val Tyr Ser Leu Asn Asp
    120             125                     130

Asp Leu Lys Pro Ala Lys Arg Glu Thr Val Leu Thr Phe Ile
        135                 140                 145

Asp Pro Glu Gly Ser Glu Val Asp Met Val Glu Glu Ile Asp
            150                 155                 160

His Ile Gly Ile Ile Ser Phe Pro Asp Phe Lys Ile Pro Ser
                165                 170

Asn Pro Arg Tyr Gly Met Trp Thr Ile Lys Ala Lys Tyr Lys
175                 180                 185

Glu Asp Phe Ser Thr Thr Gly Thr Ala Tyr Phe Glu Val Lys
    190                 195                 200

Glu Tyr Val Leu Pro His Phe Ser Val Ser Ile Glu Pro Glu
        205                 210                 215
```

<u>Column 59,</u>
Please delete lines 1-4, and insert therefor:

```
Tyr Asn Phe Ile Gly Tyr Lys Asn Phe Lys Asn Phe Glu Ile
            220             225             230

Thr Ile Lys Ala Arg Tyr Phe Tyr Asn Lys Val Val Thr Glu
                235             240
```

UNITED STATES PATENT AND TRADEMARK OFFICE
CERTIFICATE OF CORRECTION

PATENT NO. : 6,355,245 B1  
DATED : March 12, 2002  
INVENTOR(S) : Mark J. Evans et al.

Page 3 of 60

It is certified that error appears in the above-identified patent and that said Letters Patent is hereby corrected as shown below:

<u>Column 59,</u>
Please delete lines 5-28, and insert therefor:

```
Ala Asp Val Tyr Ile Thr Phe Gly Ile Arg Glu Asp Leu Lys
245             250             255

Asp Asp Gln Lys Glu Met Met Gln Thr Ala Met Gln Asn Thr
    260             265             270

Met Leu Ile Asn Gly Ile Ala Gln Val Thr Phe Asp Ser Glu
        275             280             285

Thr Ala Val Lys Glu Leu Ser Tyr Tyr Ser Leu Glu Asp Leu
            290             295             300

Asn Asn Lys Tyr Leu Tyr Ile Ala Val Thr Val Ile Glu Ser
                305             310

Thr Gly Gly Phe Ser Glu Glu Ala Glu Ile Pro Gly Ile Lys
315             320             325

Tyr Val Leu Ser Pro Tyr Lys Leu Asn Leu Val Ala Thr Pro
    330             335             340

Leu Phe Leu Lys Pro Gly Ile Pro Tyr Pro Ile Lys Val Gln
        345             350             355

Val Lys Asp Ser Leu Asp Gln Leu Val Gly Gly Val Pro Val
            360             365             370

Ile Leu Asn Ala Gln Thr Ile Asp Val Asn Gln Glu Thr Ser
                375             380

Asp Leu Asp Pro Ser Lys Ser Val Thr Arg Val Asp Asp Gly
385             390             395

Val Ala Ser Phe Val Leu Asn Leu Pro Ser Gly Val Thr Val
    400             405             410
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 59,</u>
Please delete lines 29-52, and insert therefor:

```
          Leu Glu Phe Asn Val Lys Thr Asp Ala Pro Asp Leu Pro Glu
                  415                 420                 425

Glu Asn Gln Ala Arg Glu Gly Tyr Arg Ala Ile Ala Tyr Ser
                          430                 435                 440

Ser Leu Ser Gln Ser Tyr Leu Tyr Ile Asp Trp Thr Asp Asn
                              445                 450

His Lys Ala Leu Leu Val Gly Glu His Leu Asn Ile Ile Val
          455                 460                 465

Thr Pro Lys Ser Pro Tyr Ile Asp Lys Ile Thr His Tyr Asn
                  470                 475                 480

Tyr Leu Ile Leu Ser Lys Gly Lys Ile Ile His Phe Gly Thr
                      485                 490                 495

Arg Glu Lys Phe Ser Asp Ala Ser Tyr Gln Ser Ile Asn Ile
                          500                 505                 510

Pro Val Thr Gln Asn Met Val Pro Ser Ser Arg Leu Leu Val
                              515                 520

Tyr Tyr Ile Val Thr Gly Glu Gln Thr Ala Glu Leu Val Ser
          525                 530                 535

Asp Ser Val Trp Leu Asn Ile Glu Glu Lys Cys Gly Asn Gln
                  540                 545                 550

Leu Gln Val His Leu Ser Pro Asp Ala Asp Ala Tyr Ser Pro
                      555                 560                 565

Gly Gln Thr Val Ser Leu Asn Met Ala Thr Gly Met Asp Ser
                          570                 575                 580
```

UNITED STATES PATENT AND TRADEMARK OFFICE
CERTIFICATE OF CORRECTION

PATENT NO. : 6,355,245 B1  
DATED : March 12, 2002  
INVENTOR(S) : Mark J. Evans et al.

It is certified that error appears in the above-identified patent and that said Letters Patent is hereby corrected as shown below:

<u>Column 61,</u>
Please delete lines 1-26, and insert therefor:

```
    Trp Val Ala Leu Ala Ala Val Asp Ser Ala Val Tyr Gly Val
                585                 590

Gln Arg Gly Ala Lys Lys Pro Leu Glu Arg Val Phe Gln Phe
    595             600                 605

Leu Glu Lys Ser Asp Leu Gly Cys Gly Ala Gly Gly Gly Leu
        610                 615             620

Asn Asn Ala Asn Val Phe His Leu Ala Gly Leu Thr Phe Leu
            625                 630             635

Thr Asn Ala Asn Ala Asp Asp Ser Gln Glu Asn Asp Glu Pro
                640                 645             650

Cys Lys Glu Ile Leu Arg Pro Arg Arg Thr Leu Gln Lys Lys
                655                 660

Ile Glu Glu Ile Ala Ala Lys Tyr Lys His Ser Val Val Lys
    665             670                 675

Lys Cys Cys Tyr Asp Gly Ala Cys Val Asn Asn Asp Glu Thr
        680                 685             690

Cys Glu Gln Arg Ala Ala Arg Ile Ser Leu Gly Pro Arg Cys
            695                 700             705

Ile Lys Ala Phe Thr Glu Cys Cys Val Val Ala Ser Gln Leu
                710                 715             720

Arg Ala Asn Ile Ser His Lys Asp Met Gln Leu Gly Arg Leu
                725                 730

His Met Lys Thr Leu Leu Pro Val Ser Lys Pro Glu Ile Arg
    735                 740                 745

Ser Tyr Phe Pro Glu Ser Trp Leu Trp Glu Val His Leu Val
        750                 755                 760
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 61,</u>
Please delete lines 27-52, and insert therefor:

```
Pro Arg Arg Lys Gln Leu Gln Phe Ala Leu Pro Asp Ser Leu
        765             770             775
Thr Thr Trp Glu Ile Gln Gly Ile Gly Ile Ser Asn Thr Gly
            780             785                 790
Ile Cys Val Ala Asp Thr Val Lys Ala Lys Val Phe Lys Asp
                795             800
Val Phe Leu Glu Met Asn Ile Pro Tyr Ser Val Val Arg Gly
805             810             815
Glu Gln Ile Gln Leu Lys Gly Thr Val Tyr Asn Tyr Arg Thr
    820             825             830
Ser Gly Met Gln Phe Cys Val Lys Met Ser Ala Val Glu Gly
        835             840             845
Ile Cys Thr Ser Glu Ser Pro Val Ile Asp His Gln Gly Thr
            850             855             860
Lys Ser Ser Lys Cys Val Arg Gln Lys Val Glu Gly Ser Ser
                865             870
Ser His Leu Val Thr Phe Thr Val Leu Pro Leu Glu Ile Gly
875             880             885
Leu His Asn Ile Asn Phe Ser Leu Glu Thr Trp Phe Gly Lys
    890             895             900
Glu Ile Leu Val Lys Thr Leu Arg Val Val Pro Glu Gly Val
        905             910             915
Lys Arg Glu Ser Tyr Ser Gly Val Thr Leu Asp Pro Arg Gly
            920             925             930
Ile Tyr Gly Thr Ile Ser Arg Arg Lys Glu Phe Pro Tyr Arg
                935             940
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 63,</u>
Please delete lines 1-26, and insert therefor:

```
          Ile Pro Leu Asp Leu Val Pro Lys Thr Glu Ile Lys Arg Ile
          945             950             955

Leu Ser Val Lys Gly Leu Leu Val Gly Glu Ile Leu Ser Ala
              960             965             970

Val Leu Ser Gln Glu Gly Ile Asn Ile Leu Thr His Leu Pro
              975             980             985

Lys Gly Ser Ala Glu Ala Glu Leu Met Ser Val Val Pro Val
                  990             995             1000

Phe Tyr Val Phe His Tyr Leu Glu Thr Gly Asn His Trp Asn
                      1005            1010

Ile Phe His Ser Asp Pro Leu Ile Glu Lys Gln Lys Leu Lys
          1015            1020            1025

Lys Lys Leu Lys Glu Gly Met Leu Ser Ile Met Ser Tyr Arg
              1030            1035            1040

Asn Ala Asp Tyr Ser Tyr Ser Val Trp Lys Gly Gly Ser Ala
                  1045            1050            1055

Ser Thr Trp Leu Thr Ala Phe Ala Leu Arg Val Leu Gly Gln
                      1060            1065            1070

Val Asn Lys Tyr Val Glu Gln Asn Gln Asn Ser Ile Cys Asn
                          1075            1080

Ser Leu Leu Trp Leu Val Glu Asn Tyr Gln Leu Asp Asn Gly
          1085            1090            1095

Ser Phe Lys Glu Asn Ser Gln Tyr Gln Pro Ile Lys Leu Gln
              1100            1105            1110

Gly Thr Leu Pro Val Glu Ala Arg Glu Asn Ser Leu Tyr Leu
                  1115            1120            1125
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 63,</u>
Please delete lines 27-52, and insert therefor:

```
    Thr Ala Phe Thr Val Ile Gly Ile Arg Lys Ala Phe Asp Ile
                1130            1135                    1140

Cys Pro Leu Val Lys Ile Asp Thr Ala Leu Ile Lys Ala Asp
                    1145            1150

Asn Phe Leu Leu Glu Asn Thr Leu Pro Ala Gln Ser Thr Phe
    1155                1160            1165

Thr Leu Ala Ile Ser Ala Tyr Ala Leu Ser Leu Gly Asp Lys
        1170            1175            1180

Thr His Pro Gln Phe Arg Ser Ile Val Ser Ala Leu Lys Arg
            1185            1190            1195

Glu Ala Leu Val Lys Gly Asn Pro Pro Ile Tyr Arg Phe Trp
                1200            1205                    1210

Lys Asp Asn Leu Gln His Lys Asp Ser Ser Val Pro Asn Thr
                    1215            1220

Gly Thr Ala Arg Met Val Glu Thr Thr Ala Tyr Ala Leu Leu
    1225                1230            1235

Thr Ser Leu Asn Leu Lys Asp Ile Asn Tyr Val Asn Pro Val
        1240            1245            1250

Ile Lys Trp Leu Ser Glu Glu Gln Arg Tyr Gly Gly Gly Phe
                1255            1260            1265

Tyr Ser Thr Gln Asp Thr Ile Asn Ala Ile Glu Gly Leu Thr
                1270            1275                    1280

Glu Tyr Ser Leu Leu Val Lys Gln Leu Arg Leu Ser Met Asp
                    1285            1290

Ile Asp Val Ser Tyr Lys His Lys Gly Ala Leu His Asn Tyr
    1295                1300            1305
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 65,</u>
Please delete lines 1-26, and insert therefor:

```
Lys Met Thr Asp Lys Asn Phe Leu Gly Arg Pro Val Glu Val
    1310            1315            1320

Leu Leu Asn Asp Asp Leu Ile Val Ser Thr Gly Phe Gly Ser
        1325            1330            1335

Gly Leu Ala Thr Val His Val Thr Thr Val Val His Lys Thr
            1340            1345            1350

Ser Thr Ser Glu Glu Val Cys Ser Phe Tyr Leu Lys Ile Asp
                1355            1360

Thr Gln Asp Ile Glu Ala Ser His Tyr Arg Gly Tyr Gly Asn
1365            1370            1375

Ser Asp Tyr Lys Arg Ile Val Ala Cys Ala Ser Tyr Lys Pro
    1380            1385            1390

Ser Arg Glu Glu Ser Ser Ser Gly Ser Ser His Ala Val Met
        1395            1400            1405

Asp Ile Ser Leu Pro Thr Gly Ile Ser Ala Asn Glu Glu Asp
            1410            1415            1420

Leu Lys Ala Leu Val Glu Gly Val Asp Gln Leu Phe Thr Asp
                1425            1430

Tyr Gln Ile Lys Asp Gly His Val Ile Leu Gln Leu Asn Ser
1435            1440            1445

Ile Pro Ser Ser Asp Phe Leu Cys Val Arg Phe Arg Ile Phe
    1450            1455            1460

Glu Leu Phe Glu Val Gly Phe Leu Ser Pro Ala Thr Phe Thr
        1465            1470            1475

Val Tyr Glu Tyr His Arg Pro Asp Lys Gln Cys Thr Met Phe
            1480            1485            1490
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 65,
Please delete lines 27-50, and insert therefor:

```
        Tyr Ser Thr Ser Asn Ile Lys Ile Gln Lys Val Cys Glu Gly
                        1495                1500

Ala Ala Cys Lys Cys Val Glu Ala Asp Cys Gly Gln Met Gln
        1505                1510                1515

Glu Glu Leu Asp Leu Thr Ile Ser Ala Glu Thr Arg Lys Gln
                1520                1525                1530

Thr Ala Cys Lys Pro Glu Ile Ala Tyr Ala Tyr Lys Val Ser
                    1535                1540                1545

Ile Thr Ser Ile Thr Val Glu Asn Val Phe Val Lys Tyr Lys
                        1550                1555                1560

Ala Thr Leu Leu Asp Ile Tyr Lys Thr Gly Glu Ala Val Ala
                            1565                1570

Glu Lys Asp Ser Glu Ile Thr Phe Ile Lys Lys Val Thr Cys
        1575                1580                1585

Thr Asn Ala Glu Leu Val Lys Gly Arg Gln Tyr Leu Ile Met
                1590                1595                1600

Gly Lys Glu Ala Leu Gln Ile Lys Tyr Asn Phe Ser Phe Arg
                    1605                1610                1615

Tyr Ile Tyr Pro Leu Asp Ser Leu Thr Trp Ile Glu Tyr Trp
                        1620                1625                1630

Pro Arg Asp Thr Thr Cys Ser Ser Cys Gln Ala Phe Leu Ala
                            1635                1640

Asn Leu Asp Glu Phe Ala Glu Asp Ile Phe Leu Asn Gly Cys
        1645                1650                1655
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 81,
Please delete lines 18-47, and insert therefor:

| | | | | | | | | | |
|---|---|---|---|---|---|---|---|---|---|
| ATG | GCC | GAC | ATC | CAG | ATG | ACT | CAG | TCT | CCA | 30 |
| Met | Ala | Asp | Ile | Gln | Met | Thr | Gln | Ser | Pro | |
| 1 | | | | 5 | | | | | 10 | |
| GCT | TCA | CTG | TCT | GCA | TCT | GTG | GGA | GAA | ACT | 60 |
| Ala | Ser | Leu | Ser | Ala | Ser | Val | Gly | Glu | Thr | |
| | | | | 15 | | | | | 20 | |
| GTC | ACC | ATC | ACA | TGT | GGA | GCA | AGT | GAG | AAT | 90 |
| Val | Thr | Ile | Thr | Cys | Gly | Ala | Ser | Glu | Asn | |
| | | | | 25 | | | | | 30 | |
| ATT | TAC | GGT | GCT | TTA | AAT | TGG | TAT | CAG | CGG | 120 |
| Ile | Tyr | Gly | Ala | Leu | Asn | Trp | Tyr | Gln | Arg | |
| | | | | 35 | | | | | 40 | |
| AAA | CAG | GGA | AAA | TCT | CCT | CAG | CTC | CTG | ATC | 150 |
| Lys | Gln | Gly | Lys | Ser | Pro | Gln | Leu | Leu | Ile | |
| | | | | 45 | | | | | 50 | |
| TAT | GGT | GCA | ACC | AAC | TTG | GCA | GAT | GGC | ATG | 180 |
| Tyr | Gly | Ala | Thr | Asn | Leu | Ala | Asp | Gly | Met | |
| | | | | 55 | | | | | 60 | |
| TCA | TCG | AGG | TTC | AGT | GGC | AGT | GGA | TCT | GGT | 210 |
| Ser | Ser | Arg | Phe | Ser | Gly | Ser | Gly | Ser | Gly | |
| | | | | 65 | | | | | 70 | |
| AGA | CAG | TAT | TAT | CTC | AAG | ATC | AGT | AGC | CTG | 240 |
| Arg | Gln | Tyr | Tyr | Leu | Lys | Ile | Ser | Ser | Leu | |
| | | | | 75 | | | | | 80 | |
| CAT | CCT | GAC | GAT | GTT | GCA | ACG | TAT | TAC | TGT | 270 |
| His | Pro | Asp | Asp | Val | Ala | Thr | Tyr | Tyr | Cys | |
| | | | | 85 | | | | | 90 | |
| CAA | AAT | GTG | TTA | AAT | ACT | CCT | CTC | ACG | TTC | 300 |
| Gln | Asn | Val | Leu | Asn | Thr | Pro | Leu | Thr | Phe | |
| | | | | 95 | | | | | 100 | |

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 81,</u>
Please delete line 48, through column 83, line 21, and insert therefor:

```
GGT GCT GGG ACC AAG TTG GAG CTG AAA CGG              330
Gly Ala Gly Thr Lys Leu Glu Leu Lys Arg
            105                 110

ACC GGA GGT GGC GGG TCG GGT GGC GGG GGA              360
Thr Gly Gly Gly Gly Ser Gly Gly Gly Gly
            115                 120

TCG GGT GGC GGA GGG TCG CAG GTT CAG CTG              390
Ser Gly Gly Gly Gly Ser Gln Val Gln Leu
            125                 130

CAG CAG TCT GGA GCC GAG CTG ATG AAG CCT              420
Gln Gln Ser Gly Ala Glu Leu Met Lys Pro
            135                 140

GGG GCC TCA GTG AAG ATG TCC TGC AAG GCT              450
Gly Ala Ser Val Lys Met Ser Cys Lys Ala
            145                 150

ACT GGC TAC ATA TTC AGT AAC TAC TGG ATA              480
Thr Gly Tyr Ile Phe Ser Asn Tyr Trp Ile
            155                 160

CAG TGG ATA AAG CAG AGG CCT GGA CAT GGC              510
Gln Trp Ile Lys Gln Arg Pro Gly His Gly
            165                 170

CTT GAG TGG ATT GGT GAG ATT TTA CCT GGA              540
Leu Glu Trp Ile Gly Glu Ile Leu Pro Gly
            175                 180

AGT GGT TCT ACT GAG TAC ACT GAG AAC TTC              570
Ser Gly Ser Thr Glu Tyr Thr Glu Asn Phe
            185                 190

AAG GAC AAG GCC GCA TTC ACT GCA GAT ACA              600
Lys Asp Lys Ala Ala Phe Thr Ala Asp Thr
            195                 200
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 83,</u>
Please delete lines 22-36, and insert therefor:

```
    TCC TCC AAC ACA GCC TAC ATG CAA CTC AGC              630
    Ser Ser Asn Thr Ala Tyr Met Gln Leu Ser
                    205                 210

AGC CTG ACA TCA GAG GAC TCT GCC GTC TAT              660
    Ser Leu Thr Ser Glu Asp Ser Ala Val Tyr
                    215                 220

TAC TGT GCA AGA TAT TTC TTC GGT AGT AGC              690
    Tyr Cys Ala Arg Tyr Phe Phe Gly Ser Ser
                    225                 230

CCC AAC TGG TAC TTC GAT GTC TGG GGC GCA              720
    Pro Asn Trp Tyr Phe Asp Val Trp Gly Ala
                    235                 240

GGG ACC ACG GTC ACC GTC TCC TCA TGA                  747
    Gly Thr Thr Val Thr Val Ser Ser
                    245
```

Please delete lines 46-57, and insert therefor:

```
    ATG GCC GAT ATC CAG ATG ACC CAG TCC CCG               30
    Met Ala Asp Ile Gln Met Thr Gln Ser Pro
     1               5                  10

TCC TCC CTG TCC GCC TCT GTG GGC GAT AGG               60
    Ser Ser Leu Ser Ala Ser Val Gly Asp Arg
                    15                  20

GTC ACC ATC ACC TGC GGC GCC AGC GAA AAC               90
    Val Thr Ile Thr Cys Gly Ala Ser Glu Asn
                    25                  30

ATC TAT GGC GCG CTG AAC TGG TAT CAA CGT              120
    Ile Tyr Gly Ala Leu Asn Trp Tyr Gln Arg
                    35                  40
```

UNITED STATES PATENT AND TRADEMARK OFFICE
CERTIFICATE OF CORRECTION

PATENT NO.    : 6,355,245 B1
DATED         : March 12, 2002
INVENTOR(S)   : Mark J. Evans et al.

It is certified that error appears in the above-identified patent and that said Letters Patent is hereby corrected as shown below:

<u>Column 85,</u>
Please delete lines 1-30, and insert therefor:

```
AAA CCT GGG AAA GCT CCG AAG CTT CTG ATT              150
Lys Pro Gly Lys Ala Pro Lys Leu Leu Ile
            45              50

TAC GGT GCG ACG AAC CTG GCA GAT GGA GTC              180
Tyr Gly Ala Thr Asn Leu Ala Asp Gly Val
            55              60

CCT TCT CGC TTC TCT GGA TCC GGC TCC GGA              210
Pro Ser Arg Phe Ser Gly Ser Gly Ser Gly
            65              70

ACG GAT TTC ACT CTG ACC ATC AGC AGT CTG              240
Thr Asp Phe Thr Leu Thr Ile Ser Ser Leu
            75              80

CAG CCT GAA GAC TTC GCT ACG TAT TAC TGT              270
Gln Pro Glu Asp Phe Ala Thr Tyr Tyr Cys
            85              90

CAG AAC GTT TTA AAT ACT CCG TTG ACT TTC              300
Gln Asn Val Leu Asn Thr Pro Leu Thr Phe
            95             100

GGA CAG GGT ACC AAG GTG GAA ATA AAA CGT              330
Gly Gln Gly Thr Lys Val Glu Ile Lys Arg
           105             110

ACT GGC GGT GGT GGT TCT GGT GGC GGT GGA              360
Thr Gly Gly Gly Gly Ser Gly Gly Gly Gly
           115             120

TCT GGT GGT GGC GGT TCT CAA GTC CAA CTG              390
Ser Gly Gly Gly Gly Ser Gln Val Gln Leu
           125             130

GTG CAA TCC GGC GCC GAG GTC AAG AAG CCA              420
Val Gln Ser Gly Ala Glu Val Lys Lys Pro
           135             140
```

UNITED STATES PATENT AND TRADEMARK OFFICE
CERTIFICATE OF CORRECTION

PATENT NO. : 6,355,245 B1  Page 15 of 60
DATED : March 12, 2002
INVENTOR(S) : Mark J. Evans et al.

It is certified that error appears in the above-identified patent and that said Letters Patent is hereby corrected as shown below:

<u>Column 85,</u>
Please delete lines 31-60, and insert therefor:

```
GGG GCC TCA GTC AAA GTG TCC TGT AAA GCT                 450
Gly Ala Ser Val Lys Val Ser Cys Lys Ala
            145                 150

AGC GGC TAT ATT TTT TCT AAT TAT TGG ATT                 480
Ser Gly Tyr Ile Phe Ser Asn Tyr Trp Ile
            155                 160

CAA TGG GTG CGT CAG GCC CCC GGG CAG GGC                 510
Gln Trp Val Arg Gln Ala Pro Gly Gln Gly
            165                 170

CTG GAA TGG ATG GGT GAG ATC TTA CCG GGC                 540
Leu Glu Trp Met Gly Glu Ile Leu Pro Gly
            175                 180

TCT GGT AGC ACC GAA TAT ACC GAA AAT TTT                 570
Ser Gly Ser Thr Glu Tyr Thr Glu Asn Phe
            185                 190

AAA GAC CGT GTT ACT ATG ACG CGT GAC ACT                 600
Lys Asp Arg Val Thr Met Thr Arg Asp Thr
            195                 200

TCG ACT AGT ACA GTA TAC ATG GAG CTC TCC                 630
Ser Thr Ser Thr Val Tyr Met Glu Leu Ser
            205                 210

AGC CTG CGA TCG GAG GAC ACG GCC GTC TAT                 660
Ser Leu Arg Ser Glu Asp Thr Ala Val Tyr
            215                 220

TAT TGC GCG CGT TAT TTT TTT GGT TCT AGC                 690
Tyr Cys Ala Arg Tyr Phe Phe Gly Ser Ser
            225                 230

CCG AAT TGG TAT TTT GAT GTT TGG GGT CAA                 720
Pro Asn Trp Tyr Phe Asp Val Trp Gly Gln
            235                 240
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 87,</u>
Please delete lines 1-3, and insert therefor:

```
GGA ACC CTG GTC ACT GTC TCG AGC TGA                              747
Gly Thr Leu Val Thr Val Ser Ser
                245
```

Please delete lines 13-36, and insert therefor:

```
ATG GGA ATC CAA GGA GGG TCT GTC CTG TTC                          30
Met Gly Ile Gln Gly Gly Ser Val Leu Phe
-25             -20

GGG CTG CTG CTC GTC CTG GCT GTC TTC TGC                          60
Gly Leu Leu Leu Val Leu Ala Val Phe Cys
-15             -10

CAT TCA GGT CAT AGC CTG CAG GAC ATC CAG                          90
His Ser Gly His Ser Leu Gln Asp Ile Gln
-5               1                   5

ATG ACT CAG TCT CCA GCT TCA CTG TCT GCA                         120
Met Thr Gln Ser Pro Ala Ser Leu Ser Ala
                10                  15

TCT GTG GGA GAA ACT GTC ACC ATC ACA TGT                         150
Ser Val Gly Glu Thr Val Thr Ile Thr Cys
                20                  25

GGA GCA AGT GAG AAT ATT TAC GGT GCT TTA                         180
Gly Ala Ser Glu Asn Ile Tyr Gly Ala Leu
                30                  35

AAT TGG TAT CAG CGG AAA CAG GGA AAA TCT                         210
Asn Trp Tyr Gln Arg Lys Gln Gly Lys Ser
                40                  45

CCT CAG CTC CTG ATC TAT GGT GCA ACC AAC                         240
Pro Gln Leu Leu Ile Tyr Gly Ala Thr Asn
                50                  55
```

UNITED STATES PATENT AND TRADEMARK OFFICE
CERTIFICATE OF CORRECTION

PATENT NO. : 6,355,245 B1  Page 17 of 60
DATED : March 12, 2002
INVENTOR(S) : Mark J. Evans et al.

It is certified that error appears in the above-identified patent and that said Letters Patent is hereby corrected as shown below:

<u>Column 87,</u>
Please delete line 37, through column 89, line 9, and insert therefor:

```
TTG GCA GAT GGC ATG TCA TCG AGG TTC AGT           270
Leu Ala Asp Gly Met Ser Ser Arg Phe Ser
                60                      65

GGC AGT GGA TCT GGT AGA CAG TAT TAT CTC           300
Gly Ser Gly Ser Gly Arg Gln Tyr Tyr Leu
                70                      75

AAG ATC AGT AGC CTG CAT CCT GAC GAT GTT           330
Lys Ile Ser Ser Leu His Pro Asp Asp Val
                80                      85

GCA ACG TAT TAC TGT CAA AAT GTG TTA AAT           360
Ala Thr Tyr Tyr Cys Gln Asn Val Leu Asn
                90                      95

ACT CCT CTC ACG TTC GGT GCT GGG ACC AAG           390
Thr Pro Leu Thr Phe Gly Ala Gly Thr Lys
                100                     105

TTG GAG CTG AAA CGA ACT GTG GCT GCA CCA           420
Leu Glu Leu Lys Arg Thr Val Ala Ala Pro
                110                     115

TCT GTC TTC ATC TTC CCG CCA TCT GAT GAG           450
Ser Val Phe Ile Phe Pro Pro Ser Asp Glu
                120                     125

CAG TTG AAA TCT GGA ACT GCC TCT GTT GTG           480
Gln Leu Lys Ser Gly Thr Ala Ser Val Val
                130                     135

TGC CTG CTG AAT AAC TTC TAT CCC AGA GAG           510
Cys Leu Leu Asn Asn Phe Tyr Pro Arg Glu
                140                     145

GCC AAA GTA CAG TGG AAG GTG GAT AAC GCC           540
Ala Lys Val Gln Trp Lys Val Asp Asn Ala
                150                     155
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 89,</u>
Please delete lines 10-29, and insert therefor:

```
CTC CAA TCG GGT AAC TCC CAG GAG AGT GTC                      570
Leu Gln Ser Gly Asn Ser Gln Glu Ser Val
            160                 165

ACA GAG CAG GAC AGC AAG GAC AGC ACC TAC                      600
Thr Glu Gln Asp Ser Lys Asp Ser Thr Tyr
            170                 175

AGC CTC AGC AGC ACC CTG ACG CTG AGC AAA                      630
Ser Leu Ser Ser Thr Leu Thr Leu Ser Lys
            180                 185

GCA GAC TAC GAG AAA CAC AAA GTC TAC GCC                      660
Ala Asp Tyr Glu Lys His Lys Val Tyr Ala
            190                 195

TGC GAA GTC ACC CAT CAG GGC CTG AGC TCG                      690
Cys Glu Val Thr His Gln Gly Leu Ser Ser
            200                 205

CCC GTC ACA AAG AGC TTC AAC AGG GGA GAG                      720
Pro Val Thr Lys Ser Phe Asn Arg Gly Glu
            210                 215

TGT TAG                                                      726
Cys
```

Please delete lines 39-44, and insert therefor:

```
ATG AAA TGG AGC TGG GTT ATT CTC TTC CTC                       30
Met Lys Trp Ser Trp Val Ile Leu Phe Leu
            -15                 -10

CTG TCA GTA ACT GCA GGT GTC CAC TCC CAG                       60
Leu Ser Val Thr Ala Gly Val His Ser Gln
            -5                   1
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 89,</u>
Please delete line 45, through column 91, line 15, and insert therefor:

```
GTT CAG CTG CAG CAG TCT GGA GCT GAG CTG                    90
Val Gln Leu Gln Gln Ser Gly Ala Glu Leu
          5                   10

ATG AAG CCT GGG GCC TCA GTG AAG ATG TCC                   120
Met Lys Pro Gly Ala Ser Val Lys Met Ser
         15                   20

TGC AAG GCT ACT GGC TAC ATA TTC AGT AAC                   150
Cys Lys Ala Thr Gly Tyr Ile Phe Ser Asn
         25                   30

TAC TGG ATA CAG TGG ATA AAG CAG AGG CCT                   180
Tyr Trp Ile Gln Trp Ile Lys Gln Arg Pro
         35                   40

GGA CAT GGC CTT GAG TGG ATT GGT GAG ATT                   210
Gly His Gly Leu Glu Trp Ile Gly Glu Ile
         45                   50

TTA CCT GGA AGT GGT TCT ACT GAG TAC ACT                   240
Leu Pro Gly Ser Gly Ser Thr Glu Tyr Thr
         55                   60

GAG AAC TTC AAG GAC AAG GCC GCA TTC ACT                   270
Glu Asn Phe Lys Asp Lys Ala Ala Phe Thr
         65                   70

GCA GAT ACA TCC TCC AAC ACA GCC TAC ATG                   300
Ala Asp Thr Ser Ser Asn Thr Ala Tyr Met
         75                   80

CAA CTC AGC AGC CTG ACA TCA GAG GAC TCT                   330
Gln Leu Ser Ser Leu Thr Ser Glu Asp Ser
         85                   90

GCC GTC TAT TAC TGT GCA AGA TAT TTC TTC                   360
Ala Val Tyr Tyr Cys Ala Arg Tyr Phe Phe
         95                  100
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 91,</u>
Please delete lines 16-45, and insert therefor:

```
GGT AGT AGC CCC AAC TGG TAC TTC GAT GTC            390
Gly Ser Ser Pro Asn Trp Tyr Phe Asp Val
            105                 110

TGG GGC GCA GGG ACC ACG GTC ACC GTC TCC            420
Trp Gly Ala Gly Thr Thr Val Thr Val Ser
            115                 120

TCA GCC TCC ACC AAG GGC CCA TCG GTC TTC            450
Ser Ala Ser Thr Lys Gly Pro Ser Val Phe
            125                 130

CCC CTG GCG CCC TCC TCC AAG AGC ACC TCT            480
Pro Leu Ala Pro Ser Ser Lys Ser Thr Ser
            135                 140

GGG GGC ACA GCG GCC CTG GGC TGC CTG GTC            510
Gly Gly Thr Ala Ala Leu Gly Cys Leu Val
            145                 150

AAG GAC TAC TTC CCC GAA CCG GTG ACG GTG            540
Lys Asp Tyr Phe Pro Glu Pro Val Thr Val
            155                 160

TCG TGG AAC TCA GGC GCC CTG ACC AGC GGC            570
Ser Trp Asn Ser Gly Ala Leu Thr Ser Gly
            165                 170

GTG CAC ACC TTC CCG GCT GTC CTA CAG TCC            600
Val His Thr Phe Pro Ala Val Leu Gln Ser
            175                 180

TCA GGA CTC TAC TCC CTC AGC AGC GTG GTG            630
Ser Gly Leu Tyr Ser Leu Ser Ser Val Val
            185                 190

ACC GTG CCC TCC AGC AGC TTG GGC ACC CAG            660
Thr Val Pro Ser Ser Ser Leu Gly Thr Gln
            195                 200
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 91,
Please delete lines 46-54, and insert therefor:

```
ACC TAC ATC TGC AAC GTG AAT CAC AAG CCC                690
Thr Tyr Ile Cys Asn Val Asn His Lys Pro
            205             210

AGC AAC ACC AAG GTG GAC AAG AAA GTT GAG                720
Ser Asn Thr Lys Val Asp Lys Lys Val Glu
            215             220

CCC AAA TCT TGT GAC AAA ACT CAC ACA TAA                750
Pro Lys Ser Cys Asp Lys Thr His Thr
            225
```

Column 93
Please delete lines 4-21, and insert therefor:

```
ATG AAG TGG AGC TGG GTT ATT CTC TTC CTC                 30
Met Lys Trp Ser Trp Val Ile Leu Phe Leu
            -15                 -10

CTG TCA GTA ACT GCC GGC GTC CAC TCC CAA                 60
Leu Ser Val Thr Ala Gly Val His Ser Gln
            -5                    1

GTC CAA CTG GTG CAA TCC GGC GCC GAG GTC                 90
Val Gln Leu Val Gln Ser Gly Ala Glu Val
             5                   10

AAG AAG CCA GGG GCC TCA GTC AAA GTG TCC                120
Lys Lys Pro Gly Ala Ser Val Lys Val Ser
            15                   20

TGT AAA GCT AGC GGC TAT ATT TTT TCT AAT                150
Cys Lys Ala Ser Gly Tyr Ile Phe Ser Asn
            25                   30

TAT TGG ATT CAA TGG GTG CGT CAG GCC CCC                180
Tyr Trp Ile Gln Trp Val Arg Gln Ala Pro
            35                   40
```

Page 21 of 60

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 93,
Please delete lines 22-51, and insert therefor:

```
        GGG CAG GGC CTG GAA TGG ATG GGT GAG ATC                210
        Gly Gln Gly Leu Glu Trp Met Gly Glu Ile
                        45                  50

TTA CCG GGC TCT GGT AGC ACC GAA TAT GCC                240
        Leu Pro Gly Ser Gly Ser Thr Glu Tyr Ala
                        55                  60

CAA AAA TTC CAG GGC CGT GTT ACT ATG ACT                270
        Gln Lys Phe Gln Gly Arg Val Thr Met Thr
                        65                  70

GCG GAC ACT TCG ACT AGT ACA GCC TAC ATG                300
        Ala Asp Thr Ser Thr Ser Thr Ala Tyr Met
                        75                  80

GAG CTC TCC AGC CTG CGA TCG GAG GAC ACG                330
        Glu Leu Ser Ser Leu Arg Ser Glu Asp Thr
                        85                  90

GCC GTC TAT TAT TGC GCG CGT TAT TTT TTT                360
        Ala Val Tyr Tyr Cys Ala Arg Tyr Phe Phe
                        95                  100

GGT TCT AGC CCG AAT TGG TAT TTT GAT GTT                390
        Gly Ser Ser Pro Asn Trp Tyr Phe Asp Val
                        105                 110

TGG GGT CAA GGA ACC CTG GTC ACT GTC TCG                420
        Trp Gly Gln Gly Thr Leu Val Thr Val Ser
                        115                 120

AGC GCC TCC ACC AAG GGC CCA TCG GTC TTC                450
        Ser Ala Ser Thr Lys Gly Pro Ser Val Phe
                        125                 130

CCC CTG GCG CCC TCC TCC AAG AGC ACC TCT                480
        Pro Leu Ala Pro Ser Ser Lys Ser Thr Ser
                        135                 140
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 93,
Please delete line 52, through column 95, line 27, and insert therefor:

```
GGG GGC ACA GCG GCC CTG GGC TGC CTG GTC               510
Gly Gly Thr Ala Ala Leu Gly Cys Leu Val
            145             150

AAG GAC TAC TTC CCC GAA CCG GTG ACG GTG               540
Lys Asp Tyr Phe Pro Glu Pro Val Thr Val
            155             160

TCG TGG AAC TCA GGC GCC CTG ACC AGC GGC               570
Ser Trp Asn Ser Gly Ala Leu Thr Ser Gly
            165             170

GTG CAC ACC TTC CCG GCT GTC CTA CAG TCC               600
Val His Thr Phe Pro Ala Val Leu Gln Ser
            175             180

TCA GGA CTC TAC TCC CTC AGC AGC GTG GTG               630
Ser Gly Leu Tyr Ser Leu Ser Ser Val Val
            185             190

ACC GTG CCC TCC AGC AGC TTG GGC ACC CAG               660
Thr Val Pro Ser Ser Ser Leu Gly Thr Gln
            195             200

ACC TAC ATC TGC AAC GTG AAT CAC AAG CCC               690
Thr Tyr Ile Cys Asn Val Asn His Lys Pro
            205             210

AGC AAC ACC AAG GTG GAC AAG AAA GTT GAG               720
Ser Asn Thr Lys Val Asp Lys Lys Val Glu
            215             220

CCC AAA TCT TGT GAC AAA ACT CAC ACA TAA               750
Pro Lys Ser Cys Asp Lys Thr His Thr
            225             230
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 95,</u>
Please delete line 31, through column 97, line 3, and insert therefor:

```
       ATG AAG TGG AGC TGG GTT ATT CTC TTC CTC           30
       Met Lys Trp Ser Trp Val Ile Leu Phe Leu
                       -15                 -10

CTG TCA GTA ACT GCC GGC GTC CAC TCC CAA           60
       Leu Ser Val Thr Ala Gly Val His Ser Gln
                       -5                   1

GTC CAA CTG GTG CAA TCC GGC GCC GAG GTC           90
       Val Gln Leu Val Gln Ser Gly Ala Glu Val
                        5                  10

AAG AAG CCA GGG GCC TCA GTC AAA GTG TCC          120
       Lys Lys Pro Gly Ala Ser Val Lys Val Ser
                       15                  20

TGT AAA GCT AGC GGC TAT ATT TTT TCT AAT          150
       Cys Lys Ala Ser Gly Tyr Ile Phe Ser Asn
                       25                  30

TAT TGG ATT CAA TGG GTG CGT CAG GCC CCC          180
       Tyr Trp Ile Gln Trp Val Arg Gln Ala Pro
                       35                  40

GGG CAG GGC CTG GAA TGG ATG GGT GAG ATC          210
       Gly Gln Gly Leu Glu Trp Met Gly Glu Ile
                       45                  50

TTA CCG GGC TCT GGT AGC ACC GAA TAT ACC          240
       Leu Pro Gly Ser Gly Ser Thr Glu Tyr Thr
                       55                  60

GAA AAT TTT AAA GAC CGT GTT ACT ATG ACG          270
       Glu Asn Phe Lys Asp Arg Val Thr Met Thr
                       65                  70

CGT GAC ACT TCG ACT AGT ACA GTA TAC ATG          300
       Arg Asp Thr Ser Thr Ser Thr Val Tyr Met
                       75                  80
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 97,
Please delete lines 4-33, and insert therefor:

```
GAG CTC TCC AGC CTG CGA TCG GAG GAC ACG            330
Glu Leu Ser Ser Leu Arg Ser Glu Asp Thr
            85                      90

GCC GTC TAT TAT TGC GCG CGT TAT TTT TTT            360
Ala Val Tyr Tyr Cys Ala Arg Tyr Phe Phe
            95                     100

GGT TCT AGC CCG AAT TGG TAT TTT GAT GTT            390
Gly Ser Ser Pro Asn Trp Tyr Phe Asp Val
           105                     110

TGG GGT CAA GGA ACC CTG GTC ACT GTC TCG            420
Trp Gly Gln Gly Thr Leu Val Thr Val Ser
           115                     120

AGC GCC TCC ACC AAG GGC CCA TCG GTC TTC            450
Ser Ala Ser Thr Lys Gly Pro Ser Val Phe
           125                     130

CCC CTG GCG CCC TCC TCC AAG AGC ACC TCT            480
Pro Leu Ala Pro Ser Ser Lys Ser Thr Ser
           135                     140

GGG GGC ACA GCG GCC CTG GGC TGC CTG GTC            510
Gly Gly Thr Ala Ala Leu Gly Cys Leu Val
           145                     150

AAG GAC TAC TTC CCC GAA CCG GTG ACG GTG            540
Lys Asp Tyr Phe Pro Glu Pro Val Thr Val
           155                     160

TCG TGG AAC TCA GGC GCC CTG ACC AGC GGC            570
Ser Trp Asn Ser Gly Ala Leu Thr Ser Gly
           165                     170

GTG CAC ACC TTC CCG GCT GTC CTA CAG TCC            600
Val His Thr Phe Pro Ala Val Leu Gln Ser
           175                     180
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 97,
Please delete lines 34-48, and insert therefor:

```
        TCA GGA CTC TAC TCC CTC AGC AGC GTG GTG              630
        Ser Gly Leu Tyr Ser Leu Ser Ser Val Val
                        185                 190

ACC GTG CCC TCC AGC AGC TTG GGC ACC CAG              660
        Thr Val Pro Ser Ser Ser Leu Gly Thr Gln
                        195                 200

ACC TAC ATC TGC AAC GTG AAT CAC AAG CCC              690
        Thr Tyr Ile Cys Asn Val Asn His Lys Pro
                        205                 210

AGC AAC ACC AAG GTG GAC AAG AAA GTT GAG              720
        Ser Asn Thr Lys Val Asp Lys Lys Val Glu
                        215                 220

CCC AAA TCT TGT GAC AAA ACT CAC ACA TAA              750
        Pro Lys Ser Cys Asp Lys Thr His Thr
                        225                 230
```

Column 99,
Please delete lines 2-13, and insert therefor:

```
    ATG GGA ATC CAA GGA GGG TCT GTC CTG TTC                   30
    Met Gly Ile Gln Gly Gly Ser Val Leu Phe
    -25                     -20

GGG CTG CTG CTC GTC CTG GCT GTC TTC TGC                   60
    Gly Leu Leu Leu Val Leu Ala Val Phe Cys
    -15                     -10

CAT TCA GGT CAT AGC CTG CAG GAT ATC CAG                   90
    His Ser Gly His Ser Leu Gln Asp Ile Gln
    -5                       1                  5

ATG ACC CAG TCC CCG TCC TCC CTG TCC GCC                  120
    Met Thr Gln Ser Pro Ser Ser Leu Ser Ala
                        10                  15
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 99,
Please delete lines 14-43, and insert therefor:

```
TCT GTG GGC GAT AGG GTC ACC ATC ACC TGC                150
Ser Val Gly Asp Arg Val Thr Ile Thr Cys
                 20                  25

GGC GCC AGC GAA AAC ATC TAT GGC GCG CTG                180
Gly Ala Ser Glu Asn Ile Tyr Gly Ala Leu
                 30                  35

AAC TGG TAT CAA CGT AAA CCT GGG AAA GCT                210
Asn Trp Tyr Gln Arg Lys Pro Gly Lys Ala
                 40                  45

CCG AAG CTT CTG ATT TAC GGT GCG ACG AAC                240
Pro Lys Leu Leu Ile Tyr Gly Ala Thr Asn
                 50                  55

CTG GCA GAT GGA GTC CCT TCT CGC TTC TCT                270
Leu Ala Asp Gly Val Pro Ser Arg Phe Ser
                 60                  65

GGA TCC GGC TCC GGA ACG GAT TAC ACT CTG                300
Gly Ser Gly Ser Gly Thr Asp Tyr Thr Leu
                 70                  75

ACC ATC AGC AGT CTG CAA CCT GAG GAC TTC                330
Thr Ile Ser Ser Leu Gln Pro Glu Asp Phe
                 80                  85

GCT ACG TAT TAC TGT CAG AAC GTT TTA AAT                360
Ala Thr Tyr Tyr Cys Gln Asn Val Leu Asn
                 90                  95

ACT CCG TTG ACT TTC GGA CAG GGT ACC AAG                390
Thr Pro Leu Thr Phe Gly Gln Gly Thr Lys
                100                 105

GTG GAA ATA AAA CGA ACT GTG GCT GCA CCA                420
Val Glu Ile Lys Arg Thr Val Ala Ala Pro
                110                 115
```

Page 27 of 60

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 99,</u>
Please delete line 44, through column 101, line 17, and insert therefor:

```
        TCT GTC TTC ATC TTC CCG CCA TCT GAT GAG                450
        Ser Val Phe Ile Phe Pro Pro Ser Asp Glu
                        120                 125

CAG TTG AAA TCT GGA ACT GCC TCT GTT GTG                480
        Gln Leu Lys Ser Gly Thr Ala Ser Val Val
                        130                 135

TGC CTG CTG AAT AAC TTC TAT CCC AGA GAG                510
        Cys Leu Leu Asn Asn Phe Tyr Pro Arg Glu
                        140                 145

GCC AAA GTA CAG TGG AAG GTG GAT AAC GCC                540
        Ala Lys Val Gln Trp Lys Val Asp Asn Ala
                        150                 155

CTC CAA TCG GGT AAC TCC CAG GAG AGT GTC                570
        Leu Gln Ser Gly Asn Ser Gln Glu Ser Val
                        160                 165

ACA GAG CAG GAC AGC AAG GAC AGC ACC TAC                600
        Thr Glu Gln Asp Ser Lys Asp Ser Thr Tyr
                        170                 175

AGC CTC AGC AGC ACC CTG ACG CTG AGC AAA                630
        Ser Leu Ser Ser Thr Leu Thr Leu Ser Lys
                        180                 185

GCA GAC TAC GAG AAA CAC AAA GTC TAC GCC                660
        Ala Asp Tyr Glu Lys His Lys Val Tyr Ala
                        190                 195

TGC GAA GTC ACC CAT CAG GGC CTG AGC TCG                690
        Cys Glu Val Thr His Gln Gly Leu Ser Ser
                        200                 205

CCC GTC ACA AAG AGC TTC AAC AGG GGA GAG                720
        Pro Val Thr Lys Ser Phe Asn Arg Gly Glu
                        210                 215

TGT TAG                                                726
        Cys
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 101,
Please delete lines 28-57, and insert therefor:

```
ATG GGA ATC CAA GGA GGG TCT GTC CTG TTC                           30
Met Gly Ile Gln Gly Gly Ser Val Leu Phe
-25                 -20

GGG CTG CTG CTC GTC CTG GCT GTC TTC TGC                           60
Gly Leu Leu Leu Val Leu Ala Val Phe Cys
-15                 -10

CAT TCA GGT CAT AGC CTG CAG GAT ATC CAG                           90
His Ser Gly His Ser Leu Gln Asp Ile Gln
-5                   1                 5

ATG ACC CAG TCC CCG TCC TCC CTG TCC GCC                          120
Met Thr Gln Ser Pro Ser Ser Leu Ser Ala
                 10                  15

TCT GTG GGC GAT AGG GTC ACC ATC ACC TGC                          150
Ser Val Gly Asp Arg Val Thr Ile Thr Cys
                 20                  25

GGC GCC AGC GAA AAC ATC TAT GGC GCG CTG                          180
Gly Ala Ser Glu Asn Ile Tyr Gly Ala Leu
                 30                  35

AAC TGG TAT CAA CGT AAA CCT GGG AAA GCT                          210
Asn Trp Tyr Gln Arg Lys Pro Gly Lys Ala
                 40                  45

CCG AAG CTT CTG ATT TAC GGT GCG ACG AAC                          240
Pro Lys Leu Leu Ile Tyr Gly Ala Thr Asn
                 50                  55

CTG GCA GAT GGA GTC CCT TCT CGC TTC TCT                          270
Leu Ala Asp Gly Val Pro Ser Arg Phe Ser
                 60                  65

GGA TCC GGC TCC GGA ACG GAT TTC ACT CTG                          300
Gly Ser Gly Ser Gly Thr Asp Phe Thr Leu
                 70                  75
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 103,</u>
Please delete lines 1-30, and insert therefor:

```
ACC ATC AGC AGT CTG CAG CCT GAA GAC TTC                    330
Thr Ile Ser Ser Leu Gln Pro Glu Asp Phe
                80                      85

GCT ACG TAT TAC TGT CAG AAC GTT TTA AAT                    360
Ala Thr Tyr Tyr Cys Gln Asn Val Leu Asn
                90                      95

ACT CCG TTG ACT TTC GGA CAG GGT ACC AAG                    390
Thr Pro Leu Thr Phe Gly Gln Gly Thr Lys
                100                     105

GTG GAA ATA AAA CGA ACT GTG GCT GCA CCA                    420
Val Glu Ile Lys Arg Thr Val Ala Ala Pro
                110                     115

TCT GTC TTC ATC TTC CCG CCA TCT GAT GAG                    450
Ser Val Phe Ile Phe Pro Pro Ser Asp Glu
                120                     125

CAG TTG AAA TCT GGA ACT GCC TCT GTT GTG                    480
Gln Leu Lys Ser Gly Thr Ala Ser Val Val
                130                     135

TGC CTG CTG AAT AAC TTC TAT CCC AGA GAG                    510
Cys Leu Leu Asn Asn Phe Tyr Pro Arg Glu
                140                     145

GCC AAA GTA CAG TGG AAG GTG GAT AAC GCC                    540
Ala Lys Val Gln Trp Lys Val Asp Asn Ala
                150                     155

CTC CAA TCG GGT AAC TCC CAG GAG AGT GTC                    570
Leu Gln Ser Gly Asn Ser Gln Glu Ser Val
                160                     165

ACA GAG CAG GAC AGC AAG GAC AGC ACC TAC                    600
Thr Glu Gln Asp Ser Lys Asp Ser Thr Tyr
                170                     175
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 103,
Please delete lines 31-44, and insert therefor:

```
AGC CTC AGC AGC ACC CTG ACG CTG AGC AAA                      630
Ser Leu Ser Ser Thr Leu Thr Leu Ser Lys
            180                     185

GCA GAC TAC GAG AAA CAC AAA GTC TAC GCC                      660
Ala Asp Tyr Glu Lys His Lys Val Tyr Ala
            190                     195

TGC GAA GTC ACC CAT CAG GGC CTG AGC TCG                      690
Cys Glu Val Thr His Gln Gly Leu Ser Ser
            200                     205

CCC GTC ACA AAG AGC TTC AAC AGG GGA GAG                      720
Pro Val Thr Lys Ser Phe Asn Arg Gly Glu
            210                     215

TGT TAG                                                      726
Cys
```

Please delete line 55, through column 105, line 9, and insert therefor:

```
ATG GAC ATG AGG GTC CCC GCT CAG CTC CTG                       30
Met Asp Met Arg Val Pro Ala Gln Leu Leu
            -20                     -15

GGG CTC CTG CTA CTC TGG CTC CGA GGT GCC                       60
Gly Leu Leu Leu Leu Trp Leu Arg Gly Ala
            -10                      -5

AGA TGT GAT ATC CAG ATG ACC CAG TCC CCG                       90
Arg Cys Asp Ile Gln Met Thr Gln Ser Pro
             1                       5

TCC TCC CTG TCC GCC TCT GTG GGC GAT AGG                      120
Ser Ser Leu Ser Ala Ser Val Gly Asp Arg
             10                     15
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 105,</u>
Please delete lines 10-39, and insert therefor:

```
GTC ACC ATC ACC TGC GGC GCC AGC GAA AAC        150
Val Thr Ile Thr Cys Gly Ala Ser Glu Asn
    20                  25

ATC TAT GGC GCG CTG AAC TGG TAT CAA CAG        180
Ile Tyr Gly Ala Leu Asn Trp Tyr Gln Gln
    30                  35

AAA CCC GGG AAA GCT CCG AAG CTT CTG ATT        210
Lys Pro Gly Lys Ala Pro Lys Leu Leu Ile
    40                  45

TAC GGT GCG ACG AAC CTG GCA GAT GGA GTC        240
Tyr Gly Ala Thr Asn Leu Ala Asp Gly Val
    50                  55

CCT TCT CGC TTC TCT GGA TCC GGC TCC GGA        270
Pro Ser Arg Phe Ser Gly Ser Gly Ser Gly
    60                  65

ACG GAT TTC ACT CTG ACC ATC AGC AGT CTG        300
Thr Asp Phe Thr Leu Thr Ile Ser Ser Leu
    70                  75

CAG CCT GAA GAC TTC GCT ACG TAT TAC TGT        330
Gln Pro Glu Asp Phe Ala Thr Tyr Tyr Cys
    80                  85

CAG AAC GTT TTA AAT ACT CCG TTG ACT TTC        360
Gln Asn Val Leu Asn Thr Pro Leu Thr Phe
    90                  95

GGA CAG GGT ACC AAG GTG GAA ATA AAA CGA        390
Gly Gln Gly Thr Lys Val Glu Ile Lys Arg
    100                 105

ACT GTG GCT GCA CCA TCT GTC TTC ATC TTC        420
Thr Val Ala Ala Pro Ser Val Phe Ile Phe
    110                 115
```

Page 32 of 60

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 105,
Please delete line 40, through column 107, line 9, and insert therefor:

```
    CCG CCA TCT GAT GAG CAG TTG AAA TCT GGA                    450
    Pro Pro Ser Asp Glu Gln Leu Lys Ser Gly
        120                 125

ACT GCC TCT GTT GTG TGC CTG CTG AAT AAC                    480
    Thr Ala Ser Val Val Cys Leu Leu Asn Asn
        130                 135

TTC TAT CCC AGA GAG GCC AAA GTA CAG TGG                    510
    Phe Tyr Pro Arg Glu Ala Lys Val Gln Trp
        140                 145

AAG GTG GAT AAC GCC CTC CAA TCG GGT AAC                    540
    Lys Val Asp Asn Ala Leu Gln Ser Gly Asn
        150                 155

TCC CAG GAG AGT GTC ACA GAG CAG GAC AGC                    570
    Ser Gln Glu Ser Val Thr Glu Gln Asp Ser
        160                 165

AAG GAC AGC ACC TAC AGC CTC AGC AGC ACC                    600
    Lys Asp Ser Thr Tyr Ser Leu Ser Ser Thr
        170                 175

CTG ACG CTG AGC AAA GCA GAC TAC GAG AAA                    630
    Leu Thr Leu Ser Lys Ala Asp Tyr Glu Lys
        180                 185

CAC AAA GTC TAC GCC TGC GAA GTC ACC CAT                    660
    His Lys Val Tyr Ala Cys Glu Val Thr His
        190                 195

CAG GGC CTG AGC TCG CCC GTC ACA AAG AGC                    690
    Gln Gly Leu Ser Ser Pro Val Thr Lys Ser
        200                 205

TTC AAC AGG GGA GAG TGT TAG                                711
    Phe Asn Arg Gly Glu Cys
        210
```

UNITED STATES PATENT AND TRADEMARK OFFICE
CERTIFICATE OF CORRECTION

PATENT NO. : 6,355,245 B1  
DATED : March 12, 2002  
INVENTOR(S) : Mark J. Evans et al.

It is certified that error appears in the above-identified patent and that said Letters Patent is hereby corrected as shown below:

<u>Column 107,</u>  
Please delete lines 20-49, and insert therefor:

```
ATG AAG TGG AGC TGG GTT ATT CTC TTC CTC                  30
Met Lys Trp Ser Trp Val Ile Leu Phe Leu
            -15                     -10

CTG TCA GTA ACT GCC GGC GTC CAC TCC CAA                  60
Leu Ser Val Thr Ala Gly Val His Ser Gln
             -5                       1

GTC CAA CTG GTG CAA TCC GGC GCC GAG GTC                  90
Val Gln Leu Val Gln Ser Gly Ala Glu Val
              5                      10

AAG AAG CCA GGG GCC TCA GTC AAA GTG TCC                 120
Lys Lys Pro Gly Ala Ser Val Lys Val Ser
             15                      20

TGT AAA GCT AGC GGC TAT ATT TTT TCT AAT                 150
Cys Lys Ala Ser Gly Tyr Ile Phe Ser Asn
             25                      30

TAT TGG ATT CAA TGG GTG CGT CAG GCC CCC                 180
Tyr Trp Ile Gln Trp Val Arg Gln Ala Pro
             35                      40

GGG CAG GGC CTG GAA TGG ATG GGT GAG ATC                 210
Gly Gln Gly Leu Glu Trp Met Gly Glu Ile
             45                      50

TTA CCG GGC TCT GGT AGC ACC GAA TAT GCC                 240
Leu Pro Gly Ser Gly Ser Thr Glu Tyr Ala
             55                      60

CAA AAA TTC CAG GGC CGT GTT ACT ATG ACT                 270
Gln Lys Phe Gln Gly Arg Val Thr Met Thr
             65                      70

CGT GAC ACT TCG ACT AGT ACA GTA TAC ATG                 300
Arg Asp Thr Ser Thr Ser Thr Val Tyr Met
             75                      80
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 107,
Please delete line 50, through column 109, line 21, and insert therefor:

```
GAG CTC TCC AGC CTG CGA TCG GAG GAC ACG                330
Glu Leu Ser Ser Leu Arg Ser Glu Asp Thr
            85                      90

GCC GTC TAT TAT TGC GCG CGT TAT TTT TTT                360
Ala Val Tyr Tyr Cys Ala Arg Tyr Phe Phe
            95                      100

GGT TCT AGC CCG AAT TGG TAT TTT GAT GTT                390
Gly Ser Ser Pro Asn Trp Tyr Phe Asp Val
            105                     110

TGG GGT CAA GGA ACC CTG GTC ACT GTC TCG                420
Trp Gly Gln Gly Thr Leu Val Thr Val Ser
            115                     120

AGC GCC TCC ACC AAG GGC CCA TCG GTC TTC                450
Ser Ala Ser Thr Lys Gly Pro Ser Val Phe
            125                     130

CCC CTG GCG CCC TCC TCC AAG AGC ACC TCT                480
Pro Leu Ala Pro Ser Ser Lys Ser Thr Ser
            135                     140

GGG GGC ACA GCG GCC CTG GGC TGC CTG GTC                510
Gly Gly Thr Ala Ala Leu Gly Cys Leu Val
            145                     150

AAG GAC TAC TTC CCC GAA CCG GTG ACG GTG                540
Lys Asp Tyr Phe Pro Glu Pro Val Thr Val
            155                     160

TCG TGG AAC TCA GGC GCC CTG ACC AGC GGC                570
Ser Trp Asn Ser Gly Ala Leu Thr Ser Gly
            165                     170

GTG CAC ACC TTC CCG GCT GTC CTA CAG TCC                600
Val His Thr Phe Pro Ala Val Leu Gln Ser
            175                     180
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 109,
Please delete lines 22-36, and insert therefor:

```
    TCA GGA CTC TAC TCC CTC AGC AGC GTG GTG              630
    Ser Gly Leu Tyr Ser Leu Ser Ser Val Val
                185                 190

ACC GTG CCC TCC AGC AGC TTG GGC ACC CAG              660
    Thr Val Pro Ser Ser Ser Leu Gly Thr Gln
                195                 200

ACC TAC ATC TGC AAC GTG AAT CAC AAG CCC              690
    Thr Tyr Ile Cys Asn Val Asn His Lys Pro
                205                 210

AGC AAC ACC AAG GTG GAC AAG AAA GTT GAG              720
    Ser Asn Thr Lys Val Asp Lys Lys Val Glu
                215                 220

CCC AAA TCT TGT GAC AAA ACT CAC ACA TAA              750
    Pro Lys Ser Cys Asp Lys Thr His Thr
                225                 230
```

Please delete lines 47-58, and insert therefor:

```
    ATG GCC GAT ATC CAG ATG ACC CAG TCC CCG               30
    Met Ala Asp Ile Gln Met Thr Gln Ser Pro
     1               5                  10

TCC TCC CTG TCC GCC TCT GTG GGC GAT AGG               60
    Ser Ser Leu Ser Ala Ser Val Gly Asp Arg
                 15                  20

GTC ACC ATC ACC TGC GGC GCC AGC GAA AAC               90
    Val Thr Ile Thr Cys Gly Ala Ser Glu Asn
                 25                  30

ATC TAT GGC GCG CTG AAC TGG TAT CAA CAG              120
    Ile Tyr Gly Ala Leu Asn Trp Tyr Gln Gln
                 35                  40
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 111,</u>
Please delete lines 1-30, and insert therefor:

```
AAA CCT GGG AAA GCT CCG AAG CTT CTG ATT         150
Lys Pro Gly Lys Ala Pro Lys Leu Leu Ile
            45                      50

TAC GGT GCG ACG AAC CTG GCA GAT GGA GTC         180
Tyr Gly Ala Thr Asn Leu Ala Asp Gly Val
            55                      60

CCT TCT CGC TTC TCT GGA TCC GGC TCC GGA         210
Pro Ser Arg Phe Ser Gly Ser Gly Ser Gly
            65                      70

ACG GAT TTC ACT CTG ACC ATC AGC AGT CTG         240
Thr Asp Phe Thr Leu Thr Ile Ser Ser Leu
            75                      80

CAG CCT GAA GAC TTC GCT ACG TAT TAC TGT         270
Gln Pro Glu Asp Phe Ala Thr Tyr Tyr Cys
            85                      90

CAG AAC GTT TTA AAT ACT CCG TTG ACT TTC         300
Gln Asn Val Leu Asn Thr Pro Leu Thr Phe
            95                      100

GGA CAG GGT ACC AAG GTG GAA ATA AAA CGT         330
Gly Gln Gly Thr Lys Val Glu Ile Lys Arg
            105                     110

ACT GGC GGT GGT GGT TCT GGT GGC GGT GGA         360
Thr Gly Gly Gly Gly Ser Gly Gly Gly Gly
            115                     120

TCT GGT GGT GGC GGT TCT CAA GTC CAA CTG         390
Ser Gly Gly Gly Gly Ser Gln Val Gln Leu
            125                     130

GTG CAA TCC GGC GCC GAG GTC AAG AAG CCA         420
Val Gln Ser Gly Ala Glu Val Lys Lys Pro
            135                     140
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 111,
Please delete lines 31-60, and insert therefor:

```
GGG GCC TCA GTC AAA GTG TCC TGT AAA GCT                450
Gly Ala Ser Val Lys Val Ser Cys Lys Ala
            145             150

AGC GGC TAT ATT TTT TCT AAT TAT TGG ATT                480
Ser Gly Tyr Ile Phe Ser Asn Tyr Trp Ile
            155             160

CAA TGG GTG CGT CAG GCC CCC GGG CAG GGC                510
Gln Trp Val Arg Gln Ala Pro Gly Gln Gly
            165             170

CTG GAA TGG ATG GGT GAG ATC TTA CCG GGC                540
Leu Glu Trp Met Gly Glu Ile Leu Pro Gly
            175             180

TCT GGT AGC ACC GAA TAT GCC CAA AAA TTC                570
Ser Gly Ser Thr Glu Tyr Ala Gln Lys Phe
            185             190

CAG GGC CGT GTT ACT ATG ACG CGT GAC ACT                600
Gln Gly Arg Val Thr Met Thr Arg Asp Thr
            195             200

TCG ACT AGT ACA GTA TAC ATG GAG CTC TCC                630
Ser Thr Ser Thr Val Tyr Met Glu Leu Ser
            205             210

AGC CTG CGA TCG GAG GAC ACG GCC GTC TAT                660
Ser Leu Arg Ser Glu Asp Thr Ala Val Tyr
            215             220

TAT TGC GCG CGT TAT TTT TTT GGT TCT AGC                690
Tyr Cys Ala Arg Tyr Phe Phe Gly Ser Ser
            225             230

CCG AAT TGG TAT TTT GAT GTT TGG GGT CAA                720
Pro Asn Trp Tyr Phe Asp Val Trp Gly Gln
            235             240
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 113,</u>
Please delete lines 1-3, and insert therefor:

```
GGA ACC CTG GTC ACT GTC TCG AGC TGA                    747
Gly Thr Leu Val Thr Val Ser Ser
                        245
```

<u>Column 119,</u>
Please delete lines 2-25, and insert therefor:

```
ATG GCC AAT ATT GTG CTG ACC CAA TCT CCA                 30
Met Ala Asn Ile Val Leu Thr Gln Ser Pro
 1               5                  10

GCT TCT TTG GCT GTG TCT CTA GGG CAG AGG                 60
Ala Ser Leu Ala Val Ser Leu Gly Gln Arg
                15                  20

GCC ACC ATA TCC TGC AGA GCC AGT GAA AGT                 90
Ala Thr Ile Ser Cys Arg Ala Ser Glu Ser
                25                  30

GTT GAT AGT TAT GAC AAT AGT TTT ATG CAC                120
Val Asp Ser Tyr Asp Asn Ser Phe Met His
                35                  40

TGG TAC CAG CAG AAA CCA GGA CAG CCA CCC                150
Trp Tyr Gln Gln Lys Pro Gly Gln Pro Pro
                45                  50

AAA CTC CTC ATC TTT CTT GCA TCC AAC CTA                180
Lys Leu Leu Ile Phe Leu Ala Ser Asn Leu
                55                  60

GAA TCT GGG GTC CCT GCC AGG TTC AGT GGC                210
Glu Ser Gly Val Pro Ala Arg Phe Ser Gly
                65                  70

AGT GGG TCT AGG ACA GAC TTC ACC CTC ACC                240
Ser Gly Ser Arg Thr Asp Phe Thr Leu Thr
                75                  80
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 119,
Please delete lines 26-55, and insert therefor:

```
ATT GAT CCT GTG GAG GCT GAT GAT GCT GCA                 270
Ile Asp Pro Val Glu Ala Asp Asp Ala Ala
             85                      90

ACC TAT TAC TGT CAG CAA AAT AAT GAG GTT                 300
Thr Tyr Tyr Cys Gln Gln Asn Asn Glu Val
             95                     100

CCG AAC ACG TTC GGA GGG GGG ACC AAG CTG                 330
Pro Asn Thr Phe Gly Gly Gly Thr Lys Leu
            105                     110

GAA ATA AAA CGG ACC GGA GGT GGC GGG TCG                 360
Glu Ile Lys Arg Thr Gly Gly Gly Gly Ser
            115                     120

GGT GGC GGG GGA TCG GGT GGC GGA GGG TCG                 390
Gly Gly Gly Gly Ser Gly Gly Gly Gly Ser
            125                     130

GAC GTC AAG CTC GTG GAG TCT GGG GGA GAC                 420
Asp Val Lys Leu Val Glu Ser Gly Gly Asp
            135                     140

TTA GTG AAG CTT GGA GGG TCC CTG AAA CTC                 450
Leu Val Lys Leu Gly Gly Ser Leu Lys Leu
            145                     150

TCC TGT GCA GCC TCT GGA TTC ACC TTC AGT                 480
Ser Cys Ala Ala Ser Gly Phe Thr Phe Ser
            155                     160

AGC TAT TAT ATG TCT TGG GTT CGC CAG ATT                 510
Ser Tyr Tyr Met Ser Trp Val Arg Gln Ile
            165                     170

TCA GAG AAG AGG CTG GAG TTG GTC GCA GCC                 540
Ser Glu Lys Arg Leu Glu Leu Val Ala Ala
            175                     180
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 119,
Please delete lines 56, through column 121, line 22, and insert therefor:

```
ATT AAT AGT AAT GGT GAT AGC ACC TAC TAT                    570
Ile Asn Ser Asn Gly Asp Ser Thr Tyr Tyr
            185                 190

CCA GAC ACT GTG AAG GGC CGA TTC ACC ATC                    600
Pro Asp Thr Val Lys Gly Arg Phe Thr Ile
            195                 200

TCC AGA GAC AAT GCC AAG AGC ACC CTG GAT                    630
Ser Arg Asp Asn Ala Lys Ser Thr Leu Asp
            205                 210

CTG CAA ATG AGC AGT CTG AAG TCT GAG GAC                    660
Leu Gln Met Ser Ser Leu Lys Ser Glu Asp
            215                 220

ACA GCC TTG TAT TTC TGT GTA AGA GAG ACT                    690
Thr Ala Leu Tyr Phe Cys Val Arg Glu Thr
            225                 230

TAT TAC TAC GGG ATT AGT CCC GTC TTC GAT                    720
Tyr Tyr Tyr Gly Ile Ser Pro Val Phe Asp
            235                 240

GTC TGG GGC ACA GGG ACC ACG GTC ACC GTC                    750
Val Trp Gly Thr Gly Thr Thr Val Thr Val
            245                 250

TCC TCA CTC GAG CAC CAC CAC CAC CAC CAC                    780
Ser Ser Leu Glu His His His His His His
            255                 260

TGA                                                         783
```

Page 41 of 60

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 121,
Please delete lines 32, through column 123, line 3, and insert therefor:

```
ATG GCC GAT ATC CAG ATG ACC CAG TCC CCG                30
Met Ala Asp Ile Gln Met Thr Gln Ser Pro
 1               5                   10

TCC TCC CTG TCC GCC TCT GTG GGC GAT AGG                60
Ser Ser Leu Ser Ala Ser Val Gly Asp Arg
                15                   20

GTC ACC ATC ACC TGC GGC GCC AGC GAA AAC                90
Val Thr Ile Thr Cys Gly Ala Ser Glu Asn
                25                   30

ATC TAT GGC GCG CTG AAC TGG TAT CAA CAG               120
Ile Tyr Gly Ala Leu Asn Trp Tyr Gln Gln
                35                   40

AAA CCC GGG AAA GCT CCG AAG CTT CTG ATT               150
Lys Pro Gly Lys Ala Pro Lys Leu Leu Ile
                45                   50

TAC GGT GCG ACG AAC CTG GCA GAT GGA GTC               180
Tyr Gly Ala Thr Asn Leu Ala Asp Gly Val
                55                   60

CCT TCT CGC TTC TCT GGA TCC GGC TCC GGA               210
Pro Ser Arg Phe Ser Gly Ser Gly Ser Gly
                65                   70

ACG GAT TTC ACT CTG ACC ATC AGC AGT CTG               240
Thr Asp Phe Thr Leu Thr Ile Ser Ser Leu
                75                   80

CAG CCT GAA GAC TTC GCT ACG TAT TAC TGT               270
Gln Pro Glu Asp Phe Ala Thr Tyr Tyr Cys
                85                   90

CAG AAC GTT TTA AAT ACT CCG TTG ACT TTC               300
Gln Asn Val Leu Asn Thr Pro Leu Thr Phe
                95                  100
```

Page 42 of 60

UNITED STATES PATENT AND TRADEMARK OFFICE
CERTIFICATE OF CORRECTION

PATENT NO.     : 6,355,245 B1
DATED          : March 12, 2002
INVENTOR(S)    : Mark J. Evans et al.

It is certified that error appears in the above-identified patent and that said Letters Patent is hereby corrected as shown below:

<u>Column 123,</u>
Please delete lines 4-33, and insert therefor:

```
GGA CAG GGT ACC AAG GTG GAA ATA AAA CGT                330
Gly Gln Gly Thr Lys Val Glu Ile Lys Arg
              105                 110

ACT GGC GGT GGT GGT TCT GGT GGC GGT GGA                360
Thr Gly Gly Gly Gly Ser Gly Gly Gly Gly
              115                 120

TCT GGT GGT GGC GGT TCT CAA GTC CAA CTG                390
Ser Gly Gly Gly Gly Ser Gln Val Gln Leu
              125                 130

GTG CAA TCC GGC GCC GAG GTC AAG AAG CCA                420
Val Gln Ser Gly Ala Glu Val Lys Lys Pro
              135                 140

GGG GCC TCA GTC AAA GTG TCC TGT AAA GCT                450
Gly Ala Ser Val Lys Val Ser Cys Lys Ala
              145                 150

AGC GGC TAT ATT TTT TCT AAT TAT TGG ATT                480
Ser Gly Tyr Ile Phe Ser Asn Tyr Trp Ile
              155                 160

CAA TGG GTG CGT CAG GCC CCC GGG CAG GGC                510
Gln Trp Val Arg Gln Ala Pro Gly Gln Gly
              165                 170

CTG GAA TGG ATG GGT GAG ATC TTA CCG GGC                540
Leu Glu Trp Met Gly Glu Ile Leu Pro Gly
              175                 180

TCT GGT AGC ACC GAA TAT ACC GAA AAT TTT                570
Ser Gly Ser Thr Glu Tyr Thr Glu Asn Phe
              185                 190

AAA GAC CGT GTT ACT ATG ACG CGT GAC ACT                600
Lys Asp Arg Val Thr Met Thr Arg Asp Thr
              195                 200
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 123,
Please delete lines 34-48, and insert therefor:

```
TCG ACT AGT ACA GTA TAC ATG GAG CTC TCC                630
Ser Thr Ser Thr Val Tyr Met Glu Leu Ser
            205             210

AGC CTG CGA TCG GAG GAC ACG GCC GTC TAT                660
Ser Leu Arg Ser Glu Asp Thr Ala Val Tyr
            215             220

TAT TGC GCG CGT TAT TTT TTT GGT TCT AGC                690
Tyr Cys Ala Arg Tyr Phe Phe Gly Ser Ser
            225             230

CCG AAT TGG TAT TTT GAT GTT TGG GGT CAA                720
Pro Asn Trp Tyr Phe Asp Val Trp Gly Gln
            235             240

GGA ACC CTG GTC ACT GTC TCG AGC TGA                    747
Gly Thr Leu Val Thr Val Ser Ser
            245
```

Column 125,
Please delete lines 2-13, and insert therefor:

```
ATG GCC GAT ATC CAG ATG ACC CAG TCC CCG                 30
Met Ala Asp Ile Gln Met Thr Gln Ser Pro
 1               5               10

TCC TCC CTG TCC GCC TCT GTG GGC GAT AGG                 60
Ser Ser Leu Ser Ala Ser Val Gly Asp Arg
            15              20

GTC ACC ATC ACC TGC CGT GCT AGC GAA AAC                 90
Val Thr Ile Thr Cys Arg Ala Ser Glu Asn
            25              30

ATC TAT GGC GCG CTG AAC TGG TAT CAA CAG                120
Ile Tyr Gly Ala Leu Asn Trp Tyr Gln Gln
            35              40
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 125,
Please delete lines 14-43, and insert therefor:

```
AAA CCT GGG AAA GCT CCG AAG CTT CTG ATT                     150
Lys Pro Gly Lys Ala Pro Lys Leu Leu Ile
                45                  50

TAC GGT GCG ACG AAC CTG GCA GAT GGA GTC                     180
Tyr Gly Ala Thr Asn Leu Ala Asp Gly Val
                55                  60

CCT TCT CGC TTC TCT GGA TCC GGC TCC GGA                     210
Pro Ser Arg Phe Ser Gly Ser Gly Ser Gly
                65                  70

ACG GAT TTC ACT CTG ACC ATC AGC AGT CTG                     240
Thr Asp Phe Thr Leu Thr Ile Ser Ser Leu
                75                  80

CAG CCT GAA GAC TTC GCT ACG TAT TAC TGT                     270
Gln Pro Glu Asp Phe Ala Thr Tyr Tyr Cys
                85                  90

CAG AAC GTT TTA AAT ACT CCG TTG ACT TTC                     300
Gln Asn Val Leu Asn Thr Pro Leu Thr Phe
                95                 100

GGA CAG GGT ACC AAG GTG GAA ATA AAA CGT                     330
Gly Gln Gly Thr Lys Val Glu Ile Lys Arg
               105                 110

ACT GGC GGT GGT GGT TCT GGT GGC GGT GGA                     360
Thr Gly Gly Gly Gly Ser Gly Gly Gly Gly
               115                 120

TCT GGT GGT GGC GGT TCT CAA GTC CAA CTG                     390
Ser Gly Gly Gly Gly Ser Gln Val Gln Leu
               125                 130

GTG CAA TCC GGC GCC GAG GTC AAG AAG CCA                     420
Val Gln Ser Gly Ala Glu Val Lys Lys Pro
               135                 140
```

UNITED STATES PATENT AND TRADEMARK OFFICE
CERTIFICATE OF CORRECTION

PATENT NO.     : 6,355,245 B1
DATED          : March 12, 2002
INVENTOR(S)    : Mark J. Evans et al.

It is certified that error appears in the above-identified patent and that said Letters Patent is hereby corrected as shown below:

Column 125,
Please delete line 44, through column 127, line 15, and insert therefor:

```
        GGG GCC TCA GTC AAA GTG TCC TGT AAA GCT              450
        Gly Ala Ser Val Lys Val Ser Cys Lys Ala
                        145             150

AGC GGC TAT ATT TTT TCT AAT TAT TGG ATT              480
        Ser Gly Tyr Ile Phe Ser Asn Tyr Trp Ile
                        155             160

CAA TGG GTG CGT CAG GCC CCC GGG CAG GGC              510
        Gln Trp Val Arg Gln Ala Pro Gly Gln Gly
                        165             170

CTG GAA TGG ATG GGT GAG ATC TTA CCG GGC              540
        Leu Glu Trp Met Gly Glu Ile Leu Pro Gly
                        175             180

TCT GGT AGC ACC GAA TAT GCC CAA AAA TTC              570
        Ser Gly Ser Thr Glu Tyr Ala Gln Lys Phe
                        185             190

CAG GGC CGT GTT ACT ATG ACG CGT GAC ACT              600
        Gln Gly Arg Val Thr Met Thr Arg Asp Thr
                        195             200

TCG ACT AGT ACA GTA TAC ATG GAG CTC TCC              630
        Ser Thr Ser Thr Val Tyr Met Glu Leu Ser
                        205             210

AGC CTG CGA TCG GAG GAC ACG GCC GTC TAT              660
        Ser Leu Arg Ser Glu Asp Thr Ala Val Tyr
                        215             220

TAT TGC GCG CGT TAT TTT TTT GGT TCT AGC              690
        Tyr Cys Ala Arg Tyr Phe Phe Gly Ser Ser
                        225             230

CCG AAT TGG TAT TTT GAT GTT TGG GGT CAA              720
        Pro Asn Trp Tyr Phe Asp Val Trp Gly Gln
                        235             240
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 127,</u>
Please delete lines 16-18, and insert therefor:

```
    GGA ACC CTG GTC ACT GTC TCG AGC TGA                       747
    Gly Thr Leu Val Thr Val Ser Ser
                        245
```

Please delete lines 29-52, and insert therefor:

```
    ATG GCC GAT ATC CAG ATG ACC CAG TCC CCG                    30
    Met Ala Asp Ile Gln Met Thr Gln Ser Pro
     1               5                  10

TCC TCC CTG TCC GCC TCT GTG GGC GAT AGG                    60
    Ser Ser Leu Ser Ala Ser Val Gly Asp Arg
                    15                  20

GTC ACC ATC ACC TGC GGC GCC AGC GAA AAC                    90
    Val Thr Ile Thr Cys Gly Ala Ser Glu Asn
                    25                  30

ATC TAT GGC GCG CTG AAC TGG TAT CAA CAG                   120
    Ile Tyr Gly Ala Leu Asn Trp Tyr Gln Gln
                    35                  40

AAA CCT GGG AAA GCT CCG AAG CTT CTG ATT                   150
    Lys Pro Gly Lys Ala Pro Lys Leu Leu Ile
                    45                  50

TAC GGT GCG ACG AGC CTG CAG TCT GGA GTC                   180
    Tyr Gly Ala Thr Ser Leu Gln Ser Gly Val
                    55                  60

CCT TCT CGC TTC TCT GGA TCC GGC TCC GGA                   210
    Pro Ser Arg Phe Ser Gly Ser Gly Ser Gly
                    65                  70

ACG GAT TTC ACT CTG ACC ATC AGC AGT CTG                   240
    Thr Asp Phe Thr Leu Thr Ile Ser Ser Leu
                    75                  80
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 127,
Please delete line 53, through column 129, line 24, and insert therefor:

```
    CAG CCT GAA GAC TTC GCT ACG TAT TAC TGT          270
    Gln Pro Glu Asp Phe Ala Thr Tyr Tyr Cys
                    85                      90

CAG AAC GTT TTA AAT ACT CCG TTG ACT TTC          300
    Gln Asn Val Leu Asn Thr Pro Leu Thr Phe
                    95                      100

GGA CAG GGT ACC AAG GTG GAA ATA AAA CGT          330
    Gly Gln Gly Thr Lys Val Glu Ile Lys Arg
                    105                     110

ACT GGC GGT GGT GGT TCT GGT GGC GGT GGA          360
    Thr Gly Gly Gly Gly Ser Gly Gly Gly Gly
                    115                     120

TCT GGT GGT GGC GGT TCT CAA GTC CAA CTG          390
    Ser Gly Gly Gly Gly Ser Gln Val Gln Leu
                    125                     130

GTG CAA TCC GGC GCC GAG GTC AAG AAG CCA          420
    Val Gln Ser Gly Ala Glu Val Lys Lys Pro
                    135                     140

GGG GCC TCA GTC AAA GTG TCC TGT AAA GCT          450
    Gly Ala Ser Val Lys Val Ser Cys Lys Ala
                    145                     150

AGC GGC TAT ATT TTT TCT AAT TAT TGG ATT          480
    Ser Gly Tyr Ile Phe Ser Asn Tyr Trp Ile
                    155                     160

CAA TGG GTG CGT CAG GCC CCC GGG CAG GGC          510
    Gln Trp Val Arg Gln Ala Pro Gly Gln Gly
                    165                     170

CTG GAA TGG ATG GGT GAG ATC TTA CCG GGC          540
    Leu Glu Trp Met Gly Glu Ile Leu Pro Gly
                    175                     180
```

UNITED STATES PATENT AND TRADEMARK OFFICE
CERTIFICATE OF CORRECTION

PATENT NO.   : 6,355,245 B1
DATED        : March 12, 2002
INVENTOR(S)  : Mark J. Evans et al.

It is certified that error appears in the above-identified patent and that said Letters Patent is hereby corrected as shown below:

<u>Column 129,</u>
Please delete lines 25-45, and insert therefor:

```
TCT GGT AGC ACC GAA TAT GCC CAA AAA TTC                570
Ser Gly Ser Thr Glu Tyr Ala Gln Lys Phe
            185                 190

CAG GGC CGT GTT ACT ATG ACG CGT GAC ACT                600
Gln Gly Arg Val Thr Met Thr Arg Asp Thr
            195                 200

TCG ACT AGT ACA GTA TAC ATG GAG CTC TCC                630
Ser Thr Ser Thr Val Tyr Met Glu Leu Ser
            205                 210

AGC CTG CGA TCG GAG GAC ACG GCC GTC TAT                660
Ser Leu Arg Ser Glu Asp Thr Ala Val Tyr
            215                 220

TAT TGC GCG CGT TAT TTT TTT GGT TCT AGC                690
Tyr Cys Ala Arg Tyr Phe Phe Gly Ser Ser
            225                 230

CCG AAT TGG TAT TTT GAT GTT TGG GGT CAA                720
Pro Asn Trp Tyr Phe Asp Val Trp Gly Gln
            235                 240

GGA ACC CTG GTC ACT GTC TCG AGC TGA                    747
Gly Thr Leu Val Thr Val Ser Ser
            245
```

Please delete line 56, through column 131, line 3, and insert therefor:

```
ATG GCC GAT ATC CAG ATG ACC CAG TCC CCG                 30
Met Ala Asp Ile Gln Met Thr Gln Ser Pro
 1               5                  10

TCC TCC CTG TCC GCC TCT GTG GGC GAT AGG                 60
Ser Ser Leu Ser Ala Ser Val Gly Asp Arg
            15                  20
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 131,</u>
Please delete lines 4-33, and insert therefor:

```
GTC ACC ATC ACC TGC CGT GCT AGC GAA AAC            90
Val Thr Ile Thr Cys Arg Ala Ser Glu Asn
                25                  30

ATC TAT GGC GCG CTG AAC TGG TAT CAA CAG           120
Ile Tyr Gly Ala Leu Asn Trp Tyr Gln Gln
                35                  40

AAA CCT GGG AAA GCT CCG AAG CTT CTG ATT           150
Lys Pro Gly Lys Ala Pro Lys Leu Leu Ile
                45                  50

TAC GGT GCG ACG AGC CTG CAG TCT GGA GTC           180
Tyr Gly Ala Thr Ser Leu Gln Ser Gly Val
                55                  60

CCT TCT CGC TTC TCT GGA TCC GGC TCC GGA           210
Pro Ser Arg Phe Ser Gly Ser Gly Ser Gly
                65                  70

ACG GAT TTC ACT CTG ACC ATC AGC AGT CTG           240
Thr Asp Phe Thr Leu Thr Ile Ser Ser Leu
                75                  80

CAG CCT GAA GAC TTC GCT ACG TAT TAC TGT           270
Gln Pro Glu Asp Phe Ala Thr Tyr Tyr Cys
                85                  90

CAG AAC GTT TTA AAT ACT CCG TTG ACT TTC           300
Gln Asn Val Leu Asn Thr Pro Leu Thr Phe
                95                 100

GGA CAG GGT ACC AAG GTG GAA ATA AAA CGT           330
Gly Gln Gly Thr Lys Val Glu Ile Lys Arg
               105                 110

ACT GGC GGT GGT GGT TCT GGT GGC GGT GGA           360
Thr Gly Gly Gly Gly Ser Gly Gly Gly Gly
               115                 120
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 131,
Please delete line 34, through column 133, line 3, and insert therefor:

| TCT | GGT | GGT | GGC | GGT | TCT | CAA | GTC | CAA | CTG | 390 |
| Ser | Gly | Gly | Gly | Gly | Ser | Gln | Val | Gln | Leu | |
| | | | | 125 | | | | | 130 | |
| GTG | CAA | TCC | GGC | GCC | GAG | GTC | AAG | AAG | CCA | 420 |
| Val | Gln | Ser | Gly | Ala | Glu | Val | Lys | Lys | Pro | |
| | | | | 135 | | | | | 140 | |
| GGG | GCC | TCA | GTC | AAA | GTG | TCC | TGT | AAA | GCT | 450 |
| Gly | Ala | Ser | Val | Lys | Val | Ser | Cys | Lys | Ala | |
| | | | | 145 | | | | | 150 | |
| AGC | GGC | TAT | ATT | TTT | TCT | AAT | TAT | TGG | ATT | 480 |
| Ser | Gly | Tyr | Ile | Phe | Ser | Asn | Tyr | Trp | Ile | |
| | | | | 155 | | | | | 160 | |
| CAA | TGG | GTG | CGT | CAG | GCC | CCC | GGG | CAG | GGC | 510 |
| Gln | Trp | Val | Arg | Gln | Ala | Pro | Gly | Gln | Gly | |
| | | | | 165 | | | | | 170 | |
| CTG | GAA | TGG | ATG | GGT | GAG | ATC | TTA | CCG | GGC | 540 |
| Leu | Glu | Trp | Met | Gly | Glu | Ile | Leu | Pro | Gly | |
| | | | | 175 | | | | | 180 | |
| TCT | GGT | AGC | ACC | GAA | TAT | GCC | CAA | AAA | TTC | 570 |
| Ser | Gly | Ser | Thr | Glu | Tyr | Ala | Gln | Lys | Phe | |
| | | | | 185 | | | | | 190 | |
| CAG | GGC | CGT | GTT | ACT | ATG | ACG | CGT | GAC | ACT | 600 |
| Gln | Gly | Arg | Val | Thr | Met | Thr | Arg | Asp | Thr | |
| | | | | 195 | | | | | 200 | |
| TCG | ACT | AGT | ACA | GTA | TAC | ATG | GAG | CTC | TCC | 630 |
| Ser | Thr | Ser | Thr | Val | Tyr | Met | Glu | Leu | Ser | |
| | | | | 205 | | | | | 210 | |
| AGC | CTG | CGA | TCG | GAG | GAC | ACG | GCC | GTC | TAT | 660 |
| Ser | Leu | Arg | Ser | Glu | Asp | Thr | Ala | Val | Tyr | |
| | | | | 215 | | | | | 220 | |

UNITED STATES PATENT AND TRADEMARK OFFICE
CERTIFICATE OF CORRECTION

PATENT NO. : 6,355,245 B1  Page 52 of 60
DATED : March 12, 2002
INVENTOR(S) : Mark J. Evans et al.

It is certified that error appears in the above-identified patent and that said Letters Patent is hereby corrected as shown below:

<u>Column 133,</u>
Please delete lines 4-12, and insert therefor:

```
TAT TGC GCG CGT TAT TTT TTT GGT TCT AGC                690
Tyr Cys Ala Arg Tyr Phe Phe Gly Ser Ser
                225                 230

CCG AAT TGG TAT TTT GAT GTT TGG GGT CAA                720
Pro Asn Trp Tyr Phe Asp Val Trp Gly Gln
                235                 240

GGA ACC CTG GTC ACT GTC TCG AGC TGA                    747
Gly Thr Leu Val Thr Val Ser Ser
                245
```

Please delete lines 22-45, and insert therefor:

```
ATG GCC GAT ATC CAG ATG ACC CAG TCC CCG                 30
Met Ala Asp Ile Gln Met Thr Gln Ser Pro
 1               5                  10

TCC TCC CTG TCC GCC TCT GTG GGC GAT AGG                 60
Ser Ser Leu Ser Ala Ser Val Gly Asp Arg
                15                  20

GTC ACC ATC ACC TGC CGT GCT AGC GAA AAC                 90
Val Thr Ile Thr Cys Arg Ala Ser Glu Asn
                25                  30

ATC TAT GGC GCG CTG AAC TGG TAT CAA CAG                120
Ile Tyr Gly Ala Leu Asn Trp Tyr Gln Gln
                35                  40

AAA CCC GGG AAA GCT CCG AAG CTT CTG ATT                150
Lys Pro Gly Lys Ala Pro Lys Leu Leu Ile
                45                  50

TAC GGT GCG ACG AAC CTG GCA GAT GGA GTC                180
Tyr Gly Ala Thr Asn Leu Ala Asp Gly Val
                55                  60
```

UNITED STATES PATENT AND TRADEMARK OFFICE
CERTIFICATE OF CORRECTION

PATENT NO.     : 6,355,245 B1
DATED          : March 12, 2002
INVENTOR(S)    : Mark J. Evans et al.

It is certified that error appears in the above-identified patent and that said Letters Patent is hereby corrected as shown below:

Column 133,
Please delete line 46, through column 135, line 12, and insert therefor:

```
    CCT TCT CGC TTC TCT GGA TCC GGC TCC GGA                    210
    Pro Ser Arg Phe Ser Gly Ser Gly Ser Gly
                    65                  70

ACG GAT TTC ACT CTG ACC ATC AGC AGT CTG                    240
    Thr Asp Phe Thr Leu Thr Ile Ser Ser Leu
                    75                  80

CAG CCT GAA GAC TTC GCT ACG TAT TAC TGT                    270
    Gln Pro Glu Asp Phe Ala Thr Tyr Tyr Cys
                    85                  90

CAG AAC GTT TTA AAT ACT CCG TTG ACT TTC                    300
    Gln Asn Val Leu Asn Thr Pro Leu Thr Phe
                    95                 100

GGA CAG GGT ACC AAG GTG GAA ATA AAA CGT                    330
    Gly Gln Gly Thr Lys Val Glu Ile Lys Arg
                   105                 110

ACT GGC GGT GGT GGT TCT GGT GGC GGT GGA                    360
    Thr Gly Gly Gly Gly Ser Gly Gly Gly Gly
                   115                 120

TCT GGT GGT GGC GGT TCT CAA GTC CAA CTG                    390
    Ser Gly Gly Gly Gly Ser Gln Val Gln Leu
                   125                 130

GTG CAA TCC GGC GCC GAG GTC AAG AAG CCA                    420
    Val Gln Ser Gly Ala Glu Val Lys Lys Pro
                   135                 140

GGG GCC TCA GTC AAA GTG TCC TGT AAA GCT                    450
    Gly Ala Ser Val Lys Val Ser Cys Lys Ala
                   145                 150

AGC GGC TAT ATT TTT TCT AAT TAT TGG ATT                    480
    Ser Gly Tyr Ile Phe Ser Asn Tyr Trp Ile
                   155                 160
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 135,
Please delete lines 13-39, and insert therefor:

```
CAA TGG GTG CGT CAG GCC CCC GGG CAG GGC                510
Gln Trp Val Arg Gln Ala Pro Gly Gln Gly
                165                 170

CTG GAA TGG ATG GGT GAG ATC TTA CCG GGC                540
Leu Glu Trp Met Gly Glu Ile Leu Pro Gly
                175                 180

.TCT GGT AGC ACC GAA TAT ACC GAA AAT TTT               570
Ser Gly Ser Thr Glu Tyr Thr Glu Asn Phe
                185                 190

AAA GAC CGT GTT ACT ATG ACG CGT GAC ACT                600
Lys Asp Arg Val Thr Met Thr Arg Asp Thr
                195                 200

TCG ACT AGT ACA GTA TAC ATG GAG CTC TCC                630
Ser Thr Ser Thr Val Tyr Met Glu Leu Ser
                205                 210

AGC CTG CGA TCG GAG GAC ACG GCC GTC TAT                660
Ser Leu Arg Ser Glu Asp Thr Ala Val Tyr
                215                 220

TAT TGC GCG CGT TAT TTT TTT GGT TCT AGC                690
Tyr Cys Ala Arg Tyr Phe Phe Gly Ser Ser
                225                 230

CCG AAT TGG TAT TTT GAT GTT TGG GGT CAA                720
Pro Asn Trp Tyr Phe Asp Val Trp Gly Gln
                235                 240

GGA ACC CTG GTC ACT GTC TCG AGC TGA                    747
Gly Thr Leu Val Thr Val Ser Ser
                245
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 135,</u>
Please delete line 49, through column 137, line 21, and insert therefor:

```
ATG GCC GAT ATC CAG ATG ACC CAG TCC CCG                30
Met Ala Asp Ile Gln Met Thr Gln Ser Pro
 1               5                  10

TCC TCC CTG TCC GCC TCT GTG GGC GAT AGG                60
Ser Ser Leu Ser Ala Ser Val Gly Asp Arg
                15                  20

GTC ACC ATC ACC TGC GGC GCC AGC GAA AAC                90
Val Thr Ile Thr Cys Gly Ala Ser Glu Asn
                25                  30

ATC TAT GGC GCG CTG AAC TGG TAT CAA CAG               120
Ile Tyr Gly Ala Leu Asn Trp Tyr Gln Gln
                35                  40

AAA CCC GGG AAA GCT CCG AAG CTT CTG ATT               150
Lys Pro Gly Lys Ala Pro Lys Leu Leu Ile
                45                  50

TAC GGT GCG ACG AGC CTG CAG TCT GGA GTC               180
Tyr Gly Ala Thr Ser Leu Gln Ser Gly Val
                55                  60

CCT TCT CGC TTC TCT GGA TCC GGC TCC GGA               210
Pro Ser Arg Phe Ser Gly Ser Gly Ser Gly
                65                  70

ACG GAT TTC ACT CTG ACC ATC AGC AGT CTG               240
Thr Asp Phe Thr Leu Thr Ile Ser Ser Leu
                75                  80

CAG CCT GAA GAC TTC GCT ACG TAT TAC TGT               270
Gln Pro Glu Asp Phe Ala Thr Tyr Tyr Cys
                85                  90

CAG AAC GTT TTA AAT ACT CCG TTG ACT TTC               300
Gln Asn Val Leu Asn Thr Pro Leu Thr Phe
                95                 100
```

UNITED STATES PATENT AND TRADEMARK OFFICE
CERTIFICATE OF CORRECTION

PATENT NO.   : 6,355,245 B1
DATED        : March 12, 2002
INVENTOR(S)  : Mark J. Evans et al.

It is certified that error appears in the above-identified patent and that said Letters Patent is hereby corrected as shown below:

Column 137,
Please delete lines 22-51, and insert therefor:

```
GGA CAG GGT ACC AAG GTG GAA ATA AAA CGT                330
Gly Gln Gly Thr Lys Val Glu Ile Lys Arg
            105                 110

ACT GGC GGT GGT GGT TCT GGT GGC GGT GGA                360
Thr Gly Gly Gly Gly Ser Gly Gly Gly Gly
            115                 120

TCT GGT GGT GGC GGT TCT CAA GTC CAA CTG                390
Ser Gly Gly Gly Gly Ser Gln Val Gln Leu
            125                 130

GTG CAA TCC GGC GCC GAG GTC AAG AAG CCA                420
Val Gln Ser Gly Ala Glu Val Lys Lys Pro
            135                 140

GGG GCC TCA GTC AAA GTG TCC TGT AAA GCT                450
Gly Ala Ser Val Lys Val Ser Cys Lys Ala
            145                 150

AGC GGC TAT ATT TTT TCT AAT TAT TGG ATT                480
Ser Gly Tyr Ile Phe Ser Asn Tyr Trp Ile
            155                 160

CAA TGG GTG CGT CAG GCC CCC GGG CAG GGC                510
Gln Trp Val Arg Gln Ala Pro Gly Gln Gly
            165                 170

CTG GAA TGG ATG GGT GAG ATC TTA CCG GGC                540
Leu Glu Trp Met Gly Glu Ile Leu Pro Gly
            175                 180

TCT GGT AGC ACC GAA TAT ACC GAA AAT TTT                570
Ser Gly Ser Thr Glu Tyr Thr Glu Asn Phe
            185                 190

AAA GAC CGT GTT ACT ATG ACG CGT GAC ACT                600
Lys Asp Arg Val Thr Met Thr Arg Asp Thr
            195                 200
```

UNITED STATES PATENT AND TRADEMARK OFFICE
CERTIFICATE OF CORRECTION

PATENT NO.   : 6,355,245 B1
DATED        : March 12, 2002
INVENTOR(S)  : Mark J. Evans et al.

It is certified that error appears in the above-identified patent and that said Letters Patent is hereby corrected as shown below:

Column 137,
Please delete line 52, through column 139, line 6, and insert therefor:

```
TCG ACT AGT ACA GTA TAC ATG GAG CTC TCC                 630
Ser Thr Ser Thr Val Tyr Met Glu Leu Ser
            205                     210

AGC CTG CGA TCG GAG GAC ACG GCC GTC TAT                 660
Ser Leu Arg Ser Glu Asp Thr Ala Val Tyr
            215                     220

TAT TGC GCG CGT TAT TTT TTT GGT TCT AGC                 690
Tyr Cys Ala Arg Tyr Phe Phe Gly Ser Ser
            225                     230

CCG AAT TGG TAT TTT GAT GTT TGG GGT CAA                 720
Pro Asn Trp Tyr Phe Asp Val Trp Gly Gln
            235                     240

GGA ACC CTG GTC ACT GTC TCG AGC TGA                     747
Gly Thr Leu Val Thr Val Ser Ser
            245
```

Column 139,
Please delete lines 16-27, and insert therefor:

```
ATG GCC GAT ATC CAG ATG ACC CAG TCC CCG                  30
Met Ala Asp Ile Gln Met Thr Gln Ser Pro
 1              5                       10

TCC TCC CTG TCC GCC TCT GTG GGC GAT AGG                  60
Ser Ser Leu Ser Ala Ser Val Gly Asp Arg
            15                          20

GTC ACC ATC ACC TGC CGT GCT AGC GAA AAC                  90
Val Thr Ile Thr Cys Arg Ala Ser Glu Asn
            25                          30

ATC TAT GGC GCG CTG AAC TGG TAT CAA CAG                 120
Ile Tyr Gly Ala Leu Asn Trp Tyr Gln Gln
            35                          40
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 139,
Please delete lines 28-57, and insert therefor:

```
AAA CCC GGG AAA GCT CCG AAG CTT CTG ATT              150
Lys Pro Gly Lys Ala Pro Lys Leu Leu Ile
                45                      50

TAC GGT GCG ACG AGC CTG CAG TCT GGA GTC              180
Tyr Gly Ala Thr Ser Leu Gln Ser Gly Val
                55                      60

CCT TCT CGC TTC TCT GGA TCC GGC TCC GGA              210
Pro Ser Arg Phe Ser Gly Ser Gly Ser Gly
                65                      70

ACG GAT TTC ACT CTG ACC ATC AGC AGT CTG              240
Thr Asp Phe Thr Leu Thr Ile Ser Ser Leu
                75                      80

CAG CCT GAA GAC TTC GCT ACG TAT TAC TGT              270
Gln Pro Glu Asp Phe Ala Thr Tyr Tyr Cys
                85                      90

CAG AAC GTT TTA AAT ACT CCG TTG ACT TTC              300
Gln Asn Val Leu Asn Thr Pro Leu Thr Phe
                95                     100

GGA CAG GGT ACC AAG GTG GAA ATA AAA CGT              330
Gly Gln Gly Thr Lys Val Glu Ile Lys Arg
               105                     110

ACT GGC GGT GGT GGT TCT GGT GGC GGT GGA              360
Thr Gly Gly Gly Gly Ser Gly Gly Gly Gly
               115                     120

TCT GGT GGT GGC GGT TCT CAA GTC CAA CTG              390
Ser Gly Gly Gly Gly Ser Gln Val Gln Leu
               125                     130

GTG CAA TCC GGC GCC GAG GTC AAG AAG CCA              420
Val Gln Ser Gly Ala Glu Val Lys Lys Pro
               135                     140
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

Column 141,
Please delete lines 1-30, and insert therefor:

```
        GGG GCC TCA GTC AAA GTG TCC TGT AAA GCT                    450
        Gly Ala Ser Val Lys Val Ser Cys Lys Ala
                        145                 150

AGC GGC TAT ATT TTT TCT AAT TAT TGG ATT                    480
        Ser Gly Tyr Ile Phe Ser Asn Tyr Trp Ile
                        155                 160

CAA TGG GTG CGT CAG GCC CCC GGG CAG GGC                    510
        Gln Trp Val Arg Gln Ala Pro Gly Gln Gly
                        165                 170

CTG GAA TGG ATG GGT GAG ATC TTA CCG GGC                    540
        Leu Glu Trp Met Gly Glu Ile Leu Pro Gly
                        175                 180

TCT GGT AGC ACC GAA TAT ACC GAA AAT TTT                    570
        Ser Gly Ser Thr Glu Tyr Thr Glu Asn Phe
                        185                 190

AAA GAC CGT GTT ACT ATG ACG CGT GAC ACT                    600
        Lys Asp Arg Val Thr Met Thr Arg Asp Thr
                        195                 200

TCG ACT AGT ACA GTA TAC ATG GAG CTC TCC                    630
        Ser Thr Ser Thr Val Tyr Met Glu Leu Ser
                        205                 210

AGC CTG CGA TCG GAG GAC ACG GCC GTC TAT                    660
        Ser Leu Arg Ser Glu Asp Thr Ala Val Tyr
                        215                 220

TAT TGC GCG CGT TAT TTT TTT GGT TCT AGC                    690
        Tyr Cys Ala Arg Tyr Phe Phe Gly Ser Ser
                        225                 230

CCG AAT TGG TAT TTT GAT GTT TGG GGT CAA                    720
        Pro Asn Trp Tyr Phe Asp Val Trp Gly Gln
                        235                 240
```

UNITED STATES PATENT AND TRADEMARK OFFICE
CERTIFICATE OF CORRECTION

PATENT NO. : 6,355,245 B1
DATED : March 12, 2002
INVENTOR(S) : Mark J. Evans et al.

It is certified that error appears in the above-identified patent and that said Letters Patent is hereby corrected as shown below:

<u>Column 141,</u>
Please delete lines 31-33, and insert therefor:

```
GGA ACC CTG GTC ACT GTC TCG AGC TGA                    747
Gly Thr Leu Val Thr Val Ser Ser
                245
```

Signed and Sealed this

Nineteenth Day of November, 2002

Attest:

Attesting Officer

JAMES E. ROGAN
*Director of the United States Patent and Trademark Office*